(12) United States Patent
Lee et al.

(10) Patent No.: US 7,164,019 B2
(45) Date of Patent: Jan. 16, 2007

(54) HETEROCYCLIC ANTIVIRAL COMPOUNDS

(75) Inventors: Eun Kyung Lee, San Jose, CA (US); Chris Richard Melville, Palo Alto, CA (US); David Mark Rotstein, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/147,851

(22) Filed: Jun. 8, 2005

(65) Prior Publication Data

US 2006/0014767 A1 Jan. 19, 2006

Related U.S. Application Data

(60) Provisional application No. 60/578,759, filed on Jun. 9, 2004.

(51) Int. Cl.
C07D 239/24 (2006.01)
(52) U.S. Cl. .................................. 544/335
(58) Field of Classification Search ............... 548/452; 544/335
See application file for complete search history.

(56) References Cited

U.S. PATENT DOCUMENTS 5,686,459 A * 11/1997 Diederich et al. ....... 514/266.2
2004/0053986 A1 * 3/2004 Bjorsne et al. ............. 514/412

FOREIGN PATENT DOCUMENTS

| DE | 3930266 A1 | 3/1991 |
|---|---|---|
| EP | 1 122 257 B1 | 10/2005 |
| WO | WO 95/13279 A1 | 3/1995 |
| WO | WO 95/15327 A1 | 6/1995 |
| WO | WO 96/07656 A1 | 3/1996 |
| WO | WO 97/11945 A1 | 4/1997 |
| WO | WO 98/06725 A1 | 2/1998 |
| WO | WO 00/38680 A1 | 7/2000 |
| WO | WO 00/39125 A1 | 7/2000 |
| WO | WO 00/55143 A1 | 9/2000 |
| WO | WO 00/66558 A1 | 11/2000 |
| WO | WO 00/66559 A1 | 11/2000 |
| WO | WO 01/44243 A2 | 6/2001 |
| WO | WO 01/90106 A2 | 11/2001 |
| WO | WO 02/07523 A2 | 1/2002 |
| WO | WO 02/060902 A1 | 8/2002 |
| WO | WO 03/097646 A | 11/2003 |
| WO | WO 04/056773 A1 | 7/2004 |

OTHER PUBLICATIONS

Abou-Gharbia, M., *Synthesis and Structure-Activity Relationship of Substituted Tetrahydro- and Hexahydro-1, 2-benziosothiazol-3-one, 1,1-Dioxides and Thiadiazinoes: Potential Anxiolytic Agents*, J. Med. Chem., 1989, pp. 1024-1033, vol. 32.

Agawal, L., *Chemokine receptors: emerging opportunities for new anti-HIV therapies*, Expert Opin. Ther. Targets, 2001, pp. 303-326, vol. 5(3).

Baba, M., *A small-molecule, nonpeptide CCR5 antagonist with highly potent and selective anti-HIV-1 activity*, Proc. Nat. Acad. Sci. USA, 1999, pp. 5698-5703, vol. 96.

De Clerq, E., *Emerging anti-HIV Drugs*, Exp. Opin. Emerg. Drugs, 2005, pp. 241-274, vol. 10.

Dorr, P., *Abstr. of the 11th Conf. on Retroviruses and Opportunistic Infect*, San Francisco, CA, USA, Feb. 10-14, 2003, Abstract, 12.

Dooseop, K.., *Discovery of Human CCR5 Antagonists Containing Hydantoins for the Treatment of HIV-1 Infection*, Bioorg. Med. Chem. Lett., 2001, pp. 3099-3102, vol. 11.

Dorr, P., *Maraviroc (UK-427,857), a Potent, Orally Bioavailable, and Selective Small-Molecule Inhibitor of Chemokine Receptor CCR5 with Broad-Spectrum Anti-Human Immunodeficiency Virus Type 1 Activity*, Antimicrob. Agents Chemother., 2005, pp. 4721-4732, vol. 49(11).

Finke, P., *Antagonists of the Human CCR5 Receptor as Anti-HIV-1 Agents Part 4: Synthesis and Structure-Activity Relationships for 1-[N-(Methyl)-N-(phenylsulfonyl)amino]-2-(phenyl)-4-(4-(N-(alkyl)-N-(benzyloxycarbonyl)amino)piperidin-1-yl)butanes*, Bioorg. Med. Chem. Lett. 2001, pp. 2475-2479, vol. 11.

Finke, P., *Antagonists of the Human CCR5 Receptor as anti-HIV-1 agents, Part 2: Structure-Activity Relationships for Substituted 2-Aryl-1-[N(methyl)-N-(phenylsulfonyl)amino]-4-(piperidin-1-yl)butanes*, Biorg. Med. Chem. Lett., 2001, pp. 265-270, vol. 11.

(Continued)

*Primary Examiner*—Joseph K. McKane
*Assistant Examiner*—Shawquia Young
(74) *Attorney, Agent, or Firm*—Brian L. Buckwalter

(57) ABSTRACT

Chemokine receptor antagonists, in particular, 3,7-diazabicyclo[3.3.0]octane compounds according to formula (I) are antagonists of chemokine CCR5 receptors which are useful for treating or preventing an human immunodeficiency virus (HIV) infection, or treating AIDS or ARC. The invention further provides methods for treating diseases that are alleviated with CCR5 antagonists. The invention includes pharmaceutical compositions and methods of using the compounds for the treatment of these diseases. The invention further includes processes for the preparation of compounds according to formula I.

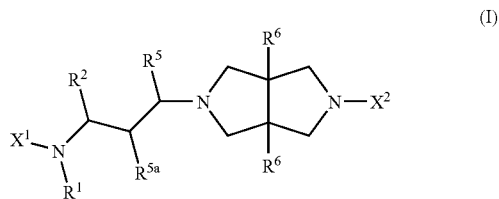

(I)

12 Claims, No Drawings

OTHER PUBLICATIONS

Finke, P., *Antagonists of the Human CCR5 Receptor as Anti-HIV-1 Agents. Part 3: a Proposed Pharmacophore Model for 1-[N-(Methyl)-N-(phenylsulfonyl)amino]-2-(phenyl)-4-[4-(substituted)piperidin-1-yl]butances*, Bioorg. Med. Chem. Lett., 2001, pp. 2469-2473, vol. 11.

Hale, J. *1,3,4-Trisubstituted Pyrrolidine CCR5 Receptor Antagonists. Part 2: Lead Optimization Affording Selective, Orally Bioavailable Compounds with Potent Anti-HIV activity*, Bioorg. Med. Chem. Lett., 2001, pp. 2741-2745, vol. 11.

Kazmierski, W., *Recent Progress in Discovery of Small-Molecule CCR5 Chemokine Receptor Ligands as HIV-1 Inhibitors*, Biorg. Med. Chem., 2003, pp. 2663-2676, vol. 11.

Macartney, M., *43rd Intersci. Conf. Antimicrob. Agents Chemother.*, Chicago, IL, USA, Sep. 14-17, 2003, Abstract, H-875;.

Maeda, K., *Novel Low Molecular Weight Spirodiketopiperazine Derivatives Potently Inhibit R5 HIV-1 Infection through Their Antagonistic Effects on CCRD*, J. Biol. Chem., 2001, pp. 35194-35200, vol. 276(37).

Maeda, K., *Spirodiketopiperazine-Based CCR5 Inhibitor Which Preserves CC-Chemokine/CCR5 Interactions and Exerts Potent Activity against R5 Human Immunodeficiency Virus Type 1 in Vitro*, J. Virol., 2004, pp. 8654-62, vol. 78(16).

Maeda, K., *The current status of, and challenges in, the development of CCR5 inhibitors as therapeutics for HIV-1 infection*, Curr. Opin. Pharmacol., 2004, pp. 447-452, vol. 4.

Obst, U., *Synthesis of Novel Nonpeptidic Thrombin Inhibitors*, Helv. Chim. Acta., 2000, pp. 855-909, vol. 83.

Palani, A., *Discovery of 4-[(Z)-(4-Bromophenyl)-(ethoxylimino)methyl]-1'-[(2,4-dimethyl-3-pyridinyl)carbonl]-4'-methyl-1,4'-bipiperidine N-Oxide (SCH 351125): An Orally Bioavailable Human CCR5 Antagonist for the Treatment of HIV Infection*, J. Med Chem., 2001, pp. 3339-3342, vol. 44(21).

Shiraishi, M., *Discovery of Novel, Potent, and Selective Small-Molecule CCR5 Antagonists as Anti-HIV-1 Agents: Synthesis and Biological Evaluation of Anilide Derivatives with a Quatemary Ammonium Moiety*, J. Med. Chem., 2000, pp. 2049-2063, vol. 43(10).

Strizki, J., *SCH-C (SCH 351125), an orally bioavailable, small molecule antagonist of the chemokine receptor CCR5, is a potent inhibitor of HIV-1 infection in vitro and in vivo*, Proc. Nat. Acad. Sci. USA, 2001, pp. 12718-12723, vol. 98.

Tagat, J., *Piperazine-Based CCR5 Antagonists as HIV-1 Inhibitors, II. Discovery of 1-[2,4-Dimethyl-3-pyridinyl)carbonyl]-4-methyl-4-[3(S)-methyl-4-[1(S)-[4-(trifluromethyl)phenyl]ethyl]-1-piperazinyl]-piperidine N1-Oxide (sch-350634), an Orally Bioavailable, Potent CCR5 Antagonist*, J. Med. Chem., 2001, pp. 3343-3346, vol. 44(21).

Watson, C., *The CCR5 Receptor-Based Mechanism of Action of 873140, a Potent Allosteric Noncompetitive HIV Entry Inhibitor*, Mol. Pharm., 2005, pp. 1268-1282, vol. 67(4).

Wood, A., *The Discovery of the CCR5 Receptor Antagonist, UK-427,857, A New Agent for the Treatment of HIV Infection and AIDS*Prog. Med. Chem., 2005, pp. 239-271, vol. 43.

\* cited by examiner

HETEROCYCLIC ANTIVIRAL COMPOUNDS

CROSS REFERENCE TO RELATED APPLICATIONS

This application claims the benefit of priority to U.S. Ser. No. 60/578,759 filed on Jun. 9, 2004 which is hereby incorporated by reference in its entirety.

FIELD OF THE INVENTION

This invention relates to octahydro-pyrrolo[3,4-c]pyrrole derivatives useful in the treatment of a variety of disorders, including those in which the modulation of CCR5 receptors is implicated. More particularly, the present invention relates to 3-(hexahydro-pyrrolo[3,4-c]pyrrol-2-yl)-1-phenyl-propylamine and [3-(hexahydro-pyrrolo[3,4-c]pyrrol-2-yl)-propyl]-phenyl-amine compounds and related derivatives, to compositions containing, to uses of such derivatives and to processes for preparing said compounds. Disorders that may be treated or prevented by the present derivatives include HIV and genetically related retroviral infections (and the resulting acquired immune deficiency syndrome, AIDS), diseases of the immune system and inflammatory diseases.

BACKGROUND OF THE INVENTION

A-M. Vandamme et al. (*Antiviral Chemistry & Chemotherapy*, 1998 9:187–203) disclose current HAART clinical treatments of HIV-1 infections in man including at least triple drug combinations. Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. In compliant drug-naive patients, HAART is effective in reducing mortality and progression of HIV-1 to AIDS. While HAART has dramatically altered the prognosis for HIV infected persons, there remain many drawbacks to the current therapy including highly complex dosing regimes and side effects which can be very severe (A. Carr and D. A. Cooper, *Lancet* 2000 356(9239):1423–1430). Moreover, these multidrug therapies do not eliminate HIV-1 and long-term treatment usually results in multidrug resistance, thus limiting their utility in long term therapy. Development of new drug therapies to provide better HIV-1 treatment remains a priority.

Compounds of the present invention modulate the activity of the chemokine CCR5 receptors. The chemokines are a large family of pro-inflammatory peptides that exert their pharmacological effect through G-protein-coupled receptors. The name "chemokine", is a contraction of "chemotactic cytokines". The chemokines are a family of leukocyte chemotactic proteins capable of attracting leukocytes to various tissues, which is an essential response to inflammation and infection. Human chemokines include approximately 50 small proteins of 50–120 amino acids that are structurally homologous. (M. Baggiolini et al., *Annu. Rev. Immunol.* 1997 15:675–705)

Modulators of the CCR5 receptor may be useful in the treatment of various inflammatory diseases and conditions, and in the treatment of infection by HIV-1 and genetically related retroviruses. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which are active in modulating, preferably antagonizing, the activity of chemokines and their receptors, are useful in the therapeutic treatment of such inflammatory and infectious diseases. The chemokine receptor CCR5 is of particular importance in the context of treating inflammatory and infectious diseases. CCR5 is a receptor for chemokines, especially for the macrophage inflammatory proteins (MIP) designated MIP-1a and MIP-1b, and for a protein which is regulated upon activation and is normal T-cell expressed and secreted (RANTES).

HIV-1 infects cells of the monocyte-macrophage lineage and helper T-cell lymphocytes by exploiting a high affinity interaction of the viral enveloped glycoprotein (Env) with the CD-4 antigen. The CD-4 antigen, however appeared to be a necessary, but not sufficient requirement for cell entry and at least one other surface protein was required to infect the cells (E. A. Berger et al., *Ann. Rev. Immunol.* 1999 17:657–700). Two chemokine receptors, either the CCR5 or the CXCR4 receptor were subsequently found to be co-receptors along with CD4 which are required for infection of cells by the human immunodeficiency virus (HIV). The central role of CCR5 in the pathogenesis of HIV was inferred by epidemiological identification of powerful disease modifying effects of the naturally occurring null allele CCR5 Δ32. The Δ32 mutation has a 32-basepair deletion in the CCR5 gene resulting in a truncated protein designated Δ32. Relative to the general population, Δ32/Δ32 homozygotes are significantly common in exposed/uninfected individuals suggesting the role of CCR5 in HIV cell entry (R. Liu et al., *Cell* 1996 86(3):367–377; M. Samson et al., *Nature* 1996 382(6593):722–725).

The HIV-1 envelope protein is comprised of two subunits: gp120, the surface subunit and gp41, the transmembrane subunit. The two subunits are non-covalently associated and form homotrimers which compose the HIV envelope. Each gp41 subunit contains two helical heptad repeat regions, HR1 and HR2 and a hydrophobic fusion region on the C-terminus.

The CD4 binding site on the gp120 of HIV appears to interact with the CD4 molecule on the cell surface that induces a conformation change in gp120 which creates or exposes a cryptic CCR5 (or CXCR4) binding site, and undergoes conformational changes which permits binding of gp120 to the CCR5 and/or CXCR-4 cell-surface receptor. The bivalent interaction brings the virus membrane into close proximity with the target cell membrane and the hydrophobic fusion region can insert into the target cell membrane. A conformation change in gp41 allows the contact between the outer leaflet of the target cell membrane and the viral membrane which produces a fusion pore whereby the virus RNA is injected into the cytoplasm. Accordingly, an agent which could inhibit binding between gp120 and chemokine receptors should prevent or moderate infection in healthy individuals and slow or halt viral progression in infected patients. (B. Tomkowicz and R. G. Collman, *Expert Opin. Ther. Targets* 2004 8(2):65–78; J. P. Moore and R. W. Doms, *Proc. Nat. Acad. Sci. USA*, 2003 100(19):10598–10602)

Viral fusion and cell entry is a complex multi-step process and each step affords the potential for therapeutic intervention. These steps include (i) CD40-gp120 interactions, (ii) CCR5 and/or CXCR-4 interactions and (iii) gp41 mediated membrane fusion. Each of these steps affords an opportunity for therapeutic intervention in preventing or slowing HIV infection RANTES, a natural ligand for the CCR5 receptor, and an analog chemically modified on the N-terminus, aminooxypentane RANTES, were found to block HIV entry into the cells. (G. Simmons et al., *Science* 1997 276:276–279). Other compounds have been demonstrated to inhibit the replication of HIV, including soluble CD4 protein and synthetic derivatives (Smith, et al., *Science* 1987 238:1704–1707), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

T20 (Entuvirtide) is a 36 amino acid peptide corresponding to residues 643–678 in the HR2 domain of gp41. T-20 binds a transient intermediate formed interaction after interaction of gp120 and the target cell which inhibits viral fusion thereby suppressing viral replication. (J. M. Kilby et al., *New Eng. J. med.* 1998 4(11):1302–1307). T-20 has been approved for clinical use.

In addition to the potential for CCR5 modulators in the management of HIV infections, the CCR5 receptor is an important regulator of immune function and compounds of the present invention may prove valuable in the treatment of disorders of the immune system. Treatment of solid organ transplant rejection, graft v. host disease, arthritis, rheumatoid arthritis, inflammatory bowel disease, atopic dermatitis, psoriasis, asthma, allergies or multiple sclerosis by administering to a human in need of such treatment an effective amount of a CCR5 antagonist compound of the present invention is also possible.

The pharmacokinetic challenges associated with large molecules, proteins and peptides resulted in the establishment of programs to identify low molecular weight antagonists of CCR5. The efforts to identify chemokine modulators have been reviewed (W. Kazmierski et al. *Biorg Med. Chem.* 2003 11:2663–76; L. Agrawal and G. Alkhatib, *Expert Opin. Ther. Targets* 2001 5(3):303–326; *Chemokine CCR5 antagonists incorporating 4-aminopiperidine scaffold, Expert Opin. Ther. Patents* 2003 13(9):1469–1473; M. A. Cascieri and M. S. Springer, *Curr. Opin. Chem. Biol.* 2000 4:420–426, and references cited therein)

Takeda's program was the first to lead to fruition with the identification of TAK-779 (M. Shiraishi et al., *J. Med. Chem.* 2000 43(10):2049–2063). Schering has advanced Sch-351125 into Phase I/II clinical studies and reported the advance of a more potent follow-up compound, Sch-417690 into Phase I studies. (S. W. McCrombie et al., WO00066559; B. M. Baroudy et al. WO00066558; A. Palani et al., *J. Med. Chem.* 2001 44(21):3339–3342; J. R. Tagat et al., *J Med. Chem.* 2001 44(21):3343–3346; J. A. Esté, *Cur. Opin. Invest. Drugs* 2002 3(3):379–383).

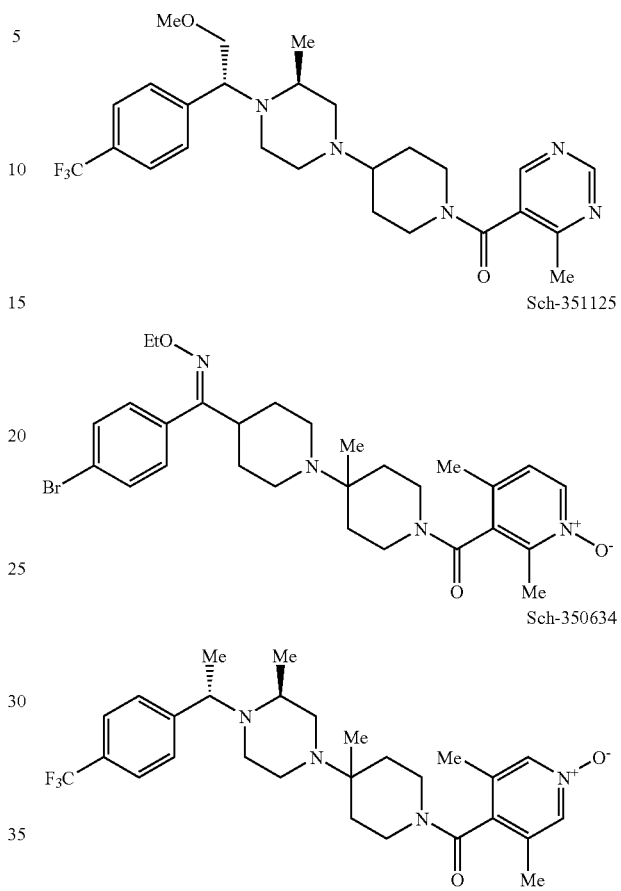

Merck has disclosed the preparation of (2S)-2-(3-chlorophenyl)-1-N-(methyl)-N-(phenylsulfonyl)amino]-4-[spiro(2,3-dihydrobenzothiophene-3,4'-piperidin-1'-yl)butane S-oxide (1) and related derivatives, trisubstituted pyrrolidines 2 and substituted piperidines 3 with good affinity for the CCR5 receptor and potent-HIV activity. (P. E. Finke et al., *Bioorg. Med. Chem. Lett.*, 2001 11:265–270; P. E. Finke et al., *Bioorg. Med. Chem. Lett.*, 2001 11:2469–2475; P. E. Finke et al., *Bioorg. Med. Chem. Lett.*, 2001 11:2475–2479; J. J. Hale et al., *Bioorg. Med. Chem. Lett.*, 2001 11:2741–22745; D. Kim et al., *Bioorg. Med. Chem. Lett.*, 2001 11:3099–3102)

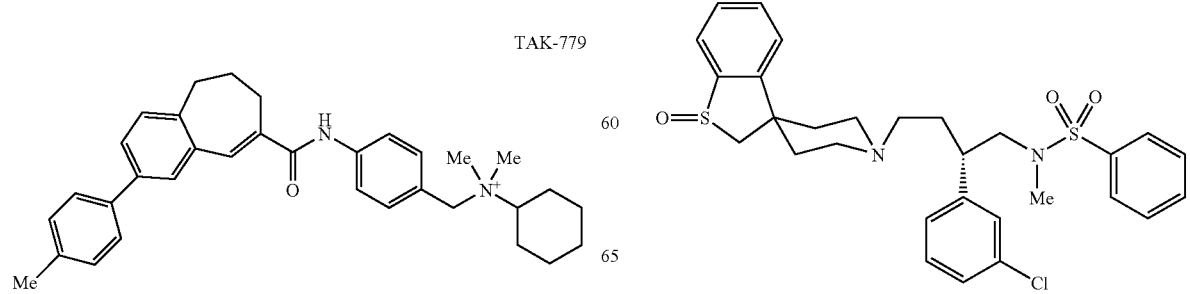

-continued

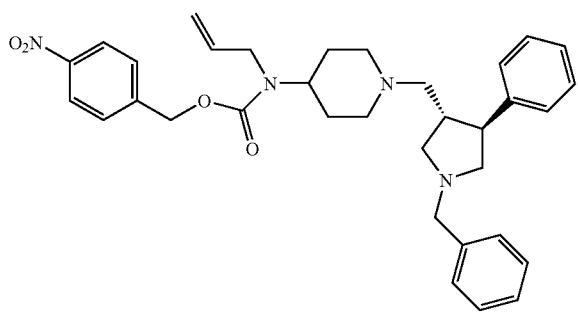
2

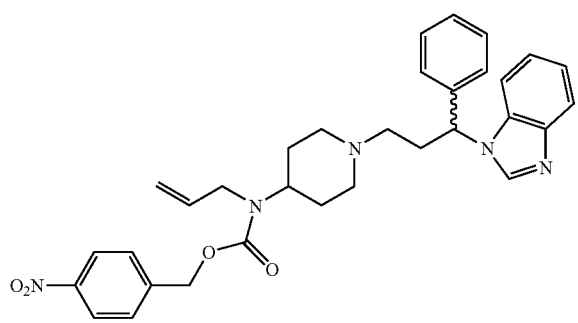
UK-427857

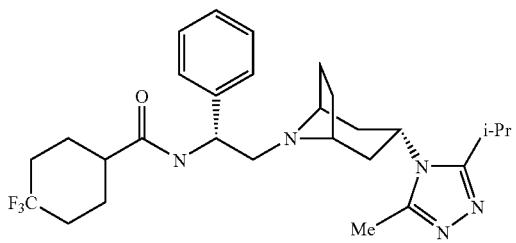

WO0039125 (D. R. Armour et al.) and WO0190106 (M. Perros et al.) disclose heterocyclic compounds that are potent and selective CCR5 antagonists. UK427857 has advanced to clinical trials and show activity against HIV-1 isolates and laboratory strains (M. J. Macartney et al., 43$^{rd}$ Intersci. Conf. Antimicrob. Agents Chemother. (Sep. 14–17, 2003, Abstract II-875).

(4)

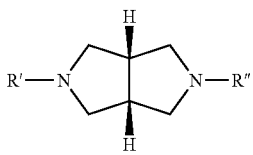

Due to their rigidity and the ease of functionalization, bicyclic and tricyclic amines have proven to be useful scaffolds in drug design. Compounds based upon the 3,7-diazabiyclo[3.3.0]octane (4: R'=R"=H) are known for use in a variety of medical applications, including inter alia as migrane (as described in WO 98/06725 and WO97/11945); antibiotics (as described in WO 97/10223 and WO 96/25691, neuroleptics (as described in WO 95/15327 and WO95/13279); serotonin reuptake inhibitors (as described in WO 96/07656); thrombin inhibitors (as described in *Helv. Chim. Acta* 2000 83:855, *Chem. & Biol.* 1997 4:287 and *Angew. Chem. Int. Ed. Eng.* 1995 34:1739); and, anxiolytic agents (*J. Med. Chem.* 1989 32:1024). In addition, compounds based upon 3,7-diazabicyclo[3.3.0]octane have been used in the treatment of gastrointestinal disorders (DE 39 30 266 A1) disorders of the glutaminergic system. WO 00/55143 discloses diamine compounds, including 3,7-diazabicyclo[3.3.0]octane compounds linked to an oxazolone which compounds are α-1 adenoreceptor modulators. EP 1 122 257 (F. Ito et al.) disclose benzimidazole compounds linked to a variety bicyclic diamine compounds including diazabicyclooctanes which compounds are ORL-1 receptor agonists. The ORL-1 receptor is an opioid receptor subtype.

WO 96/07656 (J. M. Schaus and R. D. Titus) disclosed aralkyl substituted 3,7-diazabicyclo[3.3.0]octane compounds with selective reuptake inhibitory activity. WO 97/11945 (A. Madin) disclose 3-substituted 3,7-diazabicyclo[3.3.0]octane compounds, which may be further substituted at the 7-position, with selective 5-HT$_{ID\alpha}$ activity. WO 01/44243 (D. Peters et al.) disclose novel heteroaryl 3-substituted-diazabicycloalkane compounds, which may be optionally substituted at the 7-position, which are muscarinic and nicotinic receptor modulators which are useful in the treating diseases associated with degeneration of the cholinergic system. The preferred embodiments include 3,7-diazabicyclo[3.3.0]octane compounds 4 wherein R' is a heteroaryl group and R" is hydrogen, alkyl, aryl, aralkyl or a fluorescent group.

WO 02/07523 A1 (R. Colon-Cruz et al.) discloses 3,7-diazabicyclo[3.3.0]octane compounds which are antagonists of the chemokine CCR2 and CCR3 receptors. MCP-1 is believed the natural ligand for the CCR2 receptor and interaction of the ligand with the receptor increases histamine release, calcium influx, cAMP activation, increases integrin expression and acts as a chemotactic factor for monocytes and macrophages. Compounds disclosed in the invention were claimed useful for the treatment of diseases of monocyte, lymphocyte and leukocyte accumulation and more specifically atherosclerosis, restenosis, gingivitis, psoriasis, rheumatoid arthritis, glomerulonephritis, Crohn's disease, encephalomyelitis and transplant rejection. The preferred embodiments include compounds with the generic formula 5.

(5)

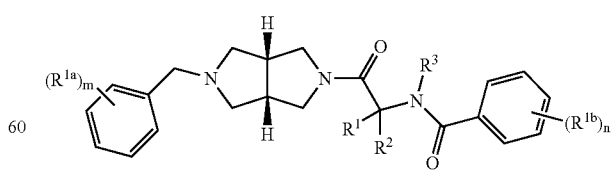

WO 02/060902 A1 (M. Björsne et al.) disclose 3,7-diazabicyclo[3.3.0]octane compounds useful in the treatment of cardiac arrhythmias. The preferred embodiments include compounds with the generic formula 6.

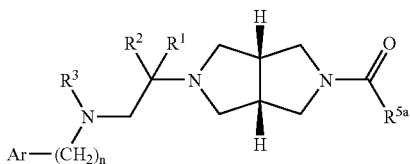

(6)

SUMMARY OF THE INVENTION

The present invention relates to a compounds according to formula I, methods for treating diseases alleviated by administration of a compound according to formula I that is a CCR5 antagonist and pharmaceutical compositions for treating diseases containing a compound according to formula I that is a CCR5 antagonist admixed with at least one carrier, diluent or

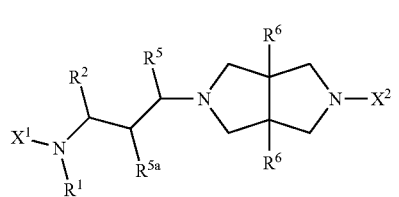

(I)

excipient, wherein:
$X^1$ is selected from the group consisting $-C(=O)R^3$, $-S(=O)_2R^3$ and $-C(=O)OR^3$;
$X^2$ is selected from the group consisting $-C(=O)R^4$, $-S(=O)_2R^4$, benzyl or $-CH_2$(pyridin-3-yl) said benzyl optionally substituted with halogen or $C_{1-3}$ alkyl;
one of $R^1$ and $R^2$ is:
  (i) phenyl optionally substituted with one to four substituents selected independently in each incidence from the group consisting of halogen, $C_{1-6}$ alkyl and $C_{1-6}$ alkoxy;
  (ii) heteroaryl selected from the group consisting of pyridinyl, pyridinyl-N-oxide, pyrimidinyl and thiazolyl said heteroaryl optionally substituted with one to three substituents independently selected from the group consisting of halogen, $C_{1-6}$ alkyl, $C_{1-6}$ haloalkyl and $C_{1-6}$ alkoxy; and,
the other of $R^1$ and $R^2$ is hydrogen;
$R^3$ is selected from the group consisting of:
  (i) phenyl optionally substituted with one to four substituents selected independently in each incidence from the group consisting of:
    (a) $C_{1-10}$ alkyl,
    (b) $C_{1-10}$ heteroalkyl,
    (c) $C_{1-6}$ haloalkyl,
    (d) $C_{1-6}$ alkoxy,
    (e) $C_{1-6}$ thioalkyl,
    (f) amino,
    (g) $C_{1-16}$ alkyl amino,
    (h) $C_{1-6}$ dialkylamino,
    (g) $C_{1-6}$ acylamino,
    (i) carbamoyl, $N-C_{1-6}$ alkylcarbamoyl or $N,N-C_{1-6}$ dialkylcarbamoyl,
    (j) ureido,
    (k) nitro,
    (l) cyano,
    (m) halogen,
    (n) $C_{1-6}$ alkylsulfonyl,
    (o) sulfamoyl, $N-C_{1-6}$ alkylsulfamoyl or $N,N-C_{1-6}$ dialkylsulfamoyl,
    (p) $C_{1-6}$ alkylsulfonamido or optionally substituted phenylsulfonamido,
    (q) optionally substituted phenoxy,
    (r) optionally substituted heteroaryloxy, and,
    (s) $-Y(CH_2)_nR^{11}$ wherein $R^{11}$ is selected from the group consisting of cyano, $-CO_2R^{12}$, $-CONR^{12}R^{13}$, $-SO_2N^{12}R^{13}$, $-NHSO_2R^{12}$ and $-NHSO_2NR^{12}R^{13}$,
    (t) $CO_2R^{12}$,
    (u) $C_{1-6}$ acyloxy,
    (v) $C_{1-6}$ alkylcarbonyl, and,
    (w) $C_{1-6}$ haloalkoxy;
  (ii) phenyl $C_{1-6}$ alkyl wherein phenyl as described in (i) above;
  (iii) heteroaryl selected from the group consisting of pyridinyl, pyridinyl-N-oxide, pyrimidinyl, pyrazinyl, pyridazinyl, isoxazolyl, isothiazolyl, pyrrolyl, furyl, thiazolyl, oxazolyl, pyrazolyl, oxadiazolyl, thiadiazolyl, imidazolyl, triazolyl, tetrazolyl, indolyl, quinolinyl, isoquinolinyl, 2,4-dimethyl-6-oxo-6H-pyranyl and thienyl said heteroaryl optionally substituted with one to three substituents selected independently in each incidence from the group consisting of $C_{1-10}$ alkyl, phenyl, $C_{1-6}$ haloalkyl, $C_{1-6}$ alkoxy, $C_{1-6}$ thioalkyl, $C_{1-6}$ alkoxycarbonyl, carbamoyl, acetyl, nitro, cyano, amino, $C_{1-3}$ alkylamino, $C_{1-3}$ dialkylamino, N-morpholino, sulfamoyl and halogen,
  (iv) heteroaryl $C_{1-6}$ alkyl wherein heteroaryl is as described above,
  (v) heterocycle selected from the group consisting of IIa–f, oxetanyl,

IIa

IIb

IIc

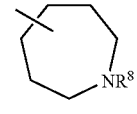

IId

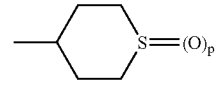

IIe

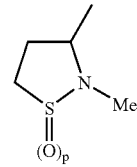

IIf tetrahydrofuranyl, tetrahydropyranyl, thiazolidinyl, oxazolidinyl, isothiazolidinyl, piperazinyl, imidazolinyl, 1,2,3,4-tetrahydroquinolinyl and N-methyl-1,2,3,4-tetrahydroisoquinolin-3-yl said heterocycle optionally substituted with 1 to 3 substituents independently selected in each occurrence from the group consisting of $C_{1-6}$ alkyl, hydroxy, $C_{1-6}$ alkylcarbonyl, carbamoyl, amino, $C_{1-6}$ alkylamino, $C_{1-6}$ dialkylamino, pyridinyl and phenylamino, and two hydrogens on a carbon bonded to a nitrogen can be replaced by oxygen (oxo), wherein:

$R^8$ is hydrogen, $C_{1-6}$-alkyl, $C_{1-6}$ haloalkyl, $C_{1-6}$ heteroalkyl, phenyl-$C_{1-6}$ alkyl, $C_{1-3}$ alkoxy-$C_{1-6}$ alkyl, pyrimidin-2-yl, $COR^9$, $COCHR^{15}NHR^7$ or $SO_2R^{10}$;

$R^9$ is selected from the group consisting of:
  (i) $C_{1-6}$ alkyl optionally substituted with one or two groups independently selected from the group consisting of $C_{1-3}$ alkoxy, $C_{1-3}$ acyloxy, hydroxyl, phenyl, amino, $C_{1-6}$ alkylamino, $C_{1-6}$ dialkylamino and, aminocarbonylpyridyl wherein said aminocarbonylpyridyl can optionally be the N-oxide and aminobenzoyl wherein said phenyl or said benzoyl radical is optionally substituted with one to three groups independently selected from the group consisting of amino, $C_{1-6}$ alkylamino, $C_{1-6}$ dialkylamino, hydroxyl, halogen and $C_{1-3}$ alkoxy,
  (ii) phenyl optionally substituted with one or two groups independently selected from the group consisting of sulfamoyl, acetylamino, halogen, $C_{1-6}$ alkyl, $C_{1-6}$ haloalkyl, and $C_{1-6}$alkoxy,
  (iii) $NH_2$, $C_{1-6}$ alkylamino, $C_{1-6}$ dialkylamino,
  (iv) $C(=O)NH_2$, $C(=O)OC_{1-6}$ alkyl, or $C(=O)OH$,
  (v) 1H indole-3-carbonyl,
  (vi) furyl, pyridinyl, or pyridinyl N-oxide,
  (vii) N-acetylpiperidin-4-yl,
  (viii) furfuryl,
  (ix) $C_{3-8}$ cycloalkyl,
  (x) $C_{1-6}$ haloalkyl,
  (xi) phenyl $C_{1-3}$ alkyl, and,
  (xii) $C_{1-6}$ alkoxy, $R^{10}$ is selected from the group consisting of:
  (i) $C_{1-6}$ alkyl,
  (ii) $C_{1-3}$ haloalkyl,
  (iii) $C_{3-8}$ cycloalkyl, and
  (iv) $NH_2$, $C_{1-3}$ alkylamino, $C_{1-3}$ dialkylamino;

(vi) heterocycle $C_{1-6}$ alkyl wherein heterocycle is as defined above;
(vii) hydrogen;
(viii) $C_{1-10}$ alkyl optionally independently substituted in each occurrence with one to three substituents independently selected at each occurrence from the group consisting of hydroxy, halogen, $C_{1-6}$ alkoxy, $C_{1-6}$ thioalkyl, $C_{1-6}$ acyloxy, $C_{1-6}$ alkoxycarbonyl, $C_{1-6}$ acylamino, $NR^{14a}R^{14b}$, cyano, $C_{1-6}$ alkylsulfonyl, phenyl, N-methyl-methyl-sulfonamido, N-piperidinyl, N-pyrrolidinyl, imidazolyl, 2-aza-bicyclo[2.2.1]hept-2-yl, carbamoyl, $C_{1-6}$ alkoxycarbonyl, and optionally substituted phenyl as defined in $R^3$ (i) above;
(ix) $C_{3-7}$ cycloalkyl or [3.1.0]bicyclohexyl, 4-oxo-cyclohexyl or 3-oxo-cyclobutyl said cycloalkyl optionally substituted with 1 to 4 fluorine, cyano, hydroxyl, $C_{1-3}$ alkyl or phenyl;
(x) $C_{1-3}$ alkyl-$C_{3-7}$ cycloalkyl said cycloalkyl optionally substituted with 1 to 4 fluorine, $C_{1-3}$ alkyl or phenyl;
(xi) $NR^{14a}R^{14b}$; and
(xii) $C(=O)OR^{14c}$;

$R^4$ is selected from the group consisting of:
  (i) aryl selected from the group consisting of:
    (a) phenyl optionally substituted with one to four substituents selected independently in each incidence from the group consisting of a phenyl substituent (i)(a) to (i)(w) as described in $R^3$, $C_{1-6}$ haloalkoxy, pyridinyl, 2-oxo-pyrrolidin-1-yl, 2,5-dimethyl-pyrrolidin-1-yl, 3-methyl-5-oxo-4,5-dihydro-pyrazol-1-yl and $NR^{14a}R^{14b}$ wherein $R^{14a}$ and $R^{14b}$ are taken together along with the nitrogen to which they are attached are $(CH_2)_r$ or $[(CH_2)_2X^3(CH_2)_2]$, —$NMe(CH_2)_2OH$;
    (b) 2,3-dihydrobenzofuran-4-yl,
    (c) benzofuran-4-yl,
    (d) 2,3-dihydrobenzofuran-7-yl,
    (e) quinolin-8-yl,
    (f) 1,2,3,4-tetrahydro-isoquinolin-5-yl,
    (g) N-acetyl-1,2,3,4-tetrahydro-isoquinolin-5-yl,
    (h) N-Boc-1,2,3,4-tetrahydro-isoquinolin-5-yl,
    (i) 1,2,3,4-tetrahydro-isoquinolin-8-yl,
    (l) N-Boc-1,2,3,4-tetrahydro-isoquinolin-8-yl,
    (k) isoquinolin-7-yl,
    (l) 1H-indol-5-yl,
    (m) 2-acetyl-1,2,3,4-tetrahydro-isoquinolin-5-yl, and
    (n) 6-fluoro-benzo[1,3]dioxin-8-yl, and,
    (o) quinolin-6-yl;
  (ii) phenyl $C_{1-6}$ alkyl wherein phenyl as described above;
  (iii) heteroaryl selected from the group consisting of pyridinyl, 2-azetidin-1-yl, pyridinyl N-oxide, pyrimidinyl, pyrazinyl, pyridazinyl, isoxazolyl, isothiazolyl, pyrrolyl, furyl, thiazolyl, oxazolyl, pyrazolyl, oxadiazolyl, thiadiazolyl, imidazolyl, triazolyl, tetrazolyl, indolyl, quinolyl, isoquinolyl, quinoxalin-2-yl, indazole, benzofuranyl, 4,5,6,7-tetrahydro-benzofuranyl, 2,4-dimethyl-6-oxo-6H-pyranyl, benzo[b]thiophenyl, 4,5,6,7-tetrahydroindazole, 1,4,5,6-tetrahydrocyclopentylpyrazolyl, imidazo[2,1-b]thiazolyl, 6-fluoro-4H-benzo[1,3]dioxin-8-yl, cinnolin-4-yl, and thienyl said heteroaryl optionally substituted with one to three substituents selected independently in each incidence from the group consisting of $C_{1-10}$ alkyl, phenyl optionally substituted with one to four substituents selected independently in each incidence from the group consisting of substituents (i)(a) to (i)(w) as described for $R^3$ above, benzyl, pyridinyl, 2-methyl-thiazolyl, acetyl, amino, $C_{1-6}$alkylamino, $C_{1-6}$ dialkylamino, aminobenzyl, $C_{1-6}$ haloalkyl, $C_{1-6}$ alkoxy, $C_{1-6}$ thioalkyl, $C_{1-6}$ alkylsulfonyl, $C_{1-6}$ alkoxycarbonyl, carboxyl, carbamoyl, nitro, cyano, sulfamoyl, —$OCH_2CO_2R^{14c}$, —$SCH_2CO_2R^{14c}$ and halogen;
  (iv) heteroaryl $C_{1-6}$ alkyl wherein heteroaryl is as described above;
  (v) heterocycle selected from the group consisting of IIa–f as described in (v) of $R^3$ above, furyl, oxetanyl, tetrahydrofuranyl, tetrahydropyranyl, thiazolidinyl, oxazolidinyl, piperazinyl, imidazolinyl, N-benzyl-morpholine, N-methyl-1,2,3,4-tetrahydroquinolin-2-yl, 4,5-dihydro-pyrazolyl, and 1,2,3,4-tetrahydroisoquinolinyl said heterocycle optionally substituted with 1 to 3 substituents independently selected in each occurrence from the group consisting of $C_{1-6}$ alkyl, acetyl, hydroxy, $C_{1-6}$ alkylcarbonyl, $C_{1-6}$ alkoxycarbonyl, carbamoyl, amino, $C_{1-6}$ alkylamino, $C_{1-6}$ dialkylamino and phenylamino, and two hydrogens on a carbon bonded to a nitrogen can be replaced by oxygen (oxo);

(vi) heterocycle $C_{1-6}$ alkyl wherein heterocycle is as defined above;

(vii) hydrogen;

(viii) $C_{1-10}$ alkyl substituted with one to three substituents independently selected at each occurrence from the group consisting of hydroxy, halogen, $C_{1-6}$ alkoxy, $C_{1-6}$ thioalkyl, acyloxy, $C_{1-6}$ acylamino, $NR^{14a}R^{14b}$, cyano, $C_{1-6}$ alkylsulfonyl, N-methyl-methyl-sulfonamido, phenyl, N-piperidinyl, N-pyrrolidinyl, imidazolyl, carbamoyl and $C_{1-6}$ alkoxycarbonyl, (ix) $C_{3-7}$ cycloalkyl optionally substituted with 1 to 4 fluorine, $C_{1-3}$ alkyl or phenyl, (x) $C_{1-3}$ alkyl-$C_{3-7}$ cycloalkyl optionally substituted with 1 to 4 fluorine, $C_{1-3}$ alkyl or phenyl; and, (xi) $NR^{14a}R^{14b}$;

$R^5$ is hydrogen, $C_{1-6}$ alkyl, $C_{1-6}$ haloalkyl, $C_{1-6}$ hydroxyalkyl, methoxymethyl, —$CO_2R^{12}$ or $CONR^{12}R^{13}$, $R^{5a}$ is hydrogen or $C_{1-6}$ alkyl;

$R^6$ is independently selected from the group consisting of hydrogen, $C_{1-10}$ alkyl, hydroxy, $C_{1-6}$ alkoxy, $C_{1-3}$ hydroxyalkyl and $C_{1-3}$ alkoxy-$C_{1-3}$ alkyl;

$R^7$ is hydrogen or Boc;

$R^{12}$ and $R^{13}$ (i) are independently hydrogen, $C_{1-6}$ alkyl or $C_{1-6}$ heteroalkyl, or (ii) $R^{12}$ and $R^3$, when both attached to a nitrogen atom, together can be $C_{2-5}$ alkylene;

$R^{14a}$ and $R^{14b}$ (i) taken independently are $R^3$, or (ii) taken together along with the nitrogen to which they are attached are $(CH_2)_r$ or $[(CH_2)_2X^3(CH_2)_2]$;

$R^{14c}$ is hydrogen or $C_{1-6}$ alkyl;

$R^{15}$ is hydrogen, methyl, iso-propyl, iso-butyl, sec-butyl, —$CH_2OH$, —$CH(OH)CH_3$, —$CH_2SH$, —$CH_2CH_2SMe$, —$(CH_2)_sCOR^{16}$ wherein $R^{16}$ is —OH or —$NH_2$ and s is 1 or 2, —$(CH_2)_t$—$NH_2$ where t is 3 or 4, —$(CH_2)_3$—$NHC(=NH)NH_2$, —$CH_2C_6H_5$, —$CH_2$-p-$C_6H_4$—OH, (3-indolinyl)methylene or (4-imidazolyl)methylene;

$X^3$ is —O—, —$S(O)_p$—, $NR^{14c}$;

Y is a direct bond, —O—, —S— or —$NR^{12}$—;

n is an integer from 1 to 6;

p is an integer from 0 to 2;

r is an integer from 3 to 6; and, pharmaceutically acceptable salts, hydrates, solvates and stereoisomers thereof.

The present invention further relates to processes for preparing compounds according to formula I. Compounds and compositions of the present invention are useful for treating diseases mediated by human immunodeficiency virus in humans. Compounds and compositions of the present invention also may be used for treatment of disorders alleviated by a CCR5 antagonist including respiratory disorders, including adult respiratory distress syndrome (ARDS), bronchitis, chronic bronchitis, chronic obstructive pulmonary disease, cystic fibrosis, asthma, emphysema, rhinitis and chronic sinusitis. Conditions triggered, affected or are in any other way correlated with T-cell trafficking in different organs may be treated with compounds of the invention. Compounds of the present invention may be useful for the treatment of such conditions and in particular, but not limited to the following for which a correlation with CCR5 or CCR5 chemokines has been established: inflammatory bowel disease, including Crohn's disease and ulcerative colitis, multiple sclerosis, rheumatoid arthritis, graft rejection, in particular but not limited to kidney and lung allografts, endometriosis, type I diabetes, renal diseases, chronic pancreatitis, inflammatory lung conditions or chronic heart failure. For recent reviews of possible applications of chemokines and chemokine receptor blockers see: Cascieri, M. A., and Springer, M. S., *The chemokine/chemokine receptor family: potential and progress for therapeutic intervention*, Curr. Opin. Chem. Biol. 2000 4(4): 420–7; A. E. I. Proudfoot *The Strategy of Blocking the Chemokine System to Combat Disease*, Immunol. Rev. 2000 177:246–256.

DETAILED DESCRIPTION OF THE INVENTION

In one embodiment of the present invention there is provided a compound according to formula I wherein $R^1$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14a}$, $R^{14b}$, $R^{14c}$, $R^{15}$, $R^{16}$, $X^1$, $X^2$, $X^3$, Y, r, s, n and p are as defined hereinabove In the following embodiments of the present invention all substituent definitions are intended to take the broadest form as disclosed in the Summary of the invention unless limited in the description of the following embodiments.

In another embodiment of the present invention there is provided a compound according to formula I wherein $R^1$ is optionally substituted phenyl; $X^1$ is —$C(=O)R^3$ or —$SO_2R^3$; $X^2$ is —$C(=O)R^4$, and $R^2$, $R^5$, $R^{5a}$ and $R^6$ are hydrogen.

In another embodiment of the present invention there is provided a compound according to formula I wherein $R^1$ is optionally substituted phenyl; $X^1$ is —$C(=O)R^3$; $X^2$ is —$C(=O)R^4$; $R^3$ is a heterocycle as defined in section (v) of $R^3$; and $R^2$, $R^5$, $R^{5a}$ $R^6$ are hydrogen.

In another embodiment of the present invention there is provided a compound according to formula I wherein $R^1$ is optionally substituted phenyl; $X^1$ is —$C(=O)R^3$; $X^2$ is —$C(=O)R^4$; $R^3$ is a heterocycle according to formulae IIa–IId as defined in section (v) of $R^3$; $R^4$ is a phenyl or heteroaryl group wherein at least one, and preferably both, atom(s) adjacent to the atom linked to $X^2$ are substituted carbon atoms and $R^2$, $R^5$, $R^{5a}$ and $R^6$ are hydrogen. A substituted carbon as used herein refers to a carbon bearing a non-hydrogen substituent.

In another embodiment of the present invention there is provided a compound according to formula I wherein $R^1$ is 4-methyl-3-chloro-phenyl; $X^1$ is —$C(=O)R^3$; $X^2$ is —$C(=O)R^4$; $R^3$ is a heterocycle according to formula IIb or IIc defined in section (v) of $R^3$; $R^4$ is 2,6-dimethyl-pyrimidin-5-yl, 2,6-dimethyl-pyridine-3-yl or 2,6-dimethyl-phenyl; and $R^2$, $R^5$, $R^{5a}$ and $R^6$ are hydrogen.

In another embodiment of the present invention there is provided a compound according to formula I wherein $R^1$ is 4-methyl-3-chloro-phenyl; $X^1$ is —$C(=O)R^3$; $X^2$ is —$C(=O)R^4$; $R^3$ is a heterocycle according to formula IIb or IIc defined in section (v) wherein the piperidinyl or pyrrolidinyl nitrogen atom is substituted by —$C(=O)CH_3$, —$C(=O)C(=O)O$-$C_{1-6}$ alkyl or —$C(=O)C(=O)OH$; $R^4$ is 2,6-dimethyl-pyrimidin-5-yl, 2,6-dimethyl-pyridine-3-yl or 2,6-dimethyl-phenyl; and $R^2$, $R^5$, $R^{5a}$ and $R^6$ are hydrogen.

In another embodiment of the present invention there is provided a compound according to formula I wherein $R^1$ is optionally substituted phenyl; $X^1$ is —C(=O)NR$^{14a}$R$^{14b}$ or —S(=O)$_2$NR$^{14a}$R$^{14b}$; is —C(=O)R$_4$; and R$^2$, R$^5$, R$^{5'}$ and R$^6$ are hydrogen.

In another embodiment of the present invention there is provided a compound according to formula I wherein R$^1$ is optionally substituted phenyl; $X^1$ is —C(=O)NR$^{14a}$R$^{14b}$ or —S(=O)$_2$NR$^{14a}$R$^{14b}$ wherein R$^{14a}$ is optionally substituted phenyl and R$^{14b}$ is hydrogen; $X^2$ is —C(=O)R$^4$; and R$^2$, R$^5$, R$^{5a}$ and R$^6$ are hydrogen. Optionally substituted phenyl refers to the substituents listed in the definition in section (i) of R$^3$.

In another embodiment of the present invention there is provided a compound according to formula I wherein R$^1$ is 4-methyl-3-chloro-phenyl; $X^1$ is —C(=O)NR$^{14a}$R$^{14b}$ or —S(=O)$_2$NR$^{14a}$R$^{14b}$ wherein R$^{14a}$ is phenyl substituted by a carboxyl or $C_{1-6}$ alkoxycarbonyl and R$^{14b}$ is hydrogen; $X^2$ is —C(=O)R$^4$; and R$^2$, R$^5$, R$^{5a}$ and R$^6$ are hydrogen. Optionally substituted phenyl refers to the substituents listed in the definition in section (i) of R$^3$.

In another embodiment of the present invention there is provided a compound according to formula I wherein R$^2$ is optionally substituted phenyl; $X^1$ is —C(=O)R$^3$ or —SO$_2$R$^3$; $X^2$ is —C(=O)R$^4$; and R$^1$R$^5$, R$^{5a}$ and R$^6$ are hydrogen.

In another embodiment of the present invention there is provided a compound according to formula I wherein R$^2$ is optionally substituted phenyl; $X^1$ is —C(=O)R$^3$; $X^2$ is —C(=O)R$^4$; and R$^1$, R$^5$, R$^{5a}$ and R$^6$ are hydrogen. In this embodiment R$^3$ is optionally substituted aryl, optionally substituted cycloalkyl, 4-oxo-cyclohexyl, 3-oxo-cyclobutyl or tetrahydrofuranyl and R$^4$ is a phenyl or heteroaryl group wherein at least one, and preferably both, atom(s) adjacent to the atom linked to $X^2$ are substituted carbon atoms.

In another embodiment of the present invention there is provided a compound according to formula I wherein R$^2$ is optionally substituted phenyl; $X^1$ is —C(=O)R$^3$; $X^2$ is —C(=O)R$^4$; and R$^1$, R$^5$, R$^{5a}$ and R$^6$ are hydrogen. In this embodiment R$^3$ is cycloalkyl optionally substituted with 1 to 4 fluorine atoms and R$^4$ is a phenyl or heteroaryl group wherein at least one, and preferably two, atom(s) adjacent to the atom linked to $X^2$ are substituted carbon atoms.

In another embodiment of the present invention there is provided a compound according to formula I wherein R$^2$ is optionally substituted phenyl; $X^1$ is —C(=O)R$^3$; $X^2$ is —C(=O)R$^4$; and R$^1$, R$^5$, R$^{5a}$ and R$^6$ are hydrogen. In this embodiment R$^3$ is cyclopentyl, 4,4-difluorocyclohexyl or 3,3-difluorocyclobutyl and R$^4$ is 2,6-dimethyl-pyrimidin-5-yl, 2,6-dimethyl-pyridine-3-yl, 2,6-dimethyl-phenyl or III.

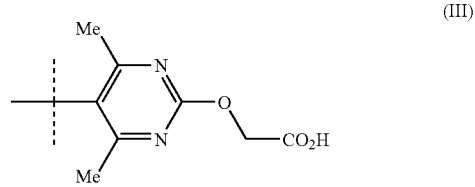

(III)

In another embodiment of the present invention there is provided a compound according to formula I wherein R$^2$ is phenyl; $X^1$ is —C(=O)R$^3$; $X^2$ is —C(=O)R$^4$; and R$^1$, R$^5$, R$^{5a}$ and R$^6$ are hydrogen. In this embodiment R$^3$ is cyclopentyl, 4,4-difluorocyclohexyl or 3,3-difluorocyclobutyl and R$^4$ is 2,6-dimethyl-pyrimidin-5-yl, 2,6-dimethyl-pyridine-3-yl, 2,6-dimethyl-phenyl or III.

In another embodiment of the present invention there is provided a compound according to formula I selected from the following:

- 1-acetyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide,
- 1-acetyl-piperidine-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide,
- [4-((3-chloro-4-methyl-phenyl)-{3-[5-(4,6-dimethyl-pyrimidin-5-carbonyl)-hexahydro-pyrrolo[3,4-c]pyrrol-2-yl]-propyl}-carbamoyl)-piperidin-1-yl]-oxo-acetic acid; compound with trifluoro-acetic acid,
- cyclopentanecarboxylic acid {(S)-1-phenyl-3-[5-(pyridine-3-carbonyl)-hexahydro-pyrrolo[3,4-c]pyrrol-2-yl]-propyl}-amide; compound with trifluoro-acetic acid,
- cyclopentanecarboxylic acid {(S)-3-[5-(4,6-dimethyl-pyrimidin-5-carbonyl)-hexahydro-pyrrolo[3,4-c]pyrrol-2-yl]-1-phenyl-propyl}-amide,
- cyclopentanecarboxylic acid {(S)-3-[5-(2,4-dimethyl-pyridine-3-carbonyl)-hexahydro-pyrrolo[3,4-c]pyrrol-2-yl]-1-phenyl-propyl}-amide,
- 3-(3-(3-Chloro-4-methyl-phenyl)-3-{3-[5-(4,6-dimethyl-pyrimidin-5-carbonyl)-hexahydro-pyrrolo[3,4-c]pyrrol-2-yl]-propyl}-ureido)-benzoic acid; compound with trifluoro-acetic acid
- 4,4-difluoro-cyclohexanecarboxylic acid {(S)-3-[5-(4,6-dimethyl-pyrimidine-5-carbonyl)-hexahydro-pyrrolo[3,4-c]pyrrol-2-yl]-1-phenyl-butyl}-amide, and,
- (5-{5-[(S)-3-(cyclopentanecarbonyl-amino)-3-phenyl-propyl]-hexahydro-pyrrolo[3,4-c]pyrrole-2-carbonyl}4,6-dimethyl-pyrimidin-2-yloxy)-acetic acid; compound with trifluoro-acetic acid.

In another embodiment of the present invention there is provided a method for treating or preventing an human immunodeficiency virus (HIV) infection, or treating AIDS or ARC, in a patient in need thereof which comprises administering to the patient in need thereof a therapeutically effective amount of a compound of according to formula I wherein R$^1$, R$^2$, R$^3$, R$^4$, R$^5$, R$^5$, R$^6$, R$^7$, R$^8$, R$^9$, R$^{10}$, R$^{11}$, R$^{12}$, R$^{13}$, R$^{14a}$, R$^{14b}$, R$^{14c}$, R$^{15}$, R$^{16}$, $X^1$, $X^2$, $X^3$, Y, r, s, n and p are as defined hereinabove.

In another embodiment of the present invention there is provided a method for treating or preventing an human immunodeficiency virus (HIV) infection, or treating AIDS or ARC, in a patient in need thereof which comprises co-administering to a patient in need thereof a therapeutically effective amount of a compound of according to formula I wherein R$^1$, R$^2$, R$^3$, R$^4$, R$^5$, R$^5$, R$^6$, R$^7$, R$^8$, R$^9$, R$^{10}$, R$^{11}$, R$^{12}$, R$^{13}$, R$^{14a}$, R$^{14b}$, R$^{14c}$, R$^{15}$, R$^{16}$, $X^1$, $X^2$, $X^3$, Y, r, s, n and p are as defined hereinabove and at least one of an HIV nucleoside reverse transcriptase inhibitors, HIV non-nucleoside reverse transcriptase inhibitors, HIV protease inhibitors or viral fusion inhibitors.

In another embodiment of the present invention there is provided a method for treating or preventing an human immunodeficiency virus (HIV) infection, or treating AIDS or ARC, in a patient in need thereof which comprises co-administering to a patient in need thereof a therapeutically effective amount of a compound of according to formula I wherein R$^1$, R$^2$, R$^3$, R$^4$, R$^5$, R$^{5a}$, R$^6$, R$^7$, R$^8$, R$^9$, R$^{10}$, R$^{11}$, R$^{12}$, R$^{13}$, R$^{14a}$, R$^{14b}$, R$^{14c}$, R$^{15}$, R$^{16}$, $X^1$, $X^2$, $X^3$, Y, r, s, n and p are as defined hereinabove and at least one of efavirenz nevirapine or delavirdine, zidovudine, didanosin, zalcitabine, stavudine; lamivudine, abacavir, adefovir and dipivoxil, saquinavir, ritonavir, nelfinavir, indinavir, amprenavir and lopinavir or T-20.

In another embodiment of the present invention there is provided a method of treating a mammal with a disease state that is alleviated by a CCR5 receptor antagonist wherein said disease state that is solid organ transplant rejection, graft v. host disease, arthritis, rheumatoid arthritis, inflammatory bowel disease, atopic dermatitis, psoriasis, asthma, allergies or multiple sclerosis comprising administering to a mammal in need thereof a therapeutically effective amount of a compound of according to formula I wherein $R^1$, $R^1$, $R^2$, $R^3$, $R^4$, $R^5$, $R^5$, $R^6$, $R^7$, $R^8$, $R^9$, $R^{10}$, $R^{11}$, $R^{12}$, $R^{13}$, $R^{14a}$, $R^{14b}$, $R^{14c}$, $R^{15}$, $R^{16}$, $X^6$, $X^2$, $X^3$, Y, r, s n and p are as defined hereinabove.

In another embodiment of the present invention there is provided a method of treating a mammal with a disease state that is alleviated by a CCR5 receptor antagonist wherein said disease state that is solid organ transplant rejection, graft v. host disease, arthritis, rheumatoid arthritis, inflammatory bowel disease, atopic dermatitis, psoriasis, asthma, allergies or multiple sclerosis comprising co-administering to a mammal in need thereof a therapeutically effective amount of a compound of according to formula I wherein $R^1$, $R^2$, $R^3$, $R^4$, $R^5$, $R^{5a}$, $R^6$, $R^7$, $R^8$, $R^9$, $R^{10}$, $R^{11}$, $R^{12}$, $R^{13}$, $R^{14a}$, $R^{14b}$, $R^{14c}$, $R^{15}$, $R^{16}$, $X^6$, $X^2$, $X^3$, Y, r, s, n and p are as defined hereinabove and at least one other immune system modulator.

In another embodiment of the present invention there is provided a method of treating a human with a disease state that is alleviated by a CCR5 receptor antagonist wherein said disease state that is solid organ transplant rejection, graft v. host disease, arthritis, rheumatoid arthritis, inflammatory bowel disease, atopic dermatitis, psoriasis, asthma, allergies or multiple sclerosis comprising co-administering to a mammal in need thereof a therapeutically effective amount of a compound of according to formula I wherein $R^1$, $R^2$, $R^3$, $R^4$, $R^5$, $R^{5a}$, $R^6$, $R^7$, $R^8$, $R^9$ $R^{10}$, $R^{11}$, $R^{12}$, $R^{13}$, $R^{14a}$, $R^{14b}$, $R^{14c}$, $R^{15}$, $R^{16}$, $X^6$, $X^2$, $X^3$, Y, r, s, n and p are as defined hereinabove and at least one other immune system modulator.

In another embodiment of the present invention there is provided a pharmaceutical composition for treating or preventing an human immunodeficiency virus (HIV) infection, or treating AIDS or ARC comprising a compound according to formula I wherein $R^1$, $R^2$, $R^3$, $R^4$, $R^5$, $R^{5a}$, $R^6$, $R^7$, $R^8$, $R^9$ $R^{10}$, $R^{11}$, $R^{12}$, $R^{13}$, $R^{14a}$, $R^{14b}$, $R^{14c}$, $R^{15}$, $R^{16}$, $X^1$, $X^2$, $X^3$, Y, r, s, n and p are as defined hereinabove admixed with at least one pharmaceutical acceptable carrier, diluent or excipient.

In another embodiment of the present invention there is provided a pharmaceutical composition for treating a mammal with a disease state that is alleviated by a CCR5 receptor antagonist wherein said disease is solid organ transplant rejection, graft v. host disease, arthritis, rheumatoid arthritis, inflammatory bowel disease, atopic dermatitis, psoriasis, asthma, allergies or multiple sclerosis comprising a compound according to formula I wherein $R^1$, $R^2$, $R^3$, $R^4$, $R^5$, $R^{5a}$, $R^6$, $R^7$, $R^8$, $R^9$ $R^{10}$, $R^{11}$, $R^{12}$, $R^{13}$, $R^{14a}$, $R^{14b}$, $R^{14c}$, $R^{15}$, $R^{16}$, $X^1$, $X^2$, $X^3$, Y, r, s, n and p are as defined hereinabove admixed with at least one pharmaceutical acceptable carrier, diluent or excipient.

In another embodiment of the present invention there is provided a process for the preparation of a compound according to formula wherein $R^1$ is hydrogen and $R^2$ is optionally substituted phenyl or optionally substituted heteroaryl comprising a reductive amination step, removal of protecting if present and acylation with an acylation agent selected to provide compounds disclosed in the present invention.

In another embodiment of the present invention there is provided a process for the preparation of a compound according to formula wherein $R^2$ is hydrogen and $R^1$ is optionally substituted phenyl or optionally substituted heteroaryl comprising an alkylation step, removal of protecting if present and acylation with an acylation agent selected to provide compounds disclosed in the present invention.

In another embodiment of the present invention there is provided a compound according to formula Ia wherein:

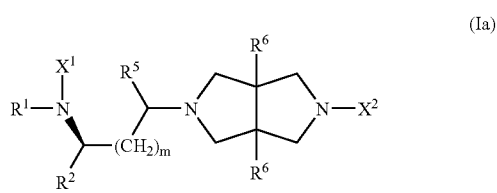

(Ia)

$X^1$ is selected from the group consisting —C(═O)$R^3$, —S(═O)$_2R^3$, —C(═O)O$R^3$ and —C(═O)NH$R^3$; $X^2$ is selected from the group consisting —C(═O)$R^4$, —S(═O)$_2R^4$ or —CH$_2$-Aryl; one of $R^1$ and $R^2$ is: (i) aryl optionally substituted with one to four substituents selected independently in each incidence from the group consisting of: (a) $C_{1-10}$ alkyl, (b) $C_{1-10}$ heteroalkyl, (c) $C_{1-6}$ haloalkyl, (d) $C_{1-6}$ alkoxy, (e) $C_{1-6}$ thioalkyl, (f) amino, (g) $C_{1-6}$ alkyl amino, (h) $C_{1-6}$ dialkylamino, (g) $C_{1-6}$ acylamino, (i) carbamoyl, N-alkylcarbamoyl, N,N-dialkylcarbamoyl, (j) ureido, (k) nitro, (l) cyano, (m) halogen, (n) $C_{1-6}$ alkylsulfonyl, (o) sulfamoyl, N-alkylsulfamoyl or N,N-dialkylsulfamoyl, (p) alkylsulfonamido or optionally substituted arylsulfonamido, (q) optionally substituted aryloxy, (r) optionally substituted heteroaryloxy, and, (s) —Y(CH$_2$)$_nR^{11}$ wherein $R^{11}$ is selected from the group consisting of cyano, —CO$_2R^{12}$, —CONR$^{12}R^{13}$, —SO$_2N^{12}R^{13}$, —NHSO$_2R^{12}$ and —NHSO$_2$NR$^{12}R^{13}R^{12}$ and $R^{13}$ (i) are independently hydrogen, $C_{1-6}$ alkyl or $C_{1-6}$ heteroalkyl, or (ii) $R^{12}$ and $R^{13}$, when both attached to a nitrogen atom, together can be $C_{2-5}$ alkylene, and Y is a direct bond, —O—, —S— or —NR$^{12}$—; or, (ii) one of $R^1$ and $R^2$ are heteroaryl selected from the group consisting of pyridinyl, pyridinyl-N-oxide, pyrimidinyl, pyrazinyl, pyridazinyl, isoxazolyl, isothiazolyl, pyrrolyl, thiazolyl and thienyl said heteroaryl optionally substituted with one to three substituents independently selected from the group of optional substituents in (i) above; and, the other of $R^1$ and $R^2$ is hydrogen; $R^3$ is selected from the group consisting of: (i) aryl optionally substituted with one to four substituents selected independently in each incidence from the group consisting of (i)(a) to (i)(s) described for $R^1$ and $R^2$ above, (ii) aryl $C_{1-6}$ alkyl wherein aryl is as described in (i) above, (iii) heteroaryl selected from the group consisting of pyridinyl, pyridinyl-N-oxide, pyrimidinyl, pyrazinyl, pyridazinyl, isoxazolyl, isothiazolyl, pyrrolyl, thiazolyl, oxazolinyl, pyrazolinyl, oxadiazolinyl, thiadiazolinyl, pyrazolyl, tetrazole, imidazolyl, triazolyl, triazolyl, indolyl, quinolinyl, isoquinolinyl and thienyl said heteroaryl optionally substituted with one to three substituents selected independently in each incidence from the group consisting of $C_{1-10}$ alkyl, aryl, $C_{1-6}$ haloalkyl, $C_{1-6}$ alkoxy, $C_{1-6}$ thioalkyl, carbamoyl, nitro, cyano, amino, $C_{1-3}$ alkylamino, $C_{1-3}$-dialkylamino, morpholino and halogen, (iv) heteroaryl $C_{1-6}$ alkyl wherein heteroaryl is as described above, (v) heterocycle selected from the group consisting of IIa–f, furfuryl, oxetanyl, tetrahydrofuranyl, tetrahydropyranyl, thiazolidinyl, oxazolidinyl, piperazinyl, imidazolinyl, 1,2,3,4-tetrahydroquinolinyl, 1,2,3,4-tetrahydroisoquinolinyl and 2-aza-bicyclo[2.2.1]heptanyl said heterocycle optionally substituted with 1 to 3 substituents independently selected in each occurrence from the group consisting of $C_{1-6}$ alkyl, hydroxy, $C_{1-6}$ alkylcarbonyl, carbamoyl, amino, alkylamino, dialkylamino and phenylamino, or the two hydrogens on a carbon bonded to a nitrogen are replaced by oxygen (oxo), wherein: $R^1$ is hydrogen, $C_{1-6}$-alkyl, $C_{1-6}$ haloalkyl, $C_{1-6}$ heteroalkyl, $COR^9$ or $SO_2R^{10}$; $R^9$ is selected from the group consisting of: (i) $C_{1-6}$ alkyl optionally substituted with one or two groups independently selected from the group consisting of $C_{1-3}$ alkoxy, $C_{1-3}$ acyloxy, hydroxyl, phenyl, amino, $C_{1-6}$ alkylamino, $C_{1-6}$ dialkylamino, aminocarbonylpyridyl wherein said aminocarbonylpyridyl can optionally be the N-oxide and aminobenzoyl wherein said phenyl or said benzoyl radical is optionally substituted with one to three groups independently selected from the group consisting of amino, alkylamino, dialkylamino, hydroxyl, halogen and $C_{1-3}$ alkoxy, (ii) phenyl optionally substituted with one or two groups independently selected from the group consisting of sulfamoyl, acetylamino, halogen, $C_{1-6}$ alkyl, $C_{1-6}$ haloalkyl, and $C_{1-6}$ alkoxy, (iii) $NH_2$, $C_{1-3}$ alkylamino, $C_{1-3}$ dialkylamino, (iv) $C(=O)NH_2$, (v) 1H indole-3-carbonyl, (vi) furyl, pyridinyl, or pyridinyl N-oxide, (vii) N-acetylpiperidin-4-yl and, (viii) furfuryl; $R^{10}$ is selected from the group consisting of: (i) $C_{1-6}$ alkyl, (ii) $C_{1-3}$ haloalkyl, (iii) $C_{1-3}$ haloalkoxy, (iv) $C_{3-8}$ cycloalkyl, (v) phenyl optionally substituted with $C_{1-3}$ alkoxy, halogen, nitro, acetamido, carboxy and, (vi) aralkyl, (vi) heterocyclyl $C_{1-6}$ alkyl wherein heterocyclyl is as defined above, (vii) hydrogen, (viii) $C_{1-10}$ alkyl substituted with one to three substituents independently selected at each occurrence with hydroxy, halogen, $C_{1-6}$ alkoxy, $C_{1-6}$ thioalkyl, acyloxy, $C_{1-6}$ acylamino, amino, alkylamino, dialkylamino, cyano, $C_{1-6}$ alkylsulfonyl, $C_{1-6}$ sulfinyl, N-piperidinyl, N-pyrrolidinyl, imidazolyl, carbamoyl and alkoxycarbonyl, (ix) $C_{3-7}$ cycloalkyl optionally substituted with 1 to 4 fluorine, $C_{1-3}$ alkyl or phenyl; (x) $C_{1-3}$ alkyl-$C_{3-7}$ cycloalkyl optionally substituted with 1 to 4 fluorine, $C_{1-3}$ alkyl or phenyl; $R^4$ is selected from the group consisting of: (i) aryl optionally substituted with one to four substituents selected independently in each incidence from the group consisting of (i)(a) to (i)(s) decribed for $R^1$ and $R^2$ above, (ii) aryl $C_{1-6}$ alkyl wherein aryl is as described above, (iii) heteroaryl selected from the group consisting of pyridinyl, pyrimidinyl, pyrazinyl, pyridazinyl, isoxazolyl, isothiazolyl, pyrrolyl, thiazolyl, oxazolinyl, pyrazolinyl, oxadiazolinyl, thiadiazolinyl, pyrazolyl, tetrazole, imidazolyl, triazolyl, triazolyl, indolyl, quinolinyl, isoquinolinyl, indazole, 4,5,6,7-tetrahydroindazole, 1,4,5,6-tetrahydrocyclopentylpyrazolyl, imidazo[2,1-b]thiazolyl and thienyl said heteroaryl optionally substituted with one to three substituents selected independently in each incidence from the group consisting of $C_{1-10}$ alkyl, aryl, $C_{1-6}$ haloalkyl, $C_{1-6}$ alkoxy, $C_{1-6}$ thioalkyl, carbamoyl, nitro, cyano and halogen, (iv) heteroaryl $C_{1-6}$ alkyl wherein heteroaryl is as described above, (v) heterocycle selected from the group consisting of azetidinyl, azepinyl, furfuryl, oxetanyl, piperidinyl, pyrrolidinyl, tetrahydrofuranyl, tetrahydropyranyl, thiazolidinyl, oxazolidinyl, piperazinyl, imidazolinyl, 1,2,3,4-tetrahydroquinolinyl and 1,2,3,4-tetrahydroisoquinolinyl and said heterocycle optionally substituted with 1 to 3 substituents independently selected in each occurence from the group consisting of $C_{1-6}$ alkyl, hydroxy, $C_{1-6}$ alkylcarbonyl, carbamoyl, amino, alkylamino, dialkylamino and phenylamino, or the two hydrogens on a carbon bonded to a nitrogen are replaced by oxygen (oxo); (vi) heterocyclyl $C_{1-6}$ alkyl wherein heterocyclyl is as defined above, (vii) hydrogen, (viii) $C_{1-10}$ alkyl substituted with one to three substituents independently selected at each occurrence with hydroxy, halogen, $C_{1-6}$ alkoxy, $C_{1-6}$ thioalkyl, acyloxy, $C_{1-6}$ acylamino, amino, alkylamino, dialkylamino, cyano, $C_{1-6}$ alkylsulfonyl, $C_{1-6}$ sulfinyl, N-piperidinyl, N-pyrrolidinyl, imidazolyl, carbamoyl and alkoxycarbonyl, (ix) $C_{3-7}$ cycloalkyl optionally substituted with 1 to 4 fluorine, $C_{1-3}$ alkyl or phenyl, (x) $C_{1-3}$ alkyl-$C_{3-7}$ cycloalkyl optionally substituted with 1 to 4 fluorine, $C_{1-3}$ alkyl or phenyl; $R^5$ is hydrogen, $C_{1-6}$ alkyl, $C_{1-4}$ haloalkyl, $C_{1-6}$ heteroalkyl, —$CO_2R^{12}$ or $CONR^{12}R^{13}$, $R^6$ is independently selected from the group consisting of hydrogen, $C_{1-10}$ alkyl, hydroxy, $C_{1-6}$ alkoxy, $C_{1-3}$ hydroxyalkyl and $C_{1-3}$ alkoxy-$C_{1-3}$ alkyl; m is 1 to 2; n is 1 to 6; p is 0 to 2; and, pharmaceutically acceptable salts, hydrates, solvates and stereoisomers thereof.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. The term -(ar)alkyl refers to either an unsubstituted alkyl or an aralkyl group. The term (hetero)aryl refers to either an aryl or a heteroaryl group.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. One or more of the carbon atoms may optionally be replaced by oxygen, sulfur, substituted or unsubstituted nitrogen atom(s). Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below.

The term "alkylene" as used herein denotes a divalent saturated linear hydrocarbon radical of 1 to 8 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, 2-ethylbutylene.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "heteroalkyl" as used herein means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, $C_{1-6}$ acyl, $C_{1-6}$ alkyl, $C_{3-8}$ cycloalkyl, or $C_{3-8}$ cycloalkyl-$C_{1-6}$ alkyl; R$^b$ and R$^c$ are independently of each other hydrogen, $C_{1-6}$ acyl, $C_{1-6}$ alkyl, $C_{3-8}$ cycloalkyl, or $C_{3-8}$ cycloalkyl-$C_{1-6}$ alkyl; and when n is 0, R$^d$ is hydrogen, $C_{1-6}$ alkyl, $C_{3-8}$ cycloalkyl, or $C_{3-8}$ cycloalkyl-$C_{1-6}$ alkyl, and when n is 1 or 2, Rd is $C_{1-6}$ alkyl, $C_{3-8}$ cycloalkyl, $C_{3-8}$ cycloalkyl-$C_{1-6}$ alkyl, amino, $C_{1-6}$ acylamino, or $C_{1-6}$ alkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

The term "acyl" as used herein denotes a group of formula —C(═O)R wherein R is hydrogen or lower alkyl as defined herein. The term or "alkylcarbonyl" as used herein denotes a group of formula C(═O)R wherein R is alkyl as defined herein. The term "arylcarbonyl" as used herein means a group of formula C(═O)R wherein R is an aryl group; the term "benzoyl" as used herein an "arylcarbonyl" group wherein R is phenyl.

The term "acylamino" as used herein denotes a group of formula —NHC(═O)R wherein R is hydrogen or lower alkyl as defined herein The term "acyloxy" as used herein denotes the radical —OC(O)R, wherein R is a lower alkyl radical as defined herein. Examples of acyloxy radicals include, but are not limited to, acetoxy, propionyloxy.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "alkylthio" or "thioalkyl" means an —S-alkyl group, wherein alkyl is as defined above such as meththio, ethylthio, n-propylthio, i-propylthio, n-butylthio, hexylthio, including their isomers. "Lower alkylthio" or "lower thioalkyl" as used herein denotes an alkylthio group with a "lower alkyl" group as previously defined. "$C_{1-10}$ alkylthio" as used herein refers to an-S-alkyl wherein alkyl is $C_{1-10}$.

The prefix "carbamoyl" as used herein means the radical —CONH$_2$. The prefix "N-alkylcarbamoyl" and "N,N-dialkylcarbamoyl" means a the radical CONHR' or CONR'R" respectively wherein the R' and R" groups are independently alkyl as defined herein. The prefix "N-arylcarbamoyl" denotes the radical CONHR' wherein R' is an aryl radical as defined herein.

The terms "amino", "alkylamino" and "dialkylamino" as used herein refer to —NH$_2$, —NHR and —NR$_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to NH$_2$(CH$_2$)n-, RHN(CH$_2$)n-, and R$_2$N(CH$_2$)n- respectively wherein n is 1 to 6 and R is alkyl as defined above. "$C_{1-10}$ alkylamino" as used herein refers to an-aminoalkyl wherein alkyl is $C_{1-10}$. The term "phenylamino" as used herein refers to —NHPh wherein Ph represents an optionally substituted phenyl group.

The term "halogen" or "halo" as used herein means fluorine, chlorine, bromine, or iodine.

The term "aryl" as used herein denotes a monovalent aromatic carbocyclic radical containing 5 to 15 carbon atoms consisting of one individual ring, or one or more fused rings in which at least one ring is aromatic in nature, which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Thus a bicyclic aryl substituents may be fused to a heterocyclyl or heteroaryl ring; however, the point of attachment of bicyclic aryl substituent is on the carbocyclic aromatic ring. Examples of aryl radicals include, phenyl, naphthyl, indanyl, anthraquinolyl, tetrahydronaphthyl, 3,4-methylenedioxyphenyl, 1,2,3,4-tetrahydroquinolin-7-yl, 1,2,3,4-tetrahydroisoquinoline-7-yl, and the like.

The term "arylalkyl" or "aralkyl" as used herein denotes the radical R'R"—, wherein R$^1$ is an aryl radical as defined herein, and R" is an alkylene radical as defined herein with the understanding that the attachment point of the arylalkyl moiety will be on the alkylene radical. R" is an alkylene chain comprising 1 to 6 methylenes. The term "phenyl $C_{1-6}$ alkyl" refers to a radical R'R" wherein R' is a phenyl group and R" is an alkylene chain comprising 1 to 6 methylenes. Examples of arylalkyl radicals include, but are not limited to, benzyl, phenylethyl, 3-phenylpropyl.

The term "aryloxy" as used herein denotes a O-aryl group, wherein aryl is as defined above. An aryloxy group can be unsubstituted or substituted with one or two suitable substituents. The term "phenoxy" refers to an aryloxy group wherein the aryl moiety is a phenyl ring.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on a heteroaryl ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazolyl, isoxazolyl, thiazolyl, isothiazolyl, triazolinyl, thiadiazolyl and oxadiaxolinyl which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heteroaryl alkyl" or "heteroaralkyl" means the radical of the formula R'R", wherein R' is an optionally substituted heteroaryl radical as defined herein, and R" is an alkylene radical as defined herein with the understanding that the attachment point of the heteroaryl radical will be on the alkylene radical. Examples of heteroarylalky radicals include, but are not limited to, 2-imidazolylmethyl, 3-pyrrolylethyl.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N, O or S(O)0–2), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. A bicyclic heterocycle can be fused to an aryl or heteroaryl ring; however, the point of attachment is on the heterocyclic ring. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "heterocycloalkyl" (or "heterocyclylalkyl") means the radical of the formula R'R", wherein R' is a heterocyclic radical as defined herein, and R" is an alkylene radical as defined herein and the attachment point of the heterocycloalkyl radical will be on the alkylene radical. Examples of heterocycloalkyl radicals include, but are not limited to, 1-piperazinylmethyl, 2-morpholinomethyl, and the like.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where $R^1$ is $C_{3-7}$ cyclolalkyl and R" is $C_{1-3}$ alkylene as defined herein.

The terms "hydroxyalkyl" and "alkoxyalkyl" as used herein denotes the radical R'R" where R' is an hydroxy radical or a alkoxy radical respectively and R" is alkylene as defined herein and the attachment point of the hydroxyalkyl or alkoxyalkyl radical will be on the alkylene radical.

The term "alkylene" as used herein denotes a divalent saturated linear hydrocarbon radical of 1 to 8 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, 2-ethyl-butylene.

The terms "alkylsulfinyl" and "arylsulfinyl" as used herein denotes a group of formula —S(═O)R wherein R is alkyl or aryl respectively and alkyl and aryl are as defined herein The terms "alkylsulfonyl" and "arylsulfonyl" as used herein denotes a group of formula —S(═O)$_2$R wherein R is alkyl or aryl respectively and alkyl and aryl are as defined herein.

The term "sulfamoyl" as used herein refers to the radical —S(O)$_2$NH$_2$. The terms "N-alkylsulfamoyl" and "N,N-dialkylsulfamoyl" as used herein refer to the radical —S(O)$_2$NR'R", wherein R' and R" are hydrogen and lower alkyl and R' and R" are independently lower alkyl respectively. Examples of N-alkylsulfamoyl substituents include, but are not limited to methylaminosulfonyl, iso-propylaminosulfonyl. Examples of N,N-dialkylsulfamoyl substituents include, but are not limited to dimethylaminosulfonyl, iso-propyl-methylaminosulfonyl. The prefix N-alkyl or N,N-dialkyl can be replaced with aryl, heteroaryl, heterocyclyl or other radical to indicate a case where the amine is substituted with a group other than alkyl.

The term "alkylsulfonamido" refers to the radical —NH—S(O)$_2$-alkyl. The term alkyl can be replaced by other chemically relevant radicals such as aryl or heteroaryl to indicate, e.g. phenylsulfonamido —NH—S(O)$_2$—Ph. "N-alkylalkylsulfonamido" refers to the radical —NR—S(O)$_2$-alkyl where R is a lower alkyl group. The term "ureido" as used herein means an —N$^1$RC(═O)N$^3$R'R" radical where R, R' and R" are independently hydrogen or lower alkyl. If the nitrogen atoms are substituted by other group other than hydrogen or lower alkyl, locants N or N' or 1 and 3 respectively are used to identify the substituted nitrogen atoms. The point of attachment of the ureido radical is denoted N or 1. For example, using this nomenclature N'-phenylureido refers to —NRC(=O)NPhR' where R and R' are as defined previously. The position of specific alkyl substituents can optionally be specifically designated using the same nomenclature.

The term "carbamate" or "urethane" as used herein refers to a ROC(=O)N$^3$R'R" radical wherein either R or R' is the core structure and the other of R, R' and R" are as defined in the specification and claims. The term "urea" as used herein refers to a group RR'NC(=O)NR"R''' wherein R is the core structure and R', R" and R''' are as defined in the specification and claims.

The term "aminocarbonylpyridyl" as used herein refers to the radical —NHCOR wherein R is 2-pyridinyl (picolinoyl), 3-pyridinyl (nicotinoyl) or 4-pyridinyl (isonicotinoyl) and the N-oxides derived therefrom.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

It will be appreciated by the skilled artisan that the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxillary) to produce diastereomers which can be separated by chromatography or by fractional crystallization after which time the chiral auxilliary is chemically removed to afford the pure enantiomers.

The compounds of formula I contain at least one basic center and suitable acid addition salts are formed from acids which form non-toxic salts. Examples of salts of inorganic acids include the hydrochloride, hydrobromide, hydroiodide, chloride, bromide, iodide, sulphate, bisulphate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 66, 1–19, 1977.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e.g., channels) that have a guest molecule (e.g., a solvent or water) trapped within.

The term "nucleoside and nucleotide reverse transcriptase inhibitors" ("NRTI's") as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA. Typical suitable NRTIs include zidovudine (AZT) available as RETROVIR® from Glaxo-Wellcome Inc.; didanosine (ddl) available as VIDEX® from Bristol-Myers Squibb Co.; zalcitabine (ddC) available as HIVID® from Roche Pharmaceuticals; stavudine (d4T) available as ZERIT® from Bristol-Myers Squibb Co.; lamivudine (3TC) available as EPIVIR® from Glaxo-Wellcome; abacavir (1592U89) disclosed in WO96/30025 and available ZIAGEN® from Glaxo-Wellcome; adefovir dipivoxil [bis (POM)-PMEA] available as PREVON® from Gilead Sciences; lobucavir (BMS-180194), a nucleoside reverse transcriptase inhibitor disclosed in EP-0358154 and EP-0736533 and under development by Bristol-Myers Squibb; BCII-10652, a reverse transcriptase inhibitor (in the form of a racemic mixture of BCII-10618 and BCII-10619) under development by Biochem Pharma; emitricitabine [(−)-FTC] licensed from Emory University under U.S. Pat. No. 5,814,639 and under development by Triangle Pharmaceuticals; beta-L-FD4 (also called beta-L-D4C and named beta-L-2',3'-dicleoxy-5-fluoro-cytidine) licensed by Yale University to Vion Pharmaceuticals; DAPD, the purine nucleoside, (−)-b-D-2,6-diamino-purine dioxolane disclosed in EP-0656778 and licensed by Emory University and the University of Georgia to Triangle Pharmaceuticals; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc.

The term "non-nucleoside reverse transcriptase inhibitors" ("NNRTI"s) as used herein means non-nucleosides that inhibit the activity of HIV-1 reverse transcriptase. Typical suitable NNRTIs include nevirapine (BI-RG-587) available as VIRAMUNE® from Roxane Laboratories; delaviradine (BHAP, U-90152) available as RESCRIPTOR® from Pfizer; efavirenz (DMP-266) a benzoxazin-2-one disclosed in WO94/03440 and available as SUSTIVA® from Bristol-Myers Squibb Co.; PNU-142721, a furopyridine-thio-pyrimide under development by Pfizer 08807; AG-1549 (formerly Shionogi # S-1153); 5-(3,5-dichlorophenyl)-thio-4-isopropyl-1-(4-pyridyl)methyl-1H-imidazol-2-ylmethyl carbonate disclosed in WO 96/10019 and under development by Agouron Pharmaceuticals, Inc.; MKC-442 (1-(ethoxy-methyl)-5-(1-methylethyl)-6-(phenylmethyl)-(2,4 (1H,3H)-pyrimidinedione) discovered by Mitsubishi Chemical Co. and under development by Triangle Pharmaceuticals; and (+)-calanolide A (NSC-675451) and B, coumarin derivatives disclosed in NIH U.S. Pat. No. 5,489,697, licensed to Med Chem Research, which is co-developing (+) calanolide A with Vita-invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character. Typical suitable PIs include saquinavir (Ro 31-8959) available in hard gel capsules as INVIRASE® and as soft gel capsules as FORTOVASE® from Roche Pharmaceuticals, Nutley, N.J. 07110-1199; ritonavir (ABT-538) available as NORVIR® from Abbott Laboratories; indinavir (MK-639) available as CRIXIVAN® from Merck & Co., Inc.; nelfnavir (AG-1343) available VIRACEPT® from Agouron Pharmaceuticals, Inc.; amprenavir (141W94), AGENERASE®, a non-peptide protease inhibitor under development by Vertex Pharmaceuticals, Inc. and available from Glaxo-Wellcome, under an expanded access program; lasinavir (BMS-234475) available from Bristol-Myers Squibb; DMP450, a cyclic urea discovered by Dupont and under development by Triangle Pharmaceuticals; BMS-2322623, an azapeptide under development by Bristol-Myers Squibb as a 2nd-generation HIV-1 PI; ABT-378 under development by Abbott; and AG-1549 an orally active imidazole carbamate discovered by Shionogi and under development by Agouron Pharmaceuticals, Inc.

Other antiviral agents include hydroxyurea, ribavirin, IL-2, IL-12, pentafuside. Hydroyurea (Droxia), a ribonucleoside triphosphate reductase inhibitor, the enzyme involved in the activation of T-cells, was discovered at the NCI and is in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748, 234, 4,752,585, and 4,949,314, and is available under the PROLEUKIN® (aldesleukin) as a lyophilized powder for IV infusion or sc administration upon reconstitution and dilution with water; a dose of about 1 to about 20 million 1 U/day, sc is preferred; a dose of about 15 million 1 U/day, sc is more preferred. IL-12 is disclosed in WO96/25171 and is administered in a dose of about 0.5 microgram/kg/day to about 10 microgram/kg/day, sc is preferred. Pentafuside (FUZEON®) a 36-amino acid synthetic peptide, disclosed in U.S. Pat. No. 5,464,933 that acts by inhibiting fusion of HIV-1 to target membranes. Pentafuside (3–100 mg/day) is given as a continuous sc infusion or injection together with efavirenz and 2 PI's to HIV-1 positive patients refractory to a triple combination therapy; use of 100 mg/day is preferred. Ribavirin, 1-.beta.-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "viral fusion inhibitors" as used herein refers to compounds which inhibit fusion of the free virus particle and introduction of the viral RNA into a host cell independent of the molecular locus of inhibitor binding. Viral fusion inhibitors therefore include, but are not limited to T-20; CD4 binding ligands including BMS-378806, BMS-488043; CCR5 binding ligands including SCH-351125, Sch-350634, Sch417690 (Schering Plough), UK4278957 (Pfizer), TAK-779 (Takeda), ONO-4128 (Ono), AK-602 (Ono, Glaxo-SmithKline), compounds 1–3 (Merck); CXCR4 binding ligands KRH-1636 (K. Ichiyama et al. *Proc. Nat. Acad. Sci USA* 2003 100(7):4185–4190), T-22 (T. Murakami et al. *J. Virol.* 1999 73(9):7489–7496), T-134 (R. Arakaki et al. *J. Virol.* 1999 73(2):1719–1723). Viral fusion inhibitors as used herein also include peptide and protein soluble receptors, antibodies, chimeric antibodies, humanized antibodies.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp) carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), di-iso-propyl-ethylamine (DIPEA), pyridine (pyr), di-iso-butylaluminumnhydride, DIBAL-H, room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2, 6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N- carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

COMPOUNDS AND PREPARATION

Compounds of the present invention can be made by a variety of methods depicked in the illustrative synthetic reaction schemes shown and descripted below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1–21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1–9 Pergamon, Oxford, 1991; *Comprehensive Heterocyclic Chemistry*, A. R. Katritzky and C. W. Rees (Eds) Pergamon, Oxford 1984, vol. 1–9; *Comprehensive Heterocyclic Chemistry II*, A. R. Katritzky and C. W. Rees (Eds) Pergamon, Oxford 1996, vol. 1–11; and Organic Reactions, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about –78° C. to about 150° C., more preferably from about 0° C. to about 125° C., and most preferably and conveniently at about room (or ambient) temperature, e.g., about 20° C.

2-Benzyl-octahydro-pyrrolo[3,4-c]pyrrole (4a) was prepared by [2,3]-dipolar cycloaddition of an imine ylide with N-benzylmaleimide as described previously (R. Colon-Cruz et al. WO 02/070523 and M. Björsne et al. WO 02/060902). Reduction of the imide, and selective debenzylation are accomplished as described therein.

The preparation of some compounds of the present invention wherein R$^2$ is phenyl is depicted in Scheme 1. The procedure in Scheme 1 is particularly suited for preparation of a series of compounds in which the amides (or ureas or sulfonamides) linked to the hexahydro-pyrrolo[3,4-c]pyrrol-2-yl] scaffold is varied. The fully elaborated 1-phenyl-1-amino-propyl side chain is introduced before deprotection of the second amine. Debenzylation of the amine allows for the elaboration of the second nitrogen atom.

Alternatively, the amide (or urea or sulfonamide) my be introduced first by acylation of 4a with e.g. 2,6-dimethyl-benzoyl chloride, 2,4-dimethyl-nicotinoyl chloride or 4,6-dimethyl-pyrimidin-5-carbonyl chloride, and subsequent debenzylation to afford 66, 54 and 44 respectively. Introduction of a Boc group and subsequent debenzylation affords 74. The accompanying examples illustrate the utility of these compounds for the preparation of compounds of the invention.

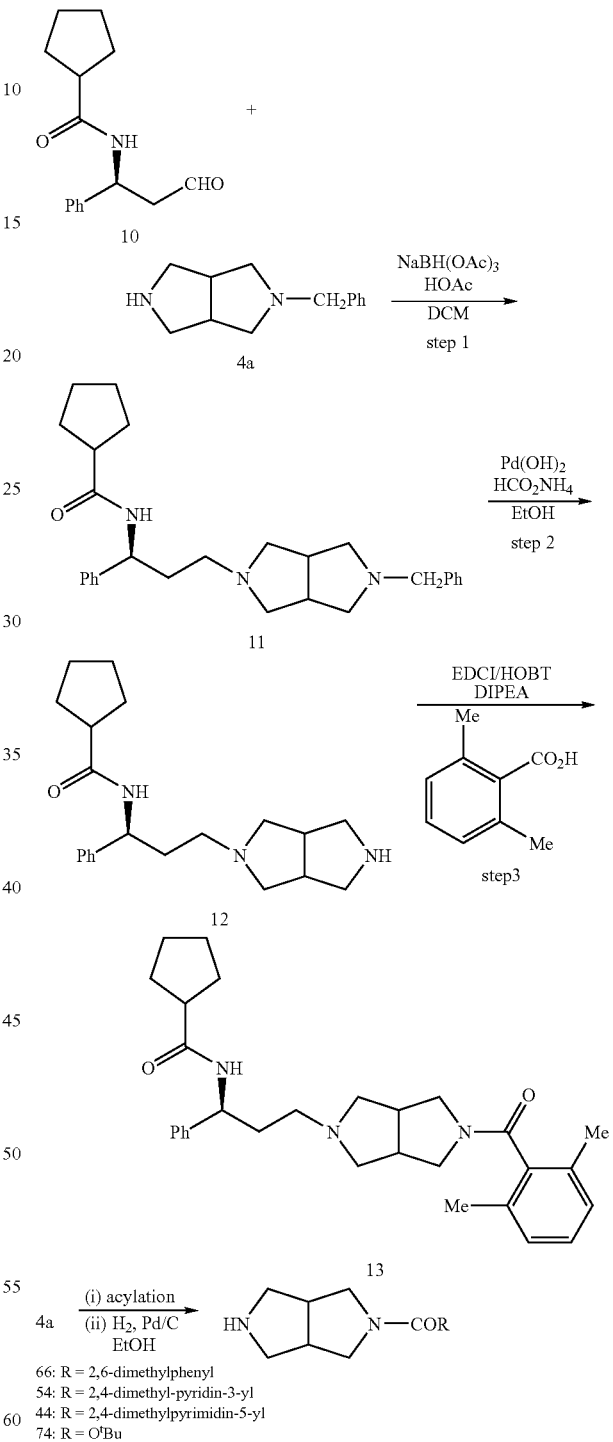

β-Aminoacylcarboxaldeydes 15b are convenient synthetic intermediates accessible by reduction of β-acylamino carboxylic acids or carboxylic acid derivatives (15a: X=OH, OR$^b$ or NR$^b$R$^c$ wherein R$^a$ is an acyl radical or a protecting group and R$^b$ and R$^c$ are typically lower alkyl), see, e.g. Example 15 Acylation of a β-amino ester (14: X is O-alkyl) is conveniently carried out with a corresponding acyl halide, carboxylic acid anhydride or chloroformate in a solvent such as DCM, chloroform, carbon tetrachloride, ether, THF, dioxane, benzene, toluene, MeCN, DMF, sodium hydroxide solution or sulpholane optionally in the presence of an inorganic or organic base at temperatures between −20 and 200° C., but preferably at temperatures between −10 and 100° C.

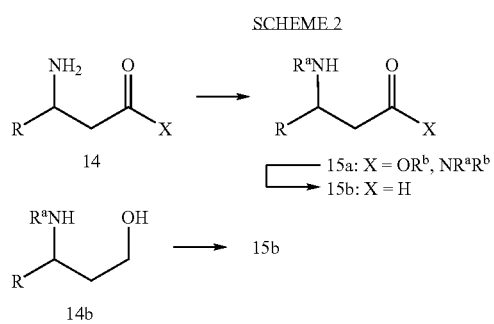

Acylation also may be carried out with the carboxylic acid in the presence of an activating agent or a dehydrating agent, e.g. in the presence of isobutyl chloroformate, thionyl chloride, trimethylchlorosilane, HCl, $H_2SO_4$, methanesulphonic acid, p-toluenesulphonic acid, phosphorus trichloride, $P_2O_5$, N,N'-dicyclohexylcarbodiimide, N,N'-dicyclohexyl-carbodiimide/N-hydroxysuccinimide or HOBt, N,N'-carbonyldiimidazole, O-(benzotriazol-1-yl)-N,N,N',N'-tetramethyluronium tetrafluoroborate/N-methylmorpholine, O-(benzotriazol-1-yl)-N,N,N',N'-tetramethyl-uronium tetrafluoroborate/N-ethyldiisopropylamine, N,N'-thionyldiimidazole or triphenylphosphine/$CCl_4$, at temperatures between −20 and 200° C., but preferably at temperatures between −10 and 100° C.

Aldehydes 15b may be prepared by reduction of the corresponding acid (15a: X=OH), ester (15a: X=$OR^b$) or amide (15a: X=$NR^bR^c$), wherein $R^b$ and $R^c$ are lower alkyl, by a hydride reducing agent in a suitable solvent. Alternatively, reduction of an acyl halide may be achieved with a suitable transition metal catalyst, a hydrogen source and in a suitable solvent. Typical hydride reducing agents are aluminum hydrides or boron hydrides such as DIBAL-H, LiAl(O-tert-Bu)$_3$H, or Me$_2$CHCH(Me)$_2$BH. Suitable solvents are inert solvents such as THF, DCM or toluene. An acid chloride (15a: X=Cl) can be reduced with a transition metal catalyst such as Pd/C or Pd/BaSO$_4$, under a hydrogen atmosphere with a modifier such as 2,4-dimethylpyridine and in solvent such as THF or toluene. Another route to β-acylamino-carboxyaldehydes 15b comprises oxidation of a β-acylaminoalcohol 14b which can be carried out by a variety of oxidizing agents, e.g. pyridine.SO$_3$.TEA. Preferably the N-acylated acid or ester is reduced to the aldehydes with DIBAL-H in DCM at −78° C. as described by D. R. Armour et al. (WO 00/38680).

The aldehyde 15b ($R^a$ is an acyl radical or a nitrogen protecting group) is incorporated onto the 2-octahydropyrrolo[3,4-c]pyrrole scaffold by reductive amination to afford diamine 11. Reductive amination is preferably carried out by combining an amine and aldehyde in the presence of a complex metal hydride such as sodium borohydride, lithium borohydride, sodium cyanoborohydride, zinc borohydride, sodium triacetoxyborohydride or borane/pyridine conveniently at a pH of 1–7. The reaction mixture optionally includes a dehydrating agent such as molecular sieves or Ti(IV)(O-i-Pr)$_4$ to facilitate formation of the intermediate imine at ambient temperature or with hydrogen in the presence of a hydrogenation catalyst, e.g. in the presence of Pd/C, at a hydrogen pressure of 1 to 5 bar, preferably at temperatures between 20° C. and the boiling temperature of the solvent used. It may also be advantageous during the reaction if reactive groups are protected during the reaction by conventional protecting groups which are cleaved again by conventional methods after the reaction. Reductive amination procedures have been reviewed: R. M. Hutchings and M. K. Hutchings *Reduction of C═N to CHNH by Metal Hydrides in Comprehensive Organic Synthesis* col. 8, I. Fleming (Ed) Pergamon, Oxford 1991 pp. 47–54.

Removal of the remaining benzyl protecting group affords amine 12. Removal of benzyl protecting groups can be readily achieved by catalytic hydrogenolysis using Pd, Pt, Ni or Rh catalysts. Acids are sometimes added to promote hydrogenolysis. Acylation of the free secondary amine affords 13. Alternatively the nitrogen atom can be alkylated with an aralkyl halide to afford I ($X^2$ is aralkyl) or sulfonylated to produce sulfonamides I ($X^2$ is $SO_2R^4$). Sulfonylation of amines is typically carried out by treating an amine with an alkyl or aryl sulfonyl chloride in the presence of an organic base, e.g. pyridine or TEA, in an inert solvent.

While the preparation of 13 exemplifies the synthesis of a compound of the invention with a cyclopentylcarboxamide, one skilled in the art will appreciate a wide variety of amides, ureas or sulfonamides can be introduced by using an analogous.

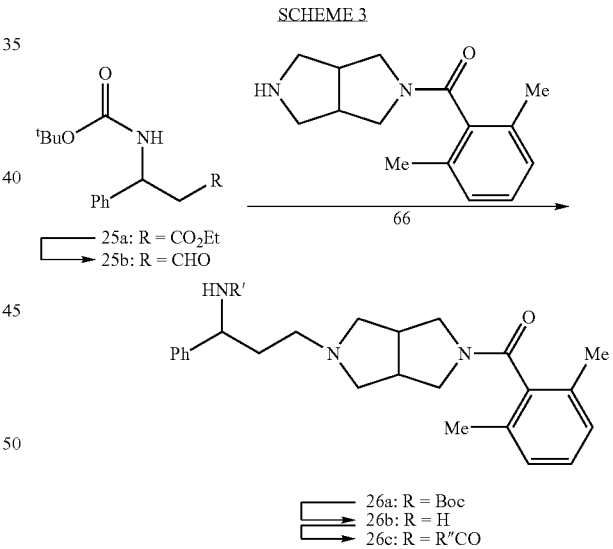

An amino protecting group, such as the Boc derivative 25b, may be utilized in place of an acyl radical during the reductive amination procedures (Scheme 3). Numerous reactions for the formation and removal of such amine protecting groups are described in standard works including, for example, "Protective Groups in Organic Chemistry", Plenum Press, London and New York, 1973; Greene, Th. and Wutts, P. G. M. *Protective Groups in Organic Synthesis*, Wiley, New York, 1999; *The Peptides*, Vol. I, Schroder and Lubke, Academic Press, London and New York, 1965; *Methoden der organischen Chemie, Houben-Weyl*, 4th Edition, Vol 15/I, Georg Thieme Verlag, Stuttgart 1974, the disclosures of which are incorporated herein by reference in their entirety. Protecting groups may be selected which are cleaved under a variety of conditions selected to be compatible with other functional groups in the molecule. Introduction of acyl groups is then accomplished after the reductive amination step by deprotection of the primary amine and acylation with a carboxylic acid as described above. Ureas, carbamates and sulfonamides are accessible by reaction of 26b with isocyanates, chloroformates and sulfonyl chlorides respectively. Scheme 3 depicts the introduction of a carboxamido group onto the diazabicyclooctane ring prior to the reductive alkylation and elaboration of the aminopropyl side chain after reductive alkylation.

SCHEME 4

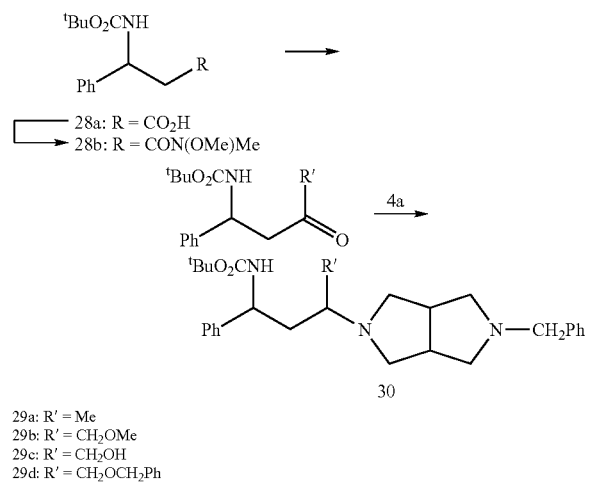

28a: R = CO₂H
28b: R = CON(OMe)Me

29a: R' = Me
29b: R' = CH₂OMe
29c: R' = CH₂OH
29d: R' = CH₂OCH₂Ph

Embodiments of the invention may have alkyl (30: R'=Me), alkoxyalkyl (30: R'=CH₂OMe or CH₂OCH₂Ph) or hydroxymethyl (30: R'=CH₂OH) substituents on the propylene linker. One route to these compounds is depicted in Scheme 4. The β-acylaminocarboxylic acid was converted to the N-methoxy-N-methyl amide and reacted with methyl lithium to afford butanone 29a which could be incorporated onto the pyrrolo[3,4-c]pyrrol-2-yl scaffold by reductive alkylation as described previously. Methoxymethyl- and benzyloxymethyl compounds were prepared by analogous methods starting from stannane organometallics as described in Examples 27 and 28. Debenzylation of 29d affords the corresponding hydroxylmethyl compound 29c, Compounds bearing a methyl or a dimethyl substituent on the linker carbon adjacent to aminomethine carbon were prepared as described in Examples 24 and 26. An example of the preparation of compounds with a hydroxyl substituent on the propylene linker is in Example 35

Examples of representative compounds encompassed by the present invention and within the scope of the claims are provided in the following Tables. These examples and preparations are provided to enable those skilled in the art to more clearly understand and to practice the present invention. They should not be considered as limiting the scope of the invention, but merely as being illustrative and representative thereof. The reagents used to introduce $X^1$ and $X^2$ are commercially available or can prepared from commercially available materials by published procedures. An examination of the compounds encompassed in the invention and working examples demonstrate that the generality of the reaction sequence and the nature of the protecting groups which can be optimized for a particular target without deviating from the general procedures discussed herein.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure encompasses both isomers. While compounds of the present invention are frequently depicted with the (S) stereochemistry, both stereoisomers are included in the present invention and both can be prepared by identical procedures from the appropriate starting material.

Representative compounds of the present invention in which $R^2$ is an aryl or heteroaryl group are compiled in Table 1.

TABLE 1

|  |  | MS[1] | mp | MW |
|---|---|---|---|---|
| I-1 | Tetrahydro-furan-3-carboxylic acid {(S)-1-phenyl-3-[5-(quinoxaline-2-carbonyl)-hexahydro-pyrrolo[3,4-c]pyrrol-2-yl]-propyl}-amide; compound with trifluoro-acetic acid | 500.3 |  | 499.61 |
| I-2 | Cyclopentanecarboxylic acid {(S)-3-[5-(3,4-dichloro-benzyl)-hexahydro-pyrrolo[3,4-c]pyrrol-2-yl]-1-phenyl-propyl}-amide; compound with trifluoro-acetic acid | 500 |  | 500.51 |
| I-3 | Cyclopentanecarboxylic acid {(S)-3-[5-(2,6-dimethyl-benzoyl)-hexahydro-pyrrolo[3,4-c]pyrrol-2-yl]-1-phenyl-propyl}-amide | 474 | 60.9–63.9 | 473.66 |
| I-4 | Cyclopentanecarboxylic acid {(S)-1-phenyl-3-[5-(pyridine-3-carbonyl)-hexahydro-pyrrolo[3,4-c]pyrrol-2-yl]-propyl}-amide; compound with trifluoro-acetic acid | 447 |  | 446.59 |
| I-5 | Cyclopentanecarboxylic acid [(S)-1-phenyl-3-(5 phenylacetyl-hexahydro-pyrrolo[3,4-c]pyrrol-2-yl)-propyl]-amide; compound with trifluoro-acetic acid | 460 |  | 459.63 |
| I-6 | 5-[(S)-3-(Cyclopentanecarbonyl-amino)-3-phenyl-propyl]-hexahydro-pyrrolo[3,4-c]pyrrole-2-carboxylic acid benzyl ester | 476 |  | 475.63 |

TABLE 1-continued

|   | | MS[1] | mp | MW |
|---|---|---|---|---|
| I-7 | Cyclopentanecarboxylic acid {(R)-2-[5-(2,6-dimethyl-benzoyl)-hexahydro-pyrrolo[3,4-c]pyrrol-2-yl]-1-phenyl-ethyl}-amide; compound with trifluoro-acetic acid | 460 | | 459.63 |
| I-8 | Cyclopentanecarboxylic acid {(S)-3-[5-(2,5-dimethyl-2H-pyrazole-3-carbonyl)-hexahydro-pyrrolo[3,4-c]pyrrol-2-yl]-1-phenyl-propyl}-amide | 464 | 70.1–72.5 | 463.62 |
| I-9 | Cyclopentanecarboxylic acid {(S)-3-[5-(1-oxy-pyridine-3-carbonyl)-hexahydro-pyrrolo[3,4-c]pyrrol-2-yl]-1-phenyl-propyl}-amide | 463 | 62.0–64.3 | 462.59 |
| I-10 | Cyclopentanecarboxylic acid {(S)-1-phenyl-3-[5-(1H-[1,2,4]triazole-3-carbonyl)-hexahydro-pyrrolo[3,4-c]pyrrol-2-yl]-propyl}-amide | 437 | 107.0–108.0 | 436.56 |
| I-11 | Cyclopentanecarboxylic acid {(S)-3-[5-(4-methoxy-2,6-dimethyl-benzoyl)-hexahydro-pyrrolo[3,4-c]pyrrol-2-yl]-1-phenyl-propyl}-amide; compound with trifluoro-acetic acid | 504.8 | | 503.68 |
| I-12 | Cyclopentanecarboxylic acid {(S)-3-[5-(2,6-dichloro-benzoyl)-hexahydro-pyrrolo[3,4-c]pyrrol-2-yl]-1-phenyl-propyl}-amide; compound with trifluoro-acetic acid | 514.7 | | 514.49 |
| I-13 | Cyclopentanecarboxylic acid {(S)-3-[5-(2-chloro-6-methyl-benzoyl)-hexahydro-pyrrolo[3,4-c]pyrrol-2-yl]-1-phenyl-propyl}-amide; compound with trifluoro-acetic acid | 494.8 | | 494.08 |
| I-14 | Cyclopentanecarboxylic acid {(S)-3-[5-(2,6-dichloro-4-methyl-benzoyl)-hexahydro-pyrrolo[3,4-c]pyrrol-2-yl]-1-phenyl-propyl}-amide; compound with trifluoro-acetic acid | 528.7 | | 528.52 |
| I-15 | Cyclopentanecarboxylic acid {(S)-3-[5-(4-butoxy-2,6-dimethyl-benzoyl)-hexahydro-pyrrolo[3,4-c]pyrrol-2-yl]-1-phenyl-propyl}-amide; compound with trifluoro-acetic acid | 546.9 | | 545.76 |
| I-16 | Cyclopentanecarboxylic acid {(S)-3-[5-(4-ethoxy-2,6-dimethyl-benzoyl)-hexahydro-pyrrolo[3,4-c]pyrrol-2-yl]-1-phenyl-propyl}-amide; compound with trifluoro-acetic acid | 518.8 | | 517.71 |
| I-17 | Cyclopentanecarboxylic acid {(S)-3-[5-(2-chloro-6-fluoro-benzoyl)-hexahydro-pyrrolo[3,4-c]pyrrol-2-yl]-1-phenyl-propyl}-amide; compound with hydrochloric acid | 498.7 | | 498.04 |
| I-18 | Cyclopentanecarboxylic acid {(S)-1-phenyl-3-[5-(2,4,6-trimethyl-benzoyl)-hexahydro-pyrrolo[3,4-c]pyrrol-2-yl]-propyl}-amide; compound with trifluoro-acetic acid | 488.8 | | 487.68 |
| I-19 | Cyclopentanecarboxylic acid {(S)-3-[5-(2-bromo-6-methyl-benzoyl)-hexahydro-pyrrolo[3,4-c]pyrrol-2-yl]-1-phenyl-propyl}-amide; compound with trifluoro-acetic acid | 540.7 | | 538.53 |
| I-20 | Cyclopentanecarboxylic acid {(S)-3-[5-(2,6-difluoro-4-methoxy-benzoyl)-hexahydro-pyrrolo[3,4-c]pyrrol-2-yl]-1-phenyl-propyl}-amide; compound with trifluoro-acetic acid | 512.8 | | 511.61 |
| I-21 | Cyclopentanecarboxylic acid {(S)-1-phenyl-3-[5-(2,4,6-trimethoxy-benzoyl)-hexahydro-pyrrolo[3,4-c]pyrrol-2-yl]-propyl}-amide; compound with trifluoro-acetic acid | 536.8 | | 535.68 |
| I-22 | Cyclopentanecarboxylic acid {(S)-3-[5-(4-chloro-2-methoxy-benzoyl)-hexahydro-pyrrolo[3,4-c]pyrrol-2-yl]-1-phenyl-propyl}-amide; compound with trifluoro-acetic acid | 510.8 | | 510.07 |
| I-23 | Cyclopentanecarboxylic acid {(S)-3-[5-(2,3-dimethyl-benzoyl)-hexahydro-pyrrolo[3,4-c]pyrrol-2-yl]-1-phenyl-propyl}-amide; compound with trifluoro-acetic acid | 474.8 | | 473.66 |
| I-24 | Cyclopentanecarboxylic acid {(S)-3-[5-(2,4-dimethyl-benzoyl)-hexahydro-pyrrolo[3,4-c]pyrrol-2-yl]-1-phenyl-propyl}-amide; compound with trifluoro-acetic acid | 474.8 | | 473.66 |
| I-25 | Cyclopentanecarboxylic acid {(S)-3-[5-(2-methoxy-4-methylsulfanyl-benzoyl)-hexahydro-pyrrolo[3,4-c]pyrrol-2-yl]-1-phenyl-propyl}-amide; compound with trifluoro-acetic acid | 522.8 | | 521.72 |
| I-26 | Cyclopentanecarboxylic acid {(S)-3-[5-(2-dimethylamino-benzoyl)-hexahydro-pyrrolo[3,4-c]pyrrol-2-yl]-1-phenyl-propyl}-amide; compound with trifluoro-acetic acid | 489.8 | | 488.67 |

TABLE 1-continued

| | | MS[1] | mp | MW |
|---|---|---|---|---|
| I-27 | Cyclopentanecarboxylic acid {(S)-1-phenyl-3-[5-(1H-pyrrole-2-carbonyl)-hexahydro-pyrrolo[3,4-c]pyrrol-2-yl]-propyl}-amide; compound with trifluoro-acetic acid | 435.8 | | 434.58 |
| I-28 | Cyclopentanecarboxylic acid {(S)-3-[5-(3,5-dimethyl-isoxazole-4-carbonyl)-hexahydro-pyrrolo[3,4-c]pyrrol-2-yl]-1-phenyl-propyl}-amide; compound with trifluoro-acetic acid | 465.8 | | 464.61 |
| I-29 | Cyclopentanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide | 476 | 48.0–49.0 | 475.63 |
| I-30 | Cyclopentanecarboxylic acid [(S)-3-(5-acetyl-hexahydro-pyrrolo[3,4-c]pyrrol-2-yl)-1-phenyl-propyl]-amide; compound with trifluoro-acetic acid | 384 | | 383.53 |
| I-31 | Cyclopentanecarboxylic acid {(S)-3-[5-(2,2-dimethyl-propionyl)-hexahydro-pyrrolo[3,4-c]pyrrol-2-yl]-1-phenyl-propyl}-amide; compound with trifluoro-acetic acid | 426 | | 425.61 |
| I-32 | N-{(S)-3-[5-(2,6-Dimethyl-benzoyl)-hexahydro-pyrrolo[3,4-c]pyrrol-2-yl]-1-phenyl-propyl}-benzenesulfonamide; compound with trifluoro-acetic acid | 518.8 | | 517.69 |
| I-33 | Cyclopropanecarboxylic acid {(S)-3-[5-(2,6-dimethyl-benzoyl)-hexahydro-pyrrolo[3,4-c]pyrrol-2-yl]-1-phenyl-propyl}-amide; compound with trifluoro acetic acid | 446.8 | | 445.6 |
| I-34 | Furan-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 472.8 | | 471.6 |
| I-35 | N-{(S)-3-[5-(2,6-Dimethyl-benzoyl)-hexahydro-pyrrolo[3,4-c]pyrrol-2-yl]-1-phenyl-propyl}-isobutyramide; compound with trifluoro-acetic acid | 448.8 | | 447.62 |
| I-36 | N-{(S)-3-[5-(2,6-Dimethyl-benzoyl)-hexahydro-pyrrolo[3,4-c]pyrrol-2-yl]-1-phenyl-propyl}-3-methyl-butyramide; compound with trifluoro-acetic acid | 462.8 | | 461.65 |
| I-37 | Thiophene-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 488.8 | | 487.67 |
| I-38 | N-{(S)-3-[5-(2,6-Dimethyl-benzoyl)-hexahydro-pyrrolo[3,4-c]pyrrol-2-yl]-1-phenyl-propyl}-2,2-dimethyl-propionamide; compound with trifluoro-acetic acid | 462.8 | | 461.65 |
| I-39 | Cyclohexanecarboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 488.9 | | 487.68 |
| I-40 | Morpholine-4-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 491.8 | | 490.64 |
| I-41 | N-{(S)-3-[5-(2,6-Dimethyl-benzoyl)-hexahydro-pyrrolo[3,4-c]pyrrol-2-yl]-1-phenyl-propyl}-2-hydroxy-2-methyl-propionamide; compound with trifluoro-acetic acid | 464.8 | | 463.62 |
| I-42 | Cyclobutanecarboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 460.8 | | 459.63 |
| I-43 | Pyrrolidine-1-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 475.8 | | 474.65 |
| I-44 | N-{(S)-3-[5-(2,6-Dimethyl-benzoyl)-hexahydro-pyrrolo[3,4-c]pyrrol-2-yl]-1-phenyl-propyl}-acetamide; compound with trifluoro-acetic acid | 420.8 | | 419.57 |
| I-45 | N-{(S)-3-[5-(2,6-Dimethyl-benzoyl)-hexahydro-pyrrolo[3,4-c]pyrrol-2-yl]-1-phenyl-propyl}-2-methoxy-acetamide; compound with trifluoro-acetic acid | 450.8 | | 449.59 |
| I-46 | N-{(S)-3-[5-(2,6-Dimethyl-benzoyl)-hexahydro-pyrrolo[3,4-c]pyrrol-2-yl]-1-phenyl-propyl}-2-hydroxy-2-phenyl-acetamide; compound with trifluoro-acetic acid | 512.8 | | 511.66 |

TABLE 1-continued

| | | MS[1] | mp | MW |
|---|---|---|---|---|
| I-47 | 2-Cyclopentyl-N-{(S)-3-[5-(2,6-dimethyl-benzoyl)-hexahydro-pyrrolo[3,4-c]pyrrol-2-yl]-1-phenyl-propyl}-acetamide; compound with trifluoro-acetic acid | 488.8 | | 487.68 |
| I-48 | N-{(S)-3-[5-(2,6-Dimethyl-benzoyl)-hexahydro-pyrrolo[3,4-c]pyrrol-2-yl]-1-phenyl-propyl}-4-methanesulfonyl-benzamide; compound with trifluoro-acetic acid | 560.8 | | 559.73 |
| I-49 | N-{(S)-3-[5-(2,6-Dimethyl-benzoyl)-hexahydro-pyrrolo[3,4-c]pyrrol-2-yl]-1-phenyl-propyl}-benzamide; compound with trifluoro-acetic acid | 482.8 | | 481.64 |
| I-50 | Furan-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 472.8 | | 471.6 |
| I-51 | 1H-Pyrrole-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 471.8 | | 470.61 |
| I-52 | 5-Methyl-thiophene-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 502.8 | | 501.69 |
| I-53 | 1-Methyl-1H-pyrrole-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 485.8 | | 484.64 |
| I-54 | 2-Acetylamino-N-{(S)-3-[5-(2,6-dimethyl-benzoyl)-hexahydro-pyrrolo[3,4-c]pyrrol-2-yl]-1-phenyl-propyl}-acetamide; compound with trifluoro-acetic acid | 477.9 | | 476.62 |
| I-55 | N-{(S)-3-[5-(2,6-Dimethyl-benzoyl)-hexahydro-pyrrolo[3,4-c]pyrrol-2-yl]-1-phenyl-propyl}-4-sulfamoyl-benzamide; compound with trifluoro-acetic acid | 561.8 | | 560.72 |
| I-56 | Tetrahydro-furan-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 476.9 | | 475.63 |
| I-57 | 2-Oxo-thiazolidine-4-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 507.8 | | 506.67 |
| I-58 | Pyrazine-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 484.8 | | 483.61 |
| I-59 | N-{(S)-3-[5-(2,6-Dimethyl-benzoyl)-hexahydro-pyrrolo[3,4-c]pyrrol-2-yl]-1-phenyl-propyl}-2-hydroxy-acetamide; compound with trifluoro-acetic acid | 436.8 | | 435.57 |
| I-60 | N-{(S)-3-[5-(2,6-Dimethyl-benzoyl)-hexahydro-pyrrolo[3,4-c]pyrrol-2-yl]-1-phenyl-propyl}-2-methyl-butyramide; compound with trifluoro-acetic acid | 462.8 | | 461.65 |
| I-61 | Tetrahydro-furan-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 476.8 | | 475.63 |
| I-62 | 2-Dimethylamino-N-{(S)-3-[5-(2,6-dimethyl-benzoyl)-hexahydro-pyrrolo[3,4-c]pyrrol-2-yl]-1-phenyl-propyl}-acetamide; compound with trifluoro-acetic acid | 463.8 | | 462.63 |
| I-63 | 1-{(S)-3-[5-(2,6-Dimethyl-benzoyl)-hexahydro-pyrrolo[3,4-c]pyrrol-2-yl]-1-phenyl-propyl}-3-phenyl-urea; compound with trifluoro-acetic acid | 497.8 | | 496.65 |
| I-64 | 1-{(S)-3-[5-(2,6-Dimethyl-benzoyl)-hexahydro-pyrrolo[3,4-c]pyrrol-2-yl]-1-phenyl-propyl}-3-isopropyl-urea; compound with trifluoro-acetic acid | 463.8 | | 462.63 |
| I-65 | 1-Acetyl-piperidine-4-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 531.9 | | 530.71 |
| I-66 | 4,4-Difluoro-cyclohexanecarboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 524.8 | | 523.66 |

TABLE 1-continued

|   | | MS[1] | mp | MW |
|---|---|---|---|---|
| I-67 | Cyclopentanecarboxylic acid [(S)-3-(5-isobutyryl-hexahydro-pyrrolo[3,4-c]pyrrol-2-yl)-1-phenyl-propyl]-amide; compound with trifluoro-acetic acid | 412 | | 411.59 |
| I-68 | Cyclopentanecarboxylic acid {(S)-3-[5-(3-methyl-butyryl)-hexahydro-pyrrolo[3,4-c]pyrrol-2-yl]-1-phenyl-propyl}-amide; compound with trifluoro-acetic acid | 426 | | 425.61 |
| I-69 | Cyclopentanecarboxylic acid [(S)-3-(5-butyryl-hexahydro-pyrrolo[3,4-c]pyrrol-2-yl)-1-phenyl-propyl]-amide; compound with trifluoro-acetic acid | 412 | | 411.59 |
| I-70 | Cyclopentanecarboxylic acid [(S)-3-(5-cyclopropanecarbonyl-hexahydro-pyrrolo[3,4-c]pyrrol-2-yl)-1-phenyl-propyl]-amide; compound with trifluoro-acetic acid | 410 | | 409.57 |
| I-71 | Cyclopentanecarboxylic acid [(S)-3-(5-cyclobutanecarbonyl-hexahydro-pyrrolo[3,4-c]pyrrol-2-yl)-1-phenyl-propyl]-amide; compound with trifluoro-acetic acid | 424 | | 423.6 |
| I-72 | Cyclopentanecarboxylic acid {(S)-3-[5-(2-methyl-butyryl)-hexahydro-pyrrolo[3,4-c]pyrrol-2-yl]-1-phenyl-propyl}-amide; compound with trifluoro-acetic acid | 426 | | 425.61 |
| I-73 | Cyclopentanecarboxylic acid {(S)-3-[5-(2-ethyl-butyryl)-hexahydro-pyrrolo[3,4-c]pyrrol-2-yl]-1-phenyl-propyl}-amide; compound with trifluoro-acetic acid | 440 | | 439.64 |
| I-74 | {(S)-3-[5-(2,6-Dimethyl-benzoyl)-hexahydro-pyrrolo[3,4-c]pyrrol-2-yl]-1-pyridin-3-yl-propyl}-carbamic acid tert-butyl ester | 479 | | 478.63 |
| I-75 | Cyclopentanecarboxylic acid {(S)-3-[5-(2,6-dimethyl-benzoyl)-hexahydro-pyrrolo[3,4-c]pyrrol-2-yl]-1-phenyl-butyl}-amide | 488 | | 487.68 |
| I-76 | Cyclopentanecarboxylic acid {(S)-3-[5-(2,6-dimethyl-benzoyl)-hexahydro-pyrrolo[3,4-c]pyrrol-2-yl]-1-pyridin-3-yl-propyl}-amide | 475 | | 474.65 |
| I-77 | Cyclopentanecarboxylic acid {3-[5-(2,6-dimethyl-benzoyl)-hexahydro-pyrrolo[3,4-c]pyrrol-2-yl]-1-phenyl-butyl}-amide | 488 | | 487.68 |
| I-78 | Cyclopentanecarboxylic acid {(S)-3-[5-(2,4-dimethyl-pyridine-3-carbonyl)-hexahydro-pyrrolo[3,4-c]pyrrol-2-yl]-1-phenyl-propyl}-amide | 475 | 68.8–73.6 | 474.65 |
| I-79 | Cyclopentanecarboxylic acid {(S)-3-[5-(2,4-dimethyl-1-oxy-pyridine-3-carbonyl)-hexahydro-pyrrolo[3,4-c]pyrrol-2-yl]-1-phenyl-propyl}-amide | 491 | 93.3–95.5 | 490.64 |
| I-80 | Cyclopentanecarboxylic acid {(S)-3-[5-(1-acetyl-pyperidine-4-carbonyl)-hexahydro-pyrrolo[3,4-c]pyrrol-2-yl]-1-phenyl-propyl}-amide; compound with trifluoro-acetic acid | 495 | | 494.68 |
| I-81 | Cyclopentanecarboxylic acid [(S)-3-(5-benzyl-hexahydro-pyrrolo[3,4-c]pyrrol-2-yl)-1-phenyl-propyl]-amide; compound with trifluoro-acetic acid | 432 | | 431.62 |
| I-82 | Cyclopentanecarboxylic acid {(S)-1-phenyl-3-[5-(2,4,6-trifluoro-benzoyl)-hexahydro-pyrrolo[3,4-c]pyrrol-2-yl]-propyl}-amide; compound with trifluoro-acetic acid | 499 | | 499.57 |
| I-83 | Cyclopentanecarboxylic acid {(S)-3-[5-(1-benzyl-5-oxo-pyrrolidine-3-carbonyl)-hexahydro-pyrrolo[3,4-c]pyrrol-2-yl]-1-phenyl-propyl}-amide; compound with trifluoro-acetic acid | 543 | | 542.72 |
| I-84 | Cyclopentanecarboxylic acid {(S)-3-[5-(2,6-dimethyl-benzyl)-hexahydro-pyrrolo[3,4-c]pyrrol-2-yl]-1-phenyl-propyl}-amide; compound with trifluoro-acetic acid | 460 | | 459.67 |
| I-85 | (1S,5R)-Bicyclo[3.1.0]hexane-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 486 | | 485.67 |
| I-86 | 4,4-Difluoro-cyclohexanecarboxylic acid [(S)-3-[5-(2,6-dimethyl-benzoyl)-hexahydro-pyrrolo[3,4-c]pyrrol-2-yl]-1-(3-fluoro-phenyl)-propyl]-amide; compound with trifluoro-acetic acid | 542 | | 541.65 |
| I-87 | N-[(S)-3-[5-(2,6-Dimethyl-benzoyl)-hexahydro-pyrrolo[3,4-c]pyrrol-2-yl]-1-(3-fluoro-phenyl)-propyl]-acetamide; compound with trifluoro-acetic acid | 438 | | 437.56 |

TABLE 1-continued

|  |  | MS[1] | mp | MW |
|---|---|---|---|---|
| I-88 | (2S,3S)-1-Methyl-5-oxo-2-pyridin-3-yl-pyrrolidine-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 580.8 |  | 579.74 |
| I-89 | 4-Dimethylamino-N-{(S)-3-[5-(2,6-dimethyl-benzoyl)-hexahydro-pyrrolo[3,4-c]pyrrol-2-yl]-1-phenyl-propyl}-butyramide; compound with trifluoro-acetic acid | 491.9 |  | 490.69 |
| I-90 | 1-Methyl-pyrrolidine-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 489.8 |  | 488.67 |
| I-91 | N-{(S)-3-[5-(2,6-Dimethyl-benzoyl)-hexahydro-pyrrolo[3,4-c]pyrrol-2-yl]-1-phenyl-propyl}-2-morpholin-4-yl-propionamide; compound with trifluoro-acetic acid | 519.9 |  | 518.7 |
| I-92 | 2-(2-Aza-bicyclo[2.2.1]hept-2-yl)-N-{(S)-3-[5-(2,6-dimethyl-benzoyl)-hexahydro-pyrrolo[3,4-c]pyrrol-2-yl]-1-phenyl-propyl}-acetamide; compound with trifluoro-acetic acid | 515.9 |  | 514.71 |
| I-93 | 1-(Furan-2-carbonyl)-4-hydroxy-pyrrolidine-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 585.8 |  | 584.71 |
| I-94 | N-{(S)-3-[5-(2,6-Dimethyl-benzoyl)-hexahydro-pyrrolo[3,4-c]pyrrol-2-yl]-1-phenyl-propyl}-2-(5-morpholin-4-yl-tetrazol-2-yl)-acetamide; compound with trifluoro-acetic acid | 573.8 |  | 572.71 |
| I-95 | 1-Methyl-piperidine-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 503.8 |  | 502.7 |
| I-96 | 1-Methyl-azepane-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 517.9 |  | 516.73 |
| I-97 | 2-Methyl-1,2,3,4-tetrahydro-isoquinoline-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 551.8 |  | 550.74 |
| I-98 | 3-(2-Aza-bicyclo[2.2.1]hept-2-yl)-N-{(S)-3-[5-(2,6-dimethyl-benzoyl)-hexahydro-pyrrolo[3,4-c]pyrrol-2-yl]-1-phenyl-propyl}-propionamide; compound with trifluoro-acetic acid | 529.9 |  | 528.74 |
| I-99 | N-{(S)-3-[5-(2,6-Dimethyl-benzoyl)-hexahydro-pyrrolo[3,4-c]pyrrol-2-yl]-1-phenyl-propyl}-2-piperidin-1-yl-acetamide; compound with trifluoro-acetic acid | 503.9 |  | 502.7 |
| I-100 | 1-Isopropyl-5-oxo-pyrrolidine-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 531.9 |  | 530.71 |
| I-101 | 1-Ethyl-piperidine-4-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 517.9 |  | 516.73 |
| I-102 | 1-Isobutyl-5-oxo-pyrrolidine-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 545.9 |  | 544.74 |
| I-103 | N-{(S)-3-[5-(2,6-Dimethyl-benzoyl)-hexahydro-pyrrolo[3,4-c]pyrrol-2-yl]-1-phenyl-propyl}-2-pyrrolidin-1-yl-acetamide; compound with trifluoro-acetic acid | 489.8 |  | 488.67 |
| I-104 | 1-Methyl-5-sulfamoyl-1H-pyrrole-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 564.8 |  | 563.72 |
| I-105 | (S)-1-Acetyl-pyrrolidine-2-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 517.8 |  | 516.68 |
| I-106 | Cyclopentanecarboxylic acid {(S)-3-[5-(2-methyl-1,2,3,4-tetrahydro-isoquinoline-3-carbonyl)-hexahydro-pyrrolo[3,4-c]pyrrol-2-yl]-1-phenyl-propyl}-amide; compound with trifluoro-acetic acid | 515.9 |  | 514.71 |

TABLE 1-continued

|  |  | MS[1] | mp | MW |
|---|---|---|---|---|
| I-107 | Cyclopentanecarboxylic acid {(S)-1-phenyl-3-[5-(1-pyrimidin-2-yl-piperidine-4-carbonyl)-hexahydro-pyrrolo[3,4-c]pyrrol-2-yl]-propyl}-amide; compound with trifluoro-acetic acid | 531.9 |  | 530.71 |
| I-108 | Cyclopentanecarboxylic acid {(S)-3-[5-(1-isobutyl-5-oxo-pyrrolidine-3-carbonyl)-hexahydro-pyrrolo[3,4-c]pyrrol-2-yl]-1-phenyl-propyl]-amide; compound with trifluoro-acetic acid | 509.9 |  | 508.7 |
| I-109 | Cyclopentanecarboxylic acid {(S)-3-[5-(1-methyl-5-sulfamoyl-1H-pyrrole-2-carbonyl)-hexahydro-pyrrolo[3,4-c]pyrrol-2-yl]-1-phenyl-propyl}-amide; compound with trifluoro-acetic acid | 528.8 |  | 527.69 |
| I-110 | Cyclopentanecarboxylic acid {(S)-3-{5-[1-(furan-2-carbonyl)-4-hydroxy-pyrrolidine-2-carbonyl]-hexahydro-pyrrolo[3,4-c]pyrrol-2-yl}-1-phenyl-propyl)-amide; compound with trifluoro-acetic acid | 549.8 |  | 548.68 |
| I-111 | Cyclopentanecarboxylic acid {(S)-3-[5-(4-benzyl-morpholine-2-carbonyl)-hexahydro-pyrrolo[3,4-c]pyrrol-2-yl]-1-phenyl-propyl}-amide; compound with trifluoro-acetic acid | 545.9 |  | 544.74 |
| I-112 | Cyclopentanecarboxylic acid {(S)-3-[5-(6-chloro-imidazo[2,1-b]thiazole-5-sulfonyl)-hexahydro-pyrrolo[3,4-c]pyrrol-2-yl]-1-phenyl-phenyl-propyl}-amide; compound with trifluoro-acetic acid | 562.7 |  | 562.16 |
| I-113 | Cyclopentanecarboxylic acid {(S)-3-[5-(5-methyl-1-phenyl-1H-pyrazole-4-sulfonyl)-hexahydro-pyrrolo[3,4-c]pyrrol-2-yl]-1-phenyl-propyl}-amide; compound with trifluoro-acetic acid | 562.8 |  | 561.75 |
| I-114 | Cyclopentanecarboxylic acid {(S)-3-[5-(5-methyl-2-phenyl-2H-[1,2,3]triazole-4-carbonyl)-hexahydro-pyrrolo[3,4-c]pyrrol-2-yl]-1-phenyl-propyl}-amide; compound with trifluoro-acetic acid | 527.8 |  | 526.68 |
| I-115 | Cyclopentanecarboxylic acid ((S)-3-{5-[3-(2-chloro-phenyl)-5-methyl-isoxazole-4-carbonyl]-hexahydro-pyrrolo[3,4-c]pyrrol-2-yl}-1-phenyl-propyl)-amide; compound with trifluoro-acetic acid | 561.8 |  | 561.12 |
| I-116 | Cyclopentanecarboxylic acid {(S)-1-phenyl-3-[5-(4,5,6,7-tetrahydro-2H-indazole-3-carbonyl)-hexahydro-pyrrolo[3,4-c]pyrrol-2-yl]-propyl}-amide; compound with trifluoro-acetic acid | 490.8 |  | 489.66 |
| I-117 | Cyclopentanecarboxylic acid {(S)-1-phenyl-3-[5-(1,4,5,6-tetrahydro-cyclopentapyrazole-3-carbonyl)-hexahydro-pyrrolo[3,4-c]pyrrol-2-yl]-propyl}-amide; compound with trifluoro-acetic acid | 476.8 |  | 475.63 |
| I-118 | Cyclopentanecarboxylic acid {(S)-3-[5-(5-ethyl-2-methyl-2H-pyrazole-3-carbonyl)-hexahydro-pyrrolo[3,4-c]pyrrol-2-yl]-1-phenyl-propyl}-amide; compound with trifluoro-acetic acid | 478.8 |  | 477.65 |
| I-119 | [(S)-3-[5-(2,6-Dimethyl-benzoyl)-hexahydro-pyrrolo[3,4-c]pyrrol-2-yl]-1-(3-fluoro-phenyl)-propyl]-carbamic acid tert-butyl ester | 496 |  | 495.64 |
| I-120 | Cyclopentanecarboxylic acid {(S)-3-[5-(4-fluoro-2,6-dimethyl-benzoyl)-hexahydro-pyrrolo[3,4-c]pyrrol-2-yl]-1-phenyl-propyl}-amide | 492 | 61.6–66.3 | 491.65 |
| I-121 | 2-Chloro-N-{(S)-3-[5-(2-chloro-6-fluoro-benzoyl)-hexahydro-pyrrolo[3,4-c]pyrrol-2-yl]-1-phenyl-propyl}-4-fluoro-benzamide; compound with trifluoro-acetic acid | 558.5 |  | 558.45 |
| I-122 | N-{(S)-3-[5-(2-Chloro-6-fluoro-benzoyl)-hexahydro-pyrrolo[3,4-c]pyrrol-2-yl]-1-phenyl-propyl}-2-trifluoromethyl-benzamide; compound with trifluoro-acetic acid | 574.6 |  | 574.02 |
| I-123 | N-{(S)-3-[5-(2-Chloro-6-fluoro-benzoyl)-hexahydro-pyrrolo[3,4-c]pyrrol-2-yl]-1-phenyl-propyl}-2-methoxy-benzamide; compound with trifluoro-acetic acid | 536.6 |  | 536.04 |
| I-124 | N-{(S)-3-[5-(2-Chloro-6-fluoro-benzoyl)-hexahydro-pyrrolo[3,4-c]pyrrol-2-yl]-1-phenyl-propyl}-4-methoxy-benzamide; compound with trifluoro-acetic acid | 536.6 |  | 536.04 |
| I-125 | N-{(S)-3-[5-(2-Chloro-6-fluoro-benzoyl)-hexahydro-pyrrolo[3,4-c]pyrrol-2-yl]-1-phenyl-propyl}-benzamide; compound with trifluoro-acetic acid | 506.6 |  | 506.02 |
| I-126 | N-{(S)-3-[5-(2-Chloro-6-fluoro-benzoyl)-hexahydro-pyrrolo[3,4-c]pyrrol-2-yl]-1-phenyl-propyl}-3,3-dimethyl-butyramide; compound with trifluoro-acetic acid | 500.7 |  | 500.05 |

TABLE 1-continued

| | | MS[1] | mp | MW |
|---|---|---|---|---|
| I-127 | N-{(S)-3-[5-(2-Chloro-6-fluoro-benzoyl)-hexahydro-pyrrolo[3,4-c]pyrrol-2-yl]-1-phenyl-propyl}-succinamic acid methyl ester; compound with trifluoro-acetic acid | 516.6 | | 516.01 |
| I-128 | 2 Chloro-N-{(S)-3-[5-(2-chloro-6-fluoro-benzoyl)-hexahydro-pyrrolo[3,4-c]pyrrol-2-yl]-1-phenyl-propyl}-benzamide; compound with trifluoro-acetic acid | 540.6 | | 540.46 |
| I-129 | N-{(S)-3-[5-(2-Chloro-6-fluoro-benzoyl)-hexahydro-pyrrolo[3,4-c]pyrrol-2-yl]-1-phenyl-propyl}-3-cyano-benzamide; compound with trifluoro-acetic acid | 531.6 | | 531.03 |
| I-130 | N-{(S)-3-[5-(2-Chloro-6-fluoro-benzoyl)-hexahydro-pyrrolo[3,4-c]pyrrol-2-yl]-1-phenyl-propyl}-2,4-difluoro-benzamide; compound with trifluoro-acetic acid | 542.6 | | 542 |
| I-131 | N-{(S)-3-[5-(2-Chloro-6-fluoro-benzoyl)-hexahydro-pyrrolo[3,4-c]pyrrol-2-yl]-1-phenyl-propyl}-2,6-difluoro-benzamide; compound with trifluoro-acetic acid | 542.6 | | 542 |
| I-132 | N-{(S)-3-[5-(2-Chloro-6-fluoro-benzoyl)-hexahydro-pyrrolo[3,4-c]pyrrol-2-yl]-1-phenyl-propyl}-3,4-difluoro-benzamide; compound with trifluoro-acetic acid | 542.5 | | 542 |
| I-133 | N-{(S)-3-[5-(2-Chloro-6-fluoro-benzoyl)-hexahydro-pyrrolo[3,4-c]pyrrol-2-yl]-1-phenyl-propyl}-2-fluoro-benzamide; compound with trifluoro-acetic acid | 524.6 | | 524.01 |
| I-134 | N-{(S)-3-[5-(2-Chloro-6-fluoro-benzoyl)-hexahydro-pyrrolo[3,4-c]pyrrol-2-yl]-1-phenyl-propyl}-4-fluoro-benzamide; compound with trifluoro-acetic acid | 524.5 | | 524.01 |
| I-135 | Furan-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 496.5 | | 495.98 |
| I-136 | N-{(S)-3-[5-(2-Chloro-6-fluoro-benzoyl)-hexahydro-pyrrolo[3,4-c]pyrrol-2-yl]-1-phenyl-propyl}-isobutyramide; compound with trifluoro-acetic acid | 472.6 | | 472 |
| I-137 | N-{(S)-3-[5-(2-Chloro-6-fluoro-benzoyl)-hexahydro-pyrrolo[3,4-c]pyrrol-2-yl]-1-phenyl-propyl}-3-methyl-butyramide; compound with trifluoro-acetic acid | 486.6 | | 486.03 |
| I-138 | 3-Chloro-N-{(S)-3-[5-(2-hloro-6-fluoro-benzoyl)-hexahydro-pyrrolo[3,4-c]pyrrol-2-yl]-1-phenyl-propyl}-4-fluoro-benzamide; compound with trifluoro-acetic acid | 558.5 | | 558.45 |
| I-139 | N-{(S)-3-[5-(2-Chloro-6-fluoro-benzoyl)-hexahydro-pyrrolo[3,4-c]pyrrol-2-yl]-1-phenyl-propyl}-2-thiophen-2-yl-acetamide; compound with trifluoro-acetic acid | 526.5 | | 526.07 |
| I-140 | N-{(S)-3-[5-(2-Chloro-6-fluoro-benzoyl)-hexahydro-pyrrolo[3,4-c]pyrrol-2-yl]-1-phenyl-propyl}-3-trifluoromethyl-benzamide; compound with trifluoro-acetic acid | 574.5 | | 574.02 |
| I-141 | N-{(S)-3-[5-(2-Chloro-6-fluoro-benzoyl)-hexahydro-pyrrolo[3,4-c]pyrrol-2-yl]-1-phenyl-propyl}-4-cyano-benzamide; compound with trifluoro-acetic acid | 531.5 | | 531.03 |
| I-142 | N-{(S)-3-[5-(2-Chloro-6-fluoro-benzoyl)-hexahydro-pyrrolo[3,4-c]pyrrol-2-yl]-1-phenyl-propyl}-4-ethoxy-benzamide; compound with trifluoro-acetic acid | 550.5 | | 550.07 |
| I-143 | N-{(S)-3-[5-(2-Chloro-6-fluoro-benzoyl)-hexahydro-pyrrolo[3,4-c]pyrrol-2-yl]-1-phenyl-propyl}-3,5-difluoro-benzamide; compound with trifluoro-acetic acid | 542.5 | | 542 |
| I-144 | Thiophene-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 512.5 | | 512.05 |
| I-145 | 4-Chloro-N-{(S)-3-[5-(2-chloro-6-fluoro-benzoyl)-hexahydro-pyrrolo[3,4-c]pyrrol-2-yl]-1-phenyl-propyl}-benzamide; compound with trifluoro-acetic acid | 540.5 | | 540.46 |
| I-146 | N-{(S)-3-[5-(2-Chloro-6-fluoro-benzoyl)-hexahydro-pyrrolo[3,4-c]pyrrol-2-yl]-1-phenyl-propyl}-3-methoxy-benzamide; compound with trifluoro-acetic acid | 536.5 | | 536.04 |
| I-147 | N-{(S)-3-[5-(2-Chloro-6-fluoro-benzoyl)-hexahydro-pyrrolo[3,4-c]pyrrol-2-yl]-1-phenyl-propyl}-3-fluoro-benzamide; compound with trifluoro-acetic acid | 524.5 | | 524.01 |

TABLE 1-continued

|  |  | MS[1] | mp | MW |
|---|---|---|---|---|
| I-148 | N-{(S)-3-[5-(2-Chloro-6-fluoro-benzoyl)-hexahydro-pyrrolo[3,4-c]pyrrol-2-yl]-1-phenyl-propyl}-3,4-dimethoxy-benzamide; compound with trifluoro-acetic acid | 566.5 |  | 566.07 |
| I-149 | N-{(S)-3-[5-(2-Chloro-6-fluoro-benzoyl)-hexahydro-pyrrolo[3,4-c]pyrrol-2-yl]-1-phenyl-propyl}-2,2-dimethyl-propionamide; compound with trifluoro-acetic acid | 586.5 |  | 486.03 |
| I-150 | Cyclohexanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 512.5 |  | 512.07 |
| I-151 | Morpholine-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 515.5 |  | 515.03 |
| I-152 | N-{(S)-3-[5-(2-Chloro-6-fluoro-benzoyl)-hexahydro-pyrrolo[3,4-c]pyrrol-2-yl]-1-phenyl-propyl}-oxalamic acid ethyl ester; compound with trifluoro-acetic acid | 502.5 |  | 501.98 |
| I-153 | Acetic acid 1-{(S)-3-[5-(2-chloro-6-fluoro-benzoyl)-hexahydro-pyrrolo[3,4-c]pyrrol-2-yl]-1-phenyl-propylcarbamoyl}-1-methyl-ethyl ester; compound with trifluoro-acetic acid | 530.5 |  | 530.04 |
| I-154 | N-{(S)-3-[5-(2-Chloro-6-fluoro-benzoyl)-hexahydro-pyrrolo[3,4-c]pyrrol-2-yl]-1-phenyl-propyl}-2-phenyl-acetamide; compound with trifluoro-acetic acid | 520.5 |  | 520.05 |
| I-155 | (1R,2R)-2-Phenyl-cyclopropanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 546.6 |  | 546.08 |
| I-156 | Cyclobutanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 484.6 |  | 484.01 |
| I-157 | Isoxazole-5-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 497.5 |  | 496.97 |
| I-158 | 5-Chloro-4-methoxy-thiophene-3-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 576.5 |  | 576.52 |
| I-159 | 4-Methyl-[1,2,3]thiadiazole-5-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 528.5 |  | 528.05 |
| I-160 | 3-{(S)-3-[5-(2-Chloro-6-fluoro-benzoyl)-hexahydro-pyrrolo[3,4-c]pyrrol-2-yl]-1-phenyl-propyl}-1,1-diethyl-urea; compound with trifluoro-acetic acid | 501.6 |  | 501.04 |
| I-161 | 3-{(S)-3-[5-(2-Chloro-6-fluoro-benzoyl)-hexahydro-pyrrolo[3,4-c]pyrrol-2-yl]-1-phenyl-propyl}-1,1-diisopropyl-urea; compound with trifluoro-acetic acid | 529.6 |  | 529.1 |
| I-162 | 3-{(S)-3-[5-(2-Chloro-6-fluoro-benzoyl)-hexahydro-pyrrolo[3,4-c]pyrrol-2-yl]-1-phenyl-propyl}-1,1-dimethyl-urea; compound with trifluoro-acetic acid | 473.6 |  | 472.99 |
| I-163 | N-{(S)-3-[5-(2-Chloro-6-fluoro-benzoyl)-hexahydro-pyrrolo[3,4-c]pyrrol-2-yl]-1-phenyl-propyl}-acetamide; compound with trifluoro-acetic acid | 444.6 |  | 443.95 |
| I-164 | N-{(S)-3-[5-(2-Chloro-6-fluoro-benzoyl)-hexahydro-pyrrolo[3,4-c]pyrrol-2-yl]-1-phenyl-propyl}-2-methoxy-acetamide; compound with trifluoro-acetic acid | 474.6 |  | 473.97 |
| I-165 | N-{(S)-3-[5-(2-Chloro-6-fluoro-benzoyl)-hexahydro-pyrrolo[3,4-c]pyrrol-2-yl]-1-phenyl-propyl}-3-cyclopentyl-propionamide; compound with trifluoro-acetic acid | 526.6 |  | 526.09 |
| I-166 | Acetic acid {(S)-3-[5-(2-chloro-6-fluoro-benzoyl)-hexahydro-pyrrolo[3,4-c]pyrrol-2-yl]-1-phenyl-propylcarbamoyl}-methyl ester; compound with trifluoro-acetic acid | 502.6 |  | 501.98 |
| I-167 | N-{(S)-3-[5-(2-Chloro-6-fluoro-benzoyl)-hexahydro-pyrrolo[3,4-c]pyrrol-2-yl]-1-phenyl-propyl}-2-(4-methoxy-phenyl)-acetamide; compound with trifluoro-acetic acid | 550.6 |  | 550.07 |

TABLE 1-continued

| | | MS[1] | mp | MW |
|---|---|---|---|---|
| I-168 | N-{(S)-3-[5-(2-Chloro-6-fluoro-benzoyl)-hexahydro-pyrrolo[3,4-c]pyrrol-2-yl]-1-phenyl-propyl}-2-cyclopentyl-acetamide; compound with trifluoro-acetic acid | 512.6 | | 512.07 |
| I-169 | N-{(S)-3-[5-(2-Chloro-6-fluoro-benzoyl)-hexahydro-pyrrolo[3,4-c]pyrrol-2-yl]-1-phenyl-propyl}-4-dimethylamino-benzamide; compound with trifluoro-acetic acid | 549.6 | | 549.09 |
| I-170 | 3,5-Dimethyl-isoxazole-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 525.6 | | 525.02 |
| I-171 | 3-{(S)-3-[5-(2-Chloro-6-fluoro-benzoyl)-hexahydro-pyrrolo[3,4-c]pyrrol-2-yl]-1-phenyl-propyl}-1-methyl-1-phenyl-urea; compound with trifluoro-acetic acid | 535.6 | | 535.06 |
| I-172 | N-{(S)-3-[5-(2-Chloro-6-fluoro-benzoyl)-hexahydro-pyrrolo[3,4-c]pyrrol-2-yl]-1-phenyl-propyl}-2-methylsulfanyl-acetamide; compound with trifluoro-acetic acid | 490.6 | | 490.04 |
| I-173 | 3-Chloro-thiophene-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 546.5 | | 546.49 |
| I-174 | {(S)-3-[5-(2-Chloro-6-fluoro-benzoyl)-hexahydro-pyrrolo[3,4-c]pyrrol-2-yl]-1-phenyl-propyl}-carbamic acid methyl ester; compound with trifluoro-acetic acid | 460.5 | | 459.95 |
| I-175 | 1-Benzyl-3-{(S)-3-[5-(2-chloro-6-fluoro-benzoyl)-hexahydro-pyrrolo[3,4-c]pyrrol-2-yl]-1-phenyl-propyl}-1-methyl-urea; compound with trifluoro-acetic acid | 549.6 | | 549.09 |
| I-176 | Cyclopentanecarboxylic acid {(S)-3-[5-(2,6-dichloro-4-methanesulfonyl-benzoyl)-hexahydro-pyrrolo[3,4-c]pyrrol-2-yl]-1-phenyl-propyl}-amide; compound with trifluoro-acetic acid | 592 | | 592.58 |
| I-177 | 3-Acetylamino-N-{(S)-3-[5-(2-chloro-6-fluoro-benzoyl)-hexahydro-pyrrolo[3,4-c]pyrrol-2-yl]-1-phenyl-propyl}-benzamide; compound with trifluoro-acetic acid | 563.6 | | 563.07 |
| I-178 | 4-Acetylamino-N-{(S)-3-[5-(2-chloro-6-fluoro-benzoyl)-hexahydro-pyrrolo[3,4-c]pyrrol-2-yl]-1-phenyl-propyl}-benzamide; compound with trifluoro-acetic acid | 563.6 | | 563.07 |
| I-179 | 1-Acetyl-piperidine-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 555.6 | | 555.09 |
| I-180 | 3-Amino-N-{(S)-3-[5-(2-chloro-6-fluoro-benzoyl)-hexahydro-pyrrolo[3,4-c]pyrrol-2-yl]-1-phenyl-propyl}-propionamide; compound with trifluoro-acetic acid | 473.6 | | 472.99 |
| I-181 | 2-Amino-N-{(S)-3-[5-(2-chloro-6-fluoro-benzoyl)-hexahydro-pyrrolo[3,4-c]pyrrol-2-yl]-1-phenyl-propyl}-acetamide; compound with trifluoro-acetic acid | 459.6 | | 458.96 |
| I-182 | (S)-Pyrrolidine-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 499.6 | | 499.03 |
| I-183 | N-{(S)-3-[5-(2-Chloro-6-fluoro-benzoyl)-hexahydro-pyrrolo[3,4-c]pyrrol-2-yl]-1-phenyl-propyl}-2-cyano-acetamide; compound with trifluoro-acetic acid | 469.6 | | 468.96 |
| I-184 | Cycloheptanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 526.6 | | 526.09 |
| I-185 | N-{(S)-3-[5-(2-Chloro-6-fluoro-benzoyl)-hexahydro-pyrrolo[3,4-c]pyrrol-2-yl]-1-phenyl-propyl}-2-cyclohexyl-acetamide; compound with trifluoro-acetic acid | 526.6 | | 526.09 |
| I-186 | N-{(S)-3-[5-(2-Chloro-6-fluoro-benzoyl)-hexahydro-pyrrolo[3,4-c]pyrrol-2-yl]-1-phenyl-propyl}-2-cyclopropyl-acetamide; compound with trifluoro-acetic acid | 484.6 | | 484.01 |
| I-187 | Furan-3-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 496.5 | | 495.98 |

TABLE 1-continued

| | | MS[1] | mp | MW |
|---|---|---|---|---|
| I-188 | N-{(S)-3-[5-(2-Chloro-6-fluoro-benzoyl)-hexahydro-pyrrolo[3,4-c]pyrrol-2-yl]-1-phenyl-propyl}-isonicotinamide; compound with trifluoro-acetic acid | 507.6 | | 507.01 |
| I-189 | N-{(S)-3-[5-(2-Chloro-6-fluoro-benzoyl)-hexahydro-pyrrolo[3,4-c]pyrrol-2-yl]-1-phenyl-propyl}-terephthalamic acid methyl ester; compound with trifluoro-acetic acid | 564.5 | | 564.05 |
| I-190 | N-{(S)-3-[5-(2-Chloro-6-fluoro-benzoyl)-hexahydro-pyrrolo[3,4-c]pyrrol-2-yl]-1-phenyl-propyl}-3-piperidin-1-yl-propionamide; compound with trifluoro-acetic acid | 541.6 | | 541.11 |
| I-191 | 1H-Pyrrole-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 495.6 | | 495 |
| I-192 | N-{(S)-3-[5-(2-Chloro-6-fluoro-benzoyl)-hexahydro-pyrrolo[3,4-c]pyrrol-2-yl]-1-phenyl-propyl}-succinamide; compound with trifluoro-acetic acid | 501.6 | | 501 |
| I-193 | 1H-Indole-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 545.6 | | 545.06 |
| I-194 | 5-Methyl-thiophene-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 526.6 | | 526.07 |
| I-195 | 1-Methyl-1H-pyrrole-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 509.6 | | 509.02 |
| I-196 | 2-Acetylamino-N-{(S)-3-[5-(2-chloro-6-fluoro-benzoyl)-hexahydro-pyrrolo[3,4-c]pyrrol-2-yl]-1-phenyl-propyl}-acetamide; compound with trifluoro-acetic acid | 501.6 | | 501 |
| I-197 | Pyridine-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 507.6 | | 507.01 |
| I-198 | N-{(S)-3-[5-(2-Chloro-6-fluoro-benzoyl)-hexahydro-pyrrolo[3,4-c]pyrrol-2-yl]-1-phenyl-propyl}-4-methylamino-benzamide; compound with trifluoro-acetic acid | 535.7 | | 535.06 |
| I-199 | N-{(S)-3-[5-(2-Chloro-6-fluoro-benzoyl)-hexahydro-pyrrolo[3,4-c]pyrrol-2-yl]-1-phenyl-propyl}-2-methylamino-benzamide; compound with trifluoro-acetic acid | 535.7 | | 535.06 |
| I-200 | N-{(S)-3-[5-(2-Chloro-6-fluoro-benzoyl)-hexahydro-pyrrolo[3,4-c]pyrrol-2-yl]-1-phenyl-propyl}-2-dimethylamino-benzamide; compound with trifluoro-acetic acid | 549.7 | | 549.09 |
| I-201 | 5-Amino-1-phenyl-1H-pyrazole-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 587.7 | | 587.1 |
| I-202 | 2,2,3,3-Tetramethyl-cyclopropanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 526.7 | | 526.09 |
| I-203 | 2-Acetylamino-N-{(S)-3-[5-(2-chloro-6-fluoro-benzoyl)-hexahydro-pyrrolo[3,4-c]pyrrol-2-yl]-1-phenyl-propyl}-4-methylsulfanyl-butyramide; compound with trifluoro-acetic acid | 575.7 | | 575.15 |
| I-204 | 2-Ethyl-5-methyl-2H-pyrazole-3-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 538.7 | | 538.06 |
| I-205 | 5-Amino-2H-[1,2,4]triazole-3-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 512.6 | | 511.99 |
| I-206 | 5-Chloro-thiophene-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 546.5 | | 546.49 |

TABLE 1-continued

|  |  | MS[1] | mp | MW |
|---|---|---|---|---|
| I-207 | (S)-2-Acetylamino-N-{(S)-3-[5-(2-chloro-6-fluoro-benzoyl)-hexahydro-pyrrolo[3,4-c]pyrrol-2-yl]-1-phenyl-propyl}-4-methylsulfanyl-butyramide; compound with trifluoro-acetic acid | 575.6 |  | 575.15 |
| I-208 | N-{(S)-3-[5-(2-Chloro-6-fluoro-benzoyl)-hexahydro-pyrrolo[3,4-c]pyrrol-2-yl]-1-phenyl-propyl}-3-diethylamino-propionamide; compound with trifluoro-acetic acid | 529.7 |  | 529.1 |
| I-209 | N-{(S)-3-[5-(2-Chloro-6-fluoro-benzoyl)-hexahydro-pyrrolo[3,4-c]pyrrol-2-yl]-1-phenyl-propyl}-2-methyl-nicotinamide; compound with trifluoro-acetic acid | 521.6 |  | 521.03 |
| I-210 | 3-Methyl-furan-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 510.6 |  | 510.01 |
| I-211 | N-{(S)-3-[5-(2-Chloro-6-fluoro-benzoyl)-hexahydro-pyrrolo[3,4-c]pyrrol-2-yl]-1-phenyl-propyl}-nicotinamide; compound with trifluoro-acetic acid | 507.5 |  | 507.01 |
| I-212 | Pyrazine-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 508.5 |  | 507.99 |
| I-213 | N-{(S)-3-[5-(2-Chloro-6-fluoro-benzoyl)-hexahydro-pyrrolo[3,4-c]pyrrol-2-yl]-1-phenyl-propyl}-2-(1-methyl-1H-imidazol-4-yl)-acetamide; compound with trifluoro-acetic acid | 524.7 |  | 524.04 |
| I-214 | 3H-Imidazole-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 496.6 |  | 495.98 |
| I-215 | N-{(S)-3-[5-(2-Chloro-6-fluoro-benzoyl)-hexahydro-pyrrolo[3,4-c]pyrrol-2-yl]-1-phenyl-propyl}-2-methanesulfonyl-acetamide; compound with trifluoro-acetic acid | 522.6 |  | 522.04 |
| I-216 | 2-Methyl-thiazole-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 527.6 |  | 527.06 |
| I-217 | N-{(S)-3-[5-(2-Chloro-6-fluoro-benzoyl)-hexahydro-pyrrolo[3,4-c]pyrrol-2-yl]-1-phenyl-propyl}-2-imidazol-1-yl-acetamide; compound with trifluoro-acetic acid | 510.7 |  | 510.01 |
| I-218 | 1-Methyl-1H-pyrazole-3-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 510.7 |  | 510.01 |
| I-219 | 1-Methyl-1H-imidazole-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 510.7 |  | 510.01 |
| I-220 | Cyclopentanecarboxylic acid {(S)-3-[5-(2,6-dichloro-4-methylsulfonyl-benzoyl)-hexahydro-pyrrolo[3,4-c]pyrrol-2-yl]-1-phenyl-propyl}-amide | MH + 560 | 67.2–72.6 | 560.59 |
| I-221 | 5-{(S)-3-Phenyl-3-[(tetrahydro-furan-3-carbonyl)-amino]-propyl}-hexahydro-pyrrolo[3,4-c]pyrrole-2-carboxylic acid phenylamide; compound with trifluoro-acetic acid | 463.3 |  | 462.59 |
| I-222 | 5-{(S)-3-Phenyl-3-[(tetrahydro-furan-3-carbonyl)-amino]-propyl}-hexahydro-pyrrolo[3,4-c]pyrrole-2-carboxylic acid (2,6-dimethyl-phenyl)-amide; compound with trifluoro-acetic acid | 491.3 |  | 490.64 |
| I-223 | Tetrahydro-furan-3-carboxylic acid [(S)-3-(5-benzenesulfonyl-hexahydro-pyrrolo[3,4-c]pyrrol-2-yl)-1-phenyl-propyl]-amide; compound with trifluoro-acetic acid | 484.2 |  | 483.63 |
| I-224 | Tetrahydro-furan-3-carboxylic acid {(S)-1-phenyl-3-[5-(thiophene-2-sulfonyl)-hexahydro-pyrrolo[3,4-c]-pyrrol-2-yl]-propyl}-amide; compound with trifluoro-acetic acid | 490.2 |  | 489.66 |
| I-225 | Tetrahydro-furan-3-carboxylic acid {(S)-3-[5-(3,5-dimethyl-isoxazole-4-sulfonyl)-hexahydro-pyrrolo[3,4-c]pyrrol-2-yl]-1-phenyl-propyl}-amide; compound with trifluoro-acetic acid | 503.2 |  | 502.63 |
| I-226 | Tetrahydro-furan-3-carboxylic acid {(S)-3-[5-(5-chloro-1,3-dimethyl-1H-pyrazole-4-sulfonyl)-hexahydro-pyrrolo[3,4-c]pyrrol-2-yl]-1-phenyl-propyl}-amide; compound with trifluoro-acetic acid | 536.3 |  | 536.09 |

TABLE 1-continued

| | | MS[1] | mp | MW |
|---|---|---|---|---|
| I-227 | 2,5-Dimethyl-4-(5-{(S)-3-phenyl-3-[(tetrahydro-furan-3-carbonyl)-amino]-propyl}-hexahydro-pyrrolo[3,4-c]pyrrole-2-sulfonyl)-furan-3-carboxylic acid methyl ester; compound with trifluoro-acetic acid | 560.3 | | 559.68 |
| I-228 | Tetrahydro-furan-3-carboxylic acid {(S)-1-phenyl-3-[5-(1,3,5-trimethyl-1H-pyrazole-4-sulfonyl)-hexahydro-pyrrolo[3,4-c]pyrrol-2-yl]-propyl}-amide; compound with trifluoro-acetic acid | 516.3 | | 515.68 |
| I-229 | 1-Methyl-5-(5-{(S)-3-phenyl-3-[(tetrahydro-furan-3-carbonyl)-amino]-propyl}-hexahydro-pyrrolo[3,4-c]pyrrole-2-sulfonyl)-1H-pyrrole-2-carboxylic acid methyl ester; compound with trifluoro-acetic acid | 545.3 | | 544.67 |
| I-230 | Tetrahydro-furan-3-carboxylic acid {(S)-3-[5-(4-cyano-benzoyl)-hexahydro-pyrrolo[3,4-c]pyrrol-2-yl]-1-phenyl-propyl}-amide; compound with trifluoro-acetic acid | 473.3 | | 472.59 |
| I-231 | Tetrahydro-furan-3-carboxylic acid {(S)-1-phenyl-3-[5-(1H-pyrrole-2-carbonyl)-hexahydro-pyrrolo[3,4-c]pyrrol-2-yl]-propyl}-amide; compound with trifluoro-acetic acid | 437.4 | | 436.55 |
| I-232 | Tetrahydro-furan-3-carboxylic acid {(S)-3-[5-(5-methoxy-1H-indole-2-carbonyl)-hexahydro-pyrrolo[3,4-c]pyrrol-2-yl]-1-phenyl-propyl}-amide; compound with trifluoro-acetic acid | 517.4 | | 516.64 |
| I-233 | Tetrahydro-furan-3-carboxylic acid {(S)-1-phenyl-3-[5-(pyridine-2-carbonyl)-hexahydro-pyrrolo[3,4-c]pyrrol-2-yl]-propyl}-amide; compound with trifluoro-acetic acid | 449.3 | | 448.56 |
| I-234 | Tetrahydro-furan-3-carboxylic acid {(S)-3-[5-(2-methylamino-benzoyl)-hexahydro-pyrrolo[3,4-c]pyrrol-2-yl]-1-phenyl-propyl}-amide; compound with trifluoro-acetic acid | 477.4 | | 476.62 |
| I-235 | Tetrahydro-furan-3-carboxylic acid {(S)-1-phenyl-3-[5-(pyrazine-2-carbonyl)-hexahydro-pyrrolo[3,4-c]pyrrol-2-yl]-propyl}-amide; compound with trifluoro-acetic acid | 450.3 | | 449.55 |
| I-236 | Tetrahydro-furan-3-carboxylic acid {(S)-3-[5-(5-methyl-isoxazole-4-carbonyl)-hexahydro-pyrrolo[3,4-c]pyrrol-2-yl]-1-phenyl-propyl}-amide; compound with trifluoro-acetic acid | 453.3 | | 452.55 |
| I-237 | Tetrahydro-furan-3-carboxylic acid {(S)-1-phenyl-3-[5-(tetrahydro-furan-2-carbonyl)-hexahydro-pyrrolo[3,4-c]pyrrol-2-yl]-propyl}-amide; compound with trifluoro-acetic acid | 442.4 | | 441.57 |
| I-238 | Tetrahydro-furan-3-carboxylic acid {(S)-3-[5-(4-acetylamino-benzoyl)-hexahydro-pyrrolo[3,4-c]pyrrol-2-yl]-1-phenyl-propyl}-amide; compound with trifluoro-acetic acid | 505.4 | | 504.63 |
| I-239 | Tetrahydro-furan-3-carboxylic acid {(S)-3-[5-(isoquinoline-7-carbonyl)-hexahydro-pyrrolo[3,4-c]pyrrol-2-yl]-1-phenyl-propyl}-amide; compound with trifluoro-acetic acid | 499.4 | | 498.62 |
| I-240 | Tetrahydro-furan-3-carboxylic acid {(S)-1-phenyl-3-[5-(quinoline-4-carbonyl)-hexahydro-pyrrolo[3,4-c]pyrrol-2-yl]-propyl}-amide; compound with trifluoro-acetic acid | 499.4 | | 498.62 |
| I-241 | Cyclopentanecarboxylic acid {(S)-3-[5-(3,5-dimethyl-benzoyl)-hexahydro-pyrrolo[3,4-c]pyrrol-2-yl]-1-phenyl-propyl}-amide | 474 | | 473.66 |
| I-242 | Tetrahydro-furan-3-carboxylic acid {(S)-3-[5-(1H-indole-2-carbonyl)-hexahydro-pyrrolo[3,4-c]pyrrol-2-yl]-1-phenyl-propyl}-amide; compound with trifluoro-acetic acid | 487.4 | | 486.61 |
| I-243 | Tetrahydro-furan-3-carboxylic acid {(S)-3-[5-(benzofuran-2-carbonyl)-hexahydro-pyrrolo[3,4-c]pyrrol-2-yl]-1-phenyl-propyl}-amide; compound with trifluoro-acetic acid | 488.4 | | 487.6 |
| I-244 | Tetrahydro-furan-3-carboxylic acid {(S)-3-[5-(benzo[b]thiophene-2-carbonyl)-hexahydro-pyrrolo[3,4-c]pyrrol-2-yl]-1-phenyl-propyl}-amide; compound with trifluoro-acetic acid | 504.4 | | 503.66 |
| I-245 | Tetrahydro-furan-3-carboxylic acid {(S)-3-[5-(1-methyl-1H-indole-2-carbonyl)-hexahydro-pyrrolo[3,4-c]pyrrol-2-yl]-1-phenyl-propyl}-amide; compound with trifluoro-acetic acid | 501.4 | | 500.64 |

TABLE 1-continued

|  |  | MS[1] | mp | MW |
|---|---|---|---|---|
| I-246 | Tetrahydro-furan-3-carboxylic acid {(S)-3-[5-(2-chloro-6-methyl-benzoyl)-hexahydro-pyrrolo[3,4-c]pyrrol-2-yl]-1-phenyl-propyl}-amide; compound with trifluoro-acetic acid | 496.4 |  | 496.05 |
| I-247 | Tetrahydro-furan-3-carboxylic acid {(S)-3-[5-(2-methoxy-3-methyl-benzoyl)-hexahydro-pyrrolo[3,4-c]pyrrol-2-yl]-1-phenyl-propyl}-amide; compound with trifluoro-acetic acid | 492.4 |  | 491.63 |
| I-248 | Tetrahydro-furan-3-carboxylic acid {(S)-3-[5-(4-methylamino-benzoyl)-hexahydro-pyrrolo[3,4-c]pyrrol-2-yl]-1-phenyl-propyl}-amide; compound with trifluoro-acetic acid | 477.4 |  | 476.62 |
| I-249 | Tetrahydro-furan-3-carboxylic acid ((S)-3-{5-[4-(3-methyl-5-oxo-4,5-dihydro-pyrazol-1-yl)-benzoyl]-hexahydro-pyrrolo[3,4-c]pyrrol-2-yl}-1-phenyl-propyl)-amide; compound with trifluoro-acetic acid | 544.5 |  | 543.66 |
| I-250 | Tetrahydro-furan-3-carboxylic acid {(S)-1-phenyl-3-[5-(tetrahydro-furan-3-carbonyl)-hexahydro-pyrrolo[3,4-c]pyrrol-2-yl]-propyl}-amide; compound with trifluoro-acetic acid | 442.4 |  | 441.57 |
| I-251 | Tetrahydro-furan-3-carboxylic acid {(S)-1-phenyl-3-[5-(thiophene-2-carbonyl)-hexahydro-pyrrolo[3,4-c]pyrrol-2-yl]-propyl}-amide; compound with trifluoro-acetic acid | 454.4 |  | 453.6 |
| I-252 | Tetrahydro-furan-3-carboxylic acid {(S)-1-phenyl-3-[5-(2-thiophen-2-yl-acetyl)-hexahydro-pyrrolo[3,4-c]pyrrol-2-yl]-propyl}-amide; compound with trifluoro-acetic acid | 468.4 |  | 467.63 |
| I-253 | Tetrahydro-furan-3-carboxylic acid {(S)-3-[5-(3-chloro-thiophene-2-carbonyl)-hexahydro-pyrrolo[3,4-c]pyrrol-2-yl]-1-phenyl-propyl}-amide; compound with trifluoro-acetic acid | 488.3 |  | 488.05 |
| I-254 | Tetrahydro-furan-3-carboxylic acid {(S)-3-[5-(2-methyl-5-phenyl-furan-3-carbonyl)-hexahydro-pyrrolo[3,4-c]pyrrol-2-yl]-1-phenyl-propyl}-amide; compound with trifluoro-acetic acid | 528.4 |  | 527.66 |
| I-255 | Tetrahydro-furan-3-carboxylic acid {(S)-3-[5-(5-fluoro-2-methyl-benzoyl)-hexahydro-pyrrolo[3,4-c]pyrrol-2-yl]-1-phenyl-propyl}-amide; compound with trifluoro-acetic acid | 480.4 |  | 479.59 |
| I-256 | Tetrahydro-furan-3-carboxylic acid ((S)-3-{5-[3-(2-oxo-pyrrolidin-1-yl)-benzoyl]-hexahydro-pyrrolo[3,4-c]pyrrol-2-yl}-1-phenyl-propyl)-amide; compound with trifluoro-acetic acid | 531.4 |  | 530.67 |
| I-257 | Tetrahydro-furan-3-carboxylic acid {(S)-3-[5-(benzo[b]thiophene-3-carbonyl)-hexahydro-pyrrolo[3,4-c]pyrrol-2-yl]-1-phenyl-propyl}-amide; compound with trifluoro-acetic acid | 504.4 |  | 503.66 |
| I-258 | 4-(5-{(S)-3-Phenyl-3-[(tetrahydro-furan-3-carbonyl)-amino]-propyl}-hexahydro-pyrrolo[3,4-c]pyrrole-2-carbonyl)-benzoic acid tert-butyl ester; compound with trifluoro-acetic acid | 548.5 |  | 547.69 |
| I-259 | 3-(5-{(S)-3-Phenyl-3-[(tetrahydro-furan-3-carbonyl)-amino]-propyl}-hexahydro-pyrrolo[3,4-c]pyrrole-2-carbonyl)-benzoic acid tert-butyl ester; compound with trifluoro-acetic acid | 548.5 |  | 547.69 |
| I-260 | Tetrahydro-furan-3-carboxylic acid {(S)-3-[5-(3,5-dimethyl-isoxazole-4-carbonyl)-hexahydro-pyrrolo[3,4-c]pyrrol-2-yl]-1-phenyl-propyl}-amide; compound with trifluoro-acetic acid | 467.4 |  | 466.58 |
| I-261 | Tetrahydro-furan-3-carboxylic acid {(S)-3-[5-(1H-indole-3-carbonyl)-hexahydro-pyrrolo[3,4-c]pyrrol-2-yl]-1-phenyl-propyl}-amide; compound with trifluoro-acetic acid | 487.4 |  | 486.61 |
| I-262 | Tetrahydro-furan-3-carboxylic acid {(S)-3-[5-(benzofuran-4-carbonyl)-hexahydro-pyrrolo[3,4-c]pyrrol-2-yl]-1-phenyl-propyl}-amide; compound with trifluoro-acetic acid | 488.4 |  | 487.6 |
| I-263 | Tetrahydro-furan-3-carboxylic acid {(S)-3-[5-(2,3-dihydro-benzofuran-4-carbonyl)-hexahydro-pyrrolo[3,4-c]pyrrol-2-yl]-1-phenyl-propyl}-amide; compound with trifluoro-acetic acid | 490.4 |  | 489.61 |
| I-264 | Tetrahydro-furan-3-carboxylic acid {(S)-3-[5-(2-methoxy-benzoyl)-hexahydro-pyrrolo[3,4-c]pyrrol-2-yl]-1-phenyl-propyl}-amide; compound with trifluoro-acetic acid | 478.4 |  | 477.6 |

TABLE 1-continued

| | | MS[1] | mp | MW |
|---|---|---|---|---|
| I-265 | Tetrahydro-furan-3-carboxylic acid {(S)-3-[5-(3-methoxy-benzoyl)-hexahydro-pyrrolo[3,4-c]pyrrol-2-yl]-1-phenyl-propyl}-amide; compound with trifluoro-acetic acid | 478.4 | | 477.6 |
| I-266 | Tetrahydro-furan-3-carboxylic acid {(S)-3-[5-(3,3-dimethyl-butyryl)-hexahydro-pyrrolo[3,4-c]pyrrol-2-yl]-1-phenyl-propyl}-amide; compound with trifluoro-acetic acid | 442.4 | | 441.61 |
| I-267 | Tetrahydro-furan-3-carboxylic acid [(S)-3-(5-cyclobutanecarbonyl-hexahydro-pyrrolo[3,4-c]pyrrol-2-yl)-1-phenyl-propyl]-amide; compound with trifluoro-acetic acid | 426.4 | | 425.57 |
| I-268 | Tetrahydro-furan-3-carboxylic acid {(S)-3-[5-(2-cyclohexyl-acetyl)-hexahydro-pyrrolo[3,4-c]pyrrol-2-yl]-1-phenyl-propyl}-amide; compound with trifluoro-acetic acid | 468.4 | | 467.65 |
| I-269 | Tetrahydro-furan-3-carboxylic acid [(S)-3-(5-cyclopentanecarbonyl-hexahydro-pyrrolo[3,4-c]pyrrol-2-yl)-1-phenyl-propyl]-amide; compound with trifluoro-acetic acid | 440.4 | | 439.6 |
| I-270 | Tetrahydro-furan-3-carboxylic acid {(S)-3-[5-(2-cyclopentyl-acetyl)-hexahydro-pyrrolo[3,4-c]pyrrol-2-yl]-1-phenyl-propyl}-amide; compound with trifluoro-acetic acid | 454.4 | | 453.62 |
| I-271 | Tetrahydro-furan-3-carboxylic acid {(S)-3-[5-(2,6-dichloro-benzoyl)-hexahydro-pyrrolo[3,4-c]pyrrol-2-yl]-1-phenyl-propyl}-amide; compound with trifluoro-acetic acid | 516.3 | | 516.47 |
| I-272 | Tetrahydro-furan-3-carboxylic acid {(S)-3-[5-(4-dimethylamino-benzoyl)-hexahydro-pyrrolo[3,4-c]pyrrol-2-yl]-1-phenyl-propyl}-amide; compound with trifluoro-acetic acid | 491.4 | | 490.64 |
| I-273 | Tetrahydro-furan-3-carboxylic acid {(S)-3-[5-(3-fluoro-benzoyl)-hexahydro-pyrrolo[3,4-c]pyrrol-2-yl]-1-phenyl-propyl}-amide; compound with trifluoro-acetic acid | 466.4 | | 465.57 |
| I-274 | Tetrahydro-furan-3-carboxylic acid [(S)-3-(5-isobutyryl-hexahydro-pyrrolo[3,4-c]pyrrol-2-yl)-1-phenyl-propyl]-amide; compound with trifluoro-acetic acid | 414.4 | | 413.56 |
| I-275 | Tetrahydro-furan-3-carboxylic acid {(S)-3-[5-(3-methyl-butyryl)-hexahydro-pyrrolo[3,4-c]pyrrol-2-yl]-1-phenyl-propyl}-amide; compound with trifluoro-acetic acid | 428.4 | | 427.59 |
| I-276 | Tetrahydro-furan-3-carboxylic acid [(S)-1-phenyl-3-(5-propionyl-hexahydro-pyrrolo[3,4-c]pyrrol-2-yl)-propyl]-amide; compound with trifluoro-acetic acid | 400.4 | | 399.53 |
| I-277 | Tetrahydro-furan-3-carboxylic acid {(S)-3-[5-(3-methyl-benzoyl)-hexahydro-pyrrolo[3,4-c]pyrrol-2-yl]-1-phenyl-propyl}-amide; compound with trifluoro-acetic acid | 462.4 | | 461.6 |
| I-278 | Tetrahydro-furan-3-carboxylic acid {(S)-3-[5-(4-methyl-benzoyl)-hexahydro-pyrrolo[3,4-c]pyrrol-2-yl]-1-phenyl-propyl}-amide; compound with trifluoro-acetic acid | 462.4 | | 461.6 |
| I-279 | Tetrahydro-furan-3-carboxylic acid {(S)-3-[5-(3-cyano-benzoyl)-hexahydro-pyrrolo[3,4-c]pyrrol-2-yl]-1-phenyl-propyl}-amide; compound with trifluoro-acetic acid | 473.3 | | 472.59 |
| I-280 | Tetrahydro-furan-3-carboxylic acid {(S)-3-[5-(4-chloro-2-ethyl-2H-pyrazole-3-carbonyl)-hexahydro-pyrrolo[3,4-c]pyrrol-2-yl]-1-phenyl-propyl}-amide; compound with trifluoro-acetic acid | 500.3 | | 500.04 |
| I-281 | Tetrahydro-furan-3-carboxylic acid {(S)-3-[5-(4-chloro-2-methyl-2H-pyrazole-3-carbonyl)-hexahydro-pyrrolo[3,4-c]pyrrol-2-yl]-1-phenyl-propyl}-amide; compound with trifluoro-acetic acid | 486.3 | | 486.01 |
| I-282 | Tetrahydro-furan-3-carboxylic acid {(S)-1-phenyl-3-[5-(2,4,5-trimethyl-thiophene-3-carbonyl)-hexahydro-pyrrolo[3,4-c]pyrrol-2-yl]-propyl}-amide; compound with trifluoro-acetic acid | 496.4 | | 495.68 |
| I-283 | Tetrahydro-furan-3-carboxylic acid {(S)-3-[5-(4-fluoro-2,6-dimethyl-benzoyl)-hexahydro-pyrrolo[3,4-c]pyrrol-2-yl]-1-phenyl-propyl}-amide; compound with trifluoro-acetic acid | 494.4 | | 493.62 |

TABLE 1-continued

|  |  | MS[1] | mp | MW |
|---|---|---|---|---|
| I-284 | Tetrahydro-furan-3-carboxylic acid [(S)-3-(5-benzoyl-hexahydro-pyrrolo[3,4-c]pyrrol-2-yl)-1-phenyl-propyl]-amide; compound with trifluoro-acetic acid | 448.4 |  | 447.58 |
| I-285 | 1-Methyl-cyclohexanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 526.6 |  | 526.09 |
| I-286 | N-{(S)-3-[5-(2-Chloro-6-fluoro-benzoyl)-hexahydro-pyrrolo[3,4-c]pyrrol-2-yl]-1-phenyl-propyl}-3-morpholin-4-yl-propionamide; compound with trifluoro-acetic acid | 543.7 |  | 543.08 |
| I-287 | N-{(S)-3-[5-(2-Chloro-6-fluoro-benzoyl)-hexahydro-pyrrolo[3,4-c]pyrrol-2-yl]-1-phenyl-propyl}-3-(4-methyl-piperazin-1-yl)-propionamide; compound with trifluoro-acetic acid | 556.7 |  | 556.12 |
| I-288 | N-{(S)-3-[5-(2-Chloro-6-fluoro-benzoyl)-hexahydro-pyrrolo[3,4-c]pyrrol-2-yl]-1-phenyl-propyl}-3-(1H-[1,2,4]triazol-3-yl)-propionamide; compound with trifluoro-acetic acid | 525.7 |  | 525.03 |
| I-289 | N-{(S)-3-[5-(2-Chloro-6-fluoro-benzoyl)-hexahydro-pyrrolo[3,4-c]pyrrol-2-yl]-1-phenyl-propyl}-2-(1H-tetrazol-5-yl)-acetamide; compound with trifluoro-acetic acid | 512.7 |  | 511.99 |
| I-290 | N-{(S)-3-[5-(2-Chloro-6-fluoro-benzoyl)-hexahydro-pyrrolo[3,4-c]pyrrol-2-yl]-1-phenyl-propyl}-3-furan-2-yl-propionamide; compound with trifluoro-acetic acid | 524.7 |  | 524.03 |
| I-291 | N-{(S)-3-[5-(2-Chloro-6-fluoro-benzoyl)-hexahydro-pyrrolo[3,4-c]pyrrol-2-yl]-1-phenyl-propyl}-3-thiophen-2-yl-propionamide; compound with trifluoro-acetic acid | 540.7 |  | 540.1 |
| I-292 | N-{(S)-3-[5-(2-Chloro-6-fluoro-benzoyl)-hexahydro-pyrrolo[3,4-c]pyrrol-2-yl]-1-phenyl-propyl}-3-pyridin-3-yl-propionamide; compound with trifluoro-acetic acid | 535.7 |  | 535.06 |
| I-293 | N-{(S)-3-[5-(2-Chloro-6-fluoro-benzoyl)-hexahydro-pyrrolo[3,4-c]pyrrol-2-yl]-1-phenyl-propyl}-3-(3H-imidazol-4-yl)-propionamide; compound with trifluoro-acetic acid | 524.7 |  | 524.04 |
| I-294 | Tetrahydro-furan-2-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 500.7 |  | 500.01 |
| I-295 | N-{(S)-3-[5-(2-Chloro-6-fluoro-benzoyl)-hexahydro-pyrrolo[3,4-c]pyrrol-2-yl]-1-phenyl-propyl}-2-(methanesulfonyl-methyl-amino)-acetamide; compound with trifluoro-acetic acid | 551.7 |  | 551.08 |
| I-296 | 4-Methoxy-thiophene-3-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 542.6 |  | 542.07 |
| I-297 | N-{(S)-3-[5-(2-Chloro-6-fluoro-benzoyl)-hexahydro-pyrrolo[3,4-c]pyrrol-2-yl]-1-phenyl-propyl}-3,3,3-trifluoro-propionamide; compound with trifluoro-acetic acid | 512.6 |  | 511.94 |
| I-298 | N-{(S)-3-[5-(2-Chloro-6-fluoro-benzoyl)-hexahydro pyrrolo[3,4-c]pyrrol-2-yl]-1-phenyl-propyl}-2-dimethylamino-acetamide; compound with trifluoro-acetic acid | 487.7 |  | 487.02 |
| I-299 | 2-Methyl-cyclopropanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 484.6 |  | 484.01 |
| I-300 | 1-Cyano-cyclopropanecarboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 495.6 |  | 495 |
| I-301 | 5-Acetyl-2,4-dimethyl-1H-pyrrole-3-carboxylic acid {(S)-3-[5-(2-chloro-6-fluoro-benzoyl)-hexahydro-pyrrolo[3,4-c]pyrrol-2-yl]-1-phenylpropyl}-amide; compound with trifluoro-acetic acid | 565.6 |  | 565.09 |
| I-302 | 2,4-Dimethyl-6-oxo-6H-pyran-3-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 552.6 |  | 552.04 |

TABLE 1-continued

|  |  | MS[1] | mp | MW |
|---|---|---|---|---|
| I-303 | 4,6-Dimethyl-pyrimidine-5-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 536.6 |  | 536.05 |
| I-304 | N-{(S)-3-[5-(2-Chloro-6-fluoro-benzoyl)-hexahydro-pyrrolo[3,4-c]pyrrol-2-yl]-1-phenyl-propyl}-2,4-dimethyl-nicotinamide; compound with trifluoro-acetic acid | 535.6 |  | 535.06 |
| I-305 | (S)-2-Amino-N-{(S)-3-[5-(2-chloro-6-fluoro-benzoyl)-hexahydro-pyrrolo[3,4-c]pyrrol-2-yl]-1-phenyl-propyl}-propionamide; compound with trifluoro-acetic acid | 473.6 |  | 472.99 |
| I-306 | (S)-2-Amino-4-methyl-pentanoic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 515.6 |  | 515.07 |
| I-307 | (S)-2-Amino-N-{(S)-3-[5-(2-chloro-6-fluoro-benzoyl)-hexahydro-pyrrolo[3,4-c]pyrrol-2-yl]-1-phenyl-propyl}-3-methyl-butyramide; compound with trifluoro-acetic acid | 501.6 |  | 501.04 |
| I-308 | N-{(S)-3-[5-(2-Chloro-6-fluoro-benzoyl)-hexahydro-pyrrolo[3,4-c]pyrrol-2-yl]-1-phenyl-propyl}-butyramide; compound with trifluoro-acetic acid | 472.5 |  | 472 |
| I-309 | N-{(S)-3-[5-(2-Chloro-6-fluoro-benzoyl)-hexahydro-pyrrolo[3,4-c]pyrrol-2-yl]-1-phenyl-propyl}-2,3-dimethyl-benzamide; compound with trifluoro-acetic acid | 534.5 |  | 534.07 |
| I-310 | N-{(S)-3-[5-(2-Chloro-6-fluoro-benzoyl)-hexahydro-pyrrolo[3,4-c]pyrrol-2-yl]-1-phenyl-propyl}-2,6-dimethyl-benzamide; compound with trifluoro-acetic acid | 534.5 |  | 534.07 |
| I-311 | N-{(S)-3-[5-(2-Chloro-6-fluoro-benzoyl)-hexahydro-pyrrolo[3,4-c]pyrrol-2-yl]-1-phenyl-propyl}-2-(4-fluoro-phenyl)-acetamide; compound with trifluoro-acetic acid | 538.6 |  | 538.04 |
| I-312 | N-{(S)-3-[5-(2-Chloro-6-fluoro-benzoyl)-hexahydro-pyrrolo[3,4-c]pyrrol-2-yl]-1-phenyl-propyl}-2-phenyl-propionamide; compound with trifluoro-acetic acid | 534.6 |  | 534.07 |
| I-313 | N-{(S)-3-[5-(2-Chloro-6-fluoro-benzoyl)-hexahydro pyrrolo[3,4-c]pyrrol-2-yl]-1-phenyl-propyl}-4-methanesulfonyl-benzamide; compound with trifluoro-acetic acid | 584.6 |  | 584.11 |
| I-314 | N-{(S)-3-[5-(2-Chloro-6-fluoro-benzoyl)-hexahydro-pyrrolo[3,4-c]pyrrol-2-yl]-1-phenyl-propyl}-2-methyl-benzamide; compound with trifluoro-acetic acid | 520.6 |  | 520.05 |
| I-315 | N-{(S)-3-[5-(2-Chloro-6-fluoro-benzoyl)-hexahydro-pyrrolo[3,4-c]pyrrol-2-yl]-1-phenyl-propyl}-3-methyl-benzamide; compound with trifluoro-acetic acid | 520.7 |  | 520.05 |
| I-316 | N-{(S)-3-[5-(2-Chloro-6-fluoro-benzoyl)-hexahydro-pyrrolo[3,4-c]pyrrol-2-yl]-1-phenyl-propyl}-4-methyl-benzamide; compound with trifluoro-acetic acid | 520.7 |  | 520.05 |
| I-317 | Cyclopentanecarboxylic acid {(S)-3-[5-(3,4-dimethyl-benzoyl)-hexahydro-pyrrolo[3,4-c]pyrrol-2-yl]-1-phenyl-propyl}-amide; compound with trifluoro acetic acid | 474 |  | 473.66 |
| I-318 | Tetrahydro-furan-3-carboxylic acid {(S)-3-[5-(4-amino-2,6-difluoro-benzoyl)-hexahydro-pyrrolo[3,4-c]pyrrol-2-yl]-1-phenyl-propyl}-amide; compound with trifluoro-acetic acid | 499.3 |  | 498.57 |
| I-319 | Tetrahydro-furan-3-carboxylic acid {(S)-3-[5-(2,4-dimethyl-6-oxo-6H-pyran-3-carbonyl)-hexahydro-pyrrolo[3,4-c]pyrrol-2-yl]-1-phenyl-propyl}-amide; compound with trifluoro-acetic acid | 494.3 |  | 493.6 |
| I-320 | Tetrahydro-furan-3-carboxylic acid {(S)-1-phenyl-3-[5-(2,4,6-trimethyl-pyrimidine-5-carbonyl)-hexahydro-pyrrolo[3,4-c]pyrrol-2-yl]-propyl}-amide; compound with trifluoro-acetic acid | 492.4 |  | 491.63 |
| I-321 | Tetrahydro-furan-3-carboxylic acid {(S)-3-[5-(1-acetyl-piperidine-4-carbonyl)-hexahydro-pyrrolo[3,4-c]pyrrol-2-yl]-1-phenyl-propyl}-amide; compound with trifluoro-acetic acid | 497.3 |  | 496.65 |
| I-322 | Tetrahydro-furan-3-carboxylic acid [(S)-3-(5-cyclohexanecarbonyl-hexahydro-pyrrolo[3,4-c]pyrrol-2-yl)-1-phenyl-propyl]-amide; compound with trifluoro-acetic acid | 454.4 |  | 453.62 |

TABLE 1-continued

|  |  | MS[1] | mp | MW |
|---|---|---|---|---|
| I-323 | Tetrahydro-furan-3-carboxylic acid {(S)-3-[5-(furan-2-carbonyl)-hexahydro-pyrrolo[3,4-c]pyrrol-2-yl]-1-phenyl-propyl}-amide; compound with trifluoro-acetic acid | 438.3 |  | 437.54 |
| I-324 | Tetrahydro-furan-3-carboxylic acid {(S)-3-[5-(furan-3-carbonyl)-hexahydro-pyrrolo[3,4-c]pyrrol-2-yl]-1-phenyl-propyl}-amide; compound with trifluoro-acetic acid | 438.3 |  | 437.54 |
| I-325 | Tetrahydro-furan-3-carboxylic acid {(S)-3-[5-(4-methanesulfonyl-benzoyl)-hexahydro-pyrrolo[3,4-c]pyrrol-2-yl]-1-phenyl-propyl}-amide; compound with trifluoro-acetic acid | 526.3 |  | 525.67 |
| I-326 | Tetrahydro-furan-3-carboxylic acid {(S)-3-[5-(2-methyl-benzoyl)-hexahydro-pyrrolo[3,4-c]pyrrol-2-yl]-1-phenyl-propyl}-amide; compound with trifluoro-acetic acid | 462.3 |  | 461.6 |
| I-327 | Tetrahydro-furan-3-carboxylic acid {(S)-1-phenyl-3-[5-(2-trifluoromethyl-benzoyl)-hexahydro-pyrrolo[3,4-c]pyrrol-2-yl]-propyl}-amide; compound with trifluoro-acetic acid | 516.3 |  | 515.57 |
| I-328 | Tetrahydro-furan-3-carboxylic acid {(S)-1-phenyl-3-[5-(thiophene-3-carbonyl)-hexahydro-pyrrolo[3,4-c]pyrrol-2-yl]-propyl}-amide; compound with trifluoro-acetic acid | 454.2 |  | 453.6 |
| I-329 | Tetrahydro-furan-3-carboxylic acid {(S)-3-[5-(2-dimethylamino-benzoyl)-hexahydro-pyrrolo[3,4-c]pyrrol-2-yl]-1-phenyl-propyl}-amide; compound with trifluoro-acetic acid | 491.3 |  | 490.64 |
| I-330 | Tetrahydro-furan-3-carboxylic acid {(S)-3-[5-(2-ethyl-5-methyl-2H-pyrazole-3-carbonyl)-hexahydro-pyrrolo[3,4-c]pyrrol-2-yl]-1-phenyl-propyl}-amide; compound with trifluoro-acetic acid | 480.3 |  | 479.62 |
| I-331 | Tetrahydro-furan-3-carboxylic acid {(S)-3-[5-(2-methyl-pyridine-3-carbonyl)-hexahydro-pyrrolo[3,4-c]pyrrol-2-yl]-1-phenyl-propyl}-amide; compound with trifluoro-acetic acid | 463.3 |  | 462.59 |
| I-332 | Tetrahydro-furan-3-carboxylic acid {(S)-3-[5-(3-methyl-furan-2-carbonyl)-hexahydro-pyrrolo[3,4-c]pyrrol-2-yl]-1-phenyl-propyl}-amide; compound with trifluoro-acetic acid | 452.3 |  | 451.56 |
| I-333 | Tetrahydro-furan-3-carboxylic acid {(S)-3-[5-(3-fluoro-2-methyl-benzoyl)-hexahydro-pyrrolo[3,4-c]pyrrol-2-yl]-1-phenyl-propyl}-amide; compound with trifluoro-acetic acid | 480.3 |  | 479.59 |
| I-334 | Tetrahydro-furan-3-carboxylic acid {(S)-3-[5-(2,6-difluoro-benzoyl)-hexahydro-pyrrolo[3,4-c]pyrrol-2-yl]-1-phenyl-propyl}-amide; compound with trifluoro-acetic acid | 484.3 |  | 483.56 |
| I-335 | Tetrahydro-furan-3-carboxylic acid {(S)-3-[5-(2-chloro-benzoyl)-hexahydro-pyrrolo[3,4-c]pyrrol-2-yl]-1-phenyl-propyl}-amide; compound with trifluoro-acetic acid | 482.3 |  | 482.02 |
| I-336 | Tetrahydro-furan-3-carboxylic acid {(S)-3-[5-(2-methyl-thiazole-4-carbonyl)-hexahydro-pyrrolo[3,4-c]pyrrol-2-yl]-1-phenyl-propyl}-amide; compound with trifluoro-acetic acid | 469.3 |  | 468.62 |
| I-337 | Tetrahydro-furan-3-carboxylic acid {(S)-3-[5-(1-methyl-1H-pyrazole-3-carbonyl)-hexahydro-pyrrolo[3,4-c]pyrrol-2-yl]-1-phenyl-propyl}-amide; compound with trifluoro-acetic acid | 452.3 |  | 451.57 |
| I-338 | Tetrahydro-furan-3-carboxylic acid {(S)-3-[5-(4-methoxy-thiophene-3-carbonyl)-hexahydro-pyrrolo[3,4-c]pyrrol-2-yl]-1-phenyl-propyl}-amide; compound with trifluoro-acetic acid | 484.2 |  | 483.63 |
| I-339 | Tetrahydro-furan-3-carboxylic acid {(S)-3-[5-(3-acetylamino-benzoyl)-hexahydro-pyrrolo[3,4-c]pyrrol-2-yl]-1-phenyl-propyl}-amide; compound with trifluoro-acetic acid | 505.3 |  | 504.63 |
| I-340 | Tetrahydro-furan-3-carboxylic acid {(S)-3-[5-(2-acetylamino-2-phenyl-acetyl)-hexahydro-pyrrolo[3,4-c]pyrrol-2-yl]-1-phenyl-propyl}-amide; compound with trifluoro-acetic acid | 519.3 |  | 518.65 |
| I-341 | Tetrahydro-furan-3-carboxylic acid {(S)-1-phenyl-3-[5-((S)-pyrrolidine-2-carbonyl)-hexahydro-pyrrolo[3,4-c]pyrrol-2-yl]-propyl}-amide; compound with trifluoro-acetic acid | 441.3 |  | 440.58 |

TABLE 1-continued

| | | MS[1] | mp | MW |
|---|---|---|---|---|
| I-342 | Tetrahydro-furan-3-carboxylic acid {(S)-3-[5-(4-chloro-2-methoxy-benzoyl)-hexahydro-pyrrolo[3,4-c]pyrrol-2-yl]-1-phenyl-propyl}-amide; compound with trifluoro-acetic acid | 512.2 | | 512.05 |
| I-343 | Tetrahydro-furan-3-carboxylic acid {(S)-3-[5-(isoquinoline-1-carbonyl)-hexahydro-pyrrolo[3,4-c]pyrrol-2-yl]-1-phenyl-propyl}-amide; compound with trifluoro-acetic acid | 499.3 | | 498.62 |
| I-344 | Tetrahydro-furan-3-carboxylic acid {(S)-1-phenyl-3-[5-(quinoline-2-carbonyl)-hexahydro-pyrrolo[3,4-c]pyrrol-2-yl]-propyl}-amide; compound with trifluoro-acetic acid | 499.3 | | 498.62 |
| I-345 | Tetrahydro-furan-3-carboxylic acid {(S)-1-phenyl-3-[5-(quinoline-3-carbonyl)-hexahydro-pyrrolo[3,4-c]pyrrol-2-yl]-propyl}-amide; compound with trifluoro-acetic acid | 499.3 | | 498.62 |
| I-346 | Tetrahydro-furan-3-carboxylic acid {(S)-1-phenyl-3-[5-(quinoline-6-carbonyl)-hexahydro-pyrrolo[3,4-c]pyrrol-2-yl]-propyl}-amide; compound with trifluoro-acetic acid | 499.3 | | 498.62 |
| I-347 | Tetrahydro-furan-3-carboxylic acid {(S)-1-phenyl-3-[5-(quinoline-8-carbonyl)-hexahydro-pyrrolo[3,4-c]pyrrol-2-yl]-propyl}-amide; compound with trifluoro-acetic acid | 499.3 | | 498.62 |
| I-348 | Tetrahydro-furan-3-carboxylic acid {(S)-3-[5-(3-carbamoyl-propionyl)-hexahydro-pyrrolo[3,4-c]pyrrol-2-yl]-1-phenyl-propyl}-amide; compound with trifluoro-acetic acid | 443.3 | | 442.56 |
| I-349 | Tetrahydro-furan-3-carboxylic acid [(S)-3-(5-cyclopropanecarbonyl-hexahydro-pyrrolo[3,4-c]pyrrol-2-yl)-1-phenyl-propyl]-amide; compound with trifluoro-acetic acid | 412.3 | | 411.54 |
| I-350 | Tetrahydro-furan-3-carboxylic acid {(S)-3-[5-(2-methyl-butyryl)-hexahydro-pyrrolo[3,4-c]pyrrol-2-yl]-1-phenyl-propyl}-amide; compound with trifluoro-acetic acid | 428.4 | | 427.59 |
| I-351 | Tetrahydro-furan-3-carboxylic acid ((S)-3-{5-[2-(methanesulfonyl-methyl-amino)-acetyl]-hexahydro-pyrrolo[3,4-c]pyrrol-2-yl}-1-phenyl-propyl)-amide; compound with trifluoro-acetic acid | 493.4 | | 492.64 |
| I-352 | Tetrahydro-furan-3-carboxylic acid {(S)-3-[5-(2,6-difluoro-4-methoxy-benzoyl)-hexahydro-pyrrolo[3,4-c]pyrrol-2-yl]-1-phenyl-propyl}-amide; compound with trifluoro-acetic acid | 514.4 | | 513.58 |
| I-353 | Tetrahydro-furan-3-carboxylic acid {(S)-1-phenyl-3-[5-(2,4,6-trifluoro-benzoyl)-hexahydro-pyrrolo[3,4-c]pyrrol-2-yl]-propyl}-amide; compound with trifluoro-acetic acid | 502.4 | | 501.55 |
| I-354 | Cyclopentanecarboxylic acid {(S)-3-[5-(2,6-dimethyl-benzoyl)-hexahydro-pyrrolo[3,4-c]pyrrol-2-yl]-4-methoxy-1-phenyl-butyl}-amide | 518 | 61.1–84.5 | 517.71 |
| I-355 | Tetrahydro-furan-3-carboxylic acid {(S)-3-[5-((R)-2-acetylamino-3-methyl-butyryl)-hexahydro-pyrrolo[3,4-c]pyrrol-2-yl]-1-phenyl-propyl}-amide; compound with trifluoro-acetic acid | 485.3 | | 484.64 |
| I-356 | Cyclopentanecarboxylic acid {(S)-3-[5-(1-methyl-5-oxo-pyrrolidine-3-carbonyl)-hexahydro-pyrrolo[3,4-c]pyrrol-2-yl]-1-phenyl-propyl}-amide; compound with trifluoro-acetic acid | 467 | | 466.62 |
| I-357 | Tetrahydro-furan-3-carboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 478.2 | | 477.61 |
| I-358 | Tetrahydro-furan-3-carboxylic acid {(S)-3-[5-(2,4-dimethyl-1-oxy-pyridine-3-carbonyl)-hexahydro-pyrrolo[3,4-c]pyrrol-2-yl]-1-phenyl-propyl}-amidetrifluoro-acetic acid; | 493.2 | | 492.62 |
| I-359 | Tetrahydro-furan-3-carboxylic acid {(S)-3-[5-(4,6-dimethyl-2-methylsulfanyl-pyrimidine-5-carbonyl)-hexahydro-pyrrolo[3,4-c]pyrrol-2-yl]-1-phenyl-propyl}-amide; compound with trifluoro-acetic acid | 524.3 | | 523.7 |
| I-360 | Cyclopentanecarboxylic acid {(S)-3-[5-(2,6-dimethyl-benzoyl)-hexahydro-pyrrolo[3,4-c]pyrrol-2-yl]-4-hydroxy-1-phenyl-butyl}-amide | 504 | 78.9–84.9 | 503.68 |

TABLE 1-continued

| | | MS[1] | mp | MW |
|---|---|---|---|---|
| I-361 | Tetrahydro-furan-3-carboxylic acid {(S)-1-phenyl-3-[5-(2,4,6-trimethoxy-benzoyl)-hexahydro-pyrrolo[3,4-c]pyrrol-2-yl]-propyl}-amide; compound with trifluoro-acetic acid | 538.5 | | 537.65 |
| I-362 | Tetrahydro-furan-3-carboxylic acid {(S)-1-phenyl-3-[5-(2,3,6-trichloro-benzoyl)-hexahydro-pyrrolo[3,4-c]pyrrol-2-yl]-propyl}-amide; compound with trifluoro-acetic acid | 550.3 | | 550.91 |
| I-363 | Tetrahydro-furan-3-carboxylic acid {(S)-3-[5-(5-methyl-2-phenyl-2H-[1,2,3]triazole-4-carbonyl)-hexahydro-pyrrolo[3,4-c]pyrrol-2-yl]-1-phenyl-propyl}-amide; compound with trifluoro-acetic acid | 529.5 | | 528.65 |
| I-364 | 2-Oxo-imidazolidine-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 514.4 | | 514 |
| I-365 | 5-Methyl-thiophene-2-carboxylic acid {(S)-3-[5-(2,4-dimethyl-1-oxy-pyridine-3-carbonyl)-hexahydro-pyrrolo[3,4-c]pyrrol-2-yl]-1-phenyl-propyl}-amidetrifluoro-acetic acid; | 519.5 | | 518.68 |
| I-366 | 2-Cyclohexyl-N-{(S)-3-[5-(2,4-dimethyl-1-oxy-pyridine-3-carbonyl)-hexahydro-pyrrolo[3,4-c]pyrrol-2-yl]-1-phenyl-propyl}-acetamidetrifluoro-acetic acid; | 519.5 | | 518.7 |
| I-367 | N-{(S)-3-[5-(2,4-Dimethyl-1-oxy-pyridine-3-carbonyl)-hexahydro-pyrrolo[3,4-c]pyrrol-2-yl]-1-phenyl-propyl}-2-(4-fluoro-phenyl)-acetamidetrifluoro-acetic acid; | 531.5 | | 530.64 |
| I-368 | N-{(S)-3-[5-(2,4-Dimethyl-1-oxy-pyridine-3-carbonyl)-hexahydro-pyrrolo[3,4-c]pyrrol-2-yl]-1-phenyl-propyl}-2-(4-methoxy-phenyl)-acetamidetrifluoro-acetic acid; | 543.5 | | 542.68 |
| I-369 | 1-{(S)-3-[5-(2,4-Dimethyl-1-oxy-pyridine-3-carbonyl)-hexahydro-pyrrolo[3,4-c]pyrrol-2-yl]-1-phenyl-propyl}-3-isopropyl-ureatrifluoro-acetic acid; | 480.5 | | 479.62 |
| I-370 | 2-Oxo-thiazolidine-4-carboxylic acid {(S)-3-[5-(2,4-dimethyl-1-oxy-pyridine-3-carbonyl)-hexahydro-pyrrolo[3,4-c]pyrrol-2-yl]-1-phenyl-propyl}-amidetrifluoro-acetic acid; | 524.4 | | 523.66 |
| I-371 | Furan-3-carboxylic acid {(S)-3-[5-2,4-dimethyl-1-oxy-pyridine-3-carbonyl)-hexahydro-pyrrolo[3,4-c]pyrrol-2-yl]-1-phenyl-propyl}-amidetrifluoro-acetic acid; | 489.4 | | 488.59 |
| I-372 | N-{(S)-3-[5-(2,4-Dimethyl-1-oxy-pyridine-3-carbonyl)-hexahydro-pyrrolo[3,4-c]pyrrol-2-yl]-1-phenyl-propyl}-3,4-difluoro-benzamidetrifluoro-acetic acid; | 535.4 | | 534.6 |
| I-373 | 1-{(S)-3-[5-(2,4-Dimethyl-1-oxy-pyridine-3-carbonyl)-hexahydro-pyrrolo[3,4-c]pyrrol-2-yl]-1-phenyl-propyl}-3-phenyl-ureatrifluoro-acetic acid; | 514.5 | | 513.64 |
| I-374 | 4,4-Difluoro-cyclohexanecarboxylic acid {(S)-3-[5-(2,4-dimethyl-1-oxy-pyridine-3-carbonyl)-hexahydro-pyrrolo[3,4-c]pyrrol-2-yl]-1-phenyl-propyl}-amidetrifluoro-acetic acid; | 541.5 | | 540.65 |
| I-375 | Tetrahydro-pyran-4-carboxylic acid {(S)-3-[5-(2,4-dimethyl-1-oxy-pyridine-3-carbonyl)-hexahydro-pyrrolo[3,4-c]pyrrol-2-yl]-1-phenyl-propyl}-amidetrifluoro-acetic acid; | 507.5 | | 506.64 |
| I-376 | Tetrahydro-furan-3-carboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 477.5 | | 476.62 |
| I-377 | 5-Methyl-thiophene-2-carboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 503.4 | | 502.68 |
| I-378 | 2-Cyclohexyl-N-{(S)-3-[5-(2,4-dimethyl-pyridine-3-carbonyl)-hexahydro-pyrrolo[3,4-c]pyrrol-2-yl]-1-phenyl-propyl}-acetamide; compound with trifluoro-acetic acid | 503.5 | | 502.7 |
| I-379 | N-{(S)-3-[5-(2,4-Dimethyl-pyridine-3-carbonyl)-hexahydro-pyrrolo[3,4-c]pyrrol-2-yl]-1-phenyl-propyl}-2-(4-fluoro-phenyl)-acetamide; compound with trifluoro-acetic acid | 515.5 | | 514.64 |
| I-380 | N-{(S)-3-[5-(2,4-Dimethyl-pyridine-3-carbonyl)-hexahydro-pyrrolo[3,4-c]pyrrol-2-yl]-1-phenyl-propyl}-2-(4-methoxy-phenyl)-acetamide; compound with trifluoro-acetic acid | 527.5 | | 526.68 |

TABLE 1-continued

|   |   | MS[1] | mp | MW |
|---|---|---|---|---|
| I-381 | Cyclohexanecarboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 489.5 |  | 488.67 |
| I-382 | Furan-3-carboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 473.4 |  | 472.59 |
| I-383 | N-{(S)-3-[5-(2,4-Dimethyl-pyridine-3-carbonyl)-hexahydro-pyrrolo[3,4-c]pyrrol-2-yl]-1-phenyl-propyl}-acetamide; compound with trifluoro-acetic acid | 421.4 |  | 420.55 |
| I-384 | N-{(S)-3-[5-(2,4-Dimethyl-pyridine-3-carbonyl)-hexahydro-pyrrolo[3,4-c]pyrrol-2-yl]-1-phenyl-propyl}-3,4-difluoro-benzamide; compound with trifluoro-acetic acid | 519.4 |  | 518.61 |
| I-385 | 1-{(S)-3-[5-(2,4-Dimethyl-pyridine-3-carbonyl)-hexahydro-pyrrolo[3,4-c]pyrrol-2-yl]-1-phenyl-propyl}-3-phenyl-urea; compound with trifluoro-acetic acid | 498.4 |  | 497.64 |
| I-386 | 4,4-Difluoro-cyclohexanecarboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 525.5 |  | 524.65 |
| I-387 | Tetrahydro-pyran-4-carboxylic acid {(S)-3-[5-(2,4-dimethyl-pyridine-3-carbonyl)-hexahydro-pyrrolo[3,4-c]phenyl-2-yl]-1-phenyl-propyl}-amide; compound with trifluoro-acetic acid | 491.4 |  | 490.64 |
| I-388 | Tetrahydro-pyran-4-carboxylic acid {(S)-3-[5-(2-chloro-6-fluoro-benzoyl)-hexahydro-pyrrolo[3,4-c]pyrrol-2-yl]-1-phenyl-propyl}-amide; compound with trifluoro-acetic acid | 514.4 |  | 514.04 |
| I-389 | (R)-Tetrahydro-furan-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 476.5 |  | 475.63 |
| I-390 | (R)-Tetrahydro-furan-3-carboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 478.4 |  | 477.61 |
| I-391 | (R)-Tetrahydro-furan-3-carboxylic acid {(S)-1-phenyl-3-[5-(2,4,5-trimethyl-thiophene-3-carbonyl)-hexahydro-pyrrolo[3,4-c]pyrrol-2-yl]-propyl}-amide; compound with trifluoro-acetic acid | 496.4 |  | 495.68 |
| I-392 | (S)-Tetrahydro-furan-3-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 476.5 |  | 475.63 |
| I-393 | (S)-Tetrahydro-furan-3-carboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 477.5 |  | 476.62 |
| I-394 | (S)-Tetrahydro-furan-3-carboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 478.5 |  | 477.61 |
| I-395 | (S)-Tetrahydro-furan-3-carboxylic acid {(S)-1-phenyl-3-[5-(2,4,5-trimethyl-thiophene-3-carbonyl)-hexahydro-pyrrolo[3,4-c]pyrrol-2-yl]-propyl}-amide; compound with trifluoro-acetic acid | 496.4 |  | 495.68 |
| I-396 | Tetrahydro-furan-3-carboxylic acid {(S)-3-[5-(5-methyl-3-phenyl-isoxazole-4-carbonyl)-hexahydro-pyrrolo[3,4-c]pyrrol-2-yl]-1-phenyl-propyl}-amide; compound with trifluoro-acetic acid | 529.4 |  | 528.65 |
| I-397 | Tetrahydro-furan-3-carboxylic acid {(S)-1-phenyl-3-[5-(quinoline-3-carbonyl)-hexahydro-pyrrolo[3,4-c]pyrrol-2-yl]-propyl}-amide; compound with trifluoro-acetic acid | 499.4 |  | 498.62 |
| I-398 | Tetrahydro-furan-3-carboxylic acid {(S)-1-phenyl-3-[5-(quinoline-4-carbonyl)-hexahydro-pyrrolo[3,4-c]pyrrol-2-yl]-propyl}-amide; compound with trifluoro-acetic acid | 499.4 |  | 498.62 |
| I-399 | Tetrahydro-furan-3-carboxylic acid {(S)-1-phenyl-3-[5-(quinoline-6-carbonyl)-hexahydro-pyrrolo[3,4-c]pyrrol-2-yl]-propyl}-amide; compound with trifluoro-acetic acid | 499.4 |  | 498.62 |

TABLE 1-continued

|   | | MS[1] | mp | MW |
|---|---|---|---|---|
| I-400 | Tetrahydro-furan-3-carboxylic acid {(S)-1-phenyl-3-[5-(quinoline-8-carbonyl)-hexahydro-pyrrolo[3,4-c]pyrrol-2-yl]-propyl}-amide; compound with trifluoro-acetic acid | 499.5 | | 498.62 |
| I-401 | (R)-Tetrahydro-furan-3-carboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 477.7 | | 476.62 |
| I-402 | Cyclopentanecarboxylic acid {(S)-3-[5-(2,6-dimethyl-4-pyridin-4-yl-benzoyl)-hexahydro-pyrrolo[3,4-c]pyrrol-2-yl]-1-phenyl-propyl}-amide; compound with trifluoro-acetic acid | 551.3 | | 550.74 |
| I-403 | Cyclopentanecarboxylic acid {(S)-3-[5-(4-cyano-2,6-dimethyl-benzoyl)-hexahydro-pyrrolo[3,4-c]pyrrol-2-yl]-1-phenyl-propyl}-amide; compound with trifluoro-acetic acid | 499.2 | | 498.67 |
| I-404 | Cyclopentanecarboxylic acid {(S)-3-[5-(2,6-dimethyl-benzoyl)-hexahydro-pyrrolo[3,4-c]pyrrol-2-yl]-1-pyridin-2-yl-propyl}-amide; compound with trifluoro-acetic acid | 475 | | 474.65 |
| I-405 | Cyclopropanecarboxylic acid {(S)-3-[5-(2,6-dimethyl-benzoyl)-hexahydro-pyrrolo[3,4-c]pyrrol-2-yl]-1-pyridin-2-yl-propyl}-amide; compound with trifluoro-acetic acid | 447 | | 446.59 |
| I-406 | 5-Methyl-thiophene-2-carboxylic acid {(S)-3-[5-(2,6-dimethyl-benzoyl)-hexahydro-pyrrolo[3,4-c]pyrrol-2-yl]-1-pyridin-2-yl-propyl}-amide; compound with trifluoro-acetic acid | 503 | | 502.68 |
| I-407 | Tetrahydro-furan-3-carboxylic acid {(S)-3-[5-(2,6-dimethyl-benzoyl)-hexahydro-pyrrolo[3,4-c]pyrrol-2-yl]-1-pyridin-2-yl-propyl}-amide; compound with trifluoro-acetic acid | 477 | | 476.62 |
| I-408 | 4,4-Difluoro-cyclohexanecarboxylic acid {(S)-3-[5-(2,6-dimethyl-benzoyl)-hexahydro-pyrrolo[3,4-c]pyrrol-2-yl]-1-pyridin-2-yl-propyl}-amide; compound with trifluoro-acetic acid | 525 | | 524.65 |
| I-409 | 1,1-Dioxo-hexahydro-1$\lambda^6$-thiopyran-4-carboxylic acid {(S)-3-[5-(2,6-dimethyl-benzoyl)-hexahydro-pyrrolo[3,4-c]pyrrol-2-yl]-1-phenyl-propyl}-amide; compound with trifluoro-acetic acid | 538 | | 537.72 |
| I-410 | Tetrahydro-furan-3-carboxylic acid ((S)-3-{5-[5-amino-1-(4-methoxy-phenyl)-1H-pyrazole-4-carbonyl]-hexahydro-pyrrolo[3,4-c]pyrrol-2-yl}-1-phenyl-propyl)-amide; compound with trifluoro-acetic acid | 559.4 | | 558.68 |
| I-411 | Tetrahydro-furan-3-carboxylic acid {(S)-1-phenyl-3-[5-(1-phenyl-5-trifluoromethyl-1H-pyrazole-4-carbonyl)-hexahydro-pyrrolo[3,4-c]pyrrol-2-yl]-propyl}-amide; compound with trifluoro-acetic acid | 582.3 | | 581.64 |
| I-412 | Tetrahydro-furan-3-carboxylic acid ((S)-3-{5-[1-(4-methoxy-phenyl)-5-trifluoromethyl-1H-pyrazole-4-carbonyl]-hexahydro-pyrrolo[3,4-c]pyrrol-2-yl}-1-phenyl-propyl)-amide; compound with trifluoro-acetic acid | 612.3 | | 611.66 |
| I-413 | Tetrahydro-furan-3-carboxylic acid ((S)-3-{5-[1-(2-methoxy-phenyl)-5-trifluoromethyl-1H-pyrazole-4-carbonyl]-hexahydro-pyrrolo[3,4-c]pyrrol-2-yl}-1-phenyl-propyl)-amide; compound with trifluoro-acetic acid | 612.3 | | 611.66 |
| I-414 | Tetrahydro-furan-3-carboxylic acid ((S)-3-{5-[1-(4-chloro-phenyl)-5-trifluoromethyl-1H-pyrazole-4-carbonyl]-hexahydro-pyrrolo[3,4-c]pyrrol-2-yl}-1-phenyl-propyl)-amide; compound with trifluoro-acetic acid | 616.3 | | 616.08 |
| I-415 | Tetrahydro-furan-3-carboxylic acid {(S)-1-phenyl-3-[5-(1-p-tolyl-5-trifluoromethyl-1H-pyrazole-4-carbonyl)-hexahydro-pyrrolo[3,4-c]pyrrol-2-yl]-propyl}-amide; compound with trifluoro-acetic acid | 596.3 | | 595.66 |
| I-416 | Tetrahydro-furan-3-carboxylic acid ((S)-3-{5-[1-(4-fluoro-phenyl)-5-trifluoromethyl-1H-pyrazole-4-carbonyl]-hexahydro-pyrrolo[3,4-c]pyrrol-2-yl}-1-phenyl-propyl)-amide; compound with trifluoro-acetic acid | 600.3 | | 599.63 |
| I-417 | Tetrahydro-furan-3-carboxylic acid {(S)-3-[5-(5-methyl-1-phenyl-1H-pyrazole-4-carbonyl)-hexahydro-pyrrolo[3,4-c]pyrrol-2-yl]-1-phenyl-propyl}-amide; compound with trifluoro-acetic acid | 528.3 | | 527.67 |

TABLE 1-continued

| | | MS¹ | mp | MW |
|---|---|---|---|---|
| I-418 | Tetrahydro-furan-3-carboxylic acid {(S)-3-[5-(5-methyl-1-p-tolyl-1H-pyrazole-4-carbonyl)-hexahydro-pyrrolo[3,4-c]pyrrol-2-yl]-1-phenyl-propyl}-amide; compound with trifluoro-acetic acid | 542.4 | | 541.69 |
| I-419 | Tetrahydro-furan-3-carboxylic acid ((S)-3-{5-[2-(4-methoxy-phenyl)-5-methyl-2H-pyrazole-3-carbonyl]-hexahydro-pyrrolo[3,4-c]pyrrol-2-yl}-1-phenyl-propyl)-amide; compound with trifluoro-acetic acid | 558.4 | | 557.69 |
| I-420 | Tetrahydro-furan-3-carboxylic acid {(S)-3-[5-(4,6-dimethyl-2-phenyl-pyrimidine-5-carbonyl)-hexahydro-pyrrolo[3,4-c]pyrrol-2-yl]-1-phenyl-propyl)-amide; compound with trifluoro-acetic acid | 554.4 | | 553.7 |
| I-421 | Tetrahydro-furan-3-carboxylic acid ((S)-3-{5-[4,6-dimethyl-2-(2-methyl-thiazol-4-yl)-pyrimidine-5-carbonyl]-hexahydro-pyrrolo[3,4-c]pyrrol-2-yl}-1-phenyl-propyl)-amide; compound with trifluoro-acetic acid | 575.3 | | 574.75 |
| I-422 | Tetrahydro-furan-3-carboxylic acid {(S)-3-[5-(4,6-dimethyl-2-pyridin-4-yl-pyrimidine-5-carbonyl)-hexahydro-pyrrolo[3,4-c]pyrrol-2-yl]-1-phenyl-propyl}-amide; compound with trifluoro-acetic acid | 555.4 | | 554.69 |
| I-423 | Tetrahydro-furan-3-carboxylic acid {(S)-3-[5-(2-bromo-pyridine-3-carbonyl)-hexahydro-pyrrolo[3,4-c]pyrrol-2-yl]-1-phenyl-propyl}-amide; compound with trifluoro-acetic acid | 529.2 | | 527.46 |
| I-424 | Tetrahydro-furan-3-carboxylic acid {(S)-3-[5-(2-fluoro-pyridine-3-carbonyl)-hexahydro-pyrrolo[3,4-c]pyrrol-2-yl]-1-phenyl-propyl}-amide; compound with trifluoro-acetic acid | 467.3 | | 466.55 |
| I-425 | Tetrahydro-furan-3-carboxylic acid {(S)-3-[5-(3-chloro-pyridine-4-carbonyl)-hexahydro-pyrrolo[3,4-c]pyrrol-2-yl]-1-phenyl-propyl}-amide; compound with trifluoro-acetic acid | 483.3 | | 483.01 |
| I-426 | Tetrahydro-furan-3-carboxylic acid {(S)-3-[5-(2-methoxy-pyridine-3-carbonyl)-hexahydro-pyrrolo[3,4-c]pyrrol-2-yl]-1-phenyl-propyl}-amide; compound with trifluoro-acetic acid | 479.3 | | 478.59 |
| I-427 | Tetrahydro-furan-3-carboxylic acid {(S)-3-[5-(2-methanesulfonyl-benzoyl)-hexahydro-pyrrolo[3,4-c]pyrrol-2-yl]-1-phenyl-propyl}-amide; compound with trifluoro-acetic acid | 526.3 | | 525.67 |
| I-428 | Tetrahydro-furan-3-carboxylic acid {(S)-1-phenyl-3-[5-(2-trifluoromethoxy-benzoyl)-hexahydro-pyrrolo[3,4-c]pyrrol-2-yl]-propyl}-amide; compound with trifluoro-acetic acid | 532.3 | | 531.57 |
| I-429 | Tetrahydro-furan-3-carboxylic acid {(S)-3-[5-(5-amino-1-phenyl-1H-pyrazole-4-carbonyl)-hexahydro-pyrrolo[3,4-c]pyrrol-2-yl]-1-phenyl-propyl}-amide; compound with trifluoro-acetic acid | 529.2 | | 528.65 |
| I-430 | Tetrahydro-furan-3-carboxylic acid ((S)-3-{5-[5-amino-1-(4-fluoro-phenyl)-1H-pyrazole-4-carbonyl]-hexahydro-pyrrolo[3,4-c]pyrrol-2-yl}-1-phenyl-propyl)-amide; compound with trifluoro-acetic acid | 547.2 | | 546.64 |
| I-431 | Tetrahydro-furan-3-carboxylic acid ((S)-3-{5-[5-amino-1-(2-methoxy-phenyl)-1H-pyrazole-4-carbonyl]-hexahydro-pyrrolo[3,4-c]pyrrol-2-yl}-1-phenyl-propyl)-amide; compound with trifluoro-acetic acid | 559.2 | | 558.68 |
| I-432 | Tetrahydro-furan-3-carboxylic acid ((S)-3-{5-[1-(4-chloro-phenyl)-5-methyl-1H-pyrazole-4-carbonyl]-hexahydro-pyrrolo[3,4-c]pyrrol-2-yl}-1-phenyl-propyl)-amide; compound with trifluoro-acetic acid | 562.2 | | 562.11 |
| I-433 | Tetrahydro-furan-3-carboxylic acid {(S)-3-[5-(3-bromo-2,6-dimethyl-benzoyl)-hexahydro-pyrrolo[3,4-c]pyrrol-2-yl]-1-phenyl-propyl}-amide; compound with trifluoro-acetic acid | 556.2 | | 554.53 |
| I-434 | Cyclopentanecarboxylic acid {(S)-3-[5-(4,6-dimethyl-pyrimidine-5-carbonyl)-hexahydro-pyrrolo[3,4-c]pyrrol-2-yl]-1-phenyl-butyl}-amide | 540 | 71.3–72.9 | 489.66 |
| I-435 | 4,4-Difluoro-cyclohexanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide | 526 | 131.8–133.2 | 525.64 |
| I-436 | Pentanoic acid {(S)-3-[5-(2,4-dimethyl-pyridine-3-carbonyl)-hexahydro-pyrrolo[3,4-c]pyrrol-2-yl]-1-phenyl-propyl]-amide; compound with trifluoro-acetic acid | 463.3 | | 462.63 |

TABLE 1-continued

| | | MS[1] | mp | MW |
|---|---|---|---|---|
| I-437 | Cyclobutanecarboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 461.3 | | 460.62 |
| I-438 | 2-Cyclopentyl-N-{(S)-3-[5-(2,4-dimethyl-pyridine-3-carbonyl)-hexahydro-pyrrolo[3,4-c]pyrrol-2-yl]-1-phenyl-propyl}-acetamide; compound with trifluoro-acetic acid | 489.3 | | 488.67 |
| I-439 | Tetrahydro-furan-3-carboxylic acid {(S)-3-[5-(2-methyl-5-trifluoromethyl-oxazole-4-carbonyl)-hexahydro-pyrrolo[3,4-c]pyrrol-2-yl]-1-phenyl-propyl}-amide; compound with trifluoro-acetic acid | 521.2 | | 520.55 |
| I-440 | Tetrahydro-furan-3-carboxylic acid {(S)-3-[5-(2-amino-6-trifluoromethyl-benzoyl)-hexahydro-pyrrolo[3,4-c]pyrrol-2-yl]-1-phenyl-propyl}-amide; compound with trifluoro-acetic acid | 531.3 | | 530.59 |
| I-441 | Tetrahydro-furan-3-carboxylic acid {(S)-3-[5-(2,6-dimethyl-4-nitro-benzoyl)-hexahydro-pyrrolo[3,4-c]pyrrol-2-yl]-1-phenyl-propyl}-amidetrifluoro-acetic acid; | 521.3 | | 520.63 |
| I-442 | N-{(S)-3-[5-(2,4-Dimethyl-pyridine-3-carbonyl)-hexahydro-pyrrolo[3,4-c]pyrrol-2-yl]-1-phenyl-propyl}-propionamide; compound with trifluoro-acetic acid | 435.3 | | 434.58 |
| I-443 | N-{(S)-3-[5-(2,4-Dimethyl-pyridine-3-carbonyl)-hexahydro-pyrrolo[3,4-c]pyrrol-2-yl]-1-phenyl-propyl}-butyramide; compound with trifluoro-acetic acid | 449.3 | | 448.61 |
| I-444 | Cyclopropanecarboxylic acid {(S)-3-[5-(2,4-dimethyl-pyridine-3-carbonyl)-hexahydro-pyrrolo[3,4-c]pyrrol-2-yl]-1-phenyl-propyl}-amide; compound with trifluoro-acetic acid | 447.3 | | 446.59 |
| I-445 | {(S)-3-[5-(2,4-Dimethyl-pyridine-3-carbonyl)-hexahydro-pyrrolo[3,4-c]pyrrol-2-yl]-2-methyl-1-phenyl-propyl}-carbamic acid tert-butyl ester | 493 | | 492.66 |
| I-446 | Cyclopentanecarboxylic acid {(S)-3-[5-(2,6-dimethyl-benzoyl)-3a,6a-dimethyl-hexahydro-pyrrolo[3,4-c]pyrrol-2-yl]-1-phenyl-propyl}-amide | 502 (M + Na) 524 | | 501.71 |
| I-447 | 5-Oxo-1-(2,2,2-trifluoro-ethyl)-pyrrolidine-3-carboxylic acid {(S)-3-[5-(2,6-dimethyl-benzoyl)-hexahydro-pyrrolo[3,4-c]pyrrol-2-yl]-1-phenyl-propyl}-amide | 571 | 93.3–94.5 | 570.65 |
| I-448 | 4,4-Difluoro-cyclohexanecarboxylic acid {(S)-3-[5-(4,6-dimethyl-pyrimidine-5-carbonyl)-hexahydro-pyrrolo[3,4-c]pyrrol-2-yl]-1-phenyl-butyl}-amide | 540 | 71.3–72.9 | 539.67 |
| I-449 | 4,4-Difluoro-cyclohexanecarboxylic acid {(S)-3-[5-(4,6-dimethyl-pyrimidine-5-carbonyl)-hexahydro-pyrrolo[3,4-c]pyrrol-2-yl]-1-phenyl-butyl}-amide | 540 | 86.4–87.0 | 539.67 |
| I-450 | Tetrahydro-furan-3-carboxylic acid {(S)-3-[5-(6-chloro-2-dimethylamino-pyridine-3-carbonyl)-hexahydro-pyrrolo[3,4-c]pyrrol-2-yl]-1-phenyl-propyl}-amide; compound with trifluoro-acetic acid | 526.1 | | 526.08 |
| I-451 | Tetrahydro-furan-3-carboxylic acid {(S)-3-[5-(4-cyano-2,5-dimethyl-thiophene-3-carbonyl)-hexahydro-pyrrolo[3,4-c]pyrrol-2-yl]-1-phenyl-propyl}-amide; compound with trifluoro-acetic acid | 507.1 | | 506.67 |
| I-452 | Tetrahydro-furan-3-carboxylic acid {(S)-3-[5-(4-iodo-2,5-dimethyl-thiophene-3-carbonyl)-hexahydro-pyrrolo[3,4-c]pyrrol-2-yl]-1-phenyl-propyl}-amide; compound with trifluoro-acetic acid | 608 | | 607.55 |
| I-453 | Tetrahydro-furan-3-carboxylic acid {(S)-3-[5-(2,5-dimethyl-thiophene-3-carbonyl)-hexahydro-pyrrolo[3,4-c]pyrrol-2-yl]-1-phenyl-propyl}-amide; compound with trifluoro-acetic acid | 482.1 | | 481.66 |
| I-454 | Tetrahydro-furan-3-carboxylic acid {(S)-3-[5-(2,5-di-tert-butyl-4-cyano-thiophene-3-carbonyl)-hexahydro-pyrrolo[3,4-c]pyrrol-2-yl]-1-phenyl-propyl}-amide; compound with trifluoro-acetic acid | 591.2 | | 590.83 |
| I-455 | 4-Oxo-cyclohexanecarboxylic acid {(S)-3-[5-(2,6-dimethyl-benzoyl)-hexahydro-pyrrolo[3,4-c]pyrrol-2-yl]-1-phenyl-propyl}-amide | 502 | 94.3–95.7 | 501.67 |
| I-456 | Cyclopentanecarboxylic acid {(S)-3-[5-(2-ethoxy-4,6-dimethyl-pyrimidine-5-carbonyl)-hexahydro-pyrrolo[3,4-c]pyrrol-2-yl]-1-phenyl-propyl}-amide | 520 | | 519.69 |

TABLE 1-continued

| | MS[1] | mp | MW |
|---|---|---|---|
| I-457 Cyclopentanecarboxylic acid {(S)-3-[5-(2,4-dimethyl-pyridine-3-carbonyl)-hexahydro-pyrrolo[3,4-c]pyrrol-2-yl]-2-methyl-1-phenyl-propyl}-amide; compound with trifluoro-acetic acid | 489 | | 488.67 |
| I-458 Cyclopropanecarboxylic acid {(S)-3-[5-(2,4-dimethyl-pyridine-3-carbonyl)-hexahydro-pyrrolo[3,4-c]pyrrol-2-yl]-2-methyl-1-phenyl-propyl}-amide; compound with trifluoro-acetic acid | 461 | | 460.62 |
| I-459 5-Methyl-thiophene-2-carboxylic acid {(S)-3-[5-(2,4-dimethyl-pyridine-3-carbonyl)-hexahydro-pyrrolo[3,4-c]pyrrol-2-yl]-2-methyl-1-phenyl-propyl}-amide; compound with trifluoro-acetic acid | 517 | | 516.71 |
| I-460 4,4-Difluoro-cyclohexanecarboxylic acid {(S)-3-[5-(2,4-dimethyl-pyridine-3-carbonyl)-hexahydro-pyrrolo[3,4-c]pyrrol-2-yl]-2-methyl-1-phenyl-propyl}-amide; compound with trifluoro-acetic acid | 539 | | 538.68 |
| I-461 Tetrahydro-furan-3-carboxylic acid {(S)-3-[5-(4-bromo-2,5-di-tert-butyl-thiophene-3-carbonyl)-hexahydro-pyrrolo[3,4-c]pyrrol-2-yl]-1-phenyl-propyl}-amide; compound with trifluoro-acetic acid | 646.1 | | 644.71 |
| I-462 Tetrahydro-furan-3-carboxylic acid {(S)-3-[5-(3,5-diethyl-isoxazole-4-carbonyl)-hexahydro-pyrrolo[3,4-c]pyrrol-2-yl]-1-phenyl-propyl}-amide; compound with trifluoro-acetic acid | 495.2 | | 494.63 |
| I-463 Cyclopentanecarboxylic acid {(S)-3-[5-(2-methanesulfonyl-4,6-dimethyl-pyrimidine-5-carbonyl)-hexahydro-pyrrolo[3,4-c]pyrrol-2-yl]-1-phenyl-propyl}-amide; compound with trifluoro-acetic acid | 554 | | 553.72 |
| I-464 (5-{5-[(S)-3-(Cyclopentanecarbonyl-amino)-3-phenyl-propyl]-hexahydro-pyrrolo[3,4-c]pyrrole-2-carbonyl}-4,6-dimethyl-pyrimidin-2-yloxy)-acetic acid methyl ester | 564 | | 563.7 |
| I-465 Cyclopentanecarboxylic acid {(S)-3-[5-(2-benylamino-4,6-dimethyl-pyrimidine-5-carbonyl)-hexahydro-pyrrolo[3,4-c]pyrrol-2-yl]-1-phenyl-propyl}-amide; compound with trifluoro-acetic acid | 581 | | 580.77 |
| I-466 (5-{5-[(S)-3-(Cyclopentanecarbonyl-amino)-3-phenyl-propyl]-hexahydro-pyrrolo[3,4-c]pyrrole-2-carbonyl}-4,6-dimethyl-pyrimidin-2-yloxy)-acetic acid; compound with trifluoro-acetic acid | 550 | | 549.67 |
| I-467 Cyclopentanecarboxylic acid {(S)-3-[5-(2,4-dimethyl-6-oxo-6H-pyran-3-carbonyl)-hexahydro-pyrrolo[3,4-c]pyrrol-2-yl]-1-phenyl-propyl}-amide | 492 | 113.0–113.7 | 491.63 |
| I-468 Cyclopentanecarboxylic acid {(S)-1-phenyl-3-[5-(2,4,6-trimethyl-benzenesulfonyl)-hexahydro-pyrrolo[3,4-c]pyrrol-2-yl]-propyl}-amide | 524.6 | | 523.74 |
| I-469 Cyclopentanecarboxylic acid {(R)-3-[5-(2-dimethylamino-4,6-dimethyl-pyrimidine-5-carbonyl)-hexahydro-pyrrolo[3,4-c]pyrrol-2-yl]-1-phenyl-propyl}-amide; compound with trifluoro-acetic acid | 519 | | 518.7 |
| I-470 N-{(S)-3-[5-(4,6-Dimethyl-pyrimidine-5-carbonyl)-hexahydro-pyrrolo[3,4-c]pyrrol-2-yl]-1-phenyl-propyl}-3,4-difluoro-benzamide; compound with trifluoro-acetic acid | 520 | | 519.59 |
| I-471 Cyclobutanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 462 | | 461.61 |
| I-472 2-Cyclopentyl-N-{(S)-3-[5-(4,6-dimethyl-pyrimidine-5-carbonyl)-hexahydro-pyrrolo[3,4-c]pyrrol-2-yl]-1-phenyl-propyl}-acetamide; compound with trifluoro-acetic acid | 490 | | 489.66 |
| I-473 5-Methyl-thiophene-2-carboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 504 | | 503.67 |
| I-474 2-Oxo-thiazolidine-4-carboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 509 | | 508.64 |
| I-475 2-Cyclohexyl-N-{(S)-3-[5-(4,6-dimethyl-pyrimidine-5-carbonyl)-hexahydro-pyrrolo[3,4-c]pyrrol-2-yl]-1-phenyl-propyl}-acetamide; compound with trifluoro-acetic acid | 504 | | 503.69 |

TABLE 1-continued

| | | MS[1] | mp | MW |
|---|---|---|---|---|
| I-476 | 3,3-Difluoro-cyclobutanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 498 | | 497.59 |
| I-477 | 3-Oxo-cyclobutanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide compound with trifluoro-acetic acid | 476 | | 475.59 |
| I-478 | N-{(S)-3-[5-(4,6-Dimethyl-pyrimidine-5-carbonyl)-hexahydro-pyrrolo[3,4-c]pyrrol-2-yl]-1-phenyl-propyl}-3,4-difluoro-benzenesulfonamide; compound with trifluoro-acetic acid | 556 | | 555.65 |
| I-479 | Cyclopropanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 448 | | 447.58 |
| I-480 | Thiophene-2-carboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 490 | | 489.64 |
| I-481 | Tetrahydro-furan-3-carboxylic acid {(S)-3-[5-(3 methyl-benzofuran-2-carbonyl)-hexahydro-pyrrolo[3,4-c]pyrrol-2-yl]-1-phenyl-propyl}-amide; compound with trifluoro-acetic acid | 502 | | 501.62 |
| I-482 | Tetrahydro-furan-3-carboxylic acid {(S)-3-[5-(7 methoxy-3-methyl-1H-indole-2-carbonyl)-hexahydro-pyrrolo[3,4-c]pyrrol-2-yl]-1-phenyl-propyl}-amide; compound with trifluoro-acetic acid | 531 | | 530.67 |
| I-483 | Tetrahydro-pyran-3-carboxylic acid {(S)-3-[5-(4,6-dimethyl-pyrimidine-5-carbonyl)-hexahydro-pyrrolo[3,4-c]pyrrol-2-yl]-1-phenyl-propyl}-amide; compound with trifluoro-acetic acid | 492 | | 491.63 |
| I-484 | Cyclopentanecarboxylic acid [(S)-3-[5-(4,6-dimethyl-pyrimidine-5-carbonyl)-hexahydro-pyrrolo[3,4-c]pyrrol-2-yl]-1-(3-fluoro-phenyl)-propyl]-amide | 494 | | 493.62 |
| I-485 | 4,4-Difluoro-cyclohexanecarboxylic acid [(S)-3-[5-(4,6-dimethyl-pyrimidine-5-carbonyl)-hexahydro-pyrrolo[3,4-c]pyrrol-2-yl]-1-(3-fluoro-phenyl)-propyl]-amide | 544 | | 543.63 |
| I-486 | 4-Hydroxy-cyclohexanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide | 506.3 | | 505.66 |
| I-487 | 4-Hydroxy-cyclohexanecarboxylic acid {(S)-3-[5-(4,6-dimethyl-Pyrimidine-5-carbonyl)-hexahydro-pyrrolo[3,4-c]pyrrol-2-yl]-1-phenyl-propyl}-amide | 506.3 | | 505.66 |
| I-488 | 3,3-Difluoro-cyclobutanecarboxylic acid {(S)-3-[5-(2,4-dimethyl-pyridine-3-carbonyl)-hexahydro-pyrrolo[3,4-c]pyrrol-2-yl]-1-phenyl-propyl}-amide | 498 | | 496.6 |

Compounds of formula I wherein R[1] is aryl are conveniently prepared by an alkylation sequence depicted in Scheme 5. 2-Benzyl-octahydro-pyrrolo[3,4-c]pyrrole (4a) is acylated prior to debenzylation as depicted in Scheme 1. The acylation can be carried out by standard techniques described above. Procedures for hydrogenolysis of the benzyl protecting group (step 2) to afford 66 are well known in the art. In other embodiments of the invention 4a may be alkylated or sulfonylated prior to hydrogenolysis of the benzyl group as described above.

SCHEME 5

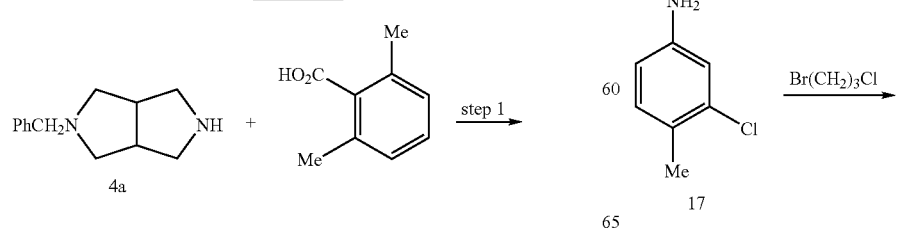

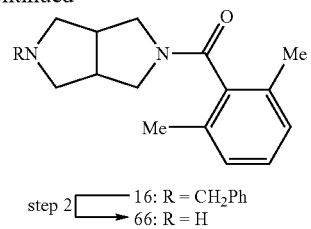

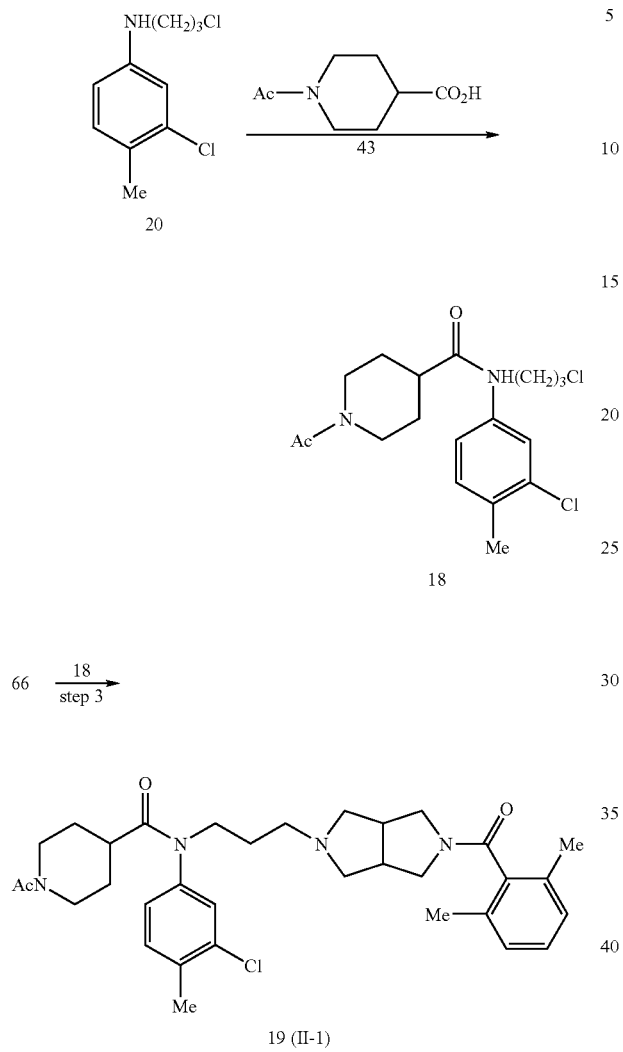

form) may be the nucleophile in a suitable solvent such as THF, DMF or 1,4-dioxane. Preferably the reaction is carried out by reacting the amine 17 and bromo-chloro-propane with either $K_2CO_3$ or $Cs_2CO_3$ dissolved in DMF or MeCN, DBU in MeCN or $K_2CO_3$ and 18-crown-6 (1,4,7,10,13,16-hexaoxacyclooctadecane) in THF. Potassium iodide is frequently added to allow for the in situ generation of an alkyl iodide. Optimal conditions for the alkylation may vary depending upon the nature of the reactants and one skilled in the art can optimize the specific reaction conditions without undue experimentation.

Acylation of the resulting secondary amine 20 by 1-acetyl-piperidine-4-carboxylic acid or the corresponding carboxylic acid chloride, or other carboxylic acids, is carried out by standard protocols as described previously. Urea and sulfonamide analogs are prepared by substituting an isocyanate or sulfonyl chloride for the carboxylic acid.

SCHEME 6

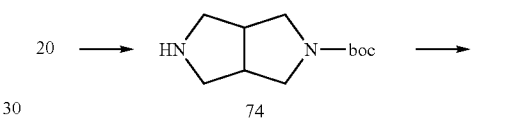

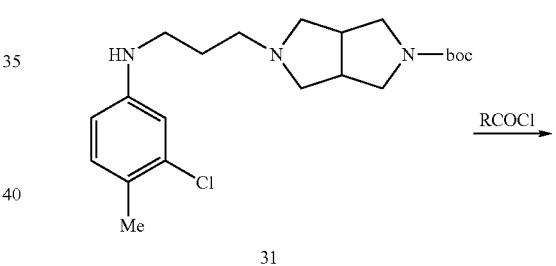

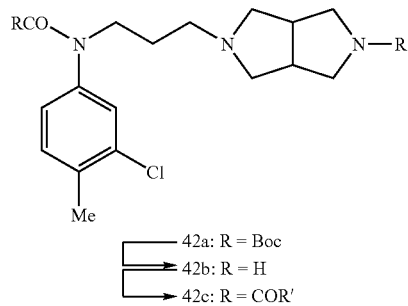

42a: R = Boc
42b: R = H
42c: R = COR'

1-Acetyl-piperidine-4-carboxylic acid (3-chloro-4-methyl-phenyl)-(3-chloro-propyl)-amide (18) was prepared by the general methodology disclosed by S. Imamura et al. (WO 01/25200). (Scheme 5) One skilled in the art will immediately recognize that 18 consists of a fragment derived from an aryl amine, a carboxylic acid and a difunctional alkylene chain. Substitution of other aryl or heteroaryl amines and other carboxylic acids readily affords analogs of 18 with other substitution on the aryl ring, with heteroaryl amines and with other acyl radicals.

Alkylation of an aryl amine 17 (or optionally a heteroaryl amine) with 1-bromo-3-chloropropane affords 20. The reaction may typically be carried out in the presence of a base such as TEA, DIPEA or DBU or an inorganic base such as $Na_2CO_3$, $NaHCO_3$, $K_2CO_3$ or $Cs_2CO_3$: optionally in the presence of a phase transfer catalyst, and in a solvent such as acetonitrile, DMF, DMSO, 1,4-dioxane, THF or toluene. While exemplified here with bromo-chloro-propane, other difunctional propylene compounds can also be employed. Alternatively, a metal salt of the amine (i.e. a deprotonated Alternative the aryl amine is sufficiently deactivated that alkylation of 74 or other octahydro-pyrrolo[3,4-c]pyrrole derivative can carried out directly with 20 without further modification of the aryl amine functionality to afford 31 which can further acylated. The reaction is exemplified in Scheme 6 utilizing a Boc protecting group which can be removed under acidic conditions for final elaboration of the compounds of the invention (conversion of 42a to 42c)

SCHEME 7

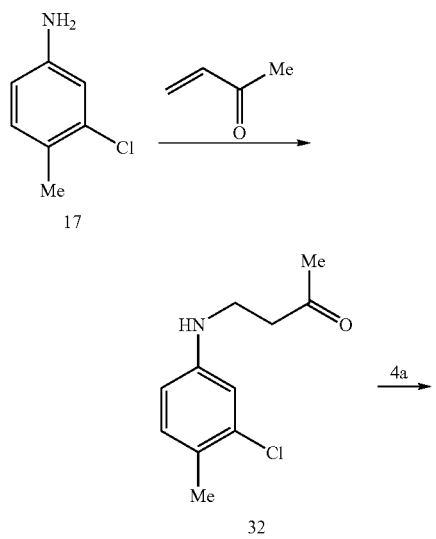

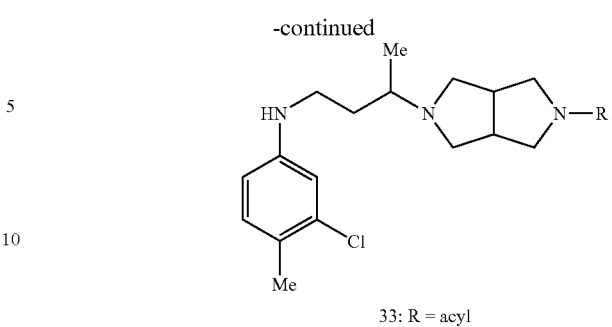

33: R = acyl

Methylation of the propylene linker can be achieved from butanone derivatives which are readily available by reacting an aryl or heteroaryl amine with methyl vinyl ketone (Scheme 7). Reductive alkylation of 32 and 66 (or other amide described herein) and acylation of 33 proceeds as described previously.

The synthesis of compounds wherein $R^6$ is other then hydrogen is exemplified in Examples 37, 38, 40 and 41.

Representative compounds of the present invention in which $R^1$ is an aryl or heteroaryl group are compiled in Table 2.

TABLE 2

|  | NAME | MS[1] | mp | MW |
|---|---|---|---|---|
| II-1 | 1-Acetyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}amide | 579 | 58.1–65.2 | 579.18 |
| II-2 | N-{3-[5-(2,6-Dimethyl-benzoyl)-hexahydro-pyrrolo[3,4-c]pyrrol-2-yl]-propyl}-N-(4-fluoro-phenyl)-benzenesulfonamide; compound with trifluoro-acetic acid | 536.6 |  | 535.68 |
| II-3 | 1-Acetyl-piperidine-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide | 580 | 91.8–96.9 | 580.17 |
| II-4 | 1-Acetyl-piperidine-4-carboxylic acid (3-chloro-4-methyl-phenyl)-{3-[5-(2,4-dimethyl-1-oxy-pyridine-3-carbonyl)-hexahydro-pyrrolo[3,4-c]pyrrol-2-yl]-propyl}-amide | 596 | 67.2–72.6 | 596.17 |
| II-5 | 4,4-Difluoro-cyclohexanecarboxylic acid {3-[5-(2-chloro-6-fluoro-benzoyl)-hexahydro-pyrrolo[3,4-c]pyrrol-2-yl]-propyl}-(3-chloro-4-methyl-phenyl)-amide; compound with trifluoro-acetic acid | 596 |  | 596.52 |
| II-6 | 1-Acetyl-piperidine-4-carboxylic acid [3-(5-benzyl-hexahydro-pyrrolo[3,4-c]pyrrol-2-yl)-propyl]-(3-chloro-4-methyl-phenyl)-amide | 537 |  | 537.14 |
| II-7 | 1-Acetyl-piperidine-4-carboxylic acid (3-chloro-4-methyl-phenyl)-{3-[5-(2,4,5-trimethyl-thiophene-3-carbonyl)-hexahydro-pyrrolo[3,4-c]pyrrol-2-yl]-propyl}-amide; compound with trifluoro-acetic acid | 599.3 |  | 599.24 |
| II-8 | 1-Acetyl-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 581.4 |  | 581.16 |
| II-9 | 1-Acetyl-piperidine-4-carboxylic acid (3-chloro-4-methyl-phenyl)-{3-[5-(2,6-difluoro-4-methoxy-benzoyl)-hexahydro-pyrrolo[3,4-c]pyrrol-2-yl]-propyl}-amide; compound with trifluoro-acetic acid | 617.4 |  | 617.13 |
| II-10 | 1-Acetyl-piperidine-4-carboxylic acid {3-[5-(2-chloro-6-fluoro-benzoyl)-hexahydro-pyrrolo[3,4-c]pyrrol-2-yl]-propyl}-(3-chloro-4-methyl-phenyl)-amide; compound with trifluoro-acetic acid | 603.3 |  | 603.56 |
| II-11 | 1-Acetyl-piperidine-4-carboxylic acid {3-[5-(2-chloro-6-methyl-benzoyl)-hexahydro-pyrrolo[3,4-c]pyrrol-2-yl]-propyl}-(3-chloro-4-methyl-phenyl)-amide; compound with trifluoro-acetic acid | 599.4 |  | 599.6 |

TABLE 2-continued

| | NAME | MS[1] | mp | MW |
|---|---|---|---|---|
| II-12 | 1-Acetyl-piperidine-4-carboxylic acid (3-chloro-4-methyl-phenyl)-{3-[5-(2,6-dichloro-4-methyl-benzoyl)-hexahydro-pyrrolo[3,4-c]pyrrol-2-yl]-propyl}-amide; compound with trifluoro-acetic acid | 633.3 | | 634.04 |
| II-13 | 1-Acetyl-piperidine-4-carboxylic acid (3-chloro-4-methyl-phenyl)-{3-[5-(2,4,6-trimethyl-benzoyl)-hexahydro-pyrrolo[3,4-c]pyrrol-2-yl]-propyl}-amide; compound with trifluoro-acetic acid | 593.4 | | 593.21 |
| II-14 | 1-Acetyl-piperidine-4-carboxylic acid (3-chloro-4-methyl-phenyl)-{3-[5-(3,5-dimethyl-isoxazole-4-carbonyl)-hexahydro-pyrrolo[3,4-c]pyrrol-2-yl]-propyl}-amide; compound with trifluoro-acetic acid | 570.4 | | 570.13 |
| II-15 | 1-Acetyl-piperidine-4-carboxylic acid (3-chloro-4-methyl-phenyl)-{3-[5-(2-dimethylamino-benzoyl)-hexahydro-pyrrolo[3,4-c]pyrrol-2-yl]-propyl}-amide; compound with trifluoro-acetic acid | 594.4 | | 594.2 |
| II-16 | 1-Acetyl-piperidine-4-carboxylic acid {3-[5-(4-chloro-2-methoxy-benzoyl)-hexahydro-pyrrolo[3,4-c]pyrrol-2-yl]-propyl}-(3-chloro-4-methyl-phenyl)-amide; compound with trifluoro-acetic acid | 615.4 | | 615.6 |
| II-17 | 1-Acetyl-piperidine-4-carboxylic acid {3-[5-(5-acetyl-2,4-dimethyl-1H-pyrrole-3-carbonyl)-hexahydro-pyrrolo[3,4-c]pyrrol-2-yl]-propyl}-(3-chloro-4-methyl-phenyl)-amide; compound with trifluoro-acetic acid | 610.5 | | 610.2 |
| II-18 | 4,4-Difluoro-cyclohexanecarboxylic acid (3-chloro-4-methyl-phenyl)-{3-[5-(2,4-dimethyl-1-oxy-pyridine-3-carbonyl)-hexahydro-pyrrolo[3,4-c]pyrrol-2-yl]-propyl}-amide | 589 | 67.0–74.1 | 589.12 |
| II-19 | 4,4-Difluoro-cyclohexanecarboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with hydrochloric acid | 573 | 152.4–161.3 | 573.12 |
| II-20 | Furan-2-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 521.4 | | 521.06 |
| II-21 | N-(3-Chloro-4-methyl-phenyl)-N-{3-[5-(2,4-dimethyl-pyridine-3-carbonyl)-hexahydro-pyrrolo[3,4-c]pyrrol-2-yl]-propyl}-isobutyramide; compound with trifluoro-acetic acid | 497.5 | | 497.08 |
| II-22 | Thiophene-2-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 537.4 | | 537.13 |
| II-23 | Cyclohexanecarboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 537.5 | | 537.14 |
| II-24 | Morpholine-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 540.5 | | 540.1 |
| II-25 | Isoxazole-5-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 522.4 | | 522.05 |
| II-26 | 4-Methyl-[1,2,3]thiadiazole-5-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 553.4 | | 553.13 |
| II-27 | Pyrrolidine-1-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 524.5 | | 524.11 |
| II-28 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3,3-dimethyl-urea; compound with trifluoro-acetic acid | 498.5 | | 498.07 |
| II-29 | N-(3-Chloro-4-methyl-phenyl)-N-{3-[5-(2,4-dimethyl-pyridine-3-carbonyl)-hexahydro-pyrrolo[3,4-c]pyrrol-2-yl]-propyl}-acetamide; compound with trifluoro-acetic acid | 496.4 | | 469.03 |

TABLE 2-continued

| | NAME | MS[1] | mp | MW |
|---|---|---|---|---|
| II-30 | N-(3-Chloro-4-methyl-phenyl)-2-cyclopentyl-N-{3-[5-(2,4-dimethyl-pyridine-3-carbonyl)-hexahydro-pyrrolo[3,4-c]pyrrol-2-yl]-propyl}-acetamide; compound with trifluoro-acetic acid | 537.5 | | 537.14 |
| II-31 | 3,5-Dimethyl-isoxazole-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 550.5 | | 550.1 |
| II-32 | N-(3-Chloro-4-methyl-phenyl)-N-{3-[5-(2,4-dimethyl-pyridine-3-carbonyl)-hexahydro-pyrrolo[3,4-c]pyrrol-2-yl]-propyl}-4-methanesulfonyl-benzamide; compound with trifluoro-acetic acid | 609.5 | | 609.19 |
| II-33 | Piperidine-1-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 538.5 | | 538.13 |
| II-34 | 1-Methyl-1H-pyrrole-2-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 534.5 | | 534.1 |
| II-35 | 1-(3-Chloro-4-methyl-phenyl)-3-(4-chloro-phenyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 580.4 | | 580.56 |
| II-36 | 1-Acetyl-piperidine-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-butyl}-amide | 594 | 60.9–62.4 | 594.2 |
| II-37 | 1-Acetyl-piperidine-4-carboxylic acid {3-[5-(2,4-dimethyl-pyridine-3-carbonyl)-hexahydro-pyrrolo[3,4-c]pyrrol-2-yl]-propyl}-p-tolyl-amide | 546 | 60.9–61.1 | 545.72 |
| II-38 | 1-Acetyl-piperidine-4-carboxylic acid (3-{5-[5-chloro-2-(2,5-dimethyl-pyrrol-1-yl)-benzoyl]-hexahydro-pyrrolo[3,4-c]pyrrol-2-yl}-propyl)-(3-chloro-4-methyl-phenyl)-amide; compound with trifluoro-acetic acid | 678.3 | | 678.7 |
| II-39 | 1-Acetyl-piperidine-4-carboxylic acid (3-chloro-4-methyl-phenyl)-{3-[5-(2-methyl-quinoline-3-carbonyl)-hexahydro-pyrrolo[3,4-c]pyrrol-2-yl]-propyl}-amide; compound with trifluoro-acetic acid | 616.3 | | 616.2 |
| II-40 | 1-Acetyl-piperidine-4-carboxylic acid (3-chloro-4-methyl-phenyl)-{3-[5-(2-chloro-4-methyl-6-pyrrolidin-1-yl-benzoyl)-hexahydro-pyrrolo[3,4-c]pyrrol-2-yl]-propyl}-amide; compound with trifluoro-acetic acid | 668.4 | | 668.71 |
| II-41 | 1-Acetyl-piperidine-4-carboxylic acid (3-chloro-4-methyl-phenyl)-(3-{5-[2-(1,1-dioxo-1$\lambda^6$-thiomorpholin-4-yl)-benzoyl]-hexahydro-pyrrolo[3,4-c]pyrrol-2-yl}-propyl)-amide; compound with trifluoro-acetic acid | 684.4 | | 684.3 |
| II-42 | 1-Acetyl-piperidine-4-carboxylic acid {3-[5-(3-bromo-2,6-dimethyl-benzoyl)-hexahydro-pyrrolo[3,4-c]pyrrol-2-yl]-propyl}-(3-chloro-4-methyl-phenyl)-amide; compound with trifluoro-acetic acid | 657.4 | | 658.08 |
| II-43 | 1-Acetyl-piperidine-4-carboxylic acid (3-chloro-4-methyl-phenyl)-{3-[5-(4,6-dimethyl-2-pyridin-4-yl-pyrimidine-5-carbonyl)-hexahydro-pyrrolo[3,4-c]pyrrol-2-yl]-propyl}-amide; compound with trifluoro-acetic acid | 658.5 | | 658.24 |
| II-44 | 5-{3-[(1-Acetyl-piperidine-4-carbonyl)-(3-chloro-4-methyl-phenyl)-amino]-propyl}-hexahydro-pyrrolo[3,4-c]pyrrole-2-carboxylic acid (2-isopropyl-phenyl)-amide; compound with trifluoro-acetic acid | 608.5 | | 608.22 |
| II-45 | 5-{3-[(1-Acetyl-piperidine-4-carbonyl)-(3-chloro-4-methyl-phenyl)-amino]-propyl}-hexahydro-pyrrolo[3,4-c]pyrrole-2-carboxylic acid (2,6-dimethyl-phenyl)-amide; compound with trifluoro-acetic acid | 594.5 | | 594.2 |
| II-46 | 1-Acetyl-piperidine-4-carboxylic acid (3-chloro-4-methyl-phenyl)-{3-[5-(2,4,6-trimethyl-benzenesulfonyl)-hexahydro-pyrrolo[3,4-c]pyrrol-2-yl]-propyl}-amide; compound with trifluoro-acetic acid | 629.5 | | 629.26 |
| II-47 | 1-Acetyl-piperidine-4-carboxylic acid (3-chloro-4-methyl-phenyl)-{3-[5-(thiophene-2-sulfonyl)-hexahydro-pyrrolo[3,4-c]pyrrol-2-yl]-propyl}-amide; compound with trifluoro-acetic acid | 593.4 | | 593.21 |

TABLE 2-continued

| | NAME | MS[1] | mp | MW |
|---|---|---|---|---|
| II-48 | 1-Acetyl-piperidine-4-carboxylic acid (3-chloro-4-methyl-phenyl)-{3-[5-(3,5-dimethyl-isoxazole-4-sulfonyl)-hexahydro-pyrrolo[3,4-c]pyrrol-2-yl]-propyl}-amide; compound with trifluoro-acetic acid | 606.5 | | 606.18 |
| II-49 | 1-Acetyl-piperidine-4-carboxylic acid {3-[5-(5-chloro-1,3-dimethyl-1H-pyrazole-4-sulfonyl)-hexahydro-pyrrolo[3,4-c]pyrrol-2-yl]-propyl}-(3-chloro-4-methyl-phenyl)-amide; compound with trifluoro-acetic acid | 639.5 | | 639.65 |
| II-50 | 4-(5-{3-[(1-Acetyl-piperidine-4-carbonyl)-(3-chloro-4-methyl-phenyl)-amino]-propyl}-hexahydro-pyrrolo[3,4-c]pyrrole-2-sulfonyl)-2,5-dimethyl-furan-3-carboxylic acid methyl ester; compound with trifluoro-acetic acid | 663.6 | | 663.23 |
| II-51 | 1-Acetyl-piperidine-4-carboxylic acid (3-chloro-4-methyl-phenyl)-{3-[5-(1,3,5-trimethyl-1H-pyrazole-4-sulfonyl)-hexahydro-pyrrolo[3,4-c]pyrrol-2-yl]-propyl}-amide; compound with trifluoro-acetic acid | 619.6 | | 619.23 |
| II-52 | 1-Acetyl-piperidine-4-carboxylic acid {3-[5-(1-acetyl-piperidine-4-carbonyl)-hexahydro-pyrrolo[3,4-c]pyrrol-2-yl]-propyl}-(3-chloro-4-methyl-phenyl)-amide; compound with trifluoro-acetic acid | 600.6 | | 600.2 |
| II-53 | 1-Acetyl-piperidine-4-carboxylic acid (3-chloro-4-methyl-phenyl)-{3-[5-(4-cyano-benzoyl)-hexahydro-pyrrolo[3,4-c]pyrrol-2-yl]-propyl}-amide; compound with trifluoro-acetic acid | 576.5 | | 576.14 |
| II-54 | 1-Acetyl-piperidine-4-carboxylic acid (3-chloro-4-methyl-phenyl)-{3-[5-(2,6-dimethoxy-benzoyl)-hexahydro-pyrrolo[3,4-c]pyrrol-2-yl]-propyl}-amide; compound with trifluoro-acetic acid | 611.6 | | 611.18 |
| II-55 | 1-Acetyl-piperidine-4-carboxylic acid (3-chloro-4-methyl-phenyl)-{3-[5-(2,4-dimethyl-benzoyl)-hexahydro-pyrrolo[3,4-c]pyrrol-2-yl]-propyl}-amide; compound with trifluoro-acetic acid | 579.6 | | 579.18 |
| II-56 | 1-Acetyl-piperidine-4-carboxylic acid (3-chloro-4-methyl-phenyl)-{3-[5-(furan-2-carbonyl)-hexahydro-pyrrolo[3,4-c]pyrrol-2-yl]-propyl}-amide; compound with trifluoro-acetic acid | 541.5 | | 541.09 |
| II-57 | 1-Acetyl-piperidine-4-carboxylic acid (3-chloro-4-methyl-phenyl)-{3-[5-(furan-3-carbonyl)-hexahydro-pyrrolo[3,4-c]pyrrol-2-yl]-propyl}-amide; compound with trifluoro-acetic acid | 541.5 | | 541.09 |
| II-58 | 1-Acetyl-piperidine-4-carboxylic acid (3-chloro-4-methyl-phenyl)-{3-[5-(pyridine-4-carbonyl)-hexahydro-pyrrolo[3,4-c]pyrrol-2-yl]-propyl}-amide; compound with trifluoro-acetic acid | 552.5 | | 552.12 |
| II-59 | 3-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-benzoic acid methyl ester; compound with trifluoro-acetic acid | 609.6 | | 609.16 |
| II-60 | 4-((3-Chloro-4-methyl-phenyl)-{3-[5-(2,6-dimethyl-benzoyl)-hexahydro-pyrrolo[3,4-c]pyrrol-2-yl]-propyl}-carbamoyl)-piperidine-1-carboxylic acid tert-butyl ester | 637.6 | | 637.26 |
| II-61 | Piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide | 537.5 | | 537.14 |
| II-62 | 1-Acetyl-piperidine-4-carboxylic acid {3-[5-(2,4-dimethyl-pyridine-3-carbonyl)-hexahydro-pyrrolo[3,4-c]pyrrol-2-yl]-propyl}-phenyl-amide | 532 | 60.1–61.1 | 531.7 |
| II-63 | 1-Acetyl-piperidine-4-carboxylic acid (3-chloro-4-methyl-phenyl)-{3-[5-(4-methanesulfonyl-benzoyl)-hexahydro-pyrrolo[3,4-c]pyrrol-2-yl]-propyl}-amide; compound with trifluoro-acetic acid | 629.2 | | 629.22 |
| II-64 | 4-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-benzoic acid methyl ester; compound with trifluoro-acetic acid | 609.3 | | 609.16 |
| II-65 | 1-Acetyl-piperidine-4-carboxylic acid (3-chloro-4-methyl-phenyl)-{3-[5-(1H-pyrrole-2-carbonyl)-hexahydro-pyrrolo[3,4-c]pyrrol-2-yl]-propyl}-amide; compound with trifluoro-acetic acid | 540.4 | | 540.1 |
| II-66 | 1-Acetyl-piperidine-4-carboxylic acid (3-chloro-4-methyl-phenyl)-{3-[5-(2-methyl-benzoyl)-hexahydro-pyrrolo[3,4-c]pyrrol-2-yl]-propyl}-amide; compound with trifluoro-acetic acid | 565.4 | | 565.15 |

TABLE 2-continued

| | NAME | MS[1] | mp | MW |
|---|---|---|---|---|
| II-67 | 1-Acetyl-piperidine-4-carboxylic acid (3-chloro-4-methyl-phenyl)-{3-[5-(2-trifluoromethyl-benzoyl)-hexahydro-pyrrolo[3,4-c]pyrrol-2-yl]-propyl}-amide; compound with trifluoro-acetic acid | 619.5 | | 619.12 |
| II-68 | 1-Acetyl-piperidine-4-carboxylic acid (3-chloro-4-methyl-phenyl)-{3-[5-(5-methyl-thiophene-2-carbonyl)-hexahydro-pyrrolo[3,4-c]pyrrol-2-yl]-propyl}-amide; compound with trifluoro-acetic acid | 571.5 | | 571.18 |
| II-69 | 1-Acetyl-piperidine-4-carboxylic acid (3-chloro-4-methyl-phenyl)-{3-[5-(1-methyl-1H-pyrrole-2-carbonyl)-hexahydro-pyrrolo[3,4-c]pyrrol-2-yl]-propyl}-amide; compound with trifluoro-acetic acid | 554.5 | | 554.13 |
| II-70 | 1-Acetyl-piperidine-4-carboxylic acid (3-chloro-4-methyl-phenyl)-{3-[5-(thiophene-3-carbonyl)-hexahydro-pyrrolo[3,4-c]pyrrol-2-yl]-propyl}-amide; compound with trifluoro-acetic acid | 557.5 | | 557.16 |
| II-71 | 1-Acetyl-piperidine-4-carboxylic acid (3-chloro-4-methyl-phenyl)-{3-[5-(pyridine-2-carbonyl)-hexahydro-pyrrolo[3,4-c]pyrrol-2-yl]-propyl}-amide; compound with trifluoro-acetic acid | 552.5 | | 552.12 |
| II-72 | 1-Acetyl-piperidine-4-carboxylic acid (3-chloro-4-methyl-phenyl)-{3-[5-(2-methylamino-benzoyl)-hexahydro-pyrrolo[3,4-c]pyrrol-2-yl]-propyl}-amide; compound with trifluoro-acetic acid | 580.6 | | 580.17 |
| II-73 | 1-Acetyl-piperidine-4-carboxylic acid (3-chloro-4-methyl-phenyl)-{3-[5-(4-methoxy-2,6-dimethyl-benzoyl)-hexahydro-pyrrolo[3,4-c]pyrrol-2-yl]-propyl}-amide; compound with trifluoro-acetic acid | 609.6 | | 609.21 |
| II-74 | 1-Acetyl-piperidine-4-carboxylic acid (3-chloro-4-methyl-phenyl)-{3-[5-(2-ethyl-5-methyl-2H-pyrazole-3-carbonyl)-hexahydro-pyrrolo[3,4-c]pyrrol-2-yl]-propyl}-amide; compound with trifluoro-acetic acid | 583.6 | | 583.17 |
| II-75 | 1-Acetyl-piperidine-4-carboxylic acid (3-chloro-4-methyl-phenyl)-{3-[5-(2-methyl-pyridine-3-carbonyl)-hexahydro-pyrrolo[3,4-c]pyrrol-2-yl]-propyl}-amide; compound with trifluoro-acetic acid | 566.5 | | 566.14 |
| II-76 | 1-Acetyl-piperidine-4-carboxylic acid (3-chloro-4-methyl-phenyl)-{3-[5-(3-methyl-furan-2-carbonyl)-hexahydro-pyrrolo[3,4-c]pyrrol-2-yl]-propyl}-amide; compound with trifluoro-acetic acid | 555.5 | | 555.12 |
| II-77 | 1-Acetyl-piperidine-4-carboxylic acid (3-chloro-4-methyl-phenyl)-{3-[5-(pyridine-3-carbonyl)-hexahydro-pyrrolo[3,4-c]pyrrol-2-yl]-propyl}-amide; compound with trifluoro-acetic acid | 552.5 | | 555.12 |
| II-78 | 1-Acetyl-piperidine-4-carboxylic acid (3-chloro-4-methyl-phenyl)-{3-[5-(3-fluoro-2-methyl-benzoyl)-hexahydro-pyrrolo[3,4-c]pyrrol-2-yl]-propyl}-amide; compound with trifluoro-acetic acid | 583.6 | | 583.14 |
| II-79 | 1-Acetyl-piperidine-4-carboxylic acid (3-chloro-4-methyl-phenyl)-{3-[5-(2,6-difluoro-benzoyl)-hexahydro-pyrrolo[3,4-c]pyrrol-2-yl]-propyl}-amide; compound with trifluoro-acetic acid | 587.6 | | 587.11 |
| II-80 | 1-Acetyl-piperidine-4-carboxylic acid{3-[5-(2-chloro-benzoyl)-hexahydro-pyrrolo[3,4-c]pyrrol-2-yl]-propyl}-(3-chloro-4-methyl-phenyl)-amide; compound with trifluoro-acetic acid | 585.5 | | 585.57 |
| II-81 | 1-Acetyl-piperidine-4-carboxylic acid (3-chloro-4-methyl-phenyl)-{3-[5-(3H-imidazole-4-carbonyl)-hexahydro-pyrrolo[3,4-c]pyrol-2-yl]-propyl}-amide; compound with trifluoro-acetic acid | 541.5 | | 541.09 |
| II-82 | 1-Acetyl-piperidine-4-carboxylic acid (3-chloro-4-methyl-phenyl)-{3-[5-(5-methyl-isoxazole-4-carbonyl)-hexahydro-pyrrolo[3,4-c]pyrrol-2-yl]-propyl}-amide; compound with trifluoro-acetic acid | 556.5 | | 556.1 |
| II-83 | 1-Acetyl-piperidine-4-carboxylic acid (3-chloro-4-methyl-phenyl)-{3-[5-(2-methyl-thiazole-4-carbonyl)-hexahydro-pyrrolo[3,4-c]pyrrol-2-yl]-propyl}-amide; compound with trifluoro-acetic acid | 572.5 | | 572.17 |
| II-84 | 1-Acetyl-piperidine-4-carboxylic acid (3-chloro-4-methyl-phenyl)-{3-[5-(1-methyl-1H-pyrazole-3-carbonyl)-hexahydro-pyrrolo[3,4-c]pyrrol-2-yl]-propyl}-amide; compound with trifluoro-acetic acid | 555.6 | | 555.12 |
| II-85 | 1-Acetyl-piperidine-4-carboxylic acid (3-chloro-4-methyl-phenyl)-{3-[5-(tetrahydro-furan-2-carbonyl)-hexahydro-pyrrolo[3,4-c]pyrrol-2-yl]-propyl}-amide; compound with trifluoro-acetic acid | 545.5 | | 545.12 |

TABLE 2-continued

| | NAME | MS[1] | mp | MW |
|---|---|---|---|---|
| II-86 | 1-Acetyl-piperidine-4-carboxylic acid (3-chloro-4-methyl-phenyl)-{3-[5-(4-methoxy-thiophene-3-carbonyl)-hexahydro-pyrrolo[3,4-c]pyrrol-2-yl]-propyl}-amide; compound with trifluoro-acetic acid | 587.5 | | 587.18 |
| II-87 | 1-Acetyl-piperidine-4-carboxylic acid (3-chloro-4-methyl-phenyl)-{3-[5-(2-methoxy-benzoyl)-hexahydro-pyrrolo[3,4-c]pyrrol-2-yl]-propyl}-amide; compound with trifluoro-acetic acid | 581.5 | | 581.15 |
| II-88 | 1-Acetyl-piperidine-4-carboxylic acid (3-chloro-4-methyl-phenyl)-{3-[5-(4-dimethylamino-benzoyl)-hexahydro-pyrrolo[3,4-c]pyrrol-2-yl]-propyl}-amide; compound with trifluoro-acetic acid | 594.6 | | 594.2 |
| II-89 | 1-Acetyl-piperidine-4-carboxylic acid (3-chloro-4-methyl-phenyl)-{3-[5-(isoquinoline-1-carbonyl)-hexahydro-pyrrolo[3,4-c]pyrrol-2-yl]-propyl}-amide; compound with trifluoro-acetic acid | 602.5 | | 602.18 |
| II-90 | 1-Acetyl-piperidine-4-carboxylic acid (3-chloro-4-methyl-phenyl)-{3-[5-(2-methyl-cyclohexanecarbonyl)-hexahydro-pyrrolo[3,4-c]pyrrol-2-yl]-propyl}-amide; compound with trifluoro-acetic acid | 571.6 | | 571.2 |
| II-91 | 1-Acetyl-piperidine-4-carboxylic acid (3-chloro-4-methyl-phenyl)-{3-[5-(quinoline-2-carbonyl)-hexahydro-pyrrolo[3,4-c]pyrrol-2-yl]-propyl}-amide; compound with trifluoro-acetic acid | 602.5 | | 602.18 |
| II-92 | 1-Acetyl-piperidine-4-carboxylic acid (3-chloro-4-methyl-phenyl)-{3-[5-(1H-indole-2-carbonyl)-hexahydro-pyrrolo[3,4-c]pyrrol-2-yl]-propyl}-amide; compound with trifluoro-acetic acid | 590.5 | | 590.16 |
| II-93 | 1-Acetyl-piperidine-4-carboxylic acid {3-[5-(benzofuran-2-carbonyl)-hexahydro-pyrrolo[3,4-c]pyrrol-2-yl]-propyl}-(3-chloro-4-methyl-phenyl)-amide; compound with trifluoro-acetic acid | 591.3 | | 591.15 |
| II-94 | 1-Acetyl-piperidine-4-carboxylic acid {3-[5-(benzo[b]thiophene-2-carbonyl)-hexahydro-pyrrolo[3,4-c]pyrrol-2-yl]-propyl}-(3-chloro-4-methyl-phenyl)-amide; compound with trifluoro-acetic acid | 607.4 | | 607.22 |
| II-95 | 1-Acetyl-piperidine-4-carboxylic acid (3-chloro-4-methyl-phenyl)-{3-[5-(1-methyl-1H-indole-2-carbonyl)-hexahydro-pyrrolo[3,4-c]pyrrol-2-yl]-propyl}-amide; compound with trifluoro-acetic acid | 604.4 | | 604.19 |
| II-96 | 1-Acetyl-piperidine-4-carboxylic acid (3-chloro-4-methyl-phenyl)-{3-[5-(2-methoxy-3-methyl-benzoyl)-hexahydro-pyrrolo[3,4-c]pyrrol-2-yl]-propyl}-amide; compound with trifluoro-acetic acid | 595.5 | | 595.18 |
| II-97 | 1-Acetyl-piperidine-4-carboxylic acid (3-chloro-4-methyl-phenyl)-{3-[5-(1H-indole-5-carbonyl)-hexahydro-pyrrolo[3,4-c]pyrrol-2-yl]-propyl}-amide; compound with trifluoro-acetic acid | 590.5 | | 590.16 |
| II-98 | 1-Acetyl-piperidine-4-carboxylic acid (3-chloro-4-methyl-phenyl)-{3-[5-(3-chloro-thiophene-2-carbonyl)-hexahydro-pyrrolo[3,4-c]pyrrol-2-yl]-propyl}-amide; compound with trifluoro-acetic acid | 591.5 | | 591.6 |
| II-99 | 1-Acetyl-piperidine-4-carboxylic acid (3-chloro-4-methyl-phenyl)-{3-[5-(2-methyl-5-phenyl-furan-3-carbonyl)-hexahydro-pyrrolo[3,4-c]pyrrol-2-yl]-propyl}-amide; compound with trifluoro-acetic acid | 631.6 | | 631.21 |
| II-100 | 1-Acetyl-piperidine-4-carboxylic acid (3-chloro-4-methyl-phenyl)-{3-[5-(5-fluoro-2-methyl-benzoyl)-hexahydro-pyrrolo[3,4-c]pyrrol-2-yl]-propyl}-amide; compound with trifluoro-acetic acid | 583.6 | | 583.14 |
| II-101 | 1-Acetyl-piperidine-4-carboxylic acid {3-[5-(1-benzyl-3,5-dimethyl-1H-pyrazole-4-carbonyl)-hexahydro-pyrrolo[3,4-c]pyrrol-2-yl]-propyl}-(3-chloro-4-methyl-phenyl)-amide; compound with trifluoro-acetic acid | 659.7 | | 659.27 |
| II-102 | 1-Acetyl-piperidine-4-carboxylic acid (3-chloro-4-methyl-phenyl)-{3-[5-(2,4,6-trimethoxy-benzoyl)-hexahydro-pyrrolo[3,4-c]pyrrol-2-yl]-propyl}-amide; compound with trifluoro-acetic acid | 641.6 | | 641.21 |
| II-103 | 1-Acetyl-piperidine-4-carboxylic acid {3-[5-(3-chloro-2,6-dimethoxy-benzoyl)-hexahydro-pyrrolo[3,4-c]pyrrol-2-yl]-propyl}-(3-chloro-4-methyl-phenyl)-amide; compound with trifluoro-acetic acid | 645.6 | | 645.62 |

TABLE 2-continued

| | NAME | MS[1] | mp | MW |
|---|---|---|---|---|
| II-104 | 1-Acetyl-piperidine-4-carboxylic acid (3-chloro-4-methyl-phenyl)-{3-[5-(3,5-dimethyl-1-phenyl-1H-pyrazole-4-carbonyl)-hexahydro-pyrrolo[3,4-c]pyrrol-2-yl]-propyl}-amide; compound with trifluoro-acetic acid | 645.6 | | 645.24 |
| II-105 | 1-Acetyl-piperidine-4-carboxylic acid (3-chloro-4-methyl-phenyl)-{3-[5-(2,6-difluoro-3-methyl-benzoyl)-hexahydro-pyrrolo[3,4-c]pyrrol-2-yl]-propyl}-amide; compound with trifluoro-acetic acid | 601.6 | | 601.13 |
| II-106 | 1-Acetyl-piperidine-4-carboxylic acid (3-chloro-4-methyl-phenyl)-{3-[5-(2-fluoro-6-trifluoromethyl-benzoyl)-hexahydro-pyrrolo[3,4-c]pyrrol-2-yl]-propyl}-amide; compound with trifluoro-acetic acid | 637.6 | | 637.11 |
| II-107 | 1-Acetyl-piperidine-4-carboxylic acid {3-[5-(6-chloro-2-fluoro-3-methyl-benzoyl)-hexahydro-pyrrolo[3,4-c]pyrrol-2-yl]-propyl}-(3-chloro-4-methyl-phenyl)-amide; compound with trifluoro-acetic acid | 617.6 | | 617.59 |
| II-108 | 1-Acetyl-piperidine-4-carboxylic acid {3-[5-(2-chloro-6-fluoro-3-methyl-benzoyl)-hexahydro-pyrrolo[3,4-c]pyrrol-2-yl]-propyl}-(3-chloro-4-methyl-phenyl)-amide; compound with trifluoro-acetic acid | 617.5 | | 617.59 |
| II-109 | 1-Acetyl-piperidine-4-carboxylic acid (3-chloro-4-methyl-phenyl)-{3-[5-(2,4,6-trifluoro-benzoyl)-hexahydro-pyrrolo[3,4-c]pyrrol-2-yl]-propyl}-amide; compound with trifluoro-acetic acid | 605.5 | | 605.1 |
| II-110 | 1-Acetyl-piperidine-4-carboxylic acid {3-[5-(3-chloro-2-fluoro-6-trifluoromethyl-benzoyl)-hexahydro-pyrrolo[3,4-c]pyrrol-2-yl]-propyl}-(3-chloro-4-methyl-phenyl)-amide; compound with trifluoro-acetic acid | 671.6 | | 671.56 |
| II-111 | 1-Methanesulfonyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide; compound with trifluoro-acetic acid | 615.6 | | 615.24 |
| II-112 | 1-Cyclopropanecarbonyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide; compound with trifluoro-acetic acid | 605.6 | | 605.22 |
| II-113 | Piperidine-1,4-dicarboxylic acid 4-((3-chloro-4-methyl-phenyl)-{3-[5-(2,6-dimethyl-benzoyl)-hexahydro-pyrrolo[3,4-c]pyrrol-2-yl]-propyl}-amide) 1-dimethylamide; compound with trifluoro-acetic acid | 608.6 | | 608.22 |
| II-114 | Piperidine-1,4-dicarboxylic acid 4-((3-chloro-4-methyl-phenyl)-{3-[5-(2,6-dimethyl-benzoyl)-hexahydro-pyrrolo[3,4-c]pyrrol-2-yl]-propyl}-amide) 1-ethylamide; compound with trifluoro-acetic acid | 608.6 | | 608.22 |
| II-115 | 1-Dimethylsulfamoyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide; compound with trifluoro-acetic acid | 644.6 | | 644.28 |
| II-116 | 1-(2,2,2-Trifluoro-acetyl)-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide; compound with trifluoro-acetic acid | 633.5 | | 633.15 |
| II-117 | 1-Acetyl-piperidine-4-carboxylic acid {3-[5-(2,6-dimethyl-benzoyl)-hexahydro-pyrrolo[3,4-c]pyrrol-2-yl]-propyl}-pyridin-2-yl-amide | 532.5 | | 531.7 |
| II-118 | 1-Acetyl-piperidine-4-carboxylic acid (3,4-dichloro-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 600 | | 600.59 |
| II-119 | 1-Acetyl-piperidine-4-carboxylic acid {3-[5-(5-amino-1-phenyl-1H-pyrazole-4-carbonyl)-hexahydro-pyrrolo[3,4-c]pyrrol-2-yl]-propyl}-(3-chloro-4-methyl-phenyl)-amide; compound with trifluoro-acetic acid | 632.5 | | 632.21 |
| II-120 | 1-Acetyl-piperidine-4-carboxylic acid (3-{5-[5-amino-1-(4-methoxy-phenyl)-1H-pyrazole-4-carbonyl]-hexahydro-pyrrolo[3,4-c]pyrrol-2-yl}-propyl)-(3-chloro-4-methyl-phenyl)-amide; compound with trifluoro-acetic acid | 662.5 | | 662.23 |

TABLE 2-continued

| | NAME | MS[1] | mp | MW |
|---|---|---|---|---|
| II-121 | 1-Acetyl-piperidine-4-carboxylic acid (3-chloro-4-methyl-phenyl)-{3-[5-(1-phenyl-5-trifluoromethyl-1H-pyrazole-4-carbonyl)-hexahydro-pyrrolo[3,4-c]pyrrol-2-yl]-propyl}-amide; compound with trifluoro-acetic acid | 685.5 | | 685.19 |
| II-122 | 1-Acetyl-piperidine-4-carboxylic acid (3-chloro-4-methyl-phenyl)-(3-{5-[1-(4-methoxy-phenyl)-5-trifluoromethyl-1H-pyrazole-4-carbonyl]-hexahydro-pyrrolo[3,4-c]pyrrol-2-yl}-propyl)-amide; compound with trifluoro-acetic acid | 715.5 | | 715.21 |
| II-123 | 1-Acetyl-piperidine-4-carboxylic acid (3-chloro-4-methyl-phenyl)-(3-{5-[1-(2-methoxy-phenyl)-5-trifluoromethyl-1H-pyrazole-4-carbonyl]-hexahydro-pyrrolo[3,4-c]pyrrol-2-yl}-propyl)-amide; compound with trifluoro-acetic acid | 715.5 | | 715.21 |
| II-124 | 1-Acetyl-piperidine-4-carboxylic acid (3-chloro-4-methyl-phenyl)-(3-{5-[1-(4-chloro-phenyl)-5-trifluoromethyl-1H-pyrazole-4-carbonyl]-hexahydro-pyrrolo[3,4-c]pyrrol-2-yl}-propyl)-amide; compound with trifluoro-acetic acid | 719.5 | | 719.63 |
| II-125 | 1-Acetyl-piperidine-4-carboxylic acid (3-chloro-4-methyl-phenyl)-{3-[5-(1-p-tolyl-5-trifluoromethyl-1H-pyrazole-4-carbonyl)-hexahydro-pyrrolo[3,4-c]pyrrol-2-yl]-propyl}-amide; compound with trifluoro-acetic acid | 699.5 | | 699.21 |
| II-126 | 1-Acetyl-piperidine-4-carboxylic acid (3-chloro-4-methyl-phenyl)-(3-{5-[1-(4-fluoro-phenyl)-5-trifluoromethyl-1H-pyrazole-4-carbonyl]-hexahydro-pyrrolo[3,4-c]pyrrol-2-yl}-propyl)-amide; compound with trifluoro-acetic acid | 703.5 | | 703.18 |
| II-127 | 1-Acetyl-piperidine-4-carboxylic acid {3-[5-(5-amino-1-p-tolyl-1H-pyrazole-4-carbonyl)-hexahydro-pyrrolo[3,4-c]pyrrol-2-yl]-propyl}-(3-chloro-4-methyl-phenyl)-amide; compound with trifluoro-acetic acid | 646.5 | | 646.23 |
| II-128 | 1-Acetyl-piperidine-4-carboxylic acid (3-{5-[5-amino-1-(4-fluoro-phenyl)-1H-pyrazole-4-carbonyl]-hexahydro-pyrrolo[3,4-c]pyrrol-2-yl}-propyl)-(3-chloro-4-methyl-phenyl)-amide; compound with trifluoro-acetic acid | 650.5 | | 650.2 |
| II-129 | 1-Acetyl-piperidine-4-carboxylic acid (3-chloro-4-methyl-phenyl)-{3-[5-(5-methyl-1-phenyl-1H-pyrazole-4-carbonyl)-hexahydro-pyrrolo[3,4-c]pyrrol-2-yl]-propyl}-amide; compound with trifluoro-acetic acid | 631.5 | | 631.22 |
| II-130 | 1-Acetyl-piperidine-4-carboxylic acid (3-chloro-4-methyl-phenyl)-{3-[5-(5-methyl-1-p-tolyl-1H-pyrazole-4-carbonyl)-hexahydro-pyrrolo[3,4-c]pyrrol-2-yl]-propyl}-amide; compound with trifluoro-acetic acid | 645.5 | | 645.24 |
| II-131 | 1-Acetyl-piperidine-4-carboxylic acid (3-chloro-4-methyl-phenyl)-{3-[5-(5-methyl-2-p-tolyl-2H-pyrazole-3-carbonyl)-hexahydro-pyrrolo[3,4-c]pyrrol-2-yl]-propyl}-amide; compound with trifluoro-acetic acid | 645.5 | | 645.24 |
| II-132 | 1-Acetyl-piperidine-4-carboxylic acid (3-chloro-4-methyl-phenyl)-(3-{5-[2-(4-methoxy-phenyl)-5-methyl-2H-pyrazole-3-carbonyl]-hexahydro-pyrrolo[3,4-c]pyrrol-2-yl}-propyl)-amide; compound with trifluoro-acetic acid | 661.5 | | 661.24 |
| II-133 | 1-Acetyl-piperidine-4-carboxylic acid (3-chloro-4-methyl-phenyl)-{3-[5-(2-methyl-4,5,6,7-tetrahydro-benzofuran-3-carbonyl)-hexahydro-pyrrolo[3,4-c]pyrrol-2-yl]-propyl}-amide; compound with trifluoro-acetic acid | 609.5 | | 609.21 |
| II-134 | 1-Acetyl-piperidine-4-carboxylic acid {3-[5-(2,6-dimethyl-benzoyl)-hexahydro-pyrrolo[3,4-c]pyrrol-2-yl]-propyl}-phenyl-amide | 531 | | 530.71 |
| II-135 | 1-Acetyl-piperidine-4-carboxylic acid {3-[5-(2-bromo-pyridine-3-carbonyl)-hexahydro-pyrrolo[3,4-c]pyrrol-2-yl]-propyl}-(3-chloro-4-methyl-phenyl)-amide; compound with trifluoro-acetic acid | 632.3 | | 631.01 |
| II-136 | 1-Acetyl-piperidine-4-carboxylic acid {3-[5-(2-acetylamino-4-fluoro-benzoyl)-hexahydro-pyrrolo[3,4-c]pyrrol-2-yl]-propyl}-(3-chloro-4-methyl-phenyl)-amide; compound with trifluoro-acetic acid | 626.4 | | 626.17 |

TABLE 2-continued

| | NAME | MS[1] | mp | MW |
|---|---|---|---|---|
| II-137 | 1-Acetyl-piperidine-4-carboxylic acid (3-chloro-4-methyl-phenyl)-{3-[5-(2-fluoro-pyridine-3-carbonyl)-hexahydro-pyrrolo[3,4-c]pyrrol-2-yl]-propyl}-amide; compound with trifluoro-acetic acid | 570.3 | | 570.11 |
| II-138 | 1-Acetyl-piperidine-4-carboxylic acid (3-chloro-4-methyl-phenyl)-{3-[5-(3-chloro-pyridine-4-carbonyl)-hexahydro-pyrrolo[3,4-c]pyrrol-2-yl]-propyl}-amide; compound with trifluoro-acetic acid | 586.3 | | 586.56 |
| II-139 | 1-Acetyl-piperidine-4-carboxylic acid (3-chloro-4-methyl-phenyl)-{3-[5-(2-methoxy-pyridine-3-carbonyl)-hexahydro-pyrrolo[3,4-c]pyrrol-2-yl]-propyl}-amide; compound with trifluoro-acetic acid | 582.3 | | 582.14 |
| II-140 | 1-Acetyl-piperidine-4-carboxylic acid (3-chloro-4 methyl-phenyl)-{3-[5-(2-methanesulfonyl-benzoyl)-hexahydro-pyrrolo[3,4-c]pyrrol-2-yl]-propyl}-amide; compound with trifluoro-acetic acid | 629.3 | | 629.22 |
| II-141 | 1-Acetyl-piperidine-4-carboxylic acid (3-chloro-4-methyl-phenyl)-{3-[5-(2-methanesulfonylamino-benzoyl)-hexahydro-pyrrolo[3,4-c]pyrrol-2-yl]-propyl}-amide; compound with trifluoro-acetic acid | 644.3 | | 644.23 |
| II-142 | 1-(3-Chloro-4-methyl-phenyl)-3-(2,6-dichloro-pyridin-4-yl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 617.2 | | 615.99 |
| II-143 | 1-(3-Chloro-4-methyl-phenyl)-3-(3,5-dimethyl-isoxazol-4-yl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 565.3 | | 565.11 |
| II-144 | 1-(3-Chloro-4-methyl-phenyl)-3-cyclopentyl-1-{3-[5-(2,4-dimethyl-pyridine-3-carbonyl)-hexahydro-pyrrolo[3,4-c]pyrrol-2-yl]-propyl}-urea; compound with trifluoro-acetic acid | 538.3 | | 538.13 |
| II-145 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-thiophen-3-yl-urea; compound with trifluoro-acetic acid | 552.3 | | 552.14 |
| II-146 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-furan-2-ylmethyl-urea; compound with trifluoro-acetic acid | 550.3 | | 550.1 |
| II-147 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-[1-(2,2,2-trifluoro-acetyl)-piperidin-3-yl]-urea; compound with trifluoro-acetic acid | 650.3 | | 649.15 |
| II-148 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-[1-(2,2,2-trifluoro-acetyl)-piperidin-4-yl]-urea; compound with trifluoro-acetic acid | 650.3 | | 649.15 |
| II-149 | 1-(3-Chloro-4-methyl-phenyl)-3-cyclohexylmethyl-1-{3-[5-(2,4-dimethyl-pyridine-3-carbonyl)-hexahydro-pyrrolo[3,4-c]pyrrol-2-yl]-propyl}-urea; compound with trifluoro-acetic acid | 566.4 | | 566.19 |
| II-150 | 1-(3-Chloro-4-methyl-phenyl)-1-{3-[5-(2,4-dimethyl pyridine-3-carbonyl)-hexahydro-pyrrolo[3,4-c]pyrrol-2-yl]-propyl}-3-(5-methyl-2-trifluoromethyl-furan-3-yl)-urea; compound with trifluoro-acetic acid | 618.3 | | 618.1 |
| II-151 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-phenyl-urea; compound with trifluoro-acetic acid | 546.3 | | 546.11 |
| II-152 | 1-(3-Chloro-4-methyl-phenyl)-3-(3-chloro-phenyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 580.2 | | 580.56 |
| II-153 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-fluoro-phenyl)-urea; compound with trifluoro-acetic acid | 564.3 | | 564.1 |
| II-154 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-p-tolyl-urea; compound with trifluoro-acetic acid | 560.3 | | 560.14 |
| II-155 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-trifluoromethoxy-phenyl)-urea; compound with trifluoro-acetic acid | 630.3 | | 630.11 |

TABLE 2-continued

| | NAME | MS[1] | mp | MW |
|---|---|---|---|---|
| II-156 | (3-(3-Chloro-4-methyl-phenyl)-3-{3-[5-(2,4-dimethyl-pyridine-3-carbonyl)-hexahydro-pyrrolo[3,4-c]pyrrol-2-yl]-propyl}-ureido)-acetic acid ethyl ester; compound with trifluoro-acetic acid | 556.3 | | 556.1 |
| II-157 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-fluoro-benzyl)-urea; compound with trifluoro-acetic acid | 578.3 | | 578.13 |
| II-158 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-methoxy-benzyl)-urea; compound with trifluoro-acetic acid | 590.3 | | 590.16 |
| II-159 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-trifluoromethyl-phenyl)-urea; compound with trifluoro-acetic acid | 614.2 | | 614.11 |
| II-160 | 3-(4-Acetyl-phenyl)-1-(3-chloro-4-methyl-phenyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 588.3 | | 588.15 |
| II-161 | 1-(3-Chloro-4-methyl-phenyl)-3-(3,4-difluoro-phenyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 582.2 | | 582.09 |
| II-162 | 1-Acetyl-piperidine-4-carboxylic acid (3-chloro-4-methyl-phenyl)-{3-[5-(2,4-dimethyl-6-oxo-6H-pyran-3-carbonyl)-hexahydro-pyrrolo[3,4-c]pyrrol-2-yl]-propyl}-amide; with trifluoro-acetic acid | 598 | | 597.15 |
| II-163 | 1-(3-Chloro-4-methyl-phenyl)-3-(4-dimethylamino-phenyl)-1-{3-[5-(2,4-dimethyl-pyridine-3-carbonyl)-hexahydro-pyrrolo[3,4-c]pyrrol-2-yl]-propyl)}-urea; compound with trifluoro-acetic acid | 589.3 | | 589.18 |
| II-164 | 4-(3-(3-Chloro-4-methyl-phenyl)-3-{3-[5-(2,4-dimethyl-pyridine-3-carbonyl)-hexahydro-pyrrolo[3,4-c]pyrrol-2-yl]-propyl}-ureido)-piperidine-1-carboxylic acid benzyl ester; compound with trifluoro-acetic acid | 687.3 | | 687.28 |
| II-165 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-methoxy-phenyl)-urea; compound with trifluoro-acetic acid | 576.3 | | 576.14 |
| II-166 | 1-(3-Chloro-4-methyl-phenyl)-3-cyclohexyl-1-{3-[5-(2,4-dimethyl-pyridine-3-carbonyl)-hexahydro-pyrrolo[3,4-c]pyrrol-2-yl]-propyl}-urea; compound with trifluoro-acetic acid | 552.4 | | 552.16 |
| II-167 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-methylsulfanyl-phenyl)-urea; compound with trifluoro-acetic acid | 592.3 | | 592.2 |
| II-168 | 1-(3-Chloro-4-methyl-phenyl)-3-(2,4-dichloro-phenyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 616.2 | | 615 |
| II-169 | 1-(3-Chloro-4-methyl-phenyl)-3-(4-chloro-2-trifluoromethyl-phenyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 648.3 | | 648.55 |
| II-170 | 1-(3-Chloro-4-methyl-phenyl)-1-{3-[5-(2,4-dimethyl-pyridine-3-carbonyl)-hexahydro-pyrrolo[3,4-c]pyrrol-2-yl]-propyl}-3-(4-methyl-benzyl)-urea; compound with trifluoro-acetic acid | 574.4 | | 574.17 |
| II-171 | 1-(3-Chloro-4-methyl-phenyl)-3-(3,4-dichloro-benzyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 630.3 | | 629.03 |
| II-172 | 1-(3-Chloro-4-methyl-phenyl)-3-(4-cyano-phenyl)-1-{3-[5-(2,4-dimethyl-pyridine-3-carbonyl)-hexahydro-pyrrolo[3,4-c]pyrrol-2-yl]-propyl}-urea; compound with trifluoro-acetic acid | 571.4 | | 571.12 |
| II-173 | 1-Acetyl-piperidine-4-carboxylic acid {3-[5-(2,6-dimethyl-benzoyl)-hexahydro-pyrrolo[3,4-c]pyrrol-2-yl]-propyl}-(3,4-dimethyl-phenyl)-amide | 559 | | 558.76 |
| II-174 | 1-Acetyl-piperidine-4-carboxylic acid (3-chloro-4-methyl-phenyl)-(3-[5-(2,4-dimethyl-pyridine-3-carbonyl)-3a,6a-dimethyl-hexahydro-pyrrolo[3,4-c]pyrrol-2-yl]-propyl}-amide; compound with trifluoro-acetic acid | 608, 610 | | 608.22 |

TABLE 2-continued

| | NAME | MS[1] | mp | MW |
|---|---|---|---|---|
| II-175 | 4,4-Difluoro-cyclohexanecarboxylic acid (3-chloro-4-methyl-phenyl)-{3-[5-(2,4-dimethyl-6-oxo-6H-pyran-3-carbonyl)-hexahydro-pyrrolo[3,4-c]pyrrol-2-yl]-propyl}-amide; compound with trifluoro-acetic acid | 590 | | 590.11 |
| II-176 | 4,4-Difluoro-cyclohexanecarboxylic acid (3-chloro-4-methyl-phenyl)-{3-[5-(3,5-dimethyl-isoxazole-4-carbonyl)-hexahydro-pyrrolo[3,4-c]pyrrol-2-yl]-propyl}-amide; compound with trifluoro-acetic acid | 563 | | 563.09 |
| II-177 | 4,4-Difluoro-cyclohexanecarboxylic acid {3-[5-(5-acetyl-2,4-dimethyl-1H-pyrrole-3-carbonyl)-hexahydro-pyrrolo[3,4-c]pyrrol-2-yl]-propyl}-(3-chloro-4-methyl-phenyl)-amide; compound with trifluoro-acetic acid | 603.1 | | 603.15 |
| II-178 | 4,4-Difluoro-cyclohexanecarboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 574.1 | | 574.11 |
| II-179 | 4,4-Difluoro-cyclohexanecarboxylic acid (3-chloro-4-methyl-phenyl)-{3-[5-(2,4,5-trimethyl-thiophene-3-carbonyl)-hexahydro-pyrrolo[3,4-c]pyrrol-2-yl]-propyl}-amide; compound with trifluoro-acetic acid | 592.1 | | 592.19 |
| II-180 | 4,4-Difluoro-cyclohexanecarboxylic acid (3-chloro-4-methyl-phenyl)-{3-[5-(2,6-dimethyl-benzoyl)-hexahydro-pyrrolo[3,4-c]pyrrol-2-yl]-propyl}-amide; compound with trifluoro-acetic acid | 572.1 | | 572.14 |
| II-181 | 4,4-Difluoro-cyclohexanecarboxylic acid (3-chloro-4-methyl-phenyl)-{3-[5-(3,5-dimethyl-1-phenyl-1H-pyrazole-4-carbonyl)-hexahydro-pyrrolo[3,4-c]pyrrol-2-yl]-propyl}-amide; compound with trifluoro-acetic acid | 638.2 | | 638.2 |
| II-182 | 4,4-Difluoro-cyclohexanecarboxylic acid (3-chloro-4-methyl-phenyl)-{3-[5-(2,6-dichloro-4-methanesulfonyl-benzoyl)-hexahydro-pyrrolo[3,4-c]pyrrol-2-yl]-propyl}-amide; compound with trifluoro-acetic acid | 692 | | 691.06 |
| II-183 | 4,4-Difluoro-cyclohexanecarboxylic acid (3-chloro-4-methyl-phenyl)-{3-[5-(4,6-dimethyl-2-pyridin-4-yl-pyrimidine-5-carbonyl)-hexahydro-pyrrolo[3,4-c]pyrrol-2-yl]-propyl}-amide; compound with trifluoro-acetic acid | 651.2 | | 651.2 |
| II-184 | 4,4-Difluoro-cyclohexanecarboxylic acid (3-chloro-4-methyl-phenyl)-{3-[5-(4,6-dimethyl-2-phenyl-pyrimidine-5-carbonyl)-hexahydro-pyrrolo[3,4-c]pyrrol-2-yl]-propyl}-amide; compound with trifluoro-acetic acid | 650.2 | | 650.21 |
| II-185 | 4,4-Difluoro-cyclohexanecarboxylic acid (3-chloro-4-methyl-phenyl)-{3-[5-(5-methyl-3-phenyl-isoxazole-4-carbonyl)-hexahydro-pyrrolo[3,4-c]pyrrol-2-yl]-propyl}-amide; compound with trifluoro-acetic acid | 625.2 | | 625.16 |
| II-186 | Cyclobutanecarboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 509.3 | | 509.09 |
| II-187 | Cyclopentanecarboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 523.3 | | 523.12 |
| II-188 | 1-(3-Chloro-4-methyl-phenyl)-1-{3-[5-(2,4-dimethyl-pyridine-3-carbonyl)-hexahydro-pyrrolo[3,4-c]pyrrol-2-yl]propyl}-3-[1-(2,2,2-trifluoro-acetyl)-piperidin-3-yl]-urea; compound with trifluoro-acetic acid | 649.3 | | 649.15 |
| II-189 | 1-Acetyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-2-hydroxy-propyl}-amide | 595 | 107.9–409.8 | 595.18 |
| II-190 | 1-Acetyl-piperidine-4-carboxylic acid (3-chloro-4-methyl-phenyl)-{3-[5-(2,4-dimethyl-pyridine-3-carbonyl)-bis-hydroxymethyl-hexahydro-pyrrolo[3,4-c]pyrrol-2-yl]-propyl}-amide | 640 | | 640.22 |
| II-191 | 4,4-Difluoro-cyclohexanecarboxylic acid {3-[5-(2,4-dimethyl-pyridine-3-carbonyl)-hexahydro-pyrrolo[3,4-c]pyrrol-2-yl]-propyl}-p-tolyl-amide | 538 | | 538.68 |
| II-192 | 4,4-Difluoro-cyclohexanecarboxylic acid {3-[5-(2,4-dimethyl-pyridine-3-carbonyl)-hexahydro-pyrrolo[3,4-c]pyrrol-2-yl]-propyl}-phenyl-amide | 525 | | 524.65 |

TABLE 2-continued

| | NAME | MS[1] | mp | MW |
|---|---|---|---|---|
| II-193 | 1-Acetyl-piperidine-4-carboxylic acid (3-chloro-4-methyl-phenyl)-{3-[5-(2-methyl-5-trifluoromethyl-oxazole-4-carbonyl)-hexahydro-pyrrolo[3,4-c]pyrrol-2-yl]-propyl}-amide; compound with trifluoro-acetic acid | 624.1 | | 624.1 |
| II-194 | 1-Acetyl-piperidine-4-carboxylic acid (3-chloro-4-methyl-phenyl)-{3-[5-(2-phenyl-5-trifluoromethyl-oxazole-4-carbonyl)-hexahydro-pyrrolo[3,4-c]pyrrol-2-yl]-propyl}-amide; compound with trifluoro-acetic acid | 686.1 | | 686.17 |
| II-195 | 1-Acetyl-piperidine-4-carboxylic acid {3-[5-(2-amino-6-trifluoromethyl-benzoyl)-hexahydro-pyrrolo[3,4-c]pyrrol-2-yl]-propyl}-(3-chloro-4-methyl-phenyl)-amide; compound with trifluoro-acetic acid | 634.1 | | 634.14 |
| II-196 | 1-Acetyl-piperidine-4-carboxylic acid (3-chloro-4-methyl-phenyl)-{3-[5-(2,6-dimethyl-4-nitro-benzoyl)-hexahydro-pyrrolo[3,4-c]pyrrol-2-yl]-propyl}-amidetrifluoro-acetic acid; | 624.3 | | 624.18 |
| II-197 | 1-Acetyl-piperidine-4-carboxylic acid (3-chloro-4-methyl-phenyl)-{3-[5-(1,3,5-trimethyl-1H-pyrazole-4-carbonyl)-hexahydro-pyrrolo[3,4-c]pyrrol-2-yl]-propyl}-amide; compound with trifluoro-acetic acid | 583.4 | | 583.17 |
| II-198 | 1-Acetyl-piperidine-4-carboxylic acid (3-chloro-4-methyl-phenyl)-{3-[5-(3,5-dimethyl-1H-pyrazole-4-carbonyl)-hexahydro-pyrrolo[3,4-c]pyrrol-2-yl]-propyl}-amide; compound with trifluoro-acetic acid | 569.3 | | 569.15 |
| II-199 | N-(3-Chloro-4-methyl-phenyl)-N-{3-[5-(2,4-dimethyl-pyridine-3-carbonyl)-hexahydro-pyrrolo[3,4-c]pyrrol-2-yl]-propyl}-propionamide; compound with trifluoro-acetic acid | 483.3 | | 483.05 |
| II-200 | N-(3-Chloro-4-methyl-phenyl)-N-{3-[5-(2,4-dimethyl-pyridine-3-carbonyl)-hexahydro-pyrrolo[3,4-c]pyrrol-2-yl]-propyl}-butyramide; compound with trifluoro-acetic acid | 497.3 | | 497.08 |
| II-201 | Pentanoic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 511.3 | | 511.11 |
| II-202 | Cyclopropanecarboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide; compound with trifluoro-acetic acid | 495.3 | | 495.06 |
| II-203 | 3-(4-Chloro-phenyl)-1-{3-[5-(2,4-dimethyl-pyridine-3-carbonyl)-hexahydro-pyrrolo[3,4-c]pyrrol-2-yl]-propyl}-1-p-tolyl-urea | 546 | 60.5–62.5 | 546.11 |
| II-204 | 1-Acetyl-piperidine-4-carboxylic acid {3-[5-(5-chloro-2-methoxy-benzoyl)-hexahydro-pyrrolo[3,4-c]pyrrol-2-yl]-propyl}-(3-chloro-4-methyl-phenyl)-amide; compound with trifluoro-acetic acid | 615.1 | | 615.6 |
| II-205 | 1-Acetyl-piperidine-4-carboxylic acid [3-(5-benzoyl-hexahydro-pyrrolo[3,4-c]pyrrol-2-yl)-propyl]-(3-chloro-4-methyl-phenyl)-amide; compound with trifluoro-acetic acid | 551.2 | | 551.13 |
| II-206 | 1-Acetyl-piperidine-4-carboxylic acid {3-[5-(2,4-bis-trifluoromethyl-benzoyl)-hexahydro-pyrrolo[3,4-c]pyrrol-2-yl]-propyl}-(3-chloro-4-methyl-phenyl)-amide; compound with trifluoro-acetic acid | 687.1 | | 687.12 |
| II-207 | 1-Acetyl-piperidine-4-carboxylic acid (3-chloro-4-methyl-phenyl)-{3-[5-(2,4-dimethoxy-benzoyl)-hexahydro-pyrrolo[3,4-c]pyrrol-2-yl]-propyl}-amide; compound with trifluoro-acetic acid | 611.2 | | 611.18 |
| II-208 | 1-Acetyl-piperidine-4-carboxylic acid (3-chloro-4-methyl-phenyl)-{3-[5-(2,3-dihydro-benzofuran-7-carbonyl)-hexahydro-pyrrolo[3,4-c]pyrrol-2-yl]-propyl}-amide; compound with trifluoro-acetic acid | 593.2 | | 593.16 |
| II-209 | 1-Acetyl-piperidine-4-carboxylic acid (3-chloro-4-methyl-phenyl)-{3-[5-(2,3-dimethoxy-benzoyl)-hexahydro-pyrrolo[3,4-c]pyrrol-2-yl]-propyl}-amide; compound with trifluoro-acetic acid | 611.3 | | 611.18 |
| II-210 | 1-Acetyl-piperidine-4-carboxylic acid (3-chloro-4-methyl-phenyl)-({3-[5-(2-chloro-5-methylsulfanyl-benzoyl)-hexahydro-pyrrolo[3,4-c]pyrrol-2-yl]-propyl}-amide; compound with trifluoro-acetic acid | 631.2 | | 631.67 |

TABLE 2-continued

|  | NAME | MS[1] | mp | MW |
|---|---|---|---|---|
| II-211 | 1-Acetyl-piperidine-4-carboxylic acid (3-chloro-4-methyl-phenyl)-{3-[5-(4-fluoro-3-trifluoromethyl-benzoyl)-hexahydro-pyrrolo[3,4-c]pyrrol-2-yl]-propyl}-amide; compound with trifluoro-acetic acid | 637.2 | | 637.11 |
| II-212 | 1-Acetyl-piperidine-4-carboxylic acid {3-[5-(3-chloro-2-fluoro-benzoyl)-hexahydro-pyrrolo[3,4-c]pyrrol-2-yl]-propyl}-(3-chloro-4-methyl-phenyl)-amide; compound with trifluoro-acetic acid | 603.2 | | 603.56 |
| II-213 | 1-Acetyl-piperidine-4-carboxylic acid (3-chloro-4-methyl-phenyl)-{3-[5-(2,3-dimethyl-benzoyl)-hexahydro-pyrrolo[3,4-c]pyrrol-2-yl]-propyl}-amide; compound with trifluoro-acetic acid | 579.3 | | 579.18 |
| II-214 | 1-Acetyl-piperidine-4-carboxylic acid (3-chloro-4-methyl-phenyl)-{3-[5-(2-ethoxy-benzoyl)-hexahydro-pyrrolo[3,4-c]pyrrol-2-yl]-propyl}-amide; compound with trifluoro-acetic acid | 595.3 | | 595.18 |
| II-215 | 1-Acetyl-piperidine-4-carboxylic acid (3-chloro-4-methyl-phenyl)-{3-[5-(2,3-difluoro-benzoyl)-hexahydro-pyrrolo[3,4-c]pyrrol-2-yl]-propyl}-amide; compound with trifluoro-acetic acid | 587.2 | | 587.11 |
| II-216 | 1-Acetyl-piperidine-4-carboxylic acid (3-chloro-4-methyl-phenyl)-{3-[5-(2-fluoro-5-methyl-benzoyl)-hexahydro-pyrrolo[3,4-c]pyrrol-2-yl]-propyl}-amide; compound with trifluoro-acetic acid | 583.3 | | 583.14 |
| II-217 | 1-Acetyl-piperidine-4-carboxylic acid {3-[5-(2-chloro-4,5-difluoro-benzoyl)-hexahydro-pyrrolo[3,4-c]pyrrol-2-yl]-propyl}-(3-chloro-4-methyl-phenyl)-amide; compound with trifluoro-acetic acid | 621.2 | | 621.55 |
| II-218 | 1-Acetyl-piperidine-4-carboxylic acid (3-chloro-4-methyl-phenyl)-{3-[5-(2,4,5-trifluoro-benzoyl)-hexahydro-pyrrolo[3,4-c]pyrrol-2-yl]-propyl}-amide; compound with trifluoro-acetic acid | 605.2 | | 605.1 |
| II-219 | 1-Acetyl-piperidine-4-carboxylic acid (3-chloro-4-methyl-phenyl)-{3-[5-(2,4-difluoro-benzoyl)-hexahydro-pyrrolo[3,4-c]pyrrol-2-yl]-propyl}-amide; compound with trifluoro-acetic acid | 587.2 | | 587.11 |
| II-220 | 1-Acetyl-piperidine-4-carboxylic acid (3-chloro-4-methyl-phenyl)-{3-[5-(2,4-dichloro-benzoyl)-hexahydro-pyrrolo[3,4-c]pyrrol-2-yl]-propyl}-amide; compound with trifluoro-acetic acid | 621.2 | | 620.02 |
| II-221 | 1-Acetyl-piperidine-4-carboxylic acid (3-chloro-4-methyl-phenyl)-{3-[5-(2,5-dichloro-benzoyl)-hexahydro-pyrrolo[3,4-c]pyrrol-2-yl]-propyl}-amide; compound with trifluoro-acetic acid | 621.2 | | 620.02 |
| II-222 | 1-Acetyl-piperidine-4-carboxylic acid (3-chloro-4-methyl-phenyl)-{3-[5-(2,3-dichloro-benzoyl)-hexahydro-pyrrolo[3,4-c]pyrrol-2-yl]-propyl}-amide; compound with trifluoro-acetic acid | 621.2 | | 620.02 |
| II-223 | 1-Acetyl-piperidine-4-carboxylic acid (3-chloro-4-methyl-phenyl)-{3-[5-(2,5-difluoro-benzoyl)-hexahydro-pyrrolo[3,4-c]pyrrol-2-yl]-propyl}-amide; compound with trifluoro-acetic acid | 587.2 | | 587.11 |
| II-224 | 1-Acetyl-piperidine-4-carboxylic acid {3-[5-(2-chloro-4-fluoro-benzoyl)-hexahydro-pyrrolo[3,4-c]pyrrol-2-yl]-propyl}-(3-chloro-4-methyl-phenyl)-amide; compound with trifluoro-acetic acid | 603.2 | | 603.56 |
| II-225 | 1-Acetyl-piperidine-4-carboxylic acid {3-[5-(4-chloro-2-fluoro-benzoyl)-hexahydro-pyrrolo[3,4-c]pyrrol-2-yl]-propyl}-(3-chloro-4-methyl-phenyl)-amide; compound with trifluoro-acetic acid | 603.2 | | 603.56 |
| II-226 | 1-Acetyl-piperidine-4-carboxylic acid (3-chloro-4-methyl-phenyl)-{3-[5-(4-methoxy-benzoyl)-hexahydro-pyrrolo[3,4-c]pyrrol-2-yl]-propyl}-amide; compound with trifluoro-acetic acid | 581.3 | | 581.15 |
| II-227 | 1-Acetyl-piperidine-4-carboxylic acid (3-chloro-4-methyl-phenyl)-{3-[5-(2-trifluoromethoxy-benzoyl)-hexahydro-pyrrolo[3,4-c]pyrrol-2-yl]-propyl}-amide; compound with trifluoro-acetic acid | 635.3 | | 635.12 |
| II-228 | 1-Acetyl-piperidine-4-carboxylic acid (3-chloro-4-methyl-phenyl)-{3-[5-(3-trifluoromethyl-benzoyl)-hexahydro-pyrrolo[3,4-c]pyrrol-2-yl]-propyl}-amide; compound with trifluoro-acetic acid | 619.3 | | 619.12 |
| II-229 | 1-Acetyl-piperidine-4-carboxylic acid (3-chloro-4-methyl-phenyl)-{3-[5-(3-methoxy-benzoyl)-hexahydro-pyrrolo[3,4-c]pyrrol-2-yl]-propyl}-amide; compound with trifluoro-acetic acid | 581.3 | | 581.15 |

TABLE 2-continued

| | NAME | MS[1] | mp | MW |
|---|---|---|---|---|
| II-230 | Acetic acid 2-(5-{3-[(1-acetyl-piperidine-4-carbonyl)-(3-chloro-4-methyl-phenyl)-amino]-propyl}-hexahydro-pyrrolo[3,4-c]pyrrole-2-carbonyl)-phenyl ester; compound with trifluoro-acetic acid | 609.3 | | 609.16 |
| II-231 | 1-Acetyl-piperidine-4-carboxylic acid {3-[5-(2-bromo-benzoyl)-hexahydro-pyrrolo[3,4-c]pyrrol-2-yl]-propyl}-(3-chloro-4-methyl-phenyl)-amide; compound with trifluoro-acetic acid | 631.2 | | 630.02 |
| II-232 | 1-Acetyl-piperidine-4-carboxylic acid {3-[5-(5-bromo-2-chloro-benzoyl)-hexahydro-pyrrolo[3,4-c]pyrrol-2-yl]-propyl}-(3-chloro-4-methyl-phenyl)-amide; compound with trifluoro-acetic acid | 665.2 | | 664.47 |
| II-233 | 1-Acetyl-piperidine-4-carboxylic acid {3-[5-(4-acetyl-benzoyl)-hexahydro-pyrrolo[3,4-c]pyrrol-2-yl]-propyl}-(3-chloro-4-methyl-phenyl)-amide; compound with trifluoro-acetic acid | 593.3 | | 593.16 |
| II-234 | 1-Acetyl-piperidine-4-carboxylic acid (3-chloro-4-methyl-phenyl)-{3-[5-(2,5-dimethoxy-benzoyl)-hexahydro-pyrrolo[3,4-c]pyrrol-2-yl]-propyl}-amide; compound with trifluoro-acetic acid | 611.3 | | 611.18 |
| II-235 | 2-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-benzoic acid methyl ester; compound with trifluoro-acetic acid | 609.3 | | 609.16 |
| II-236 | 1-Acetyl-piperidine-4-carboxylic acid {3-[5-(2,5-bis-trifluoromethyl-benzoyl)-hexahydro-pyrrolo[3,4-c]pyrrol-2-yl]-propyl}-(3-chloro-4-methyl-phenyl)-amide; compound with trifluoro-acetic acid | 687.3 | | 687.12 |
| II-237 | 1-Acetyl-piperidine-4-carboxylic acid (3-chloro-4-methyl-phenyl)-{3-[5-(2,3,4-trifluoro-benzoyl)-hexahydro-pyrrolo[3,4-c]pyrrol-2-yl]-propyl}-amide; compound with trifluoro-acetic acid | 605.3 | | 605.1 |
| II-238 | 1-Acetyl-piperidine-4-carboxylic acid (3-chloro-4-methyl-phenyl)-{3-[5-(2-fluoro-3-trifluoromethyl-benzoyl)-hexahydro-pyrrolo[3,4-c]pyrrol-2-yl]-propyl}-amide; compound with trifluoro-acetic acid | 637.3 | | 637.11 |
| II-239 | 1-Acetyl-piperidine-4-carboxylic acid (3-chloro-4-methyl-phenyl)-{3-[5-(2,4-dichloro-5-fluoro-benzoyl)-hexahydro-pyrrolo[3,4-c]pyrrol-2-yl]-propyl}-amide; compound with trifluoro-acetic acid | 639.2 | | 638.01 |
| II-240 | 1-Acetyl-piperidine-4-carboxylic acid (3-chloro-4-methyl-phenyl)-{3-[5-(4-fluoro-2-trifluoromethyl-benzoyl)-hexahydro-pyrrolo[3,4-c]pyrrol-2-yl]-propyl}-amide; compound with trifluoro-acetic acid | 637.3 | | 637.11 |
| II-241 | 1-Acetyl-piperidine-4-carboxylic acid (3-chloro-4-methyl-phenyl)-{3-[5-(3-fluoro-5-trifluoromethyl-benzoyl)-hexahydro-pyrrolo[3,4-c]pyrrol-2-yl]-propyl}-amide; compound with trifluoro-acetic acid | 637.3 | | 637.11 |
| II-242 | 1-Acetyl-piperidine-4-carboxylic acid {3-[5-(2 acetyl-benzoyl)-hexahydro-pyrrolo[3,4-c]pyrrol-2-yl]-propyl}-(3-chloro-4-methyl-phenyl)-amide; compound with trifluoro-acetic acid | 593.3 | | 593.16 |
| II-243 | 1-Acetyl-piperidine-4-carboxylic acid {3-[5-(4-bromo-2-methyl-benzoyl)-hexahydro-pyrrolo[3,4-c]pyrrol-2-yl]-propyl}-(3-chloro-4-methyl-phenyl)-amide; compound with trifluoro-acetic acid | 645.2 | | 644.05 |
| II-244 | 1-Acetyl-piperidine-4-carboxylic acid {3-[5-(2-bromo-3-methyl-benzoyl)-hexahydro-pyrrolo[3,4-c]pyrrol-2-yl]-propyl}-(3-chloro-4-methyl-phenyl)-amide; compound with trifluoro-acetic acid | 645.2 | | 644.05 |
| II-245 | 1-Acetyl-piperidine-4-carboxylic acid {3-[5-(2-bromo-5-methyl-benzoyl)-hexahydro-pyrrolo[3,4-c]pyrrol-2-yl]-propyl}-(3-chloro-4-methyl-phenyl)-amide; compound with trifluoro-acetic acid | 645.2 | | 644.05 |
| II-246 | 1-Acetyl-piperidine-4-carboxylic acid {3-[5-(3-bromo-2-methyl-benzoyl)-hexahydro-pyrrolo[3,4-c]pyrrol-2-yl]-propyl}-(3-chloro-4-methyl-phenyl)-amide; compound with trifluoro-acetic acid | 645.2 | | 644.05 |
| II-247 | 1-Acetyl-piperidine-4-carboxylic acid {3-[5-(3,5-bis-trifluoromethyl-benzoyl)-hexahydro-pyrrolo[3,4-c]pyrrol-2-yl]-propyl}-(3-chloro-4-methyl-phenyl)-amide; compound with trifluoro-acetic acid | 687.2 | | 687.12 |
| II-248 | 1-Acetyl-piperidine-4-carboxylic acid (3-chloro-4-methyl-phenyl)-{3-[5-(2-fluoro-benzoyl)-hexahydro-pyrrolo[3,4-c]pyrrol-2-yl]-propyl}-amide; compound with trifluoro-acetic acid | 569.3 | | 569.12 |

TABLE 2-continued

| | NAME | MS[1] | mp | MW |
|---|---|---|---|---|
| II-249 | 1-Acetyl-piperidine-4-carboxylic acid (3-chloro-4-methyl-phenyl)-{3-[5-(3-fluoro-4-trifluoromethyl-benzoyl)-hexahydro-pyrrolo[3,4-c]pyrrol-2-yl]-propyl}-amide; compound with trifluoro-acetic acid | 637.3 | | 637.11 |
| II-250 | 1-Acetyl-piperidine-4-carboxylic acid (3-chloro-4-methyl-phenyl)-{3-[5-(2,5-dimethyl-benzoyl)-hexahydro-pyrrolo[3,4-c]pyrrol-2-yl]-propyl}-amide; compound with trifluoro-acetic acid | 579.3 | | 579.18 |
| II-251 | 1-Acetyl-piperidine-4-carboxylic acid (3-chloro-4-methyl-phenyl)-{3-[5-(4-trifluoromethyl-benzoyl)-hexahydro-pyrrolo[3,4-c]pyrrol-2-yl]-propyl}-amide; compound with trifluoro-acetic acid | 619.3 | | 619.12 |
| II-252 | 1-Acetyl-piperidine-4-carboxylic acid {3-[5-(2-bromo-5-methoxy-benzoyl)-hexahydro-pyrrolo[3,4-c]pyrrol-2-yl]-propyl}-(3-chloro-4-methyl-phenyl)-amide; compound with trifluoro-acetic acid | 661.2 | | 660.05 |
| II-253 | 1-Acetyl-piperidine-4-carboxylic acid {3-[5-(2-chloro-3-methyl-benzoyl)-hexahydro-pyrrolo[3,4-c]pyrrol-2-yl]-propyl}-(3-chloro-4-methyl-phenyl)-amide; compound with trifluoro-acetic acid | 599.3 | | 599.6 |
| II-254 | 1-Acetyl-piperidine-4-carboxylic acid (3-chloro-4-methyl-phenyl)-{3-[5-(3-dimethylamino-benzoyl)-hexahydro-pyrrolo[3,4-c]pyrrol-2-yl]-propyl}-amide; compound with trifluoro-acetic acid | 594.3 | | 594.2 |
| II-255 | 1-Acetyl-piperidine-4-carboxylic acid (3-chloro-4-methyl-phenyl)-{3-[5-(2-iodo-benzoyl)-hexahydro-pyrrolo[3,4-c]pyrrol-2-yl]-propyl}-amide; compound with trifluoro-acetic acid | 677.2 | | 677.02 |
| II-256 | 1-Acetyl-piperidine-4-carboxylic acid (3-chloro-4-methyl-phenyl)-{3-[5-(2-ethyl-benzoyl)-hexahydro-pyrrolo[3,4-c]pyrrol-2-yl]-propyl}-amide; compound with trifluoro-acetic acid | 579.3 | | 579.18 |
| II-257 | 1-Acetyl-piperidine-4-carboxylic acid (3-chloro-4-methyl-phenyl)-[3-(5-{4-[(2-hydroxy-ethyl)-methyl-amino]-benzoyl}-hexahydro-pyrrolo[3,4-c]pyrrol-2-yl)-propyl]-amide; compound with trifluoro-acetic acid | 624.3 | | 624.22 |
| II-258 | 1-Acetyl-piperidine-4-carboxylic acid (3-chloro-4-methyl-phenyl)-{3-[5-(6-fluoro-4H-benzo[1,3]dioxine-8-carbonyl)-hexahydro-pyrrolo[3,4-c]pyrrol-2-yl]-propyl}-amide; compound with trifluoro-acetic acid | 627.2 | | 627.15 |
| II-259 | 1-Acetyl-piperidine-4-carboxylic acid (3-chloro-4-methyl-phenyl)-{3-[5-(2,5-dibromo-benzoyl)-hexahydro-pyrrolo[3,4-c]pyrrol-2-yl]-propyl}-amide; compound with trifluoro-acetic acid | 709 | | 708.92 |
| II-260 | 1-Acetyl-piperidine-4-carboxylic acid (3-chloro-4-methyl phenyl)-{3-[5-(4-methoxy-2-methyl-benzoyl)-hexahydro-pyrrolo[3,4-c]pyrrol-2-yl]-propyl}-amide; compound with trifluoro-acetic acid | 595.3 | | 595.18 |
| II-261 | 1-Acetyl-piperidine-4-carboxylic acid (3-chloro-4-methyl-phenyl)-{3-[5-(5-fluoro-2-methoxy-benzoyl)-hexahydro-pyrrolo[3,4-c]pyrrol-2-yl]-propyl}-amide; compound with trifluoro-acetic acid | 599.2 | | 599.14 |
| II-262 | 1-Acetyl-piperidine-4-carboxylic acid (3-chloro-4-methyl-phenyl)-{3-[5-(3-methoxy-2-methyl-benzoyl)-hexahydro-pyrrolo[3,4-c]pyrrol-2-yl]-propyl}-amide; compound with trifluoro-acetic acid | 595.2 | | 595.18 |
| II-263 | 1-Acetyl-piperidine-4-carboxylic acid (3-chloro-4-methyl-phenyl)-{3-[5-(5-fluoro-2-trifluoromethyl-benzoyl)-hexahydro-pyrrolo[3,4-c]pyrrol-2-yl]-propyl}-amide; compound with trifluoro-acetic acid | 637.2 | | 637.11 |
| II-264 | 1-Acetyl-piperidine-4-carboxylic acid (3-chloro-4-methyl-phenyl)-{3-[5-(cinnoline-4-carbonyl)-hexahydro-pyrrolo[3,4-c]pyrrol-2-yl]-propyl}-amide; compound with trifluoro-acetic acid | 603.2 | | 603.16 |
| II-265 | 1-Acetyl-piperidine-4-carboxylic acid (3-chloro-4-methyl-phenyl)-{3-[5-(2,6-dimethoxy-pyridine-3-carbonyl)-hexahydro-pyrrolo[3,4-c]pyrrol-2-yl]-propyl}-amide; compound with trifluoro-acetic acid | 612.2 | | 612.17 |
| II-266 | 1-Acetyl-piperidine-4-carboxylic acid (3-chloro-4-methyl-phenyl)-{3-[5-(4-trifluoromethyl-pyridine-3-carbonyl)-hexahydro-pyrrolo[3,4-c]pyrrol-2-yl]-propyl}-amide; compound with trifluoro-acetic acid | 620.2 | | 620.11 |

TABLE 2-continued

| | NAME | MS[1] | mp | MW |
|---|---|---|---|---|
| II-267 | 1-Acetyl-piperidine-4-carboxylic acid (3-chloro-4-methyl-phenyl)-{3-[5-(4-methyl-pyridine-3-carbonyl)-hexahydro-pyrrolo[3,4-c]pyrrol-2-yl]-propyl}-amide; compound with trifluoro-acetic acid | 566.2 | | 566.14 |
| II-268 | 1-Acetyl-piperidine-4-carboxylic acid (3-chloro-4-methyl-phenyl)-{3-[5-(3-methyl-pyridine-2-carbonyl)-hexahydro-pyrrolo[3,4-c]pyrrol-2-yl]-propyl}-amide; compound with trifluoro-acetic acid | 566.2 | | 566.14 |
| II-269 | 1-Acetyl-piperidine-4-carboxylic acid {3-[5-(2,6-dimethyl-benzoyl)-hexahydro-pyrrolo[3,4-c]pyrrol-2-yl]-propyl}-pyrimidin-2-yl-amide; compound with trifluoro-acetic acid | 533 | | 532.69 |
| II-270 | 5-Oxo-1-(2,2,2-trifluoro-ethyl)-pyrrolidine-3-carboxylic acid (3-chloro-4-methyl-phenyl)-{3-[5-(2,6-dimethyl-benzoyl)-hexahydro-pyrrolo[3,4-c]pyrrol-2-yl]-propyl}-amide | 619 | 68.8–72.9 | 619.12 |
| II-271 | 1-Acetyl-piperidine-4-carboxylic acid {3-[5-(6-chloro-2-dimethylamino-pyridine-3-carbonyl)-hexahydro-pyrrolo[3,4-c]pyrrol-2-yl]-propyl}-(3-chloro-4-methyl-phenyl)-amide; compound with trifluoro-acetic acid | 629.1 | | 629.63 |
| II-272 | 1-Acetyl-piperidine-4-carboxylic acid (3-chloro-4-methyl-phenyl)-{3-[5-(4-cyano-2,5-dimethyl-thiophene-3-carbonyl)-hexahydro-pyrrolo[3,4-c]pyrrol-2-yl]-propyl}-amide; compound with trifluoro-acetic acid | 610.1 | | 610.22 |
| II-273 | 1-Acetyl-piperidine-4-carboxylic acid (3-chloro-4-methyl-phenyl)-{3-[5-(4-iodo-2,5-dimethyl-thiophene-3-carbonyl)-hexahydro-pyrrolo[3,4-c]pyrrol-2-yl]-propyl}-amide; compound with trifluoro-acetic acid | 711 | | 711.1 |
| II-274 | 1-Acetyl-piperidine-4-carboxylic acid (3-chloro-4-methyl-phenyl)-{3-[5-(2,5-dimethyl-thiophene-3-carbonyl)-hexahydro-pyrrolo[3,4-c]pyrrol-2-yl]-propyl}-amide; compound with trifluoro-acetic acid | 585.1 | | 585.21 |
| II-275 | 1-Acetyl-piperidine-4-carboxylic acid (3-chloro-4-methyl-phenyl)-{3-[5-(3,6-dimethoxy-pyridazine-4-carbonyl)-hexahydro-pyrrolo[3,4-c]pyrrol-2-yl]-propyl}-amide; compound with trifluoro-acetic acid | 613.1 | | 613.16 |
| II-276 | 1-Acetyl-piperidine-4-carboxylic acid {3-[5-(4-bromo-2,5-di-tert-butyl-thiophene-3-carbonyl)-hexahydro-pyrrolo[3,4-c]pyrrol-2-yl]-propyl}-(3-chloro-4-methyl-phenyl)-amide; compound with trifluoro-acetic acid | 749.1 | | 748.27 |
| II-277 | 1-Acetyl-piperidine-4-carboxylic acid (3-chloro-4-methyl-phenyl)-{3-[5-(2,5-di-tert-butyl-4-cyano-thiophene-3-carbonyl)-hexahydro-pyrrolo[3,4-c]pyrrol-2-yl]-propyl}-amide; compound with trifluoro-acetic acid | 694.2 | | 694.38 |
| II-278 | 3-(4-Chloro-phenyl)-1-{3-[5-(2,4-dimethyl-pyridine-3-carbonyl)-hexahydro-pyrrolo[3,4-c]pyrrol-2-yl]-propyl}-1-phenyl-urea; compound with trifluoro acetic acid | 532 | | 532.09 |
| II-279 | 1,1-Dioxo-hexahydro-1λ[6]-thiopyran-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide | 586 | 101.3–102.7 | 586.19 |
| II-280 | 1-Acetyl-piperidine-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-2-hydroxy-propyl}-amide | 596 | 97.3–98.1 | 596.17 |
| II-281 | Cyclopentanecarboxylic acid {3-[5-(2,4-dimethyl-pyridine-3-carbonyl)-hexahydro-pyrrolo[3,4-c]pyrrol-2-yl]-cyclohexyl}-phenyl-amide | 515 | 108.7–109.3 | 514.71 |
| II-282 | Cyclopentanecarboxylic acid {3-[5-(2,4-dimethyl-pyridine-3-carbonyl)-hexahydro-pyrrolo[3,4-c]pyrrol-2-yl]-propyl}-phenyl-amide; compound with trifluoroacetic acid | 475 | 130.3–130.7 | 474.65 |
| II-283 | 1-Acetyl-piperidine-4-carboxylic acid {3-[5-(4-chloro-2-methyl-benzoyl)-hexahydro-pyrrolo[3,4-c]pyrrol-2-yl]-propyl}-(3-chloro-4-methyl-phenyl)-amide; compound with trifluoro-acetic acid | 599.1 | | 599.6 |
| II-284 | 1-Acetyl-piperidine-4-carboxylic acid {3-[5-(3-chloro-2-methyl-benzoyl)-hexahydro-pyrrolo[3,4-c]pyrrol-2-yl]-propyl}-(3-chloro-4-methyl-phenyl)-amide; compound with trifluoro-acetic acid | 599.1 | | 599.6 |

TABLE 2-continued

| | NAME | MS[1] | mp | MW |
|---|---|---|---|---|
| II-285 | 1-Acetyl-piperidine-4-carboxylic acid (3-chloro-4-methyl-phenyl)-{3-[5-(2-chloro-3-trifluoromethyl-benzoyl)-hexahydro-pyrrolo[3,4-c]pyrrol-2-yl]-propyl}-amide; compound with trifluoro-acetic acid | 653.1 | | 653.57 |

TABLE 2

| | NAME | MS[1] | mp | MW |
|---|---|---|---|---|
| II-286 | 1-Acetyl-piperidine-4-carboxylic acid {3-[5-(3-bromo-2-methoxy-benzoyl)-hexahydro-pyrrolo[3,4-c]pyrrol-2-yl]-propyl}-(3-chloro-4-methyl-phenyl)-amide; compound with trifluoro-acetic acid | 661 | | 660.05 |
| II-287 | 1-Acetyl-piperidine-4-carboxylic acid {3-[5-(5-chloro-2-methyl-benzoyl)-hexahydro-pyrrolo[3,4-c]pyrrol-2-yl]-propyl}-(3-chloro-4-methyl-phenyl)-amide; compound with trifluoro-acetic acid | 599.1 | | 599.6 |
| II-288 | 1-Acetyl-piperidine-4-carboxylic acid (3-chloro-4-methyl-phenyl)-{3-[5-(3-chloro-pyridine-2-carbonyl)-hexahydro-pyrrolo[3,4-c]pyrrol-2-yl]-propyl}-amide; compound with trifluoro-acetic acid | 586.1 | | 586.56 |
| II-289 | 1-Acetyl-piperidine-4-carboxylic acid (3-chloro-4-methyl-phenyl)-{3-[5-(4-methyl-2-methylsulfanyl-pyrimidine-5-carbonyl)-hexahydro-pyrrolo[3,4-c]pyrrol-2-yl]-propyl}-amide; compound with trifluoro-acetic acid | 613.1 | | 613.22 |
| II-290 | 1-Acetyl-piperidine-4-carboxylic acid {3-[5-(2-chloro-4-methanesulfonyl-benzoyl)-hexahydro-pyrrolo[3,4-c]pyrrol-2-yl]-propyl}-(3-chloro-4-methyl-phenyl)-amide; compound with trifluoro-acetic acid | 663.1 | | 663.66 |
| II-291 | 1-Acetyl-piperidine-4-carboxylic acid {3-[5-(2-chloro-3-fluoro-benzoyl)-hexahydro-pyrrolo[3,4-c]pyrrol-2-yl]-propyl}-(3-chloro-4-methyl-phenyl)-amide; compound with trifluoro-acetic acid | 603.1 | | 603.56 |
| II-292 | 1-Acetyl-piperidine-4-carboxylic acid {3-[5-(4-bromo-2-chloro-benzoyl)-hexahydro-pyrrolo[3,4-c]pyrrol-2-yl]-propyl}-(3-chloro-4-methyl-phenyl)-amide; compound with trifluoro-acetic acid | 665 | | 664.47 |
| II-293 | 1-Acetyl-piperidine-4-carboxylic acid (3-chloro-4-methyl-phenyl)-{3-[5-(2-cyano-benzoyl)-hexahydro-pyrrolo[3,4-c]pyrrol-2-yl]-propyl}-amide; compound with trifluoro-acetic acid | 576.1 | | 576.14 |
| II-294 | 1-Acetyl-piperidine-4-carboxylic acid (3-chloro-4-methyl-phenyl)-{3-[5-(2,2,3,3-tetramethyl-cyclopropanecarbonyl)-hexahydro-pyrrolo[3,4-c]pyrrol-2-yl]-propyl}-amide; compound with trifluoro-acetic acid | 571.2 | | 571.2 |
| II-295 | 1-Acetyl-piperidine-4-carboxylic acid (3-chloro-4-methyl-phenyl)-{3-[5-(2-ethyl-butyryl)-hexahydro-pyrrolo[3,4-c]pyrrol-2-yl]-propyl}-amide; compound with trifluoro-acetic acid | 545.2 | | 545.16 |
| II-296 | 1-Acetyl-piperidine-4-carboxylic acid {3-[5-(2-chloro-4-fluoro-benzenesulfonyl)-hexahydro-pyrrolo[3,4-c]pyrrol-2-yl]-propyl}-(3-chloro-4-methyl-phenyl)-amide; compound with trifluoro-acetic acid | 639 | | 639.62 |
| II-297 | 1-Acetyl-piperidine-4-carboxylic acid (3-chloro-4-methyl-phenyl)-{3-[5-(4-cyano-benzenesulfonyl)-hexahydro-pyrrolo[3,4-c]pyrrol-2-yl]-propyl}-amide; compound with trifluoro-acetic acid | 612.1 | | 612.19 |
| II-298 | {1-[4-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-piperidine-1-carbonyl]-2-methyl-propyl}-carbamic acid tert-butyl ester; compound with trifluoro-acetic acid | 738.2 | | 738.37 |
| II-299 | [4-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-piperidin-1-yl]-oxo-acetic acid methyl ester; compound with trifluoro-acetic acid | 625.1 | | 625.17 |

TABLE 2-continued

| | NAME | MS[1] | mp | MW |
|---|---|---|---|---|
| II-300 | 4-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-piperidine-1-carboxylic acid methyl ester; compound with trifluoro-acetic acid | 597.1 | | 597.16 |
| II-301 | 1-(2-Amino-3-methyl-butyryl)-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 638.2 | | 638.25 |
| II-302 | 1-(2-Methoxy-ethyl)-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 597.2 | | 597.2 |
| II-303 | [4-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-piperidin-1-yl]-oxo-acetic acid; compound with trifluoro-acetic acid | 611.1 | | 611.14 |
| II-304 | 1-Acetyl-piperidine-4-carboxylic acid {3-[5-(6-chloro-2,4-dimethyl-pyridine-3-carbonyl)-hexahydro-pyrrolo[3,4-c]pyrrol-2-yl]-propyl}-(3-chloro-4-methyl-phenyl)-amide; compound with trifluoro-acetic acid | 614 | oil | 614.61 |
| II-305 | 1-Acetyl-piperidine-4-carboxylic acid (3-chloro-4-methyl-phenyl)-{3-[5-(2,4-dimethyl-6-methylsulfanyl-pyridine-3-carbonyl)-hexahydro-pyrrolo[3,4-c]pyrrol-2-yl]-propyl}-amide; compound with trifluoro-acetic acid | 626 | oil | 626.26 |
| II-306 | Cyclopentanecarboxylic acid {3-[5-(2,6-dimethyl-benzoyl)-hexahydro-pyrrolo[3,4-c]pyrrol-2-yl]-propyl}-(4-trifluoromethyl-pyrimidin-2-yl)-amide | 544 | | 543.63 |
| II-307 | 1-Acetyl-piperidine-4-carboxylic acid (3-chloro-4-methyl-phenyl)-{3-[5-(4-cyano-2-fluoro-benzoyl)-hexahydro-pyrrolo[3,4-c]pyrrol-2-yl]-propyl}-amide; compound with trifluoro-acetic acid | 594 | | 594.13 |
| II-308 | 1-Acetyl-piperidine-4-carboxylic acid (3-chloro-4-methyl-phenyl)-{3-[5-(2-dimethylamino-pyridine-3-carbonyl)-hexahydro-pyrrolo[3,4-c]pyrrol-2-yl]-propyl}-amide; compound with trifluoro-acetic acid | 595 | | 595.18 |
| II-309 | 1-Acetyl-piperidine-4-carboxylic acid (3-chloro-4-methyl-phenyl)-{3-[5-(4-dimethylamino-pyridine-3-carbonyl)-hexahydro-pyrrolo[3,4-c]pyrrol-2-yl]-propyl}-amide; compound with trifluoro-acetic acid | 595.1 | | 595.18 |
| II-310 | Cyclopentanecarboxylic acid (3-chloro-4-methyl-phenyl)-{3-[5-(2,6-dimethyl-benzoyl)-hexahydro-pyrrolo[3,4-c]pyrrol-2-yl]-2-methyl-propyl}-amide | 536 | | 536.16 |
| II-311 | 1-Acetyl-piperidine-4-carboxylic acid (3-chloro-4-methyl-phenyl)-{3-[5-(4,6-dimethyl-pyrimidine-5-carbonyl)-3a,6a-dimethyl-hexahydro-pyrrolo[3,4-c]pyrrol-2-yl]-propyl}-amide | 609; 611 | | 609.21 |
| II-312 | 1-Acetyl-piperidine-4-carboxylic acid (3-chloro-4-methyl-phenyl)-{3-[5-(2,4-dimethyl-1-oxy-pyridine-3-carbonyl)-3a,6a-dimethyl-hexahydro-pyrrolo[3,4-c]pyrrol-2-yl]-propyl}-amide | 624; 626 (M + Na) 646; 648 | | 624.22 |
| II-313 | 1-Acetyl-piperidine-4-carboxylic acid (3-chloro-4-methyl-phenyl)-{3-[5-(4-dimethylamino-pyrimidine-5-carbonyl)-hexahydro-pyrrolo[3,4-c]pyrrol-2-yl]-propyl}-amide | 569 | | 596.17 |
| II-314 | 1-Acetyl-piperidine-4-carboxylic acid (3-chloro-4-methyl-phenyl)-{3-[5-(4-dimethylamino-2-methylsulfanyl-pyrimidine-5-carbonyl)-hexahydro-pyrrolo[3,4-c]pyrrol-2-yl]-propyl}-amide | 642 | | 642.27 |
| II-315 | 1-Acetyl-piperidine-4-carboxylic acid (3-chloro-4-methyl-phenyl)-{3-[5-(4-dimethylamino-pyridine-3-sulfonyl)-hexahydro-pyrrolo[3,4-c]pyrrol-2-yl]-propyl}-amide; compound with trifluoro-acetic acid | 630.8 | | 631.24 |
| II-316 | [4-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-3-chloro-phenoxy]-acetic acid; compound with trifluoro-acetic acid | 658.8 | | 659.61 |
| II-317 | 1-Acetyl-piperidine-4-carboxylic acid {3-[5-(5-bromo-2-methylsulfanyl-pyrimidine-4-carbonyl)-hexahydro-pyrrolo[3,4-c]pyrrol-2-yl]-propyl}-(3-chloro-4-methyl-phenyl)-amide; compound with trifluoro-acetic acid | 678 | | 678.09 |

TABLE 2-continued

| | NAME | MS[1] | mp | MW |
|---|---|---|---|---|
| II-318 | 1-Dimethylsulfamoyl-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 646.3 | | 646.25 |
| II-319 | 1-(2,2,2-Trifluoro-acetyl)-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 635 | | 635.13 |
| II-320 | 1-Dimethylsulfamoyl-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 618 | | 618.12 |
| II-321 | 1-(2,2,2-Trifluoro-acetyl)-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 607 | | 607.07 |
| II-322 | 1-Methanesulfonyl-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 589 | | 589.16 |
| II-323 | Cyclopentanecarboxylic acid (3-chloro-4-methyl-phenyl)-{3-[5-(2,6-dimethyl-benzoyl)-hexahydro-pyrrolo[3,4-c]pyrrol-2-yl]-2-hydroxy-propyl}-amide; compound with trifluoro-acetic acid | 538 | | 538.13 |
| II-324 | 4-Oxo-cyclohexanecarboxylic acid (3-chloro-4-methyl-phenyl)-{3-[5-(2,6-dimethyl-benzoyl)-hexahydro-pyrrolo[3,4-c]pyrrol-2-yl]-propyl}-amide; compound with trifluoro-acetic acid | 550 | | 550.14 |
| II-325 | [5-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-4,6-dimethyl-pyridin-2-ylsulfanyl]-acetic acid; compound with trifluoro-acetic acid | 670 | | 670.27 |
| II-326 | Cyclopentanecarboxylic acid {3-[5-(4,6-dimethyl-pyrimidine-5-carbonyl)-hexahydro-pyrrolo[3,4-c]pyrrol-2-yl]-propyl}-(3-fluoro-phenyl)-amide; compound with trifluoro-acetic acid | 494 | | 493.62 |
| II-327 | 4,4-Difluoro-cyclohexanecarboxylic acid {3-[5-(4,6-dimethyl-pyrimidine-5-carbonyl)-hexahydro-pyrrolo[3,4-c]pyrrol-2-yl]-propyl}-(3-fluoro-phenyl)-amide | 544 | | 543.63 |
| II-328 | 3-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-pyrrolidine-1-carboxylic acid tert-butyl ester | 625 | | 625.21 |
| II-329 | 1-Acetyl-piperidine-4-carboxylic acid {2-[5-(4,6-dimethyl-pyrimidine-5-carbonyl)-hexahydro-pyrrolo[3,4-c]pyrrol-2-yl]-ethyl}-(3-fluoro-phenyl)-amide | 537 | | 536.65 |
| II-330 | 2-Cyclopentyl-N-{2-[5-(4,6-dimethyl-pyrimidine-5-carbonyl)-hexahydro-pyrrolo[3,4-c]pyrrol-2-yl]-ethyl}-N-(3-fluoro-phenyl)-acetamide | 494 | | 493.62 |
| II-331 | N-{2-[5-(4,6-Dimethyl-pyrimidine-5-carbonyl)-hexahydro-pyrrolo[3,4-c]pyrrol-2-yl]-ethyl}-N-(3-fluoro-phenyl)-propionamide | 440 | | 439.53 |
| II-332 | N-{2-[5-(4,6-Dimethyl-pyrimidine-5-carbonyl)-hexahydro-pyrrolo[3,4-c]pyrrol-2-yl]-ethyl}-N-(3-fluoro-phenyl)-3-methyl-butyramide | 468 | | 467.59 |
| II-333 | 1-Acetyl-piperidine-4-carboxylic acid {3-[5-(4,6-dimethyl-pyrimidine-5-carbonyl)-hexahydro-pyrrolo[3,4-c]pyrrol-2-yl]-propyl}-p-tolyl-amide | 547 | | 546.71 |
| II-334 | 1-Acetyl-piperidine-4-carboxylic acid {3-[5-(2,4-dimethyl-1-oxy-pyridine-3-carbonyl)-hexahydro-pyrrolo[3,4-c]pyrrol-2-yl]-propyl)}-p-tolyl-amide | 562 | | 561.72 |
| II-335 | 1-Acetyl-piperidine-4-carboxylic acid (3-chloro-4-methyl-phenyl)-{3-[5-(6-dimethylamino-2-ethoxy-pyridine-3-carbonyl)-hexahydro-pyrrolo[3,4-c]pyrrol-2-yl]-propyl}-amide | 639 | | 639.24 |
| II-336 | 1,1-Dioxo-hexahydro-1$\lambda^6$-thiopyran-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide | 587 | | 587.18 |

TABLE 2-continued

| | NAME | MS[1] | mp | MW |
|---|---|---|---|---|
| II-337 | 5-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-3,4-dihydro-1H-isoquinoline-2-carboxylic acid tert-butyl ester | 706 | | 706.32 |
| II-338 | 1-Acetyl-piperidine-4-carboxylic acid (3-chloro-4-methyl-phenyl)-{3-[5-(1,2,3,4-tetrahydro-isoquinoline-5-carbonyl)-hexahydro-pyrrolo[3,4-c]pyrrol-2-yl]-propyl}-amide | 606 | | 606.21 |
| II-339 | 1-Acetyl-piperidine-4-carboxylic acid {3-[5-(2-acetyl-1,2,3,4-tetrahydro-isoquinoline-5-carbonyl)-hexahydro-pyrrolo[3,4-c]pyrrol-2-yl]-propyl}-(3-chloro-4-methyl-phenyl-amide | 648 | | 648.24 |
| II-340 | 4-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-3,5-dimethyl-1H-pyrrole-2-carboxylic acid ethyl ester | 640 | | 640.22 |
| II-341 | [3-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-pyrrolidin-1-yl]-oxo-acetic acid methyl ester | 611 | | 611.14 |
| II-342 | 5-{3-[(1-Acetyl-piperidine-4-carbonyl)-(3-chloro-4-methyl-phenyl)-amino]-propyl}-hexahydro-pyrrolo[3,4-c]pyrrole-2-carboxylic acid methyl-phenyl-amide; compound with trifluoro-acetic acid | 580 | | 580.17 |
| II-343 | 5-{3-[(1-Acetyl-piperidine-4-carbonyl)-(3-chloro-4-methyl-phenyl)-amino]-propyl}-hexahydro-pyrrolo[3,4-c]pyrrole-2-carboxylic acid benzylamide; compound with trifluoro-acetic acid | 580 | | 580.17 |
| II-344 | 1-(3-Chloro-4-methyl-phenyl)-1-{3-[5-(4,6-dimethyl-pyrimidine-5-carbonyl)-hexahydro-pyrrolo[3,4-c]pyrrol-2-yl]-propyl}-3-methyl-3-phenyl-urea; compound with trifluoro-acetic acid | 561 | | 561.13 |
| II-345 | 1-Acetyl-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 553 | | 553.1 |
| II-346 | 1-Propionyl-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 567 | | 567.13 |
| II-347 | {2-[3-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-azetidin-1-yl]-2-oxo-ethoxy}-acetic acid; compound with trifluoro-acetic acid | 627 | | 627.14 |
| II-348 | 4-[3-((3-Chloro-4-methyl-phenyl)-(3-[5-(4,6-dimethyl-pyrimidine-5-carbonyl)-hexahydro pyrrolo[3,4-c]pyrrol-2-yl]-propyl}-carbamoyl)-azetidin-1-yl]-4-oxo-butyric acid; compound with trifluoro-acetic acid | 611 | | 611.14 |
| II-349 | 3-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-azetidine-1-carboxylic acid methyl ester; compound with trifluoro-acetic acid | 569 | | 569.1 |
| II-350 | [3-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-azetidin-1-yl]-oxo-acetic acid methyl ester; compound with trifluoro-acetic acid | 597 | | 597.11 |
| II-351 | 1-Cyclopropanecarbonyl-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 579 | | 579.14 |
| II-352 | 1-Butyryl-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 581 | | 581.16 |
| II-353 | 1-(2-Methoxy-acetyl)-azetidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 583 | | 583.13 |

TABLE 2-continued

| | NAME | MS[1] | mp | MW |
|---|---|---|---|---|
| II-354 | 1-Acetyl-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-2,2-dimethl-propyl}-amide | 609 | | 609.21 |
| II-355 | 4-(5-{3-[(1-Acetyl-piperidine-4-carbonyl)-(3-chloro-4-methyl-phenyl)-amino]-propyl}-hexahydro-pyrrolo[3,4-c]pyrrole-2-sulfonyl)-3,5-dimethyl-1H-pyrrole-2-carboxylic acid ethyl ester | 676 | | 676.27 |
| II-356 | 1-Acetyl-piperidine-4-carboxylic acid {3-[5-(2-azetidin-1-yl-pyridine-3-carbonyl)-hexahydro-pyrrolo[3,4-c]pyrrol-2-yl]-propyl}-(3-chloro-4-methyl-phenyl)-amide | 607 | | 607.2 |
| II-357 | 4-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-1,3,5-trimethyl-1H-pyrrole-2-carboxylic acid ethyl ester | 654 | | 654.25 |
| II-358 | 5-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-1,2,4-trimethyl-1H-pyrrole-3-carboxylic acid ethyl ester | 654 | | 654.25 |
| II-359 | 4-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-3,5-dimethyl-1H-pyrrole-2-carboxylic acid | 612 | | 612.17 |
| II-360 | 1-Acetyl-piperidine-4-carboxylic acid {3-[5-(2,6-bis-dimethylamino-pyridine-3-carbonyl)-hexahydro-pyrrolo[3,4-c]pyrrol-2-yl]-propyl}-(3-chloro-4-methyl-phenyl)-amide | 638 | | 638.25 |
| II-361 | 1-Acetyl-piperidine-4-carboxylic acid (3-chloro-4-methyl-phenyl)-{3-[5-(5-methyl-1-phenyl-1H-pyrazole-4-sulfonyl)-hexahydro-pyrrolo[3,4-c]pyrrol-2-yl]-propyl}-amide | 667 | | 667.27 |
| II-362 | 4-Oxo-cyclohexanecarboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide | 552 | | 552.12 |
| II-363 | 1-Acetyl-piperidine-4-carboxylic acid (3-chloro-4-methyl-phenyl)-{3-[5-(2-methyl-pyridine-3-sulfonyl)-hexahydro-pyrrolo[3,4-c]pyrrol-2-yl]-propyl}-amide | 602 | | 602.2 |
| II-364 | 1-Acetyl-piperidine-4-carboxylic acid (3-chloro-4-methyl-phenyl)-{3-[5-(3-methyl-benzofuran-2-carbonyl)-hexahydro-pyrrolo[3,4-c]pyrrol-2-yl]-propyl}-amide; compound with trifluoro-acetic acid | 605 | | 605.18 |
| II-365 | 1-Acetyl-piperidine-4-carboxylic acid (3-chloro-4-methyl-phenyl)-{3-[5-(7-methoxy-3-methyl-1H-indole-2-carbonyl)-hexahydro-pyrrolo[3,4-c]pyrrol-2-yl]-propyl}-amide; compound with trifluoro-acetic acid | 634 | | 634.22 |
| II-366 | Tetrahydro-pyran-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 540 | | 540.1 |
| II 367 | N-(3-Chloro-4-methyl-phenyl)-N-{3-[5-(4,6-dimethyl-pyrimidine-5-carbonyl)-hexahydro-pyrrolo[3,4-c]pyrrol-2-yl]-propyl}-acetamide; compound with trifluoro-acetic acid | 470 | | 470.01 |
| II-368 | Cyclopropanecarboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 496 | | 496.05 |
| II-369 | 1-Acetyl-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 567 | | 567.13 |
| II-370 | 1-(2,2,2-Trifluoro-acetyl)-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 621 | | 621.1 |
| II-371 | 1-Methanesulfonyl-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 603 | | 603.18 |

TABLE 2-continued

| | NAME | MS[1] | mp | MW |
|---|---|---|---|---|
| II-372 | 1-Cyclopropanecarbonyl-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 593 | | 593.17 |
| II-373 | 3-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-pyrrolidine-1-carboxylic acid methyl ester; compound with trifluoro-acetic acid | 583 | | 583.13 |
| II-374 | 1-Dimethylsulfamoyl-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 632 | | 632.23 |
| II-375 | [3-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-pyrrolidin-1-yl]-oxo-acetic acid; compound with trifluoro-acetic acid | 597 | | 597.11 |
| II-376 | 2-(5-{3-[(1-Acetyl-piperidine-4-carbonyl)-(3-chloro-4-methyl-phenyl)-amino]-propyl}-hexahydro-pyrrolo[3,4-c]pyrrole-2-sulfonyl)-benzoic acid methyl ester; compound with trifluoro-acetic acid | 645 | | 645.22 |
| II-377 | 2-(5-{3-[(1-Acetyl-piperidine-4-carbonyl)-(3-chloro-4-methyl-phenyl)-amino]-propyl}-hexahydro-pyrrolo[3,4-c]pyrrole-2-sulfonyl)-benzoic acid; compound with trifluoro-acetic acid | 631 | | 631.19 |
| II-378 | 1-Methanesulfonyl-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 617 | | 617.21 |
| II-379 | Pyrrolidine-1,3-dicarboxylic acid 3-((3-chloro-4-methyl-phenyl)-{3-[5-(4,6-dimethyl-pyrimidine-5-carbonyl)-hexahydro-pyrrolo[3,4-c]pyrrol-2-yl]-propyl}-amide) 1-dimethylamide; compound with trifluoro-acetic acid | 596 | | 596.17 |
| II-380 | 1-Cyclopropanesulfonyl-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 629 | | 629.22 |
| II-381 | 1-Isobutyryl-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 595 | | 595.18 |
| II-382 | 1-Propionyl-pyrrolidine-3-carboxylic acid (3-chloro 4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 581 | | 581.16 |
| II-383 | 1-(2,2,2-Trifluoro-ethyl)-pyrrolidine-3-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide; compound with trifluoro-acetic acid | 607 | | 607.12 |
| II-384 | 4-(5-{3-[(1-Acetyl-piperidine-4-carbonyl)-(3-chloro-4-methyl-phenyl)-amino]-propyl}-hexahydro-pyrrolo[3,4-c]pyrrole-2-sulfonyl)-3,5-dimethyl-1H-pyrrole-2-carboxylic acid | 648.3 | | 648.22 |
| II-385 | 8-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-3,4-dihydro-1H-isoquinoline-2-carboxylic acid tert-butyl ester | 706 | | 706.32 |
| II-386 | 1-Acetyl-piperidine-4-carboxylic acid (3-chloro-4-methyl-phenyl)-{3-[5-(1-methyl-1H-imidazole-2-carbonyl)-hexahydro-pyrrolo[3,4-c]pyrrol-2-yl]-propyl}-amide | 555 | | 555.12 |
| II-387 | 4-Hydroxy-cyclohexanecarboxylic acid (3-chloro-4-methyl-phenyl)-{3-[5-(4,6-dimethyl-pyrimidine-5-carbonyl)-hexahydro-pyrrolo[3,4-c]pyrrol-2-yl]-propyl}-amide | 554 | | 554.13 |
| II-388 | 1-Acetyl-piperidine-4-carboxylic acid (3-chloro-4-methyl-phenyl)-{3-[5-(1,2,3,4-tetrahydro-isoquinoline-8-carbonyl)-hexahydro-pyrrolo[3,4-c]pyrrol-2-yl]-propyl}-amide | 606 | | 606.21 |

TABLE 2-continued

| | NAME | MS[1] | mp | MW |
|---|---|---|---|---|
| II-389 | 1-Acetyl-piperidine-4-carboxylic acid (5-chloro-thiazol-2-yl)-{3-[5-(2,6-dimethyl-benzoyl)-hexahydro-pyrrolo[3,4-c]pyrrol-2-yl]-propyl}-amide; compound with trifluoro-acetic acid | 572 | | 572.17 |
| II-390 | 3-[4-(5-{3-[(1-Acetyl-piperidine-4-carbonyl)-(3-chloro-4-methyl-phenyl)-amino]-propyl}-hexahydro-pyrrolo[3,4-c]pyrrole-2-carbonyl)-3,5-dimethyl-pyrazol-1-yl]-benzoic acid methyl ester | 703 | | 703.28 |
| II-391 | 1-Acetyl-piperidine-4-carboxylic acid (5-chloro-thiazol-2-yl)-{3-[5-(2,6-dimethyl-benzoyl)-hexahydro-pyrrolo[3,4-c]pyrrol-2-yl]-propyl}-amide; compound with trifluoro-acetic acid | 572 | | 572.17 |
| II-392 | 3-(3-(3-Chloro-4-methyl-phenyl)-3-{3-[5-(4,6-dimethyl-pyrimidine-5-carbonyl)-hexahydro-pyrrolo[3,4-c]pyrrol-2-yl]-propyl}-ureido)-benzoic acid; compound with trifluoro-acetic acid | 591 | | 591.1 |
| II-393 | 3-(3-(3-Chloro-4-methyl-phenyl)-3-{3-[5-(4,6-dimethyl-pyrimidine-5-carbonyl)-hexahydro-pyrrolo[3,4-c]pyrrol-2-yl]-propyl}-ureido)-benzoic acid ethyl ester; compound with trifluoro-acetic acid | 619 | | 619.16 |

[1]The observed mass spectra are (M)+ or (M + H)+ and are consistent with the compound

DOSAGE AND ADMINISTRATION

The compounds of the present invention may be formulated in a wide variety of oral administration dosage forms and carriers. Oral administration can be in the form of tablets, coated tablets, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxy-ethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor, HIV protease inhibitor and/or a viral fusion inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLE 1

Cyclopentanecarboxylic acid {3-[5-(2,6-dimethyl-benzoyl)-hexahydro-pyrrolo[3,4-c]pyrrol-2-yl]-1-phenyl-propyl}-amide (I-3; Scheme 1)

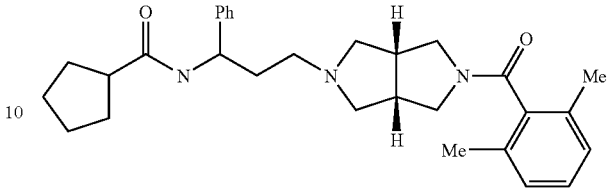

step 1—A solution of 2-benzyl-octahydro-pyrrolo[3,4-c]pyrrole (4a, 1.22 g, 4.97 mmol) in DCM (20 mL) was added to a solution of cyclopentanecarboxylic acid (3-oxo-1-phenyl-propyl)-amide (10, 1.0 g, 4.97 mmol) in toluene (8 mL) containing HOAc (0.34 mL). Sodium triacetoxyborohydride (1.26 g, 5.96 mmol) was added in two portion separated by 0.5 h and reaction stirred for 18 h at room temperature. The reaction was quenched by addition a solution 0.5 M of KOH (30 mL) and product extracted with DCM 3×50 mL). The combined organic extracts dried (MgSO$_4$) and concentrated in vacuo. The crude product was purified by flash chromatography on silica gel eluting with 4% (10% ammonium hydroxide in methanol) in DCM to afford 11 as a viscous liquid (0.62 g, 29% theory): $^1$H NMR (CDCl$_3$) δ 1.46–1.64 (m, 2H), 1.65–1.94 (m, 7H), 1.96–2.11 (m, 1H), 2.23–2.44 (m, 4H), 2.45–2.83 (m, 9H), 3.59 (q, 2H, J=18.2, 12.8 Hz), 5.11 (q, 1H, J=6.2, 5.8 Hz), 7.07–7.39 (m, 10H), 7.93 (d, 1H, J=7.1 Hz); MS (ES+) m/z 432 (M+H)$^+$.

step 2—Palladium hydroxide (0.2 g) and ammonium formate (2.92 g, 0.046 mol) were added to a solution of cyclopentanecarboxylic acid [3-(5-benzyl-hexahydro-pyrrolo[3,4-c]pyrrol-2-yl)-1-phenyl-propyl]-amide (11, 2.0 g, 0.004 mol) in EtOH (50 mL). The solution was heated at reflux for 2 h and filtered through a CELITE® pad. The resulting solution was concentrated in vacuo and crude product purified by flash column chromatography on silica gel (CH$_2$Cl$_2$:MeOH:NH$_4$OH=60:10:1) to afford 12: $^1$H NMR (DMSO-d$_6$) δ 1.4–1.8 (m, 11H), 2.15–2.42 (m, 6H), 2.55–2.65 (m, 2H), 2.75–2.85 (m, 2H), 4.33 (q, 1H), 7.15–7.35 (m, 5H), 8.2 (dd, 1H); $^{13}$C NMR (DMSO-d$_6$) δ 25.96, 26.00, 30.15, 30.45, 35.60, 39.07, 39.35, 39.62, 39.90, 40.18, 40.46, 40.74, 41.37, 43.43, 44.61, 51.02, 52.14, 54.02, 60.20, 60.30, 126.64, 126.82, 128.51, 144.46, 174.81; MS (ES+) m/z 341 (M+H)$^+$;

step 3—To a solution of cyclopentanecarboxylic acid [3-(hexahydro-pyrrolo[3,4-c]pyrrol-2-yl)-1-phenyl-propyl]-amide (12 0.20 g, 0.585 mmol) in dichloromethane at rt was added 2,6-dimethylbenzoic acid was added to a solution. To the resulting solution was added sequentially EDCI (0.14 g, 0.760 mmol), HOBt (0.10 g, 0.760 mmol) and diisopropylethylamine (0.3 mL, 1.755 mmol) were added to the mixture. The mixture was stirred overnight at rt. The reaction mixture was washed with 5% NaHCO$_3$ solution and dried (MgSO$_4$) and concentrated in vacuo. The crude product was purified by flash column chromatography on silica gel (5% MeOH/CH$_2$Cl$_2$) to afford 13: mp 60.9–63.9° C.; $^1$H NMR (DMSO-d$_6$) δ 1.4–1.9 (m, 10H), 2.1 (s, 3H), 2.2 (s, 3H), 2.3–2.5 (m, 5H), 3.35 (m, 1H), 3.5 (dd, 1H), 3.75 (m, 1H), 4.88 (m, 1H), 7.05 (d, 2H), 7.15–7.35 (m, 6H), 8.0 (d, 1H); $^{13}$C NMR (DMSO-d$_6$) δ 18.85, 18.98, 25.96, 26.00, 30.12, 30.42, 35.73, 39.05, 39.33, 39.60, 39.88, 41.69, 44.56, 50.49, 51.05, 52.37, 53.11, 60.37, 126.64, 126.67, 126.89, 127.53, 127.61, 128.31, 128.52, 133.05, 138.25, 144.39, 167.72, 174.81; MS (ES+) m/z 473 (M+H)$^+$; Anal. (C$_{30}$H$_{39}$N$_3$O$_3$ 0.15M CH$_2$Cl$_2$) C; calcd, 74.45; found, 74.55; H; calcd, 8.14; found, 7.74; N; calcd, 8.64; found, 8.95.

EXAMPLE 2

1-Acetyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl} (II-1)

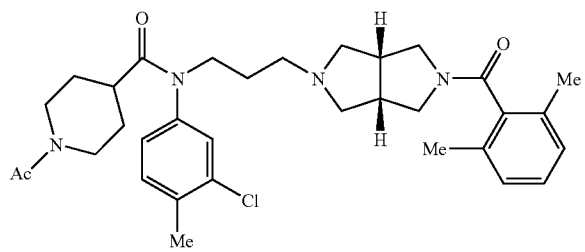

step 1—1-chloro-3-iodopropane (3.0 mL, 28.49 mmol) and cesium carbonate (18.0 g, 56.49 mol) were added to a solution of 2-chloro-4-aminotoluene (4 g, 28.49 mmol) in DMF (8 mL). The mixture was stirred overnight at RT. Water (15 mL) was added to the mixture and the resulting solution was extracted with hexane. The organic layer was washed with water again and dried ($MgSO_4$). The crude product was purified by flash column chromatography on silica gel (5% EtOAc/hexane) to afford 20: $^1$H NMR ($CHCl_3$) δ 1.5 (s, 1H), 2.05 (m, 2H), 2.25 (s, 3H), 3.3 (t, 2H), 3.65 (t, 2H), 6.4 (dd, 1H), 6.65 (d, 1H), 7.0 (d, 1H)

step 2—A solution of (3-chloro-4-methyl-phenyl)-(3-chloro-propyl)-amine (20, 3.20 g, 14.70 mmol) in $CH_2Cl_2$ (100 mL) was cooled to 0° C. After the mixture was treated with triethylamine (4.9 mL, 35.28 mmol) and 1-acetyl-piperidine-4-carbonyl chloride (5.57 g, 29.40 mmol), it was allowed to stir for 5 h at 0° C. Saturated $NaHCO_3$ was added to the mixture and the mixture was stirred for 20 min. The solvent was evaporated and the mixture was extracted with EtOAc. The organic layer was washed with 2N HCl and brine, dried ($MgSO_4$) and purified by flash column chromatography on silica gel (5% MeOH/EtOAc) to afford 18: $^1$H NMR ($CHCl_3$) δ 1.55–1.8 (br, 4H), 2.0 (m, 3H), 2.05 (s, 3H), 2.3–2.4 (m, 2H), 2.45 (s, 3H), 3.52 (t, 2H), 3.3 (t, 2H), 6.97 (dd, 1H), 7.18 (t, 1H), 7.32 (d, 1H); $^{13}$C NMR ($CHCl_3$) δ 20.19, 21.68, 28.94, 31.17, 39.64, 42.64, 48.03, 126.63, 128.79, 132.47, 135.79, 137.12, 141.27, 169.27, 174.58; ms (ES+) m/z 370 (M+H).

step 3—To a solution of solution of 2-benzyl-octahydro-pyrrolo[3,4-c]pyrrole (4b, 1.03 g, 5.11 mmol) in DCM (30 mL) at rt was added 2,6-dimethylbenzoic acid (1.53 g, 10.22 mmol), BOP-Cl (2.60 g, 10.22 mmol), DMAP (1.24 g, 10.22 mmol) and $Et_3N$ (1.5 mL, 10.22 mmol). The reaction mixture was stirred overnight at RT and washed with 5% $NaHCO_3$ and brine. The resulting was dried ($MgSO_4$), filtered and evaporated in vacuo. The crude product was purified by flash chromatography on silica gel ($CH_2Cl_2$:MeOH:$NH_4$OH/4000:10:1) to afford 16: ms (ES+) m/z=235 (M+H)$^+$;

step 4—Palladium hydroxide (0.13 g) and ammonium formate (2.45 g, 0.038 mol) were added to a solution of (5-benzyl-hexahydro-pyrrolo[3,4-c]pyrrol-2-yl)-(2,6-dimethyl-phenyl)-methanone (16, 1.30 g, 3.88 mmol) in EOH (30 mL). The solution was heated at reflux for 2 h and filtered through a CELITE® pad. The volatile solvents were removed by evaporation in vacuo and the crude reaction product was purified by flash column chromatography on silica gel ($CH_2Cl_2$:MeOH:$NH_4$OH/120:10:1) to afford 66: $^1$H NMR ($CHCl_3$) δ 2.13 (s, 1H), 2.25 (s, 3H), 2.28 (s, 3H), 2.65 (dd, 1H), 2.2–2.95 (m, 3H), 3.08–3.25 (m, 2H), 3.35 (dd, 1H), 3.65 (dd, 1H), 3.85–3.95 (m, 1H), 7.0 (m, 2H), 7.15 (q, 1H); ms (ES+) m/z 245 (M+H).

step 5—1-Acetyl-piperidine-4-carboxylic acid(3-chloro-4-methyl-phenyl)-(3-chloro-propyl)-amide (17, 0.22 g, 0.61 mmol) and (2,6-dimethyl-phenyl)-(hexahydro-pyrrolo[3,4-c]pyrrol-2-yl)-methanone (18, 0.15 g, 0.61 mmol) were dissolved in MeCN (15 mL). $K_2CO_3$ (0.25 g, 1.84 mmol) and potassium iodide (0.11 g, 0.67 mmol) were added to the mixture and the resulting solution was heated at reflux overnight. The mixture was cooled, diluted with water and extracted with EtOAc. The combined EtOAc extracts were washed with brine and dried ($MgSO_4$) and evaporated. The crude product was purified by flash column chromatography on silica gel (5% MeOH/$CH_2Cl_2$) to afford 19: mp 58.1–65.2° C.; $^1$H NMR (DMSO-$d_6$) δ 1.5–1.65 (m, 6H), 1.95 (s, 3H), 2.12 (d, 6H), 2.23–2.52 (m, 12H), 2.68–2.85 (m, 4H), 3.2–3.25 (m, 1H), 3.45 (dd, 1H), 3.6–3.7 (m, 3H), 7.05 (d, 2H), 7.1–7.2 (m, 2H), 7.35 (d, 1H), 7.43 (d, 1H); $^{13}$C NMR (DMSO-$d_6$) δ 18.84, 18.93, 19.60, 21.53, 26.64, 28.37, 29.04, 39.05, 39.33, 39.61, 39.88, 41.63, 45.23, 47.46, 50.62, 52.37, 53.13, 60.18, 60.60, 127.42, 127.52, 127.57, 128.29, 128.62, 132.43, 132.96, 133.05, 134.13, 135.64, 138.24, 141.63, 167.65, 168.18, 173.47; ms (ES+) m/z 578 (M+H); Anal. ($C_{33}H_{43}ClN_4O_3$-0.2M $CH_2Cl_2$) C; calcd, 66.89; found, 66.70; H; calcd, 7.34; found, 7.10; N; calcd, 9.40 found, 9.50.

EXAMPLE 3

2-Acetylamino-N-{3-[5-(2-chloro-6-fluoro-benzoyl)-hexahydro-pyrrolo[3,4-c]pyrrol-2-yl]-phenyl-propyl}-acetamide (I-196)

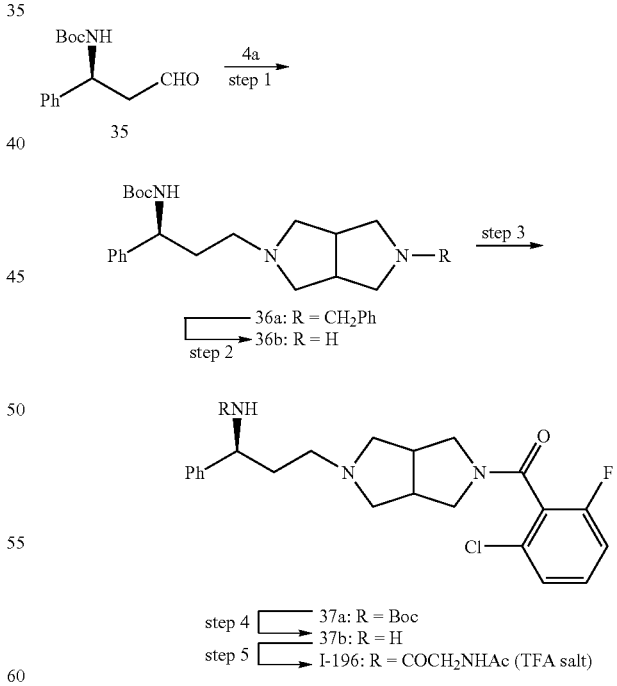

step 1—A solution of 4a (6.25 g, 31 mmol) in DCM (200 mL) was added to 35 (1.0 g, 4.97 mmol). To the resulting mixture was added NaBH(OAc)$_3$ (9.86 g, 47 mmol) in two portions and the reaction stirred for 18 h at RT. The reaction was washed with a solution 5% $NaHCO_3$ (100 mL). The organic phase was dried ($Na_2SO_4$) and concentrated in vacuo. The crude product was purified by flash chromatography on silica gel eluting with DCM/3.5% MeOH (containing 10% NH₄OH) to afford 6.8 g (46%) of 36a as a viscous liquid: MS (ES+) m/z 436 (M+H)⁺.

step 2—Palladium hydroxide (0.2 g) and ammonium formate (6.3 g, 0.100 mol) were added to a solution of 36a (4.36 g, 0.010 mol) in EtOH (200 mL). The solution was heated at reflux for 2 h and filtered through a CELITE® pad. The resulting solution was concentrated in vacuo to afford to afford 3.5 g (100%) of 36b: ms (ES+) m/z 346 (M+H)⁺.

step 3—To a solution of 36b (3.5 g, 10.0 mmol) in DMF (100 ml) at RT was added 2-chloro-6-fluorobenzoic acid (1.75 g, 10.0 mmol). To the resulting solution were added sequentially EDCI (2.0 g, 10.0 mmol), HOBt (1.35 g, 10.0 mmol) and NaHCO₃ (3.4 g, 40.0 mmol) and the mixture was stirred overnight at RT. The solvent was evaporated under reduced pressure and the residue was dissolved in DCM (100 ml). The organics were washed with 2% HCl, water, saturated. NaHCO₃ solution, dried (Na₂SO₄) and concentrated in vacuo. The crude product was purified by flash column chromatography on silica gel (3.5% MeOH/DCM) to afford 3.3 g (66%) of 37a: MS (ES+) m/z 502 (M+H)⁺.

step 4—To a solution of 37a (3.3 g, 6.6 mmol) in DCM (50 ml) was added a solution of ethereal HCl (100 mL, 1 N in ether). The reaction stirred 18 h. The solution was evaporated under reduced pressure to afford 3.6 g (110%) of 37b HCl as a white solid: MS (ES+) m/z 401 (M+H)⁺.

step 5—Acetylamino-acetic acid (6.1 mg, 52.5 μmol) was weighed into the reaction vessel and resin-bound carbodimide (78 mg, 2.0 equiv) was added. HOBt (60 μmol, 1.7 equiv. in 10% DMF in DCM, 1.0 ml) was added and the reaction was shaken for 1 h. A solution of 37b HCl in DCM (35 μmol, 500 μl, with 30 μl DIEA) was added. The reaction was shaken for 72 h. The resin was filtered, washed with DCM (3×1.0 mL) and the solvent was evaporated under reduced pressure. The residue was purified by reverse-phase preparative HPLC to afford I-196: ms (ES+) m/z 501 (M+H)⁺.

EXAMPLE 4

N-{3-[5-(2-Chloro-6-fluoro-benzoyl)-hexahydro-pyrrolo[3,4-c]pyrrol-2-yl]-1-phenyl-propyl}-2-phenyl-propionamide (I-312)

I-312 was synthesized in the same manner as example 3 except in step 5, acetylamino-acetic acid was replaced with 2-methylphenyl acetic acid to afford I-312 which was isolated as the TFA salt: ms (ES+) m/z 534 (M+H)⁺.

EXAMPLE 5

1-{3-[5-(2,4-Dimethyl-1-oxy-pyridine-3-carbonyl)-hexahydro-pyrrolo[3,4-c]pyrrol-2-yl]-1-phenyl-propyl}-3-phenyl-urea (I-373)

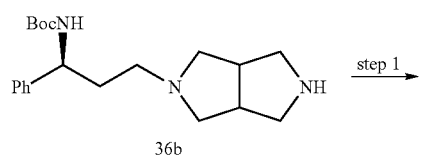

36b

-continued

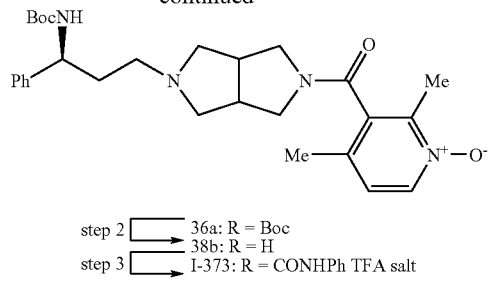

step 2 ⎡ 36a: R = Boc
       ⎣ 38b: R = H
step 3 ⎣ I-373: R = CONHPh TFA salt step 1—To a solution of 36b (0.456 g, 1.1 mmol) in DMF (10 ml) at RT was added 2,4-dimethyl-3-pyridine carboxylic acid N-oxide (0.184 g, 1.1 mmol). To the resulting solution were added sequentially EDCI (0.221 g, 1.2 mmol), HOBt (0.149 g, 1.1 mmol) and NaHCO₃ (0.370 g, 4.4 mmol). The mixture was stirred overnight at RT then evaporated under reduced pressure. The residue was dissolved in DCM (25 ml). The organics were washed with 2% HCl, water, saturated. NaHCO₃ solution, dried (Na₂SO₄) and concentrated in vacuo. The crude product was purified by flash column chromatography on silica gel (3.5% MeOH/CH₂Cl₂) to afford 0.360 g (66%) of 38a: ms (ES+) m/z 495 (M+H)⁺.

step 2—To a solution of 38a (0.36 g, 0.73 mmol) in DCM (20 ml) was added a solution of HCl (1 N in ether, 20 ml). The reaction stirred 18 h. The solution was evaporated under reduced pressure to afford 0.31 g (100%) of 38b HCl as a white solid: ms (ES+) m/z 395 (M+H)⁺.

step 3—Phenyl isocyanate (8.1 mg, 75 μmol) was weighed into the reaction vessel and 38b HCl (50 μmol) in DCM (500 μl containing 60 μl DIEA) was added. The reaction was shaken for 18 h. The solvent was evaporated under reduced pressure. The residue was purified by reverse-phase preparative HPLC to afford I-373: ms (ES+) mL/z 514 (M+H)⁺.

EXAMPLE 6

2-Cyclohexyl-N-{3-[5-(2,4-dimethyl-pyridine-3-carbonyl)-hexahydro-pyrrolo[3,4-c]pyrrol-2-yl]-1-phenyl-propyl}-acetamide, TFA salt (I-378)

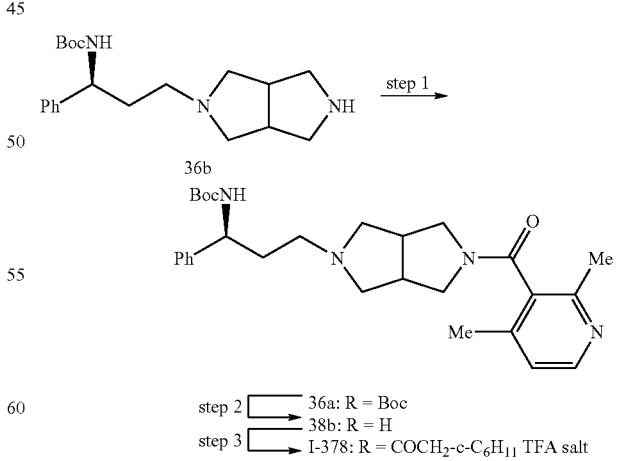

step 2 ⎡ 36a: R = Boc
       ⎣ 38b: R = H
step 3 ⎣ I-378: R = COCH₂-c-C₆H₁₁ TFA salt step 1—Prepared as described in step I of Example 5 except 2,4-dimethyl-3-pyridine carboxylic acid N-oxide was replaced with 2,4-dimethyl-3-pyridine carboxylic acid to afford 0.643 g (61%) of 39a: ms (ES+) m/z 479 (M+H)⁺.

step 2—Prepared as described in step 2 of Example 5 except 39a from step 1 was used to afford 0.790 g (100%) of 39b HCl salt: ms (ES+) m/z 379 (M+H)+.

step 3—Cyclohexylacetic acid (10.6 mg, 75 μmol) was weighed into the reaction vessel and 39b.2HCl (50 μmol) in DCM (500 μl containing with 60 μl DIPEA) was added. The reaction was shaken for 18 h and the solvent was evaporated under reduced pressure. The residue was purified by reverse-phase preparative HPLC to afford I-378 as a TFA salt: ms (ES+) m/z 503 (M+H)+.

EXAMPLE 7

Tetrahydro-furan-3-carboxylic acid {3-[5-(4,6-dimethyl-2-pyridin-4-yl-pyrimidine-5-carbonyl)-hexahydro-pyrrolo[3,4-c]pyrrol-2-yl]-1-phenyl-propyl}-amide, TFA salt (I-422)

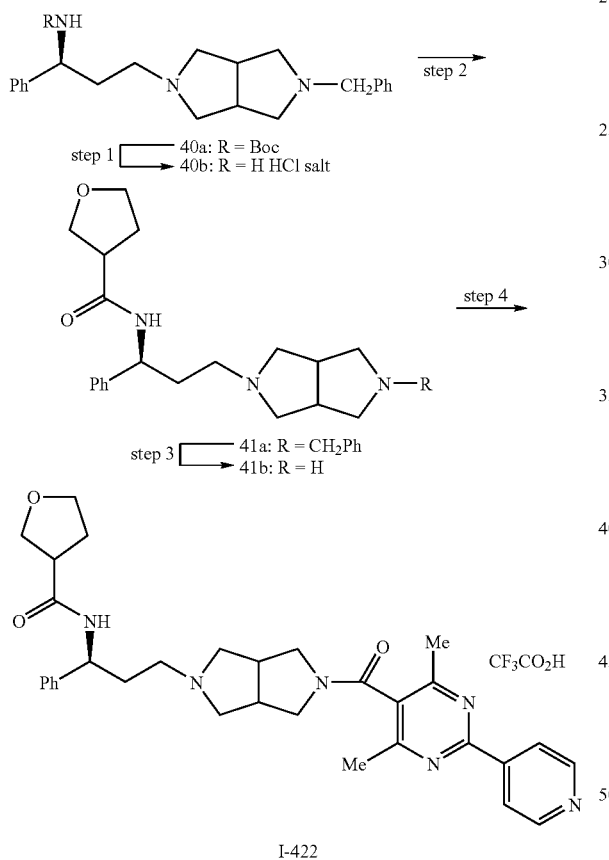

step 1—To a solution of 40a (5.85 g, 13.4 mmol) in DCM (50 ml) was added a solution of HCl (1 N in ether, 50 ml) and the reaction stirred 18 h. The solution was evaporated under reduced pressure to afford 6.3 g (100%) 40b HCl as a white solid: ms (ES+) m/z 336 (M+H)+.

step 2—To a solution of 40b HCl (6.3 g, 13.4 mmol) in DMF (50 ml) at RT was added tetrahydro-3-furoic acid (1.29 ml, 13.4 mmol). To the resulting solution were added sequentially EDCI (2.7 g, 14.1 mmol), HOBt (1.81 g, 13.4 mmol) and NaHCO₃ (4.5 g, 53.6 mmol). The mixture was stirred overnight at RT. The solvent was evaporated under reduced pressure and the residue was dissolved in DCM (25 ml). The organic phase was washed with 2% HCl, water, saturated NaHCO₃ solution, dried (Na₂SO₄) and concentrated in vacuo. The crude product was purified by flash column chromatography on silica gel (3.5% MeOH/DCM) to afford 5.23 g (90% theory) of 41a: ms (ES+) m/z 434 (M+H)+.

step 3—Palladium hydroxide (0.2 g) and ammonium formate (3.0 g, 46 mmol) were added to a solution of 41a (2.0 g, 4.6 mmol) in EtOH (100 mL). The solution was heated to reflux for 5 h and filtered through a CELITE® pad. The resulting solution was concentrated in vacuo to afford 1.40 g (89%) of 41b: ms (ES+) m/z 344 (M+H)+.

step 3—4,6-Dimethyl-2-pyridin-4-yl-pyrimidine-5-carboxylic acid (18.7 mg, 75 μmol, prepared as described in T. Gebhard et al. *J. Med. Chem.* 2004 47(8):1939–1955 and WO2002081449 A1) was weighed into a reaction vessel and resin-bound carbodimide (120 mg, 2.0 equiv) was added. HOBt (85 μmol, in 10% DMF/DCM, 1.0 ml) was added. The reaction was shaken for 18 h. A solution of 41b (50 μmol) in DCM (500 μl containing 60 μl DIEA) was added. The reaction shakin continued for 18 h. The resin was filtered and washed with DMF (1.0 ml) and DCM (2×1.0 mL). The residue was purified by reverse-phase preparative HPLC to afford I-422: ms (ES+) m/z 555 (M+H)+.

EXAMPLE 8

1-(3-Chloro-4-methyl-phenyl)-3-cyclohexylmethyl-1-{3-[5-(2,4-dimethyl-pyridine-3carbonyl)-hexahydro-pyrrolo[3,4-c]pyrrol-2-yl]-propyl}-urea, TFA salt (II-149)

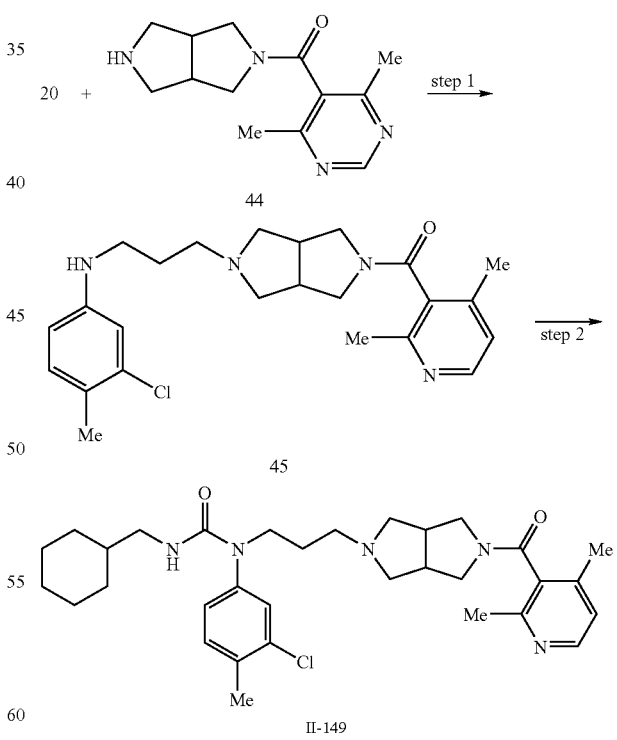

step 1—To a solution of 44 (0.90 g, 3.7 mmol) in MeCN (80 ml) were added sequentially 20 (0.887 mg, 4.1 mmol), KI (0.681 g, 4.1 mmol) and DIPEA (1.3 mL, 7.4 mmol). The reaction mixture was heated at 80° C. for 18 h. The reaction was quenched with water and thrice extracted with EtOAc.

The organic phase was dried ($Na_2SO_4$), filtered and evaporated. The crude product was purified by flash column chromatography on silica gel eluting with 3.5% MeOH/DCM (containing 0.4% ammonia) to afford 1.06 g (67%) of 45: ms (ES+) m/z 426 (M+H)+.

step 2—A flask was charged with cyclohexaneaminemethyl isocyanate (7.5 mg, 52.5 µmol) and 45 (35 µmol) in DCM (500 µL) was added. The reaction was shaken for 18 h. The residue was purified by reverse-phase preparative HPLC to I-149: ms (ES+) m/z 566 (M+H)+.

EXAMPLE 9

1-Acetyl-piperidine-4-carboxylic acid {3-[5-(2-acetyl-1,2,3,4-tetrahydro-isoquinoline-5-carbonyl)hexahydro-pyrrolo[3,4-c]pyrrol-2-yl]-propyl}-(3-chloro-4-methyl-phenyl)-amide (II-339)

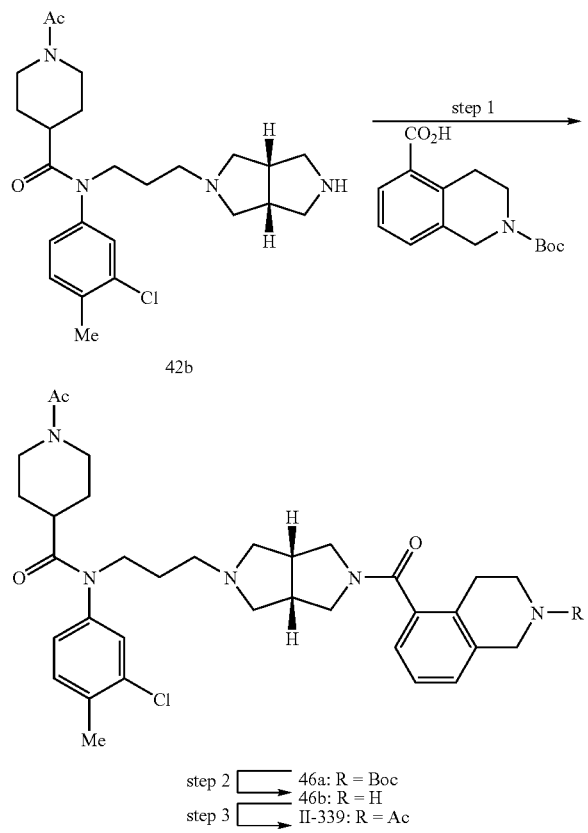

1-Acetyl-piperidine-4-carboxylic acid (3-chloro-4-methyl-phenyl)-[3-(hexahydro-pyrrolo[3,4-c]pyrrol-2-yl)-propyl]-amide (42b) was prepared by the procedures described in Example 2 except 4a was first alkylated with 18 as described in step 4 and the benzyl protecting group was removed by catalytic hydrogenolysis as described in step 3.

step 1—To a solution of 42b (0.1 g, 0.224 mmol), boc-5-hydroxycarbonyl-1,2,3,4-tetrahydroisoquinoline (62 mg, 0.224 mmol, Arch Corp. catalog # AR02230), EDCI (51 mg, 0.268 mmol) and HOBT (41 mg, 0.268 mmol) in DMF (2 mL) at RT was added DIPEA (80 µL, 0.336 mmol). The resulting mixture was stirred at RT for 16 h then partitioned between EtOAc and water. The aqueous layer was back extracted twice with EtOAc. The combined organic layers were dried ($Na_2SO_4$), filtered and evaporated. The residue was purified by $SiO_2$ chromatography eluting with a gradient of 100% DCM (2 min isocratic run time) to a 1:1 mixture DCM of a solution of DCM/MeOH/$NH_4OH$ (80/10/1) over 20 minutes at a 25 mL/min flow rate to afford 0.142 g (90%) of 46a as a light pink foam: $^{13}$C NMR ($CDCl_3$) δ 20.19, 21.77, 26.62, 27.20, 28.74, 28.89, 29.56, 39.78, 41.09, 41.28, 42.47, 45.93, 48.47, 50.99, 53.00, 54.34, 60.27, 60.75, 80.31, 124.34, 126.71, 128.88, 131.62, 132.39, 135.64, 136.88, 141.53, 155.20, 168.99, 169.15, 174.30; MS (ES+) m/z 706 (M+H)+.

step 2—To a solution of 46a (0.11 g, 0.156 mmol) in DCM (2.5 mL) at RT was added TFA (0.5 mL). The resulting solution was stirred at RT for 2 h then evaporated. The residue was purified by $SiO_2$ chromatography eluting with a gradient of 100% DCM to 100% of a solution of DCM/MeOH/$NH_4OH$ (80/10/1) over 20 minutes then maintained this composition for another 10 min at a flow rate of 25 mL/min which afforded 0.060 g (64%) of 46b: $^1$H NMR ($CD_3OD$) δ $^1$1.51–1.78 (m, 6H), 2.30–2.56 (m, 11H), 2.61 (dd, 1H, J=9, 8 Hz), 2.69–2.98 (m, 6H), 3.00–3.14 (m, 3H), 3.42 (dd, 1H, J=12, 6 Hz), 3.58 (dd, 1H, J=15, 3 Hz), 3.63–3.93 (m, 5H), 4.02 (m, 2H), 4.43 (bd, 1H, J=12 Hz), 7.03–7.26 (m, 4H), 7.37–7.47 (m, 2H); $^{13}$C NMR ($CD_3OD$) δ 20.19, 21.54, 26.90, 28.05, 29.78, 30.37, 41.28, 42.34, 42.54, 43.52, 44.29, 47.16, 50.27, 52.30, 54.21, 55.72, 61.91, 125.38, 127.75, 128.40, 128.93, 130.11, 132.08, 133.77, 137.16, 138.32, 138.85, 171.40, 171.83; MS (ES+) m/z 606 (M+H)+.

step 3—A solution of 46b (30 mg, 49.5 µmol), pyridine (0.5 mL) and $Ac_2O$ (0.5 mL) was stirred at RT for 16 h then diluted with MeOH (2 mL). The resulting mixture was stirred at RT for 1 h then evaporated and co-evaporated with toluene. The residue was purified by $SiO_2$ chromatography eluting with a gradient of 100% DCM to a 1:1 solution of DCM and DCM/MeOH/$NH_4OH$ (80/10/1) over 20 minutes at a flow rate of 25 mL/min which afforded 22 mg (66%) II-339; $^1$H NMR ($CD_3OD$) δ 1.51–1.78 (m, 6H), 2.05 (s, 3H), 2.19 and 2.16 (2s, 3H), 2.28–2.55 (m, 8H), 2.60 (m, 1H), 2.73–2.96 (m, 5H), 3.04 (m, 1H), 3.43 (m, 1H), 3.55–3.90 (m, 7H), 4.43 (bd, 1H, J=12 Hz), 4.71 (d, 2H, J=15 Hz), 7.16 (m, 2H), 7.29 (m, 2H), 7.42 (m, 2H), two proton signals are hidden under the deuterated methanol signals; $^{13}$C NMR ($CD_3OD$) δ 19.77, 21.12, 21.42, 21.66, 26.81, 27.59, 29.37, 29.95, 40.62, 40.85, 41.92, 42.08, 43.13, 44.82, 45.16, 46.74, 52.00, 53.78, 55.42, 61.05, 61.51, 125.37, 125.52, 127.90, 128.00, 128.46, 128.71, 129.71, 133.35, 135.46, 135.81, 136.21, 138.01, 142.38, 170.66, 171.42, 172.21, 176.17; MS (ES+) m/z 648 (M+H)+.

EXAMPLE 10

3-[4-(5-{3-[(1-Acetyl-piperidine-4-carbonyl)-(3-chloro-4-methyl-phenyl)-amino]-propyl}hexahydro-pyrrolo[3,4-c]pyrrole-2-carbonyl)-3,5-dimethyl-pyrazol-1-yl]-benzoic acid methyl ester (II-390)

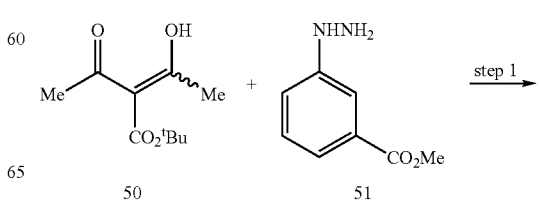

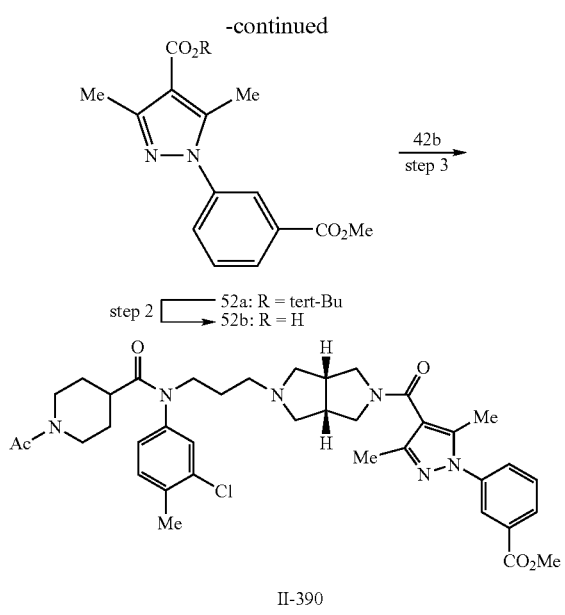

II-390 step 1—To a suspension of 3-hydrazinobenzoic acid (1.52 g, 9.99 mmol) (CAS # 38235-71-1) in water (20 mL) and HOAc (20 mL) at RT was added 50 (2 g, 9.99 mmol, prepared according to the procedure described in *Org. Prep. Proc. Int.* 2001 34(4):357–409). The resulting mixture was stirred at RT for 30 min before being poured into 400 mL of a 1:1 mixture of iced cold water and EtOAc. The aqueous layer was extracted once with EtOAc. The combined organic layers were washed with saturated aqueous NaHCO$_3$ until the aqueous extract remained basic. The organic layers were dried (Na$_2$SO$_4$), filtered and evaporated. The residue was used directly in without further purification or characterization. To the residue dissolved in DCM (100 mL) was added trimethylsilyldiazomethane (5 mL of 2M in hexane solution, 10 mmol) at RT. The resulting mixture was stirred at RT for 30 min then quenched by adding methanol. The mixture was stirred at RT for 30 min then evaporated. The residue was purified by SiO$_2$ chromatography eluting with a hexane/EtOAc gradient (100% hexane for 2 minutes then a gradient to 20% EtOAc over 20 min which was maintained for an additional 10 min) at a flow rate of 55 mL/min to afford 1.09 g (33%) of 52a: $^1$H NMR (CDCl$_3$) δ 1.59 (s, 9H), 2.48 (s, 3H), 2.52 (s, 3H), 3.94 (s, 3H), 7.54–7.64 (m, 1H), 8.07 (m, 1H), 8.09 (m, 1H); MS (ES+) m/z 331 (M+H).

step 2—To a solution of 52a (1.088 g, 3.293 mmol) in DCM (50 mL) and triethylsilane (5 mL) was added TFA (5 mL). The resulting mixture was stirred at RT for 48 h then evaporated to afford 0.9 g (99% theory) of 52b: $^1$H NMR (DMSO-d$_6$) δ 2.27 (s, 3H), 2.39 (s, 3H), 3.78 (s, 3H), 7.58 (m, 1H), 7.71 (m, 1H), 7.87–7.95 (m, 2H); MS (ES+) m/z 502 (M+H)$^+$.

step 3—To a solution of 42b (75 mg, 0.168 mmol), 52b (51 mg, 0.185 mmol), EDCI (39 mg, 0.201 mmol), HOBT (31 mg, 0.201 mmol) and DMF (1.5 mL) was added DIPEA (0.15 mL, 0.839 mmol). The resulting mixture was stirred at RT for 16 h then partitioned between EtOAc and water. The aqueous layer was extracted twice with EtOAc. The combined extracts were dried (Na$_2$SO$_4$), filtered and evaporated. The residue was purified by SiO$_2$ chromatography eluting with a gradient of 100% DCM (1 min isocratic) to a 1:1 solution of DCM and DCM/MeOH/NH$_4$OH (80/10/1) over 20 min followed by 2:8 for 10 min at a flow rate of 25 mL/min which afforded 66 mg (56% theory) of II-390: $^1$H NMR (CD$_3$OD) δ 1.45–1.78 (m, 6H), 2.04 (s, 3H), 2.27 (s, 3H), 2.30 (s, 3H), 2.31–2.53 (m, 9H), 2.53–2.73 (m, 2H), 2.77–2.97 (m, 3H), 3.58–3.78 (m, 6H), 3.84 (bd, 1H, J=10 Hz), 3.94 (s, 3H), 4.42 (bd, 1H, J=12 Hz), 7.16 (dd, 1H, J=6.2 Hz), 7.38 (1H, J=2 Hz), 7.41 (d, 1H, J=6 Hz), 7.67 (m, 1H), 7.75 (m, 1H), 8.11 (m, 2H); $^{13}$C NMR (CD$_3$OD) δ 12.26, 12.99, 20.18, 24.54, 28.02, 29.76, 30.35, 41.25, 42.32, 43.54, 47.14, 50.28, 52.22, 53.43, 54.22, 55.24, 61.41, 61.90, 118.72, 127.55, 128.39, 130.09, 130.69, 131.13, 131.30, 133.24, 133.75, 136.62, 138.31, 140.79, 140.93, 142.75, 149.05, 166.81, 167.77, 171.82, 176.56; MS (ES+) m/z 703 (M+H)$^+$.

EXAMPLE 11

4,4-Difluoro-cyclohexanecarboxylic acid {3-[5-(4,6-dimethyl-pyrimidine-5-carbonyl)-hexahydro-pyrrolo[3,4-c]pyrrol-2-yl]-1-phenyl-propyl}-amide (I-435)

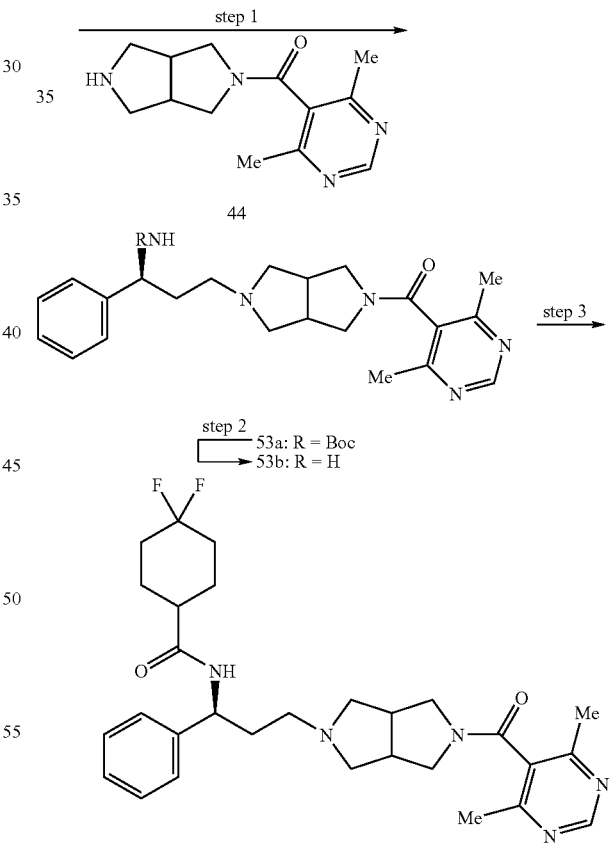

I-435 step 1—To the mixture of 35 (0.20 g, 0.82 mmol, CAS 135865-78-0) and 44 (0.18 g, 0.75 mmol) in DCM (10 mL) was added sodium triacetoxyborohydride (0.24 g, 1.12 mmol) and the resulting solution was stirred at RT for 3 h. The mixture was diluted with DCM and washed with saturated NaHCO₃. The organic layer was dried (MgSO₄), filtered and evaporated. The crude product and purified by SiO₂ column chromatography eluting with DCM:MeOH:NH₄OH (140:10:1) to afford 0.29 g (80%) of 53a: ms (ES+) m/z 480 (M+H).

step 2—Methanolic HCl (10 mL, 1.25 M) was added to 53a (0.29 g, 0.60 mmol) and the mixture was heated at 50° C. for 2 h. The mixture was concentrated in vacuo to afford 53b which used in the next step without additional without purification.

step 3—To a solution of 4,4-difluoro-cyclohexanecarboxylic acid (0.13 g, 0.78 mmol) in toluene (5 mL) was added thionyl chloride (66 μL, 0.90 mmol). It was heated to reflux for 2 h. The solvent and the excess of thionyl chloride were evaporated and the residual acid chloride was diluted with DCM (4 mL) and toluene (2 mL). The acid chloride solution was added to a mixture of 53b in saturated Na₂CO₃ (5 mL) and H₂O (3 mL) and stirred at RT for 4 h. The reaction mixture was diluted with H₂O and extracted with DCM. The organic layer was dried (MgSO₄), filtered evaporated. The crude product was purified by SiO₂ column chromatography eluting with DCM:MeOH:NH₄OH (120:10:1) afford 0.16 g (50%) of I-435: mp 131.8–133.2° C.; ms (ES+) m/z 526 (M+H).

EXAMPLE 12

1-Acetyl-piperidine-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-propyl}-amide (II-3)

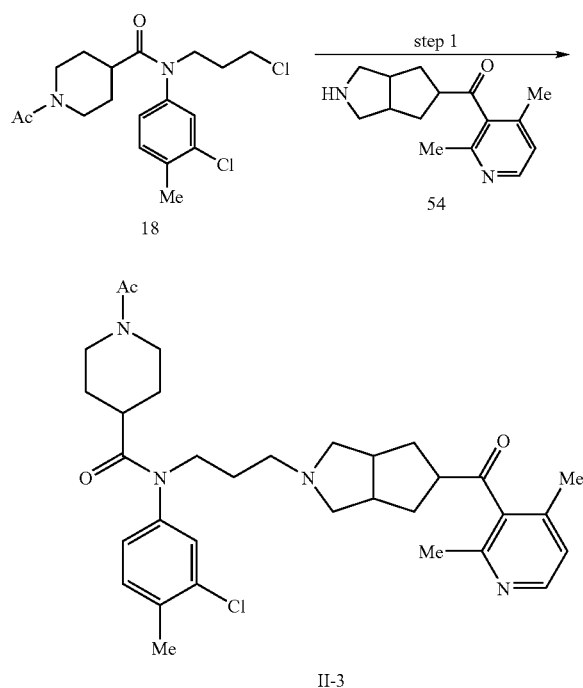

To a solution of 18 (0.35 g, 1.15 mmol), 54 (0.18 g, 0.76 mmol) and MeCN (10 mL) were added K₂CO₃ (0.31 g, 2.30 mmol) and KI (0.25 g, 1.53 mmol) and the resulting solution was heated at reflux overnight. The mixture was cooled, diluted with water and extracted with EtOAc. The combined EtOAc extracts were washed with brine and dried (MgSO₄) and evaporated. The crude product was purified by SiO₂ column chromatography eluting with DCM:MeOH:NH₄OH (150:10:1) to afford 0.25 g (57%) of II-3: mp 81.5–83.6° C.; ¹H NMR (DMSO-d₆) δ 1.3–1.6(m, 8H), 1.95 (s, 3H), 2.15 (s, 3H), 2.3 (s, 3H), 2.35 (s, 3H), 2.65–2.85 (m, 5H), 3.2–3.3 (m, 1H), 3.4–3.8 (m, 6H), 4.2–4.3 (d, 1H), 7.1 (m, 1H), 7.15–7.25 (d, 1H), 7.45 (d, 1H), 8.3 (d, 1H); ms (ES+) m/z 580 (M+H); Anal. (C₃₂H₄₂ClN₅O₃. 0.3M (CH₂Cl₂) C; calcd, 65.78; found, 65.74; H; calcd, 7.38; found, 7.30; N; calcd, 12.07; found, 11.58.

EXAMPLE 13

Cyclopentanecarboxylic acid {3-[5-(4,6-dimethyl-pyrimidine-5-carbonyl)-hexahydro-pyrrolo[3,4-c]pyrrol-2-yl]-1-phenyl-propyl}-amide (I-29)

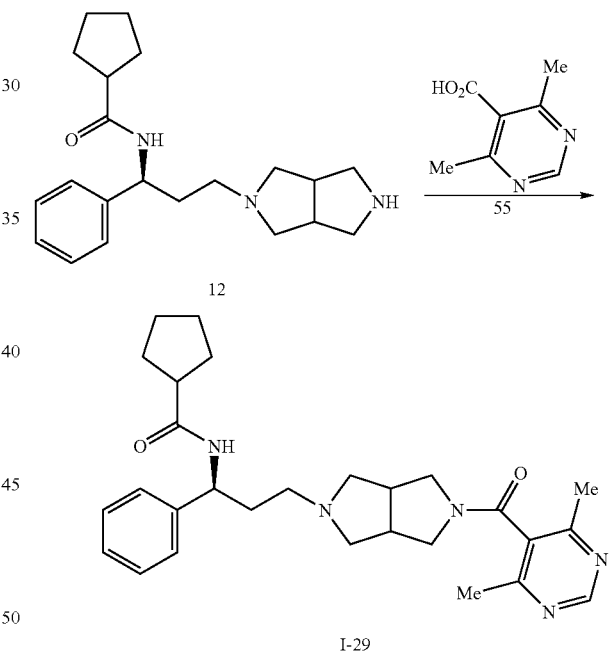

To a solution of 12 (0.24 g, 0.70 mmol) in DCM (10 mL) were added 4,6-dimethyl-pyrimidine-5-carboxylic acid (55, 0.12 g, 0.84 mmol), EDCI (0.17 g, 0.91 mmol), HOBt (0.12 g, 0.91 mmol) and DIPEA (0.36 mL, 2.10 mmol). The mixture was stirred at RT for 3 h. The reaction mixture was washed with saturated NaHCO₃ and the organic layer was dried (Na₂SO₄). The crude product was purified by SiO₂ column chromatography eluting with DCM:MeOH:NH₄OH (150:10:1) to afford 0.27 g (81%) of I-29: mp 48.0–49.0° C.; ms (ES+) m/z 476 (M+H); Anal. (C₂₈H₃₇N₅O₂. 0.2M CH₂Cl₂) C; calcd, 68.76; found, 68.61; H; calcd, 7.65; found, 7.51; N; calcd, 14.22; found, 14.28.

EXAMPLE 14

(S)-4,4-Difluoro-cyclohexanecarboxylic acid [3-[5-(4,6-dimethyl-pyrimidine-5-carbonyl)-hexahydro-pyrrolo[3,4-c]pyrrol-2-yl]-1-(3-fluoro-phenyl)-propyl]-amide (I-485)

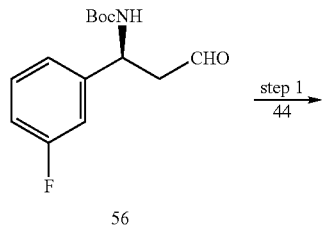

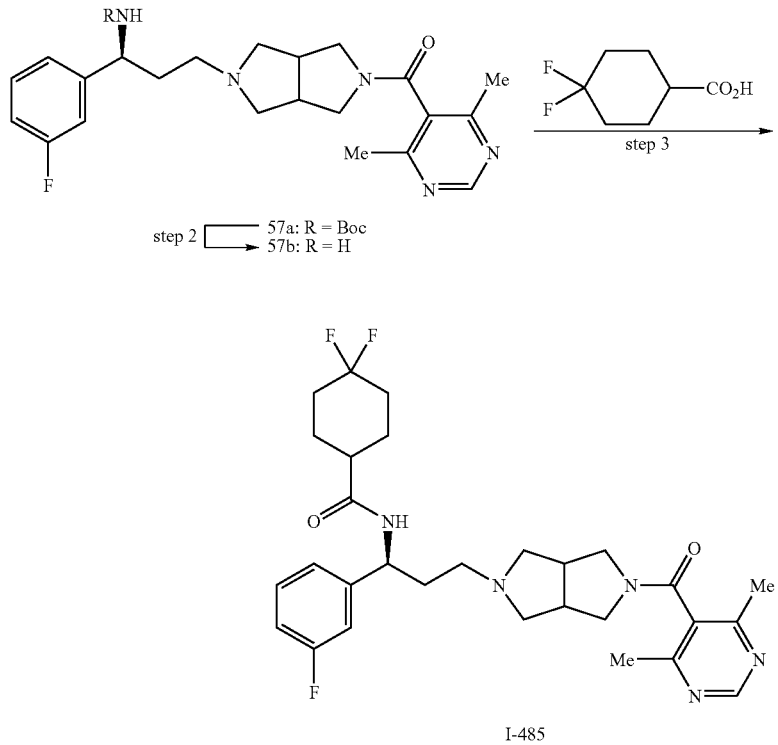

step 1—To a solution of 56 (562 mg, 2.1 mmol, prepared as described in WO2004/018425) and 44 (518 mg, 2.1 mmol) in DCM (20 mL) containing HOAc (0.31 mL) was added NaBH(OAc)$_3$ (579 mg, 2.73 mmol) in 1 portion and the reaction mixture was stirred for 18 hrs at RT. The reaction was quenched by the addition of 10% K$_2$CO$_3$ (20 mL) and stirring continued for 30 min. The product was twice extracted with DCM (25 mL). The combined extracts were dried (MgSO$_4$) and concentrated in vacuo. The crude product was purified by flash chromatography on silica eluting with DCM/5% MeOH (containing 2% NH$_4$OH) to afford 821 mg (79% theory) of 57a as a white foam: ms (ES+) m/z 498 (M+H)$^+$.

step 2—A solution of 57a (821 mg, 1.65 mmol) dissolved in 10 M HCl in MeOH (40 mL) was heated at 65° C. for 2 h. The MeOH was evaporated under reduced pressure and the residue cautiously partitioned between DCM (35 mL) and 20% K$_2$CO$_3$ solution. The aqueous layer was extracted with DCM (2×35 mL). The combined organic extracts were dried (Na$_2$SO$_4$) and concentrated in vacuo to afford 641 mg (98%) of 57b as a viscous liquid: ms (ES+) m/z 398 (M+H)$^+$.

step 3—To a solution of 57b (98 mg, 0.25 mmol) in DCM (4 mL) at RT was added 4,4-difluorocyclohexanecarboxylic acid (49 mg, 0.30 mmol). To the resulting solution was added sequentially EDCI (61.4 mg, 0.32 mmol), HOBt (43 mg. 0.32 mmol) and DIPEA (0.13 mL, 0.74 mmol). The mixture was stirred for 4 h. The reaction mixture washed with brine and dried (Na$_2$SO$_4$), then concentrated in vacuo. The crude product was flash chromatographed on silica eluting with DCM/7.5% MeOH (containing 2% NH$_4$OH) to afford 113 mg (84%) of I-485 as a white foam: ms (ES+) m/z 544 (M+H)$^+$.

EXAMPLE 15

5-Methyl-thiophene-2-carboxylic acid {(S)-3-[5-(2,6-dimethyl-benzoyl)-hexahydro-pyrrolo[3,4-c]pyrrol-2-yl]-1-pyridin-2-yl-propyl}-amide; compound with trifluoro-acetic acid (I-406)

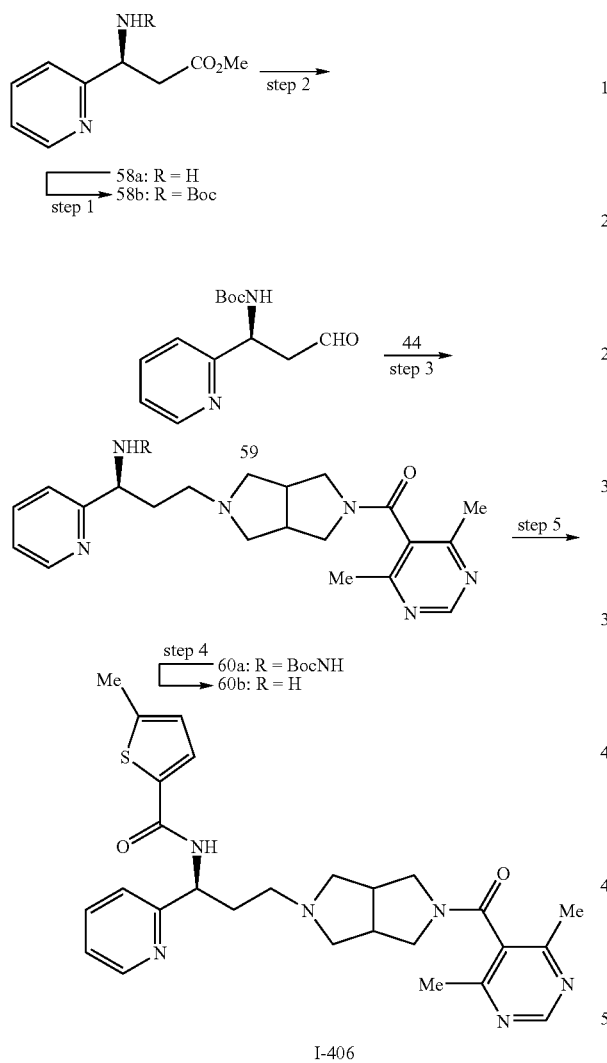

I-406 step 1—To a cold (0°) mixture of $Na_2CO_3$ (418 mg, 3.95 mmol) in $THF:H_2O$ (2:1) was added in one portion (S)-3-amino-3-pyridin-2-yl-propionic acid methyl ester dihydrochloride (58a, 200 mg, 0.79 mmol; prepared as described for the isomeric 3-pyridyl analog in *J. Org. Chem.* 2002 67:7819). A solution of $(BOC)_2O$ (189 mg, 0.86 mmol) in THF (2 mL) was added in 1 portion and the reaction stirred at 0° C. for 1 h, then at RT for 2 hrs. The product was extracted with EtOAc (2×25 mL). The combined organic extracts were dried ($MgSO_4$) and concentrated in vacuo. The crude product was purified by flash chromatography on silica eluting with DCM/5.0% MeOH (containing 2% $NH_4OH$) to afford 157 mg (71%) of 58b as a viscous liquid: ms (ES+) m/z 281 $(M+H)^+$.

step 2—To a soln of 58b (561 mg, 2.0 mmol) in DCM (20 mL) cooled to −78° was added DIBAL-H (4.0 mL of a 1.0 M DCM solution, 4.0 mmol) dropwise at a rate that maintained the temperature below −70° C. After 1 h the reaction was quenched by the addition of MeOH (5 mL) and $H_2O$ (1 mL) at −78° C., then allowed to warm to RT. The mixture was filtered through a CELITE® pad. The filtrate was dried ($Na_2SO_4$) and concentrated in vacuo. The crude product was purified by flash chromatography on silica eluting with DCM/6.0% MeOH (containing 2% $NH_4OH$) to afford 416 mg (83%) of 59 as a viscous liquid; ms (ES+) m/z 251 $(+H)^+$.

step 3—To a solution of 59 (220 mg, 0.88 mmol) and 44 (215 mg, 0.88 mmol) in DCM (10 mL) containing HOAc (0.13 mL) was added $NaBH(OAc)_3$ (224 mg, 1.05 mmol) in 1 portion and the reaction was stirred for 5 h. The reaction was quenched by adding 10% $K_2CO_3$ soln (10 mL) and stirred for an additional 30 min. The product was extracted with DCM (2×20 mL). The combined extracts were dried ($Na_2SO_4$) and concentrated in vacuo. The crude product was purified by flash chromatography on silica eluting with DCM/7.5% MeOH (containing 2% $NH_4OH$) to afford 304 mg (72%) of 60a as a viscous liquid: ms (ES+) m/z 479 $(M+H)^+$.

step 4—A solution of 60a (304 mg, 0.64 mmol) in 10 M HCl and MeOH (10 mL) heated at 65° C. for 2 h. The MeOH was evaporated under reduced pressure and the residue cautiously partitioned between DCM (35 mL) and 20% $K_2CO_3$ solution (20 mL). The aqueous layer was reextracted with DCM (2×35 mL). The combined organic extracts were dried ($Na_2SO_4$) and concentrated in vacuo to afford 60b as a viscous liquid. (254 mg) which was used in the next step without further purification: ms (ES+) m/z 379 $(M+H)^+$.

step 5—To 5-methyl-2-thiophencarboxylic acid (10.7 mg, 0.075 mmol) and HOBt (1.0 mL 0.06 M soln in DCM:DMF, 9:1) was added resin-bound carbodiimide (81 mg) and the mixture was stirred for 18 h. A solution of 60b (500 μL of 0.1 M soln in DCM) was added and stirring was continued for 18 h. The reaction mixture was concentrated in vacuo and purified by reverse phase HPLC to afford I-406: ms (ES+) m/z 503 $(M+H)^+$.

EXAMPLE 16

(3S, 3'S)-Tetrahydro-furan-3-carboxylic acid {3-[5-(2,6-dimethyl-benzoyl)-hexahydro-pyrrolo[3,4-c]pyrrol-2-yl]-1-phenyl-propyl}-amide (I-390)

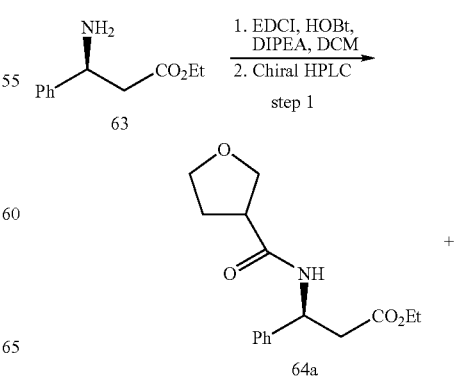

EXAMPLE 17

1-Dimethylsulfamoyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-propyl}-amide (I-115)

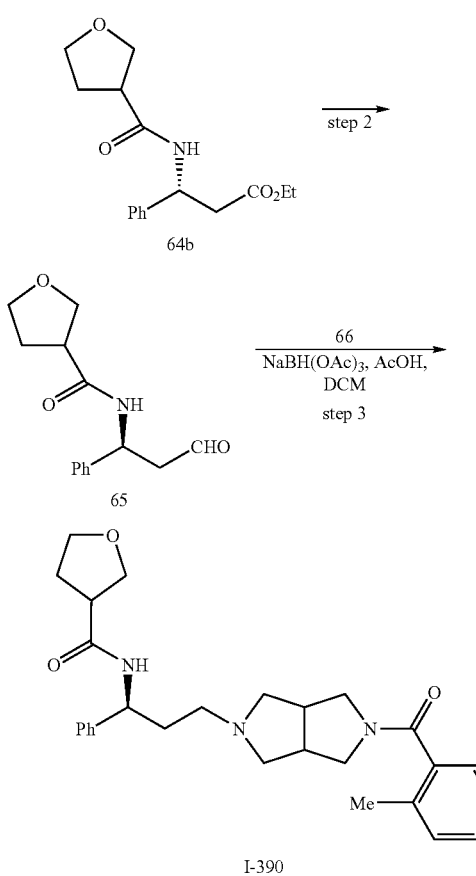

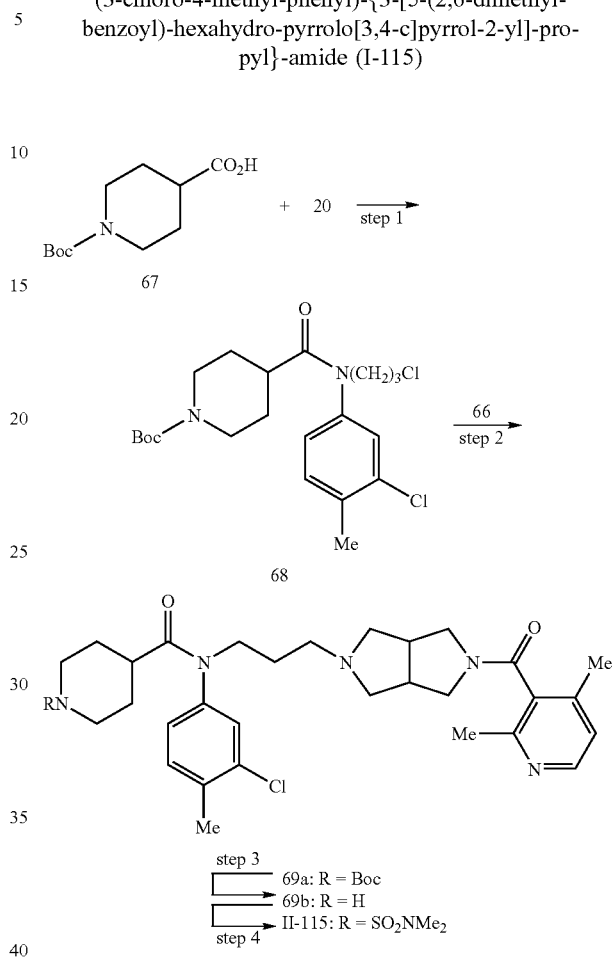

step 1—To a mixture of tetrahydro-3-furoic acid (1.55 g, 13.34 mmol) and (S)-3-amino-3-phenylpropanoic acid ethyl ester hydrochloride (63, 3.06 g, 13.34 mmol) in 50 mL of DCM at RT were added sequentially EDCI (3.42 g, 16.01 mmol), HOBt (2.16 g, 16.01 mmol) and DIPEA (11.62 mL, 66.74 mmol). The mixture was stirred overnight at RT. The reaction mixture was washed with 5% $NaHCO_3$ solution, dried ($MgSO_4$) and concentrated in vacuo. The crude product was purified by preparative HPLC using a Chiralcel OD-H column, eluting with 20% 2-propanol/hexanes to afford 1.5 g of (3S, 3'S)-3-phenyl-3-[(tetrahydro-furan-3-carbonyl)-amino]-propionic acid ethyl ester 64a: retention time: 14.71 min, mp 84.6–85.9° C., ms (ES+) m/z=291 $M^+$.

step 2—A DIBAL-H (1M solution in DCM, 7.5 mL, 7.5 mmol) was cooled to −78° C. and added drop-wise to a solution of 64a (1.1 g, 3.7 mmol) and DCM (20 mL) cooled to −78° C. with stirring. Stirring was continued for 2 h at −78° C., then 2N hydrochloric acid (1 ml) was added drop-wise at −78° C. and mixture allowed to warm to RT. Additional 2N HCl (20 mL) was added, the layers were separated and aqueous phase thrice extracted with DCM (3×). Combined organic layers were dried ($MgSO_4$) and concentrated. The crude product was purified by $SiO_2$ chromatography eluting with EtOAc/DCM (0 to 100% EtOAc) to afford 0.33 g of 65: MS (ES+) m/z=248 $(M+H)^+$.

Step 3 was carried out as described in step 3 of Example 14 to afford I-390: MS (ES+) m/z=476 $(M+H)^+$.

step 1—To a stirred mixture of Boc-isonipecotic acid (67, 2.12 g, 9.22 mmol), pyridine (1.9 mL, 23.6 mmol), and DCM (13 mL) under a nitrogen atmosphere and at RT was added $SOCl_2$ (0.8 mL, 11 mmol) was added. After 25 min, a solution of 20 (2.21 g, 10.16 mmol), TEA (4.5 mL, 32.33 mmol), and DMAP (0.12 g, 0.92 mmol) in DCM (16 mL) was added dropwise and stirring was continued for 72 h. 5% HCl (20 mL) was added dropwise, layers separated and aqueous layer thrice extracted with DCM. The combined organic layers were dried ($MgSO_4$) and concentrated. The crude product was purified by $SiO_2$ chromatography eluting with a EtOAc/hexanes gradient (0 to 30%) to afford 2.2 g of 68: ms (ES+) m/z=451$(M+Na)^+$.

step 2—4—To a solution of 68 (0.52 g, 1.2 mmol) and 66 (0.3 g, 1.2 mmol) dissolved in MeCN (30 mL) were added $K_2CO_3$ (0.33 g, 2.4 mmol) and potassium iodide (0.22 g, 1.32 mmol) and the resulting mixture was heated at reflux overnight. Additional 68 was added (0.2 g, 0.46 mmol) and heating continued for 6 h. A third aliquot of 68 was added (0.2 g, 0.46 mmol) and reaction continued for an additional 18 h. The mixture was cooled to RT, diluted with water and extracted with EtOAc. The combined EtOAc extracts were washed with brine, dried ($MgSO_4$) and evaporated. The crude product was purified by flash chromatography on silica gel eluting with MeOH containing 10% NH₄OH/ DCM (0 to 4%) to afford 0.244 g of 69a: ms(ES+) m/z 637 (M+H)⁺.

step 3—To 69a (0.24 g, 0.37 mmol) dissolved in DCM (9 mL) was added TFA (1 mL) and the mixture was stirred at RT overnight. The solvents were evaporated, and the residue suspended in toluene and re-evaporated (twice). The residue was purified by flash chromatography on silica gel eluting with MeOH containing 10% NH₄OH/DCM (0 to 7%) to afford 0.194 g of 69b: MS(ES+) m/z 537 (M+H)⁺.

step 4—To a RT solution of 69b (0.019 g, 0.035 mmol) and DIPEA (0.02 mL, 0.105 mmol) in 1 mL of DCM was added dimethylsulfamoyl chloride (0.01 g, 0.07 mmol) and the mixture stirred overnight at rt. The reaction mixture was concentrated in vacuo and purified by reverse phase HPLC to afford II-115: ms (ES+) m/z 644 (M+H)⁺.

EXAMPLE 18

3-(4-Chloro-phenyl)-1-{3-[(3aS,6aR)-5-(2,4-dimethyl-pyridine-3-carbonyl)-hexahydro-pyrrolo[3,4-c]pyrrol-2-yl]-propyl}-1-p-tolyl-urea (II-203 step 2—To a solution of 71 (0.16 g, 0.41 mmol) in DCM (5 mL) were added 1-chloro-4-isocyanato-benzene (0.09 g, 0.62 mmol) and TEA (0.13 mL, 0.91 mmol). The mixture was allowed to stir at RT for 2 h then was diluted with DCM and washed with water. The organic layer was dried (Na₂SO₄), filtered and concentrated. The crude product was purified by flash column chromatography on silica gel (CH₂Cl₂:MeOH:NH₄OH/200:10: 1) to afford 0.19 g (yield 83%) of II-203: mp 60.5–62.5° C., ms (ES+) m/z 546 (M+H).

EXAMPLE 19

3-(3-(3-Chloro-4-methyl-phenyl)-3-{3-[5-(4,6-dimethyl-pyrimidine-5-carbonyl)-hexahydro-pyrrolo[3,4-c]pyrrol-2-yl]-propyl}-ureido)-benzoic acid ethyl ester; compound with trifluoro-acetic acid (II-393) and 3-(3-(3-chloro-4-methyl-phenyl)-3-{3-[5-(4,6-dimethyl-pyrimidine-5-carbonyl)-hexahydro-pyrrolo[3,4-c]pyrrol-2-yl]-propyl}-ureido)-benzoic acid (II-392)

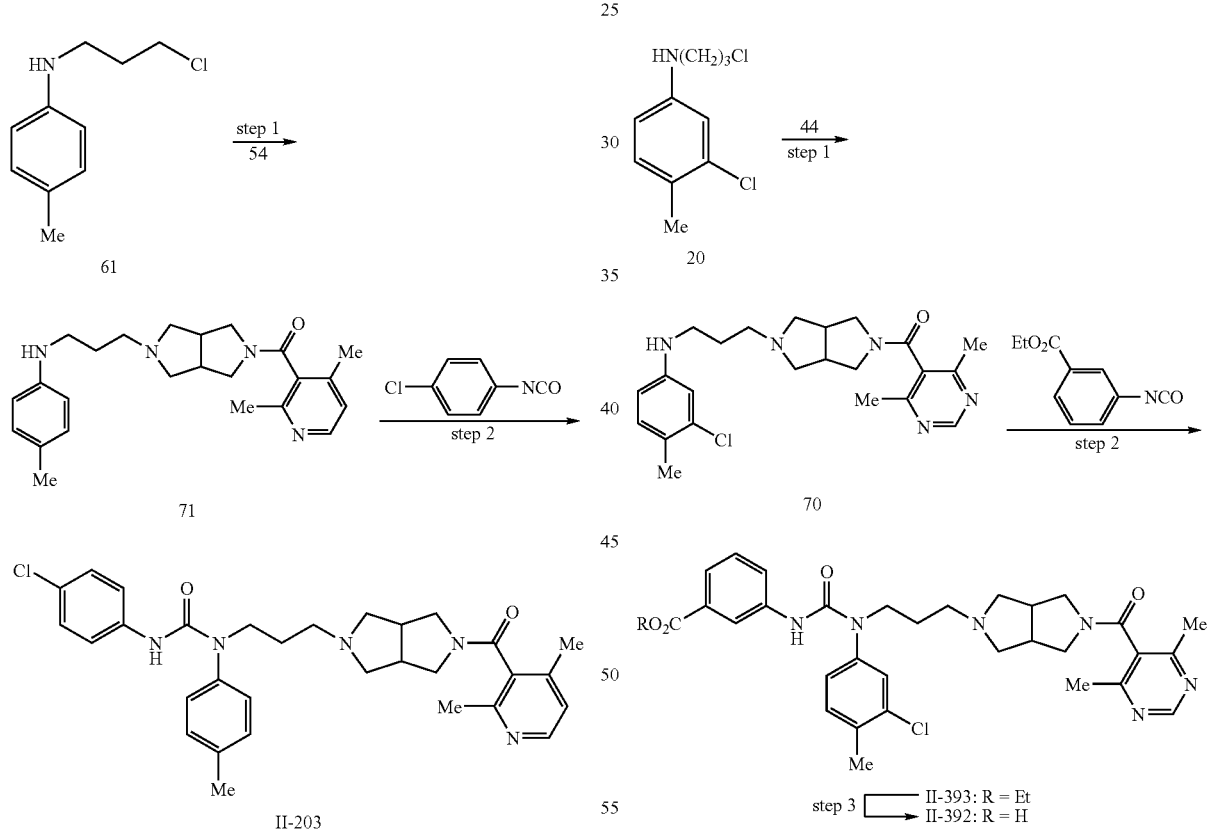

step 1—To a solution of 61 (0.20 g, 1.13 mmol) and 54 (0.18 g, 0.75 mmol) dissolved in MeCN (10 mL) were K₂CO₃ (0.20 g, 1.51 mmol) and potassium iodide (0.18 g, 1.13 mmol) and the resulting solution was heated at reflux overnight. The mixture was cooled, diluted with water and extracted with EtOAc. The combined EtOAc extracts were washed with brine, dried (MgSO₄) and evaporated. The crude product was purified by flash column chromatography on silica gel (DCM:MeOH:NH₄OH/130:10:1) to afford 0.16 g (54%) of 71: ms (ES+) m/z 393 (M+H);

step—To a solution of 20 (1.77 g, 8.12 mmol) and 44 (2.0 g, 8.12 mmol) dissolved in MeCN (10 mL) was added NaHCO₃ (1.36 g, 16.24 mmol) and KI (1.34 g, 8.12 mmol). The resulting mixture was heated at reflux overnight. The mixture was cooled, diluted with water and extracted with EtOAc. The combined EtOAc extracts were washed with brine, dried (MgSO₄) and evaporated. The crude product was purified by flash chromatography on silica gel eluting with MeOH (containing 10% NH₄OH)/DCM (0 to 4%) to afford 2.7 g of 70: ms (ES+) m/z 428 (M+H)⁺.

step 2 and 3—A solution of ethyl 3-isocyanatobenzoate and 70 and THF is shaken overnight at RT. The solvent is evaporated which afforded II-393 which could be purified by SiO₂ chromatography. The crude product was dissolved in MeOH (1 mL) and treated with a 10% solution of NaOH (excess). The reaction mixture was shaken overnight at RT. The reaction mixture is acidified with TFA, solvents evaporated, the crude was dissolved in 5% MeOH/DCM, filtered and concentrated to afford the carboxylic acid II-392: ms (ES+) m/z 591 (M+H)⁺.

EXAMPLE 20

1-Acetyl-piperidine-4-carboxylic acid {3-[5-(2-bromo-3-methyl-benzoyl)-hexahydro-pyrrolo[3,4-c]pyrrol-2-yl]-propyl}-(3-chloro-4-methyl-phenyl)-amide (II-244)

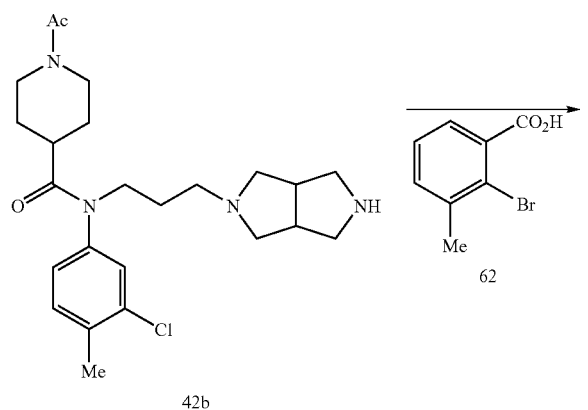

A mixture of 2-bromo-3-methyl-benzoic acid (62, 0.016 g, 0.075 mmol), resin-bound carbodiimide (0.078 g, 0.15 mmol) and HOBT (0.012 g, 0.085 mmol) in DCM:DMF (1 mL, 10:1) was shaken for 18 h. A solution of 42b (0.022 g, 0.05 mmol) and DIPEA (0.03 mL, 0.17 mmol) and DCM (1 mL) was added. Shaking was continued for 24 h, the resin filtered and washed with DMF (1 mL) and twice with DCM (1 mL). The reaction mixture was concentrated in vacuo and purified by reverse phase HPLC to afford II-244: ms (ES+) m/z 644 (M+H)⁺.

EXAMPLE 21

[4-((3-Chloro-4-methyl-phenyl)-{3-[5-(4,6-dimethyl-pyrimidine-5-carbonyl)-hexahydro-pyrrolo[3,4-c]pyrrol-2-yl]-propyl}-carbamoyl)-piperidin-1-yl]-oxo-acetic acid, hydrochloride salt (II-303)

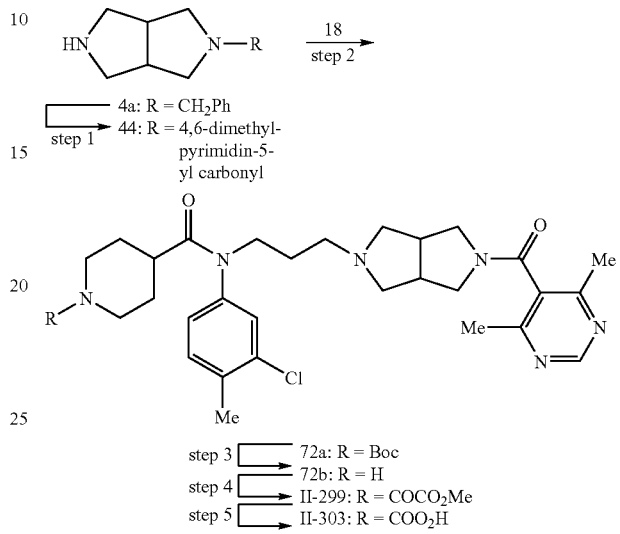

step 1—To a mixture of 4,6-dimethyl-pyrimidine-5-carboxylic acid (0.85 g, 5.58 mmol, T. J. Kress et. al. *Heterocycles* 1994 38:1375) and 4a (1.13 g, 5.58 mmol, C. J. Ohnmacht et al. *J. Heterocycl. Chem.* 1983 20:321) in DCM (25 mL) at RT was added sequentially EDCI (1.43 g, 6.7 mmol), HOBt (0.9 g, 6.7 mmol) and DIPEA (3.9 mL, 22.34 mmol) and the mixture was stirred overnight at RT. The reaction mixture was washed with 5% NaHCO₃ solution, dried (MgSO₄) and concentrated in vacuo. The crude product was purified by flash chromatography on silica gel eluting with MeOH (containing 10% NH₄OH)/DCM (0 to 4%) to afford 1.5 g of (5-benzyl-hexahydro-pyrrolo[3,4-c]pyrrol-2-yl)-(4,6-dimethyl-pyrimidin-5-yl)-methanone: ms (ES+) m/z 337 (M+H)⁺. To a solution of amide from the previous step (1.5 g, 4.45 mmol) in MeOH (50 mL) was added ammonium formate (2.81 g, 44.58 mmol). Palladium on charcoal previously wetted with MeOH was slowly added and the mixture heated to reflux for 8 h. The catalyst was filtered and solvent evaporated. The residue was purified by flash chromatography on silica gel eluting with MeOH (containing 10% NH₄OH)/DCM (0 to 4%) to afford 0.941 g of 44b: ms (ES+) m/z 247 (M+H)⁺.

step 2—To a solution of 18 (0.6 g, 1.39 mmol) and 44 (0.31 g, 1.27 mmol) and MeCN (20 mL) were added DIPEA (0.44 mL, 2.54 mmol) and KI (0.23 g, 1.39 mmol) and the resulting mixture was heated at reflux overnight. The mixture was cooled, diluted with water and extracted with EtOAc. The combined EtOAc extracts were washed with brine, dried (MgSO₄) and evaporated. The crude product was purified by flash chromatography on silica gel with eluting with MeOH (containing 10% NH₄OH)/DCM (0 to 4%) to afford 0.347 g of 72a: ms (ES+) m/z 639 (M+H)⁺.

step 3—To a solution of 72a dissolved in DCM (9 mL) was added TFA (1 mL) and the mixture was stirred at RT overnight. The solvents were evaporated and the residue suspended in toluene and evaporated again (2×). The residue purified by flash chromatography on silica gel eluting with gradient DCM/MeOH (containing 10% NH₄OH) (0 to 4% MeOH) to afford 0.347 g of 72b: ms(ES+) m/z 539 (M+H)⁺.

step 4—To a mixture of 72b (0.3 g, 0.55 mmol) and methyl oxalyl chloride (0.057 mL, 0.61 mmol) in DCM (5 mL) at RT was added DIPEA (0.145 mL, 0.83 mmol). The reaction mixture was stirred overnight at RT then washed with 5% NaHCO₃ solution, back extracted with DCM (5×), dried (MgSO₄) and concentrated in vacuo. The crude product was purified by flash chromatography on silica gel eluting with MeOH (containing 10% NH₄OH)/DCM (0 to 4%) to afford 0.304 g of II-299: mp, 60.3–62° C.; Anal, calcd. for C₃₂H₄₁ClN₆O₅ (containing 0.15 mol of CH₂Cl₂): C, 60.53; H, 6.53; N, 13.17. Found: C, 60.59; H, 6.49; N, 12.99; MS(ES+) m/z 625 (M+H)⁺.

step 5—To a solution of II-299 (0.194 g, 0.31 mmol) in MeOH (3 mL) was added a solution of NaOH (0.019 g, 0.47 mmol) in water (1 mL). The mixture was stirred overnight at RT. The solvents were evaporated with a nitrogen stream, redissolved in MeOH, acidified with HCl (1M solution in ethyl ether), stirred for 15 min at RT then concentrated in vacuo. The residue dissolved in DCM, stirred for 15 min and filtered to remove NaCl. Cyclohexane was added and an oily phase separated. The solvents were decanted and product dried in vacuo to afford 0.12 g of II-303: mp 172.4–175.2° C.; Anal. calcd. for C₃₁H₃₉ClN₆O₅ (containing 1 mol of HCl and 0.55 mol of CH₂Cl₂): C, 54.58; H, 5.97; N, 12.10. Found: C, 54.66; H. 5.88; N. 12.03; MS(ES+) m/z 611 (M+H)⁺.

EXAMPLE 22

1-Acetyl-piperidine-4-carboxylic acid {3-[5-(2-aze-tidin-1-yl-pyridine-3-carbonyl)-hexahydro-pyrrolo[3,4-c]pyrrol-2-yl]-propyl}-(3-chloro-4-methyl-phenyl)-amide (II-356)

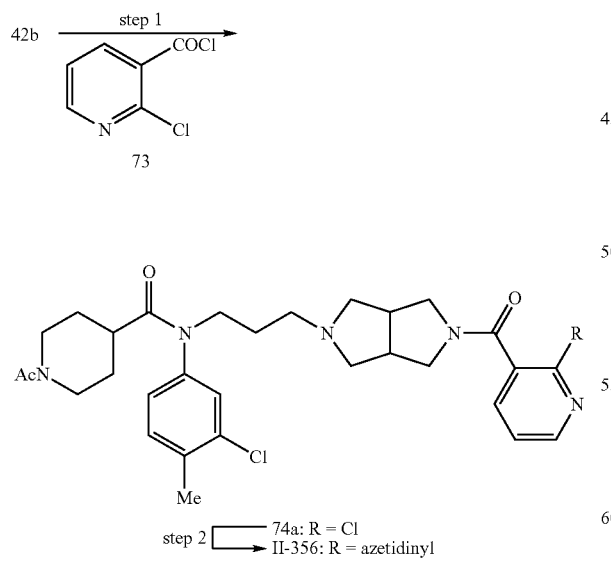

To a mixture of 42b (0.063 g, 0.138 mmol) and 2-chloronicotinoyl chloride (73, 0.027 g, 0.15 mmol) in DCM (3 mL) at RT was added DIPEA (0.05 mL, 0.27 mmol). The mixture was stirred overnight at RT and the solvent was evaporated. The residue as obtained contained 74a and was treated with a solution of azetidine (0.1 mL, excess) in THF (2 mL). The reaction mixture was heated at 800 C with stirring for 4 h. The reaction mixture was cooled to RT and the solvents evaporated in vacuo. The crude product was purified by flash chromatography on silica gel eluting with MeOH (containing 10% NH₄OH)/DCM (0 to 4% MeOH/NH₄OH). The recovered material was dissolved in DCM and cyclohexane was added which resulted in the separation of an oil. The solvents were decanted and product dried in vacuo to afford 0.045 g of II-356: mp 72.9–74° C.; Anal. calcd. for C₃₃H₄₃ClN₆O₃ (containing 0.5 mol of H₂O): C, 65.69; H, 7.66; N, 12.77. Found: C, 65.99; H, 7.47; N, 12.61; ms (ES+) m/z 607 (M+H)

EXAMPLE 23

(5-{(5-[(S)-3-(Cyclopentanecarbonyl-amino)-3-phenyl-propyl]-hexahydro-pyrrolo[3,4-c]pyrrole-2-carbonyl)}-4,6-dimethyl-pyrimidin-2-yloxy)-acetic acid; compound with trifluoro-acetic acid, (I-466)

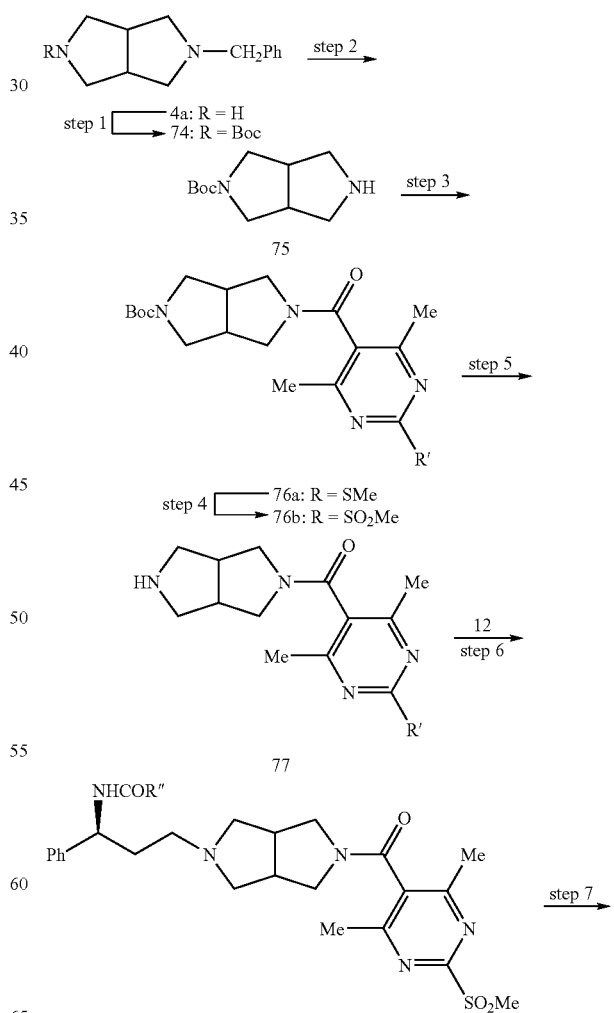

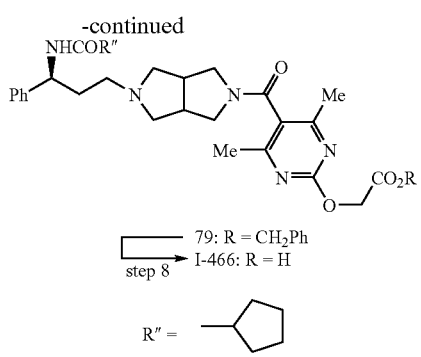

79: R = CH₂Ph
step 8 → I-466: R = H

R'' = cyclopentyl step 1—A solution of (BOC)₂O (15.7 g, 72 mmol) in THF (20 mL) was added to a solution of 4a (12 g, 59.3 mmol) in THF (100 mL) at RT, and resulting solution was stirred for 18 h then concentrated in vacuo. The residue was dissolved in EtOAc (100 mL), and the organic phase was washed with saturated NaHCO₃ (25 mL), 1M citric acid (25 mL) and brine (1×25 mL), dried (MgSO₄) and concentrated in vacuo. The crude product was purified by flash chromatography on SiO₂ eluting with 10% EtOAc/DCM to afford 11.7 g (65%) of 74: $^1$H NMR (CDCl₃) δ 1.46 (s, 9H), 2.37–2.40 (m, 2H), 2.62–2.68 (m, 2H), 2.76–2.79 (m, 2H), 3.25 (m, 2H), 3.51–3.57 (m, 2H), 3.58 (s, 2H), 7.23–7.31 (m, 5H); MS (ES+) m/z 303 (M+H)⁺.

step 2—Palladium hydroxide (0.1 g) was added to a solution of 74 (1.0 g, 3.3 mmol) in EtOH (50 mL). The solution was hydrogenated under atmospheric pressure overnight and filtered through a CELITE® pad. The resulting solution was concentrated in vacuo to afford 0.6 g (85%) of 75: MS (ES+) m/z 213 (M+H)⁺.

step 3—A solution of 75 (0.6 g, 2.82 mmol), dimethylsulfamoyl chloride (0.3 mL, 2.82 mmol), 4,6-dimethyl-2-methylsulfanyl-pyrimidine-5-carboxylic acid (0.56 g, 2.82 mmol), N,N-dimethylbutyl amine (1.16 mL, 8.4 mmol), and DMAP (34 mg, 0.000282 mol) in DMF (5 mL) was stirred at 65° C. overnight. DMF was removed in vacuo. The residue was dissolved in EtOAc (30 mL), washed with saturated NaHCO₃ (25 mL), 1M citric acid (25 mL), brine (25 mL), dried (MgSO₄) and concentrated in vacuo. The crude product was purified by flash chromatography on SiO₂ eluting with 20% MeOH/DCM to afford 0.6 g (54%) of 76a: MS (ES+) m/z 393 (M+H)⁺.

step 4—A solution of 76a (1 g, 2.54 mmol) in DCM (15 mL) was cooled to 0° C. and MCPBA (1.3 g, 7.6 mmol) was added in portions. Stirring was continued for 2 h. The reaction mixture was diluted with DCM (15 mL), washed with saturated NaHCO₃ (25 mL), brine (25 mL), dried (MgSO₄) and concentrated in vacuo. The crude product was purified by flash chromatography on silica gel eluting with 10% MeOH/CH₂Cl₂ to afford 0.34 g (31%) of 76b: MS (ES+) m/z 425 (M+H)⁺.

step 5—The carbamate 76b (0.12 g, 0.00028 mole) was dissolved in 50% TFA/DCM (5 mL) and stirred at RT for 1 h. Solvents were removed in vacuo, and residue was dried in vacuo for 5 h at 40° C. to afford 0.12 g of 77: ms (ES+) m/z 325 (M+H)⁺.

step 6—Cyclopentanecarboxylic acid (3-oxo-1-phenyl-propyl)-amide (12, 0.41 g, 1.68 mmol) was added to a solution of 77 TFA salt (0.51 g, 1.18 mmol) in DCM (5 mL), and NaBH(OAc)₃ (0.35 g, 1.65 mmol) was added. The reaction was stirred at RT for 18 h, diluted with EtOAc (25 mL), washed with saturated NaHCO₃ (25 mL), brine (25 mL), dried (MgSO₄) and concentrated in vacuo. The crude product was purified by flash chromatography on silica gel eluting with 10% MeOH/DCM to afford 0.4 g (61%) of 78: MS (ES+) m/z 554 (M+H)⁺.

step 7—To a mixture of 78 (0.14 g, 2.51 mmol) and Cs₂CO₃ (0.16 g, 5.0 mmol) in DMF (2 mL) was added benzyl glycolate (0.05 g, 3 mmol), and resulting mixture was stirred at 70° C. for 8 h. DMF was removed in vacuo and residue was purified by flash chromatography on silica gel eluting with 10% MeOH/DCM to afford 0.1 g (62%) 79: MS (ES+) m/z 640 (M+H)⁺.

step 8—Palladium on carbon (20 mg) was added to a solution of 79 (0.1 g, 0.15 mmol) on EtOH (20 mL). The solution was hydrogenated under atmospheric pressure overnight and filtered through a CELITE® pad. The resulting solution was concentrated in vacuo to afford 78 mg (91%) of I466: mp 117.3–119.0° C., ms (ES+) m/z 550 (M+H)⁺.

EXAMPLE 24

Cyclopentanecarboxylic acid (3-chloro-4-methyl-phenyl)-{3-[5-(2,6-dimethyl-benzoyl)-hexahydro-pyrrolo[3,4-c]pyrrol-2-yl]-2-methyl-propyl}-amide (II-310)

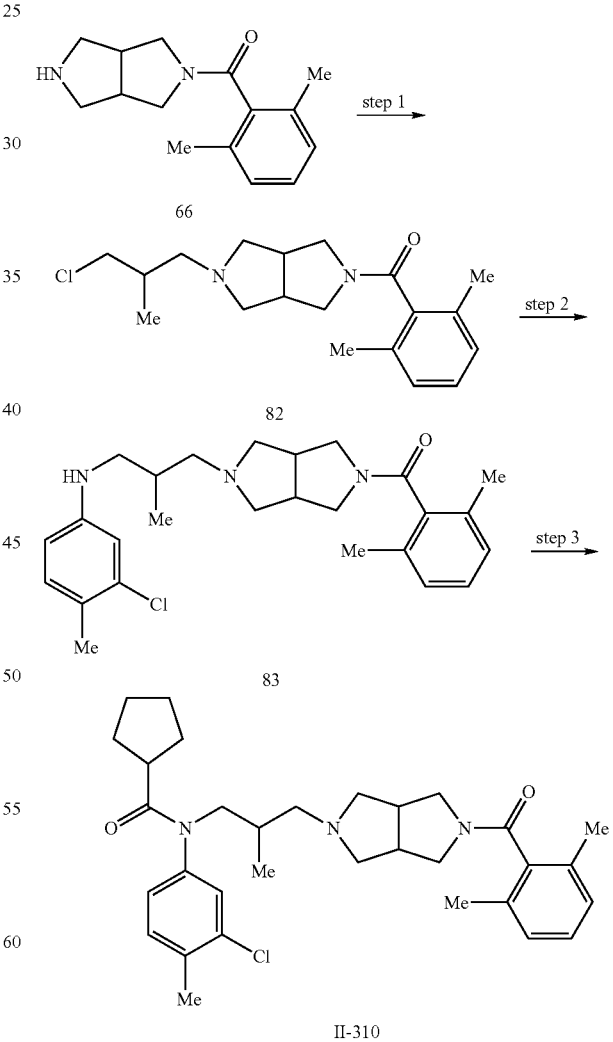

step 1—1-Bromo-3-chloro-2-methyl-propane (0.17 mL, 1.45 mmol) and TEA (0.24 mL, 1.71 mmol) were added to a solution of (2,6-dimethyl-phenyl)-(hexahydro-pyrrolo[3,4-c]pyrrol-2-yl)-methanone (66, 358 mg, 1.47 mmol) in DMF (6 mL). The mixture was stirred overnight at RT. Water was added and the mixture was extracted with DCM. The organic layer was dried (Na$_2$SO$_4$) and concentrated. The crude product was purified by SiO$_2$ column chromatography on silica gel eluting with a DCM: MeOH:NH$_4$OH gradient (98:1.4:0.14 to 96:3.5:0.35 over 40 min.) to afford 82 (224 mg, 46%): ms (LCMS) m/z 335 (M+H).

step 2—To a solution of 82 (224 mg, 0.67 mmol) dissolved in DMF (3 mL) was added KI (120 mg, 0.72 mmol), 3-chloro-4-methyl-phenylamine (105 mg, 0.74 mmol) and DIPEA (0.12 mL, 0.69 mmol) and the reaction mixture was stirred at 80° C. for 4 h. The mixture was allowed to cool to RT, diluted with water and extracted with DCM. The combined DCM extracts were dried (Na$_2$SO$_4$) and concentrated. The crude product was purified by SiO$_2$ column chromatography eluting with a CH$_2$Cl$_2$:MeOH:NH$_4$OH (99:0.7:0.07) to afford 83 (146 mg, 49%) as an off-white solid: ms (LCMS) m/z 440 (M+H).

step 3—Cyclopentanecarbonyl chloride (0.07 mL, 0.06 mmol) and DIPEA (0.02 mL, 0.11 mmol) were added to a solution of 83 (28.5 mg, 0.06 mmol) in toluene (1 µL). The resulting solution was stirred at 50° C. for 1 hour. The mixture was allowed to cool to room temperature, diluted with water and extracted with DCM. The combined DCM extracts were dried (Na$_2$SO$_4$) and concentrated. The crude product was purified by SiO$_2$ column chromatography eluting with a DCM:MeOH:NH$_4$OH gradient (99:0.7:0.07 to 96:3.5:0.35 over 50 min.) to afford II-310 (14 mg, 40%): $^1$H NMR (CDCl$_2$) δ 0.9 (d, 3H), 1.35–1.45 (m, 2H), 1.55 (s, 3H), 1.6–1.85 (m, 5), 2.1–2.5 (m, 15H), 2.65–2.9 (m, 3H), 3.22–3.3 (m, 1H), 3.4–3.9 (m, 4H), 6.95–7.4 (m, 3H), 7.1–7.3 (m, 3H); ms (ES+) m/z 536 (M+H).

EXAMPLE 25

Cyclopentanecarboxylic acid {(S)-3-[5-(2,6-dimethyl-benzoyl)-hexahydro-pyrrolo[3,4-c]pyrrol-2-yl]-1-phenyl-butyl}-amide (I-75)

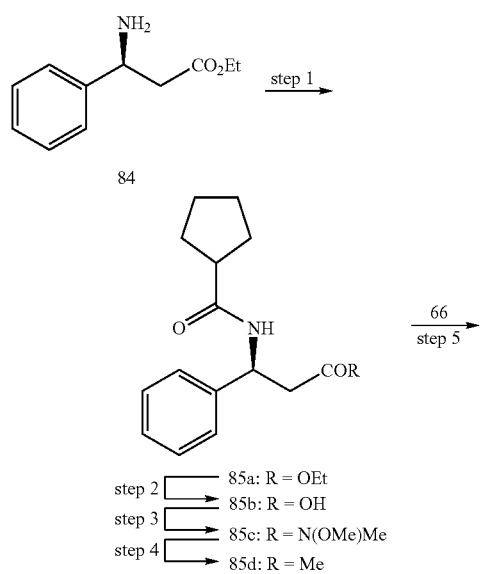

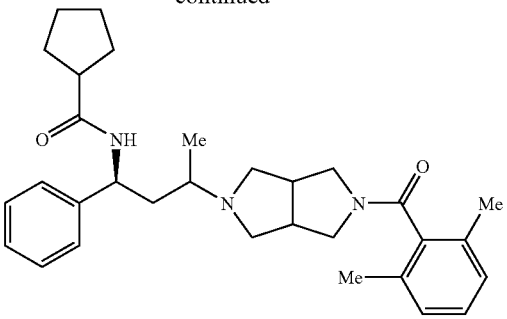

I-75 steps 1 and 2—To a solution of (S)-3-amino-3-phenyl-propanoic acid ethyl ester hydrochloride (84, 5.0 g, 21.76 mmol) in H$_2$O (50 mL), saturated Na$_2$CO$_3$ (50 mL), DCM (50 mL) and toluene (20 mL) was added cyclopentylcarboxylic acid chloride (2.9 mL, 23.93 mmol). The reaction was stirred overnight at RT. The mixture was extracted with DCM and the organic layer was dried (MgSO$_4$), filtered and concentrated in vacuo. The residue containing 85a was redissolved in H$_2$O (50 mL) and THF (50 mL) LiOH.H$_2$O (2.73 g, 65.06 mmol) was added. After 3 h, the mixture was washed with ether. The aqueous layer was acidified with 2N HCl and extracted with EtOAc. The organic layer was dried (MgSO$_4$), filtered and evaporated to afford 5.56 g (97%) of 85b; $^1$H NMR (CDCl$_3$) δ 1.5–1.65(m, 2H), 1.65–1.95 (m, 6H), 2.55 (t, 1H), 2.8–3.0 (qd, 2H), 5.4–5.5 (m, 1H), 6.4–6.45 (d, 1H), 7.2–7.45 (m, 5H).

step 3—N,O-dimethylhydroxylamine hydrochloride (0.92 g, 9.50 mmol), O-(7-azabenzotriazol-1-yl)N,N,N',N'-tetramethyluronium hexafluorophosphate (3.61 g, 9.50 mmol) and DIPEA (5.5 mL, 31.68 mmol) were added to a solution of 85b (2.07 g, 7.92 mmol) in DCM (80 mL). The reaction mixture was stirred overnight at RT, poured into 2N NaOH solution and stirred for 10 min. The organic layer was washed with H$_2$O, 2N HCl and brine, dried (MgSO$_4$) and concentrated in vacuo. The crude product was purified by SiO$_2$ column chromatography eluting with n-hexane:EtOAc (1:2) to afford 1.24 g of 85c (yield 51%): $^1$H NMR (CDCl$_3$) δ 1.55–1.65 (m, 2H), 1.65–1.95 (m, 6H), 2.65 (q, 1H), 2.8 (dd, 1H), 3.1 (s, 3H) 3.1–3.2 (dd, 1H), 3.45 (s, 3H), 5.43 (m, 1H), 7.15–7.45 (m, 5H), 7.4 (d 1H).

step 4—To a solution of 85c (1.06 g, 3.50 mmol) in THF (15 mL) was added dropwise at −78° C. MeMgCl (3.7 mL, 3M in THF). The mixture was warmed to RT over 3 h and it was stirred at RT one additional hour. The reaction was quenched with 1N K$_2$HPO$_4$ extracted with Et$_2$O. The organic layer was washed with saturated NaHCO$_3$ and brine, dried (MgSO$_4$), filtered and concentrated in vacuo. The crude product was purified by SiO$_2$ column chromatography on eluting with n-hexane:EtOAc (1:1) to afford 0.89 g (98%) of 85d.

step 5—To a solution of (2,6-dimethyl-phenyl)-(hexahydro-pyrrolo[3,4-c]pyrrol-2-yl)-methanone (66, 0.12 g, 0.52 mmol) in DCM (7 mL) and THF (7 mL) was added cyclopentanecarboxylic acid (3-oxo-1-phenyl-butyl)-amide (85d, 0.15 g, 0.57 mmol). Titanium tetraisopropoxide (0.34 mL, 1.15 mmol) was added to the mixture. After 30 min NaBH(OAc)$_3$ (0.16 g, 0.78 mmol) was added and the mixture stirred at RT for 4 h. Saturated NaHCO$_3$ was added to the mixture and it was stirred for 10 min. The mixture was extracted with DCM and the organic layer was dried (MgSO$_4$), filtered and evaporated. The crude product was purified by SiO$_2$ chromatography on silica gel eluting with DCM:MeOH:NH$_4$OH (150:10:1) to afford I-75: ms (ES+)

m/z 488 (M+H); Anal. (C$_{31}$H$_{41}$N$_3$O$_2$.0.3M H$_2$O)C; calcd, 75.51; found 75.53; H; calcd, 8.50; found, 8.29; N; calcd, 8.52; found, 8.53.

EXAMPLE 26

1-Acetyl-piperidine-4-carboxylic acid (3-chloro-4-methyl-phenyl)-{3-[5-(4,6-dimethyl-pyrimidine-5-carbonyl)-hexahydro-pyrrolo[3,4-c]pyrrol-2-yl]-2,2-dimethyl-propyl}-amide (II-354)

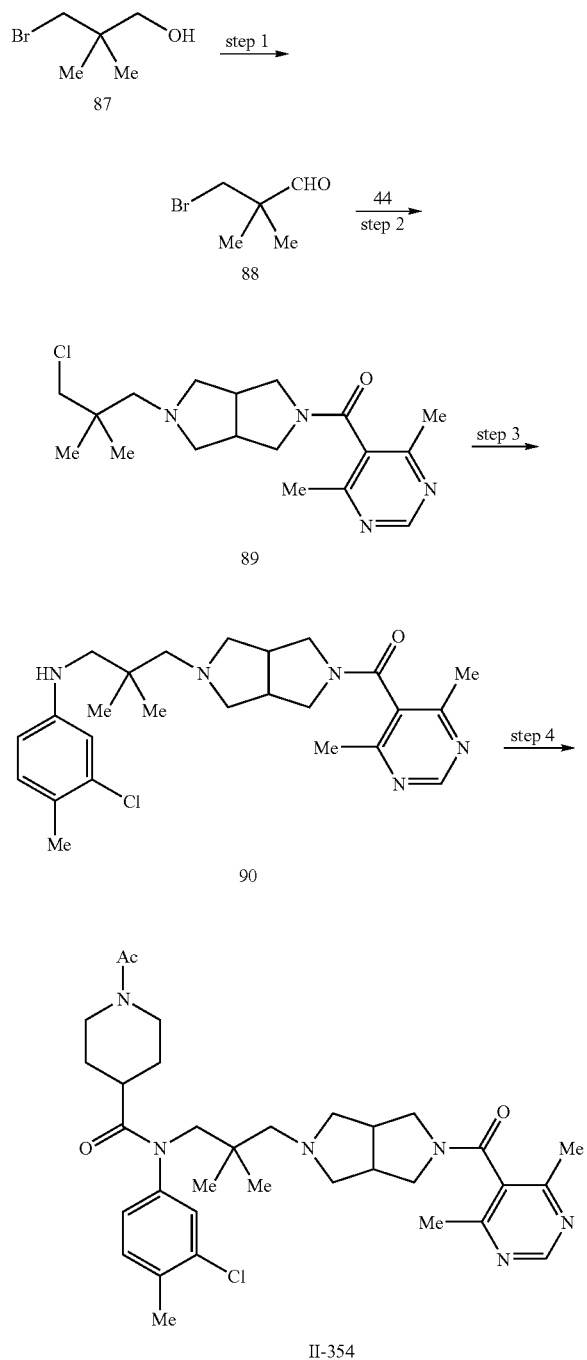

step 1—The Dess-Martin reagent (1.12 g, 2.64 mmol) was added to a solution of 3-bromo-2,2-dimethyl-propan-1-ol (87, 0.37 mL, 3.00 mmol) in DCM (20 mL) maintained 0° C. The reaction mixture was stirred at 0° C. for 1 h. The ice bath was removed and the reaction mixture was stirred at RT for additional 30 min. Et$_2$O (40 mL) was added, and the mixture was poured onto 20 mL of a 9:1 mixture of aqueous saturated NaHCO$_3$ and aqueous saturated Na$_2$S$_2$O$_3$. The mixture was stirred until a clear solution was obtained (10 minutes). The layers were separated, and the Et$_2$O layer was washed with saturated aqueous NaHCO$_3$ (2×) and water (2×). The organic layer was dried (Na$_2$SO$_4$) and concentrated to afford 88 (393 mg). The crude product was used for the next step without further purification.

step 2—A solution of 3-bromo-2,2-dimethyl-propionaldehyde (88, 393 mg, 23.8 mmol) and 44 (620 mg, 25.2 mmol) in DCM (6 mL) was treated with HOAc (0.2 mL, 34.9 mmol) and NaBH(OAc)$_3$ (530 mg, 25.0 mmol). The reaction mixture was stirred for 2 h at RT and then quenched by the addition of aqueous NaOH (2 M, 2.4 mL, 0.48 mmol). The mixture was extracted with DCM. The combined DCM extracts were dried (Na$_2$SO$_4$) and concentrated. The crude product was purified by SiO$_2$ column chromatography eluting with a CH$_2$Cl$_2$:MeOH:NH$_4$OH gradient (99:0.7:0.07 to 96:3.5:0.35 over 50 min.) to afford 89 (95 mg, 10%): ms (LCMS) m/z 397 (M+H).

step 3—A solution of 89 (95 mg, 0.24 mmol) in MeCN (1 mL) was treated with 3-chloro-4-methyl-phenylamine (76 mg, 0.53 mmol) and TEA (0.035 mL, 0.25 mmol). The reaction mixture was stirred at 50° C. overnight. The mixture was allowed to cool to RT, diluted with water and extracted with DCM. The combined CH$_2$Cl$_2$ extracts were dried (Na$_2$SO$_4$) and concentrated. The crude product was purified by SiO$_2$ column chromatography eluting with a CH$_2$Cl$_2$:MeOH:NH$_4$OH gradient (99:0.7:0.07 to 96:3.5:0.35 over 50 min.) to afford 90 (25 mg, 23%): ms (LCMS) m/z 456 (M+H).

step 4—1-Acetyl-piperidine-4-carbonyl chloride (24 mg, 0.13 mmol) and TEA (0.02 mL, 0.14 mmol) were added to a solution of 90 (25 mg, 0.054 mmol) in DCM (2 mL). The resulting solution was stirred overnight. The mixture was diluted with water and extracted with DCM. The combined DCM extracts were dried (Na$_2$SO$_4$) and concentrated. The crude product was purified by SiO$_2$ column chromatography eluting with a CH$_2$Cl$_2$:MeOH:NH$_4$OH gradient (98:1.4:0.14 to 93:6:0.6 over 50 min.) to afford II-354 (9 mg, 27%): $^1$H NMR (DMSO-d$_6$) δ 0.75 (s, 6H), 1.2–1.6 (m, 4H), 1.95 (s, 3H), 2.1 (s, 2H), 2.2–2.5 (m, 16H), 2.65–2.85 (m, 4H), 3.25–3.35 (m, 1H), 3.6–3.8 (m, 4H), 4.2–4.3 (m, 1H), 7.25–7.5 (m, 3H), 8.95 (s, 1H); ms (ES+) m/z 609 (M+H).

EXAMPLE 27

Cyclopentanecarboxylic acid {3-[5-(2,6-dimethyl-benzoyl)-hexahydro-pyrrolo[3,4-c]pyrrol-2-yl]-4-methoxy-1-phenyl-butyl}-amide. (I-354)

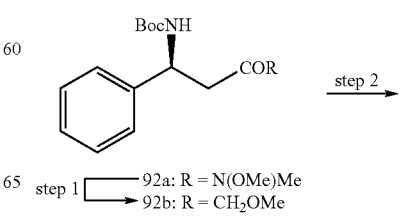

step 1 ┌─ 92a: R = N(OMe)Me
        └▶ 92b: R = CH$_2$OMe

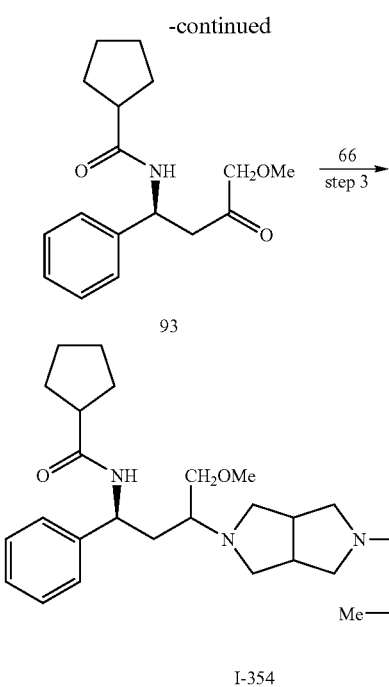

step 1—To a solution of tributyl-methoxymethyl-stannane (0.71 g, 2.14 mmol, T. S. Kaufman *Syn. Lett.* 1997 12:1377–1378) in THF (5 mL) was added n-BuLi (1.4 mL, 1.5M in hexane) dropwise at −78° C. and the reaction was stirred for 10 min at −78° C. A solution of 92a (0.22 g, 0.71 mmol) in THF (3 mL) was added to the mixture slowly and after the addition the reaction mixture was stirred for 30 min at −78° C. Sat. NH$_4$Cl was added to the mixture and it was warmed up to RT. The mixture was extracted with EtOAc and the organic layer was washed with brine, dried (MgSO$_4$), filtered and concentrated in vacuo The crude product was purified by SiO$_2$ column chromatography eluting with n-hexane:EtOAc (2:1) to afford 0.13 g (62%) of 92b: $^1$H NMR (CDCl$_3$) δ 1.42 (s, 9H), 2.85–3.1 (dd, 2H), 3.35 (s, 3H), 3.85 (s, 2H), 5.1 (br, 1H), 5.38 (br, 1H), 7.2–7.4 (m, 5H).

step 2—Methanolic HCl (17 mL, 1.25 M) was added to 92b (0.31 g, 1.05 mmol) and the mixture was heated at 50° C. for 2 h. The mixture was concentrated in vacuo and dried in vacuo. The crude product was dissolved in a mixture of saturated Na$_2$CO$_3$ (4 mL), H$_2$O (2 mL), DCM (2 mL) and toluene (1 mL) and the resulting mixture was treated with cyclopentylcarboxylic acid chloride (0.18 mL, 1.48 mmol). After stirring overnight the solution was extracted with DCM and the organic layer was washed with brine, dried (Na$_2$SO$_4$) and concentrated in vacuo. The crude product was purified by SiO$_2$ column chromatography eluting with n-hexane:EtOAc (1:1) to afford 0.23 g (76%) of 93. mp 89.5–92.2° C.; ms (ES+) m/z 290 (M+H).

step 3—To a solution of 93 (0.15 g, 0.63 mmol) in DCE (7 mL) and THF (7 mL) was added 66 (0.18 g, 0.63 mmol). Titanium tetraisopropoxide (0.41 mL, 1.39 mmol) was added to the mixture and after 30 min NaBH(OAc)$_3$ (0.20 g, 0.95 mmol) was added and the reaction stirred at rt overnight. Saturated NaHCO$_3$ was added to the mixture and stirring continued for 10 min. The mixture was filtered through a CELITE® pad and extracted with DCM. The organic layer was dried (MgSO$_4$), filtered and concentrated in vacuo. The crude product was purified by SiO$_2$ column chromatography eluting with 5% MeOH/EtOAc to afford 0.32 g (50%) of II-354: ms (ES+) m/z 517 (M+H); Anal. (C$_{32}$H$_{43}$N$_3$O$_3$.0.15M DCM) C; calcd, 72.80; found, 72.55; H; calcd, 8.23; found, 8.22; N; calcd, 7.92; found, 7.93.

EXAMPLE 28

Cyclopentanecarboxylic acid {3-[5-(2,6-dimethyl-benzoyl)-hexahydro-pyrrolo[3,4-c]pyrrol-2-yl]4-hydroxy-1-phenyl-butyl}-amide (I-360)

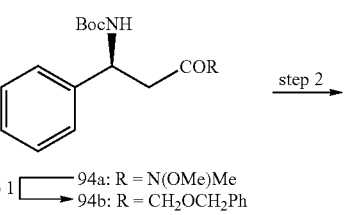

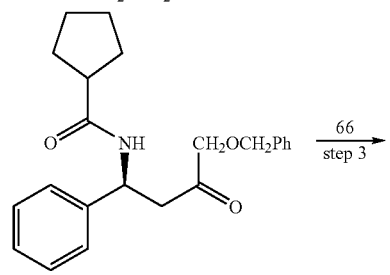

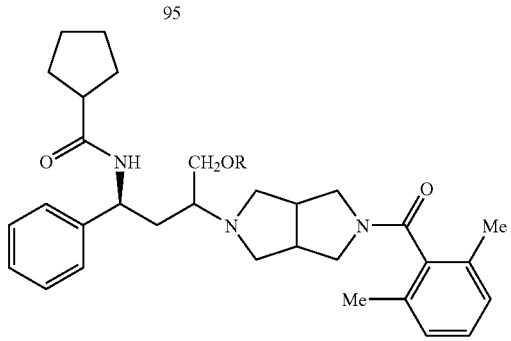

Steps 1 to 3 were carried out as described in Example 27 except benzyloxymethyl-tributyl-stannane was used in place of methoxymethyl-tributyl-stannane in step 1.

step 4—To a solution of 96 (0.21 g, 0.35 mmol) and EtOH (6 mL) was added 2N HCl (2 mL) and Pd/C (0.02 g). The mixture was stirred at RT overnight under H$_2$ atmosphere. The catalyst was filtered through a CELITE® pad and the filtrate was concentrated in vacuo. The crude product was purified by SiO$_2$ column chromatography eluting with CH$_2$Cl$_2$:MeOH:NH$_4$OH (120:10:1) to afford 0.10 g (56%) of I-360: mp 78.9–84.9° C.; ms (ES+) m/z 504 (M+H).

EXAMPLE 29

4,4-Difluoro-cyclohexanecarboxylic acid {3-[5-(4,6-dimethyl-pyrimidine-5-carbonyl)-hexahydro-pyrrolo[3,4-c]pyrrol-2-yl]-1-phenyl-butyl}-amide (I-448)

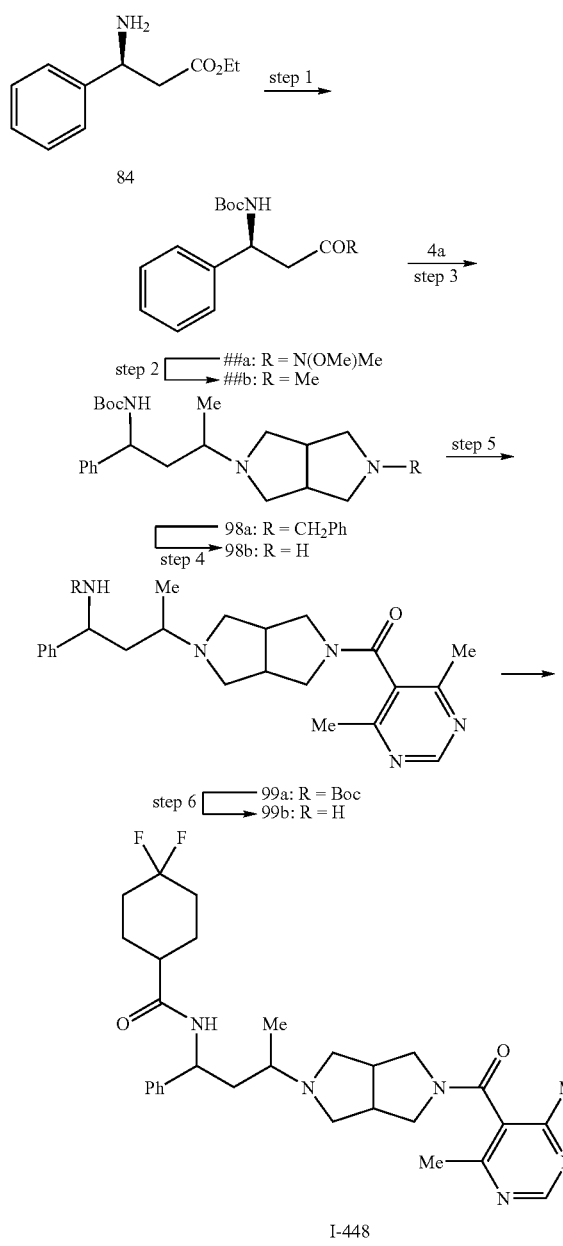

I-448

Formation of the N-Boc derivative of 84 was carried out using stand protocols. Steps 2 and 3 were carried out as described for steps 4 and 5 of example 25 except the N-protecting groups were Boc and benzyl in the present example. Silica chromatography of 98a eluting with DCM:MeOH:NH$_4$OH (150:10:1) afforded 0.72 g (57%): $^1$H NMR (DMSO-d$_6$) δ 0.9–0.95 (m, 3H), 1.35 (s, 9H), 1.45–1.7 (m 1H), 1.8–2.2 (m, 1H), 2.25–2.38 (m, 4H), 2.45–2.7 (m, 6H), 3.55 (q, 2H), 4.6–4.75 (1H), 7.25–7.32 (m, 10H).

step 4—Palladium on carbon (0.07 g) and ammonium formate (1.01 g, 16.01 mmol) were added to a solution of 98a (0.72 g, 1.60 mmol) in MeOH (30 mL). The solution was heated at reflux for 2 h and filtered through a CELITE® pad. The resulting solution was concentrated in vacuo and crude product purified by SiO$_2$ column chromatography eluting with DCM:MeOH:NH$_4$OH (90:10:1) to afford 98b.

steps—To a solution of [3-(hexahydro-pyrrolo[3,4-c]pyrrol-2-yl)-1-phenyl-butyl]-carbamic acid tert-butyl ester 98b (0.22 g, 0.63 mmol) in DCM (10 mL) were added 4,6-dimethyl-pyrimidine-5-carboxylic acid (0.11 g, 0.76 mmol), EDCI (0.16 g, 0.82 mmol), HOBt (0.11 g, 0.82 mmol) and DIPEA (0.33 mL, 1.90 mmol). The mixture was stirred at RT overnight. The mixture was washed with saturated. NaHCO$_3$ and the organic layer was dried (Na$_2$SO$_4$). The crude product was purified by SiO$_2$ column chromatography eluting with CH$_2$Cl$_2$:MeOH:NH$_4$OH (160:10:1) to afford 0.30 g (95%) of 99a:

step 6—Methanolic HCl (5 mL, 1.25 M) was added to 99a (0.30 g, 0.61 mmol) and the mixture was heated at 50° C. for 2 h. The mixture was concentrated in vacuo and purified by SiO$_2$ column chromatography eluting with CH$_2$Cl$_2$:MeOH:NH$_4$OH (120:10:1) to afford 0.17 g (70%) of 99b:

step 7—To a solution of 99b (0.17 g, 0.43 mmol) in DCM (10 mL) were added 4,4-difluoro-cyclohexanecarboxylic acid (0.08 g, 0.51 mmol), EDCI (0.10 g, 0.56 mmol), HOBt (0.07 g, 0.56 mmol) and DIPEA (0.22 mL, 1.29 mmol). The mixture was stirred at RT overnight. The mixture was washed with saturated. NaHCO$_3$ and the organic layer was dried (Na$_2$SO$_4$). The crude product was purified by SiO$_2$ column chromatography eluting with DCM:MeOH:NH$_4$OH (150:10:1) to afford 0.22 g (95%) of I-448: mp 86.4–87.0° C.; ms (ES+) m/z 540 (M+H).

EXAMPLE 30

Cyclopentanecarboxylic acid {3-[5-(5-methyl-1-phenyl-1H-pyrazole-4-sulfonyl)-hexahydro-pyrrolo[3,4-c]pyrrol-2-yl]-1-phenyl-propyl}-amide (I-113)

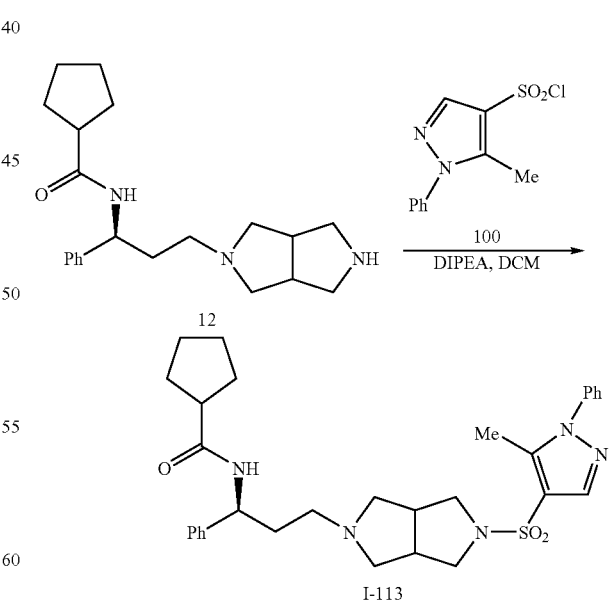

I-113

To a solution of 12 (0.012 g, 0.035 mmol), DIPEA (0.02 mL, 0.105 mmol) and DCM (1 mL) at RT was added 5-methyl-1-phenyl-1H-pyrazole-4-sulfonyl chloride (100 0.018 g, 0.07 mmol) and the mixture stirred overnight at rt.

The reaction mixture was concentrated in vacuo and purified by reverse phase HPLC: MS (ES+) m/z 562 (M+H)+ to afford I-113.

EXAMPLE 31

4-Acetyl-piperidine-1-carboxylic acid (3-chloro-4-methyl-phenyl)-{3-[5-(2-methyl-pyridine-3-sulfonyl)-hexahydro-pyrrolo[3,4-c]pyrrol-2-yl]-propyl}-amide (II-363)

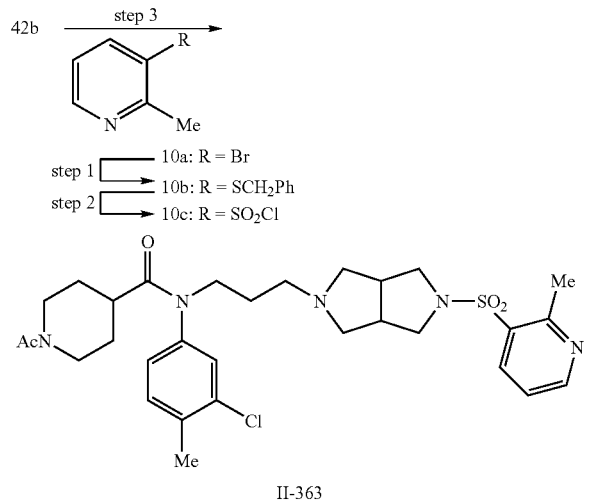

step 1—Benzylmercaptan (664 mg, 0.63 in L, 5.34 mmol) was dissolved in 8.5 mL DMF under an atmosphere of $N_2$. NaH (214 mg 60% as an oil dipersion, 5.34 mmol) was added portionwise with stirring, then stirred for an additional 15 min. To the solution was added 3-bromo-2-methyl-pyridine (102a, 707 mg, 4.11 mmol) in one portion and the mixture heated in an oil bath at 130° C. for 4 h. The reaction mixture was cooled to RT and partitioned between $H_2O$ (50 mL) and hexane (50 mL). The hexane layer was separated, washed with $H_2O$ (50 mL), dried over $MgSO_4$, then concentrated in vacuo. The crude product was purified by flash chromatography on silica gel eluting with EtOAc:hexane (1:2) to afford 522 mg (44%) of 102b as a viscous liquid: ms (ES+) m/z 216 (M+H)+.

step 2—A solution of 102b (414 mg, 1.92 mmol) in glacial HOAc (8.3 mL) and $H_2O$ (0.83 mL) was cooled to 0° C. Chlorine gas was bubbled into the mixture for 15 min, and the resulting solution was stirred for an additional 20 min. The mixture was diluted with DCM (50 mL), washed with brine, saturated $NaHCO_3$ solution, brine, dried ($MgSO_4$), and concentrated in vacuo. The crude product was purified by flash chromatography on silica eluting with EtOAc:hexane (1:2) to afford 285 mg (76%) of 102c as a pale yellow liquid: ms (ES+) m/z 191 (M+).

step 3—A solution of 102c (47 mg, 0.25 mmol), DIPEA (35 mg, 0.05 mL, 0.27 mmol) and 42b (100 mg, 0.22 mmol) in DCM (3.5 mL) was stirred for 2 h then concentrated in vacuo. The crude product was purified by flash chromatography on silica eluting with DCM/8% MeOH (containing 2% $NH_4OH$) to afford 133 mg (99%) of II-363 as a viscous liquid.

EXAMPLE 32

N-{3-[5-(2,6-Dimethyl-benzoyl)-hexahydro-pyrrolo[3,4-c]pyrrol-2-yl]-propyl}-N-(4-fluoro-phenyl)-benzenesulfonamide (II-2)

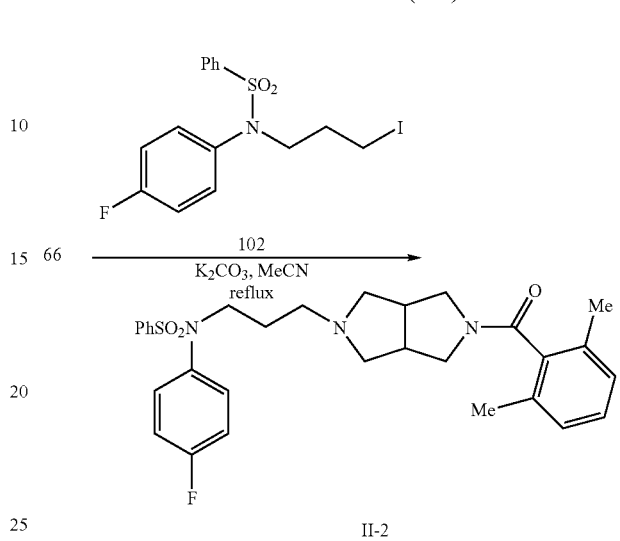

To a solution of 66 (0.012 g, 0.05 mmol) in MeCN (1 mL) at RT were added N-(4-fluoro-phenyl)-N-(3-iodo-propyl)-benzenesulfonamide (102, 0.025 g, 0.06 mmol) and $K_2CO_3$ (0.01 g, 0.075 mmol). The reaction mixture was shaken at 80° C. for 48 h. After cooling to RT, the mixture was diluted with DCM (5 mL), filtered and evaporated in vacuo. The crude product was purified by reverse phase HPLC to afford II-2: MS (ES+) m/z=536 (M+H)+.

EXAMPLE 33

N-{3-[5-(2,6-Dimethyl-benzoyl)-hexahydro-pyrrolo[3,4-c]pyrrol-2-yl]-1-phenyl-propyl}-benzenesulfonamide (I-32)

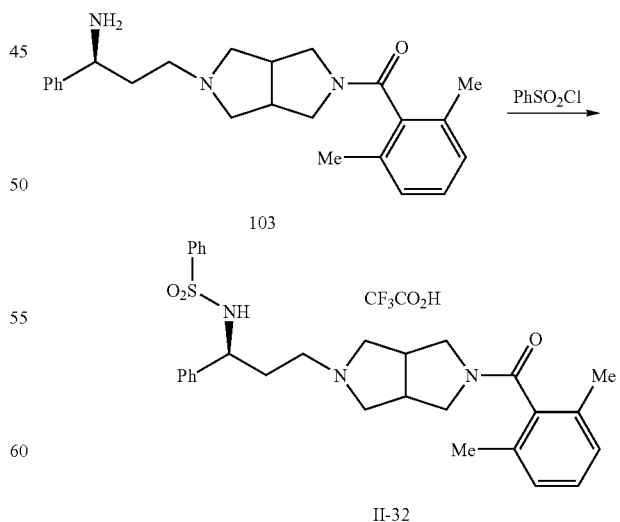

A solution of 103 (35 µmol) in DCM was added to benzenesulfonyl chloride (9.3 mg 53 µmol) and DIPEA (30 µl) was added. The reaction was shaken for 18 h. The solution was evaporated under reduced pressure and purified by preperative HPLC to afford II-32: ms (ES+) m/z 518 (M+H)+.

EXAMPLE 34

1-Acetyl-piperidine-4-carboxylic acid {3-[5-(2-chloro-4-fluoro-benzenesulfonyl)-hexahydro-pyrrolo[3,4-c]pyrrol-2-yl]-propyl}-(3-chloro-4-methyl-phenyl)-amide (II-296)

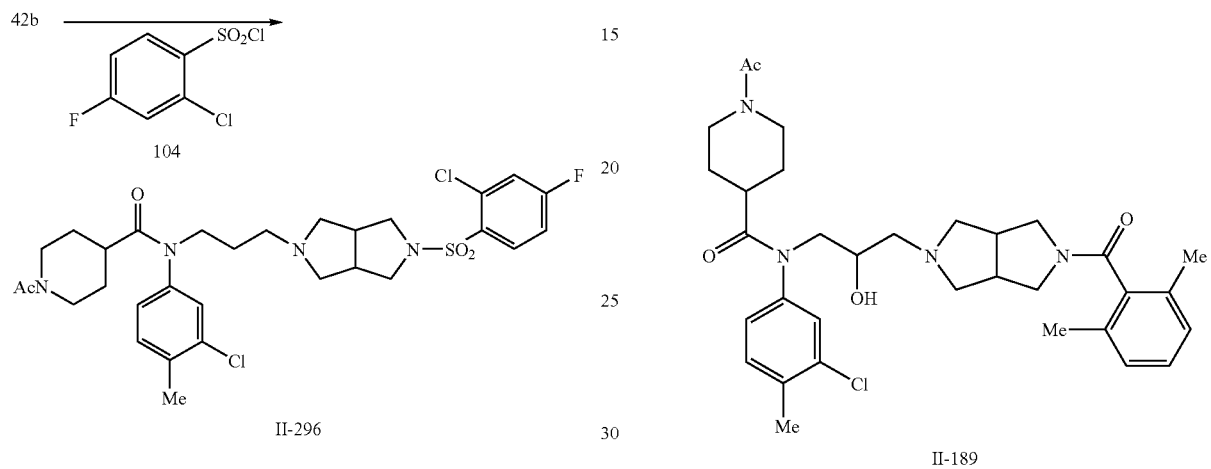

To a solution of 42b (0.016 g, 0.035 mmol) and DIPEA (0.02 mL, 0.105 mmol) in DCM (1 mL) at RT was added 2-chloro-4-fluorobenzenesulfonyl chloride (104, 0.016 g, 0.07 mmol) and the mixture shaken overnight at rt. The reaction mixture was concentrated in vacuo and purified by reverse phase HPLC to afford II-296: ms (ES+) m/z 639 (M+H)+.

EXAMPLE 35

1-Acetyl-piperidine-4-carboxylic acid (3-chloro-4-methyl-phenyl)-{3-[5-(2,6-dimethyl-benzoyl)-hexahydro-pyrrolo[3,4-c]pyrrol-2-yl]-2-hydroxy-propyl}-amide (II-189)

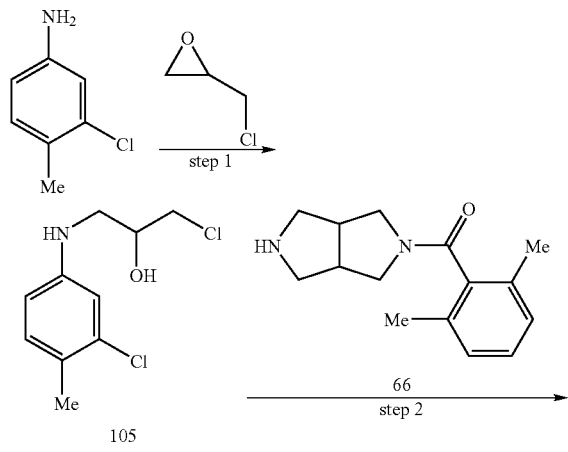

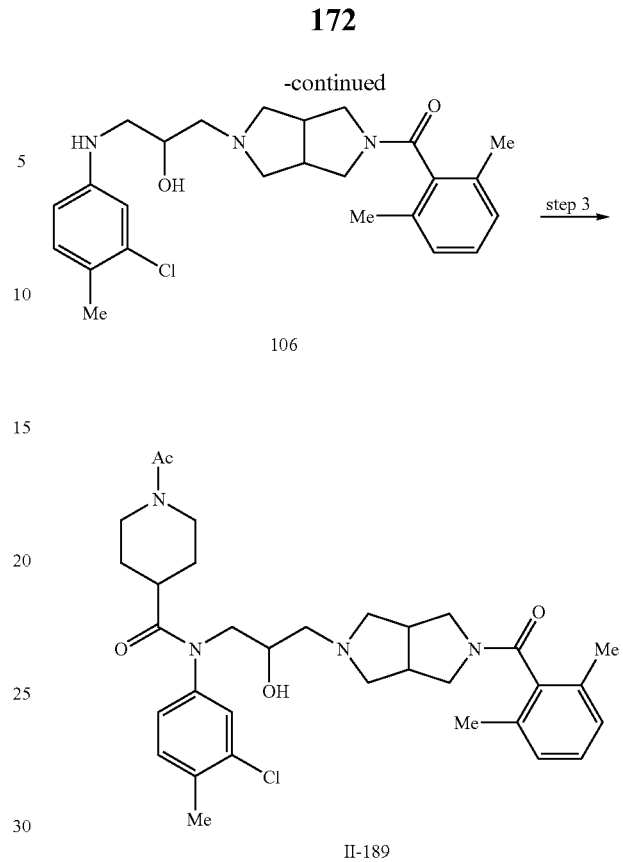

step 1—A solution of 3-chloro-4-methyl-phenylamine (3.0 g, 21.18 mmol) and 2-chloromethyl-oxirane (0.83 mL, 10.59 mmol) and EtOH (30 mL) were heated to reflux overnight. The mixture was concentrated in vacuo and purified by SiO$_2$ column chromatography eluting with n-hexane:EtOAc (5:1) to afford 2.23 g (90%) of 105: $^1$H NMR (CDCl$_3$) δ 2.25 (s, 3H), 3.18 (dd, 1H), 3.35 (dd, 1H), 3.6–3.75 (m, 2H), 4.0–4.15 (m, 1H) 6.45 (dd, 1H), 6.65 (dd, 1H), 7.0 (d, 1H)

step 2—To a solution of 105 (0.12 g, 0.52 mmol) and 66 (0.11 g, 0.47 mmol) and MeCN (10 mL) was added K$_2$CO$_3$ (0.13 g, 0.94 mmol) and KI (0.09 g, 0.56 mmol) and the resulting solution was heated at reflux overnight. The mixture was cooled, diluted with water and extracted with EtOAc. The combined EtOAc extracts were washed with brine, dried (MgSO$_4$), filtered and evaporated. The crude product was purified by SiO$_2$ column chromatography eluting with DCM:MeOH:NH$_4$OH (120:10:1) to afford 0.13 g (62%) of 106.

step 3—To a solution of 106 (0.13 g, 0.29 mmol) in DCE (5 mL) were added 1-acetyl-piperidine-4-carbonyl chloride (0.16 g, 0.82 mmol) and pyridine (0.94 mL, 1.17 mL). The solution was heated at 50° C. overnight. The mixture was cooled, diluted with DCM and washed with saturated NaHCO$_3$. The organic layer was dried (Na$_2$SO$_4$), filtered and evaporated. The crude product was purified by SiO$_2$ column chromatography eluting with CH$_2$Cl$_2$:MeOH:NH$_4$OH (150:10:1) to afford 0.12 g (68%) of II-189: mp 107.9–109.8° C.; ms (ES+) m/z 595 (M+H).

EXAMPLE 36

1-Acetyl-piperidine-4-carboxylic acid (3-chloro-4-methyl-phenyl)-{3-[5-(2,4-dimethyl-pyridine-3-carbonyl)-hexahydro-pyrrolo[3,4-c]pyrrol-2-yl]-butyl}-amide (II-36)

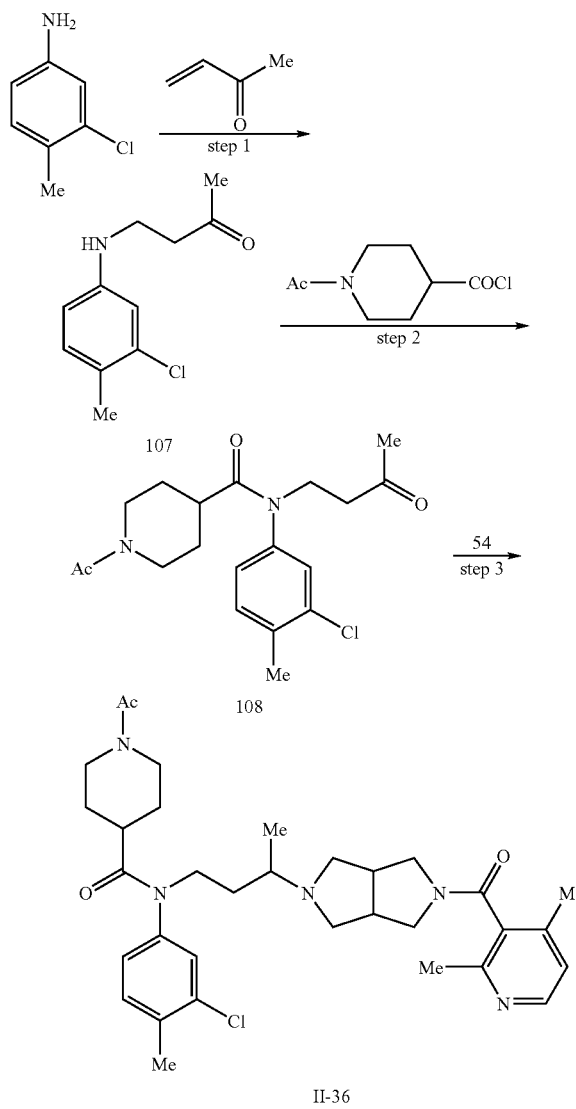

step 1—To a mixture of 3-chloro-4-methyl-phenylamine (2.5 g, 17.65 mmol) and trifluoromethanesulfonimide (0.33 g, 1.20 mmol) in MeCN (20 mL) was added methyl vinyl ketone (1 mL, 12.05 mmol) at RT. After 1 h silica gel and $Na_2CO_3$ (200 mg) were added to the mixture and it was concentrated in vacuo. The crude product was purified by $SiO_2$ column chromatography eluting with n-hexane:EtOAc (4:1) to afford 1.3 g (51%) of 107: NMR (CDCl$_3$) δ 2.15 (s, 3H), 2.25 (s, 3H), 2.73 (t, 2H), 3.35 (t, 2H), 3.93 (br, 1H), 6.4 (dd, 1H), 6.6 (d, 1H), 6.98 (d, 1H);

step 2—To a solution of 107 (1.3 g, 6.14 mmol) in DCM (30 mL) were added 1-acetyl-piperidine-4-carbonyl chloride (3.49 g, 18.42 mmol) and TEA (3 mL, 22.09 mmol) at 0° C. After 20 min the solution was heated at 40° C. overnight. The mixture was diluted with DCM and washed sequentially with $H_2O$, 2N HCl, saturated NaHCO$_3$ and brine. The organic layer was dried ($Na_2SO_4$), filtered and evaporated. The crude product was purified by $SiO_2$ column chromatography eluting with 5% MeOH/EtOAc to afford 1.28 g 957%) of 108: $^1$H NMR (CDCl$_3$) δ 1.6–1.85 (m, 4H), 2.05 (s, 3H), 2.45 (s, 3H), 2.68 (t, 2H), 2.85 (t, 1H), 3.28 (d, 1H), 3.85–3.95 (m. 2H), 4.5 (d, 1H), 6.98 (dd, 1H), 7.2 (d, 1H), 7.33 (d, 1H).

step 3—To a solution of 108 (0.17 g, 0.48 mmol) in THF (7 mL) was added a solution of 54 (0.10 g, 0.40 mmol) in DCM (7 mL). Titanium tetra-isopropoxide (0.26 mL, 0.89 mmol) was added to the mixture. After stirring for 40 min, NaBH(OAc)$_3$ (0.13 g, 0.61 mmol) was added to the mixture and stirring was continued at RT overnight. Saturated NaHCO$_3$ was added to the mixture and it was stirred for 10 min. The mixture was filtered through a CELITE pad and the filtrate was extracted with DCM. The organic layer was dried over (MgSO$_4$) and purified by SiO$_2$ column chromatography eluting with DCM:MeOH:NH$_4$OH (150:10:1) afford 0.15 g (64%) of II-36: mp 60.9–62.4° C.; ms (ES+) m/z 594 (M+H).

EXAMPLE 37

Cyclopentanecarboxylic acid {3-[5-(2,6-dimethyl-benzoyl)-3a,6a-dimethyl-hexahydro-pyrrolo[3,4-c]pyrrol-2-yl]-1-phenyl-propyl}-amide (I-446)

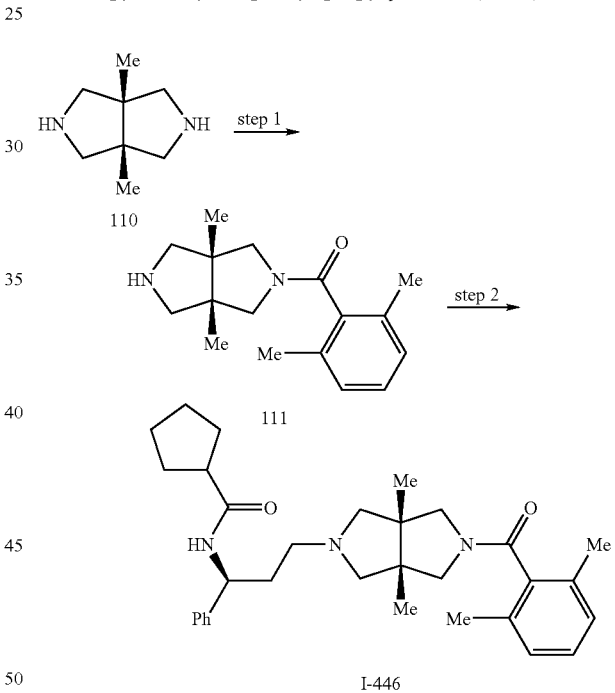

step 1—Butyllithium 2.5M in hexanes (2 mL, 5 mmol) was added dropwise at 0° C. to a suspension of 110 (0.35 g, 3 mmol, prepared as described in *J. Org. Chem.* 1996, 61:8897–8903) ( ) in THF (8 mL). The resulting mixture was stirred at 0° C. for 15 min then 2,6-dimethyl-benzoyl chloride (0.421 g, 3 mmol) in THF (2 mL) was added. The reaction mixture was stirred at 0° C. for 15 min then quenched by addition of MeOH (7 mL) and evaporated. The residue was partitioned between EtOAc and water. The organic layer was dried (MgSO$_4$), filtered and evaporated. The residue was purified by flash chromatography on silica gel eluting with a gradient from 100% DCM to a 1:1 solution of DCM and DCM/MeOH/NH$_4$OH 80/10/1 to afford 52 mg (8%) of 111: $^1$H NMR (CDCl$_3$) δ 1.01 (s, 3H), 1.11 (s, 3H), 2.26 (s, 6H), 2.83 (d, 1H, J=12 Hz), 2.90 (d, 1H, J=12 Hz), 2.95 (d, 1H, J=12 Hz), 2.96 (d, 1H, J=12 Hz), 3.09 (d, 1H, J=12 Hz), 3.15 (d, 1H, J=12 Hz), 3.54 (d, 1H, J=12 Hz), 3.84 (d, 1H, J=12 Hz), 7.03 (bd, 2H, J=9 Hz), 7.15 (dd, 1H, J=9; 8 Hz); MS (ES+) m/z 273 (M+H)+.

step 2—A mixture of 11 (52 mg, 0.191 mmol), aldehyde 10 (56 mg, 0.228 mmol), sodium triacetoxyborohydride (81 mg, 0.382 mmol) and HOAc (30 µl, 0.524 mmol) in DCM (5 mL) was stirred at RT for 48 h before being partitioned between DCM and a solution of 5% aqueous NaHCO$_3$. The aqueous layer was back extracted three times with DCM. The combined organic layers were dried over magnesium sulfate, filtered and evaporated. The residue was purified by SiO$_2$ flash chromatography on silica gel eluting with gradient of DCM (100%) to a solution 6:4 solution of DCM and DCM/MeOH/NH$_4$OH (80/10/1) to afford (I-446) (50 mg, 54% theoretical). $^1$H NMR (DMSO-d$_6$) δ TO BE ADDED; $^{13}$C NMR (DMSO-d$_6$) δ 18.86, 18.99, 25.96, 26.01, 30.13, 30.43, 35.74, 41.69, 44.57, 50.50, 51.06, 52.37, 53.12, 60.37, 126.64, 126.68, 126.89, 127.54, 127.61, 128.32, 128.53, 133.06, 138.25, 144.40, 167.72, 174.81; MS (ES+) m/z 502 (M+H)+.

EXAMPLE 38

1-Acetyl-piperidine-4-carboxylic acid (5-chloro-thiazol-2-yl)-{3-[5-(2,6-dimethyl-benzoyl)-hexahydro-pyrrolo[3,4-c]pyrrol-2-yl]-propyl}-amide (II-389)

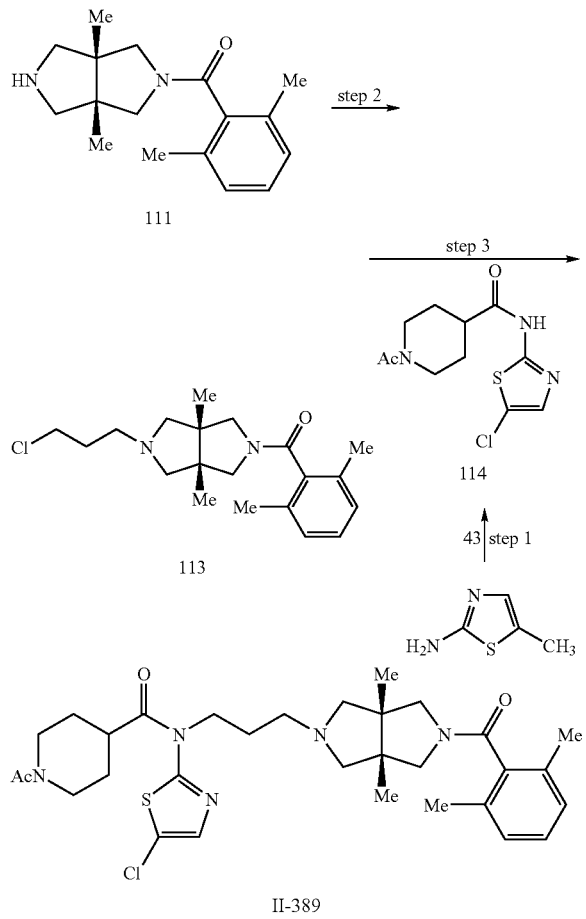

step 1—To a solution of 5-chloro-thiazol-2-ylamine hydrochloride (115, 216 mg, 1.26 mmol) in DCM (3 mL) was added 1-acetyl-piperidine-4-carbonyl chloride (43, 282 mg, 1.49 mmol) and TEA (0.41 mL, 2.92 mmol). The mixture was stirred for 12 h at RT. The reaction was quenched with water and the mixture was extracted with DCM. The organic layer was dried (Na$_2$SO$_4$), concentrated and purified by SiO$_2$ chromatography on (100% EtOAc) to afford 93 mg (26%) of 114: $^1$H NMR (CDCl$_3$, 1 H not observed) δ 1.66–2.04 (m, 4H), 2.12 (s, 3H), 2.54–2.71 (m, 1H), 2.72–2.84 (m, 1H), 3.10–3.25 (m, 1H), 3.85–3.99 (m, 1H), 4.54–4.65 (m, 1H), 7.23 (s, 1H).

step 2—To a solution of (2,6-dimethyl-phenyl)-(hexahydro-pyrrolo[3,4-c]pyrrol-2-yl)-methanone (111, 964 mg, 3.95 mmol) in DMF (7 mL) was added 1-chloro-3-iodo-propane (0.6 mL, 5.58 mmol) and Cs$_2$CO$_3$ (1.7 g, 5.21 mol) The mixture was stirred overnight at RT. Water was added to the mixture and the resulting solution was extracted with EtOAc. The organic layer was dried (Na$_2$SO$_4$) and concentrated. The crude product was purified by flash column chromatography on silica gel eluting with a DCM: MeOH: NH$_4$OH gradient (99:0.7:0.07 to 96:3.5:0.35 over 50 min.) to afford 0.828 g (65%) of 113: ms (LCMS) m/z 321 (M+H).

step 3—1-Acetyl-piperidine-4-carboxylic acid (5-chloro-thiazol-2-yl)-amide (114, 79 mg, 0.28 mmol) was dissolved in DMF (3 mL) and the resulting solution was cooled to 0° C. NaH (29 mg, 60% dispersion in mineral oil) was added and the mixture was heated to 50° C. for 2 h. A solution of 113 (88 mg, 0.28 mmol) and DMF (0.6 mL) was added dropwise and the reaction mixture was stirred at 90° C. for 9 h. The mixture was cooled, diluted with water and extracted with DCM. The combined DCM extracts were dried (MgSO$_4$) and concentrated. The crude product was purified by preparative HPLC to afford 20.5 mg (13%) of II-389 as a TFA salt: $^1$H NMR (DMSO-d$_6$) δ 1.4–1.6 (m, 2H), 1.85–1.95 (m, 2H), 2.0 (s, 3H), 2.05–2.22 (m, 9H), 2.55–2.65 (m, 1H), 2.9–3.0 (m, 1H), 3.2–3.3 (m, 7H), 3.5–3.9 (m, 7H), 4.15–4.2 (m, 2H), 7.05–7.2 (m, 3H), 7.6 (s, 1H); ms (ES+) m/z 572 (M+H).

EXAMPLE 39

(S)-Cyclopropanecarboxylic acid {3-[5-(2,4-dimethyl-pyridine-3-carbonyl)-hexahydro-pyrrolo[3,4-c]pyrrol-2-yl]-2-methyl-1-phenyl-propyl}-amide (I-458)

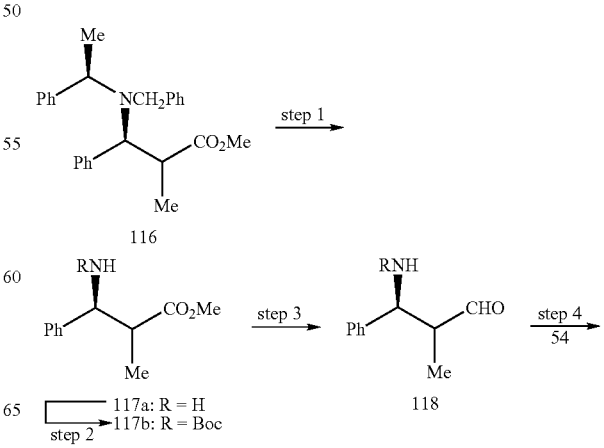

-continued

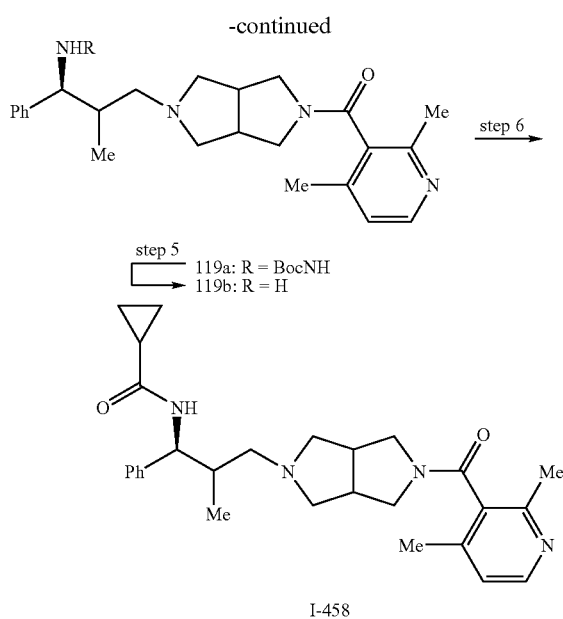

step 1—A solution of (2R, 3S, αR)3-[benzyl-(1-phenyl-ethyl)-amino]-2-methyl-3-phenyl-propionic acid methyl ester (116, 1.00 g, 2.58 mmol, prepared as described in *J. Chem. Soc. Perkin Trans.* 1 1994 1129) and MeOH:EtOAc: 10% HCl solution (25 mL) containing Pd(OH)$_2$—C (0.50 g) and hydrogenated (1 atm) for 24 h. The reaction mixture was filtered through a CELITE® pad to remove the catalyst. The filtrate was concentrated in vacuo and the residue partitioned between Et$_2$O (40 mL) and saturated NaHCO$_3$ solution (25 mL). The organic layer was dried (MgSO$_4$) and concentrated in vacuo to afford 408 mg (80%) of 117a as a pale yellow liquid: ms (ES+) m/z 194 (M+H)$^+$.

step 2—A solution of (2R, 3S)-3-amino-2-methyl-3-phenyl-propionic acid methyl ester (117a, 400 mg, 2.06 mmol) in THF (5 mL) was cooled to 0° C. A cold solution of NaOH (166 mg, 4.14 mmol) in H$_2$O (3.75 mL) was added to the above solution followed by a solution of (BOC)$_2$O in THF (2.5 mL) and the mixture stirred at RT for 5 h. The reaction mixture was extracted with EtOAc (2×50 mL) and the combined organic extracts were dried (MgSO$_4$) and concentrated in vacuo to afford 117b as a waxy solid: ms (ES+) m/z 237 (M−C$_4$H$_8$)$^+$.

step 3—To a solution of 117b (355 mg, 1.21 mmol) in DCM (20 mL) cooled to −78° C. was added DIBAL-H (2.42 mL of 1 M DCM solutionn, 2.42 mmol) dropwise at such a rate to maintain the temperature below −70° C. After 2 h the reaction was quenched by the slow addition of MeOH (2 mL) and then allowed to warm to RT. The reaction mixture was filtered through a CELITE® pad. The filtrate was dried (Na$_2$SO$_4$) and concentrated in vacuo. The crude product was purified by flash chromatography on silica eluting with EtOAc:hexane (1:3) to afford 118 as a white solid: $^1$H-NMR showed this material to be a 1:1.38 ratio of diastereomers.

step 4—To a solution of 118 (197 mg, 0.75 mmol) and 54 (184 mg, 0.75 mmol) in DCM (16 mL) containing HOAc (0.11 mL) was added NaBH(OAc)$_3$ (191 mg, 0.90 mmol) in 1 portion and the reaction was stirred for 18 h at RT. The reaction was quenched by the addition of 10% K$_2$CO$_3$ solution (10 mL) and stirred for 20 min. The product was extracted with DCM (2×20 mL) and the combined extracts were dried (Na$_2$SO$_4$) and concentrated in vacuo. The crude product was purified by flash chromatography on silica eluting with DCM/7.5% MeOH (containing 2% NH$_4$OH) to afford 290 mg (79%) of 119a as an off-white foam: ms (ES+) m/z 493 (M+H)$^+$.

step 5—A solution of 119a (258 mg, 0.52 mmol) dissolved in 10 M HCl in MeOH (8 mL) was heated at 65° C. for 2 h. The MeOH was evaporated under reduced pressure and the residue cautiously partitioned between DCM (25 mL) and 20% K$_2$CO$_3$ soln (15 mL). The aqueous layer was reextracted with DCM (2×20 mL). The combined extracts were dried (Na$_2$SO$_4$) and concentrated in vacuo to afford 194 mg (95%) of 119b as a viscous liquid: MS (ES+) m/z 393 (M+H)$^+$.

step 6—To a solution of 119b (500 μL of 0.1 M DCM soln, 0.050 mmol) and DIPEA (0.03 mL) was added cyclopropanecarbonyl chloride (6.8 μL, 7.8 mg, 0.075 mmol) and the resulting mixture stirred at room temp for 18 hrs. The reaction mixture was concentrated in a stream of N$_2$ and purified by reverse phase HPLC to afford I-458: ms (ES+) m/z 461 (M+H)$^+$.

EXAMPLE 40

1-Acetyl-piperidine-4-carboxylic acid (3-chloro-4-methyl-phenyl)-{3-[5-(2,4-dimethyl-pyridine-3-carbonyl)-3a,6a-dimethyl-hexahydro-pyrrolo[3,4-c]pyrrol-2-yl]-propyl}-amide (II-174)

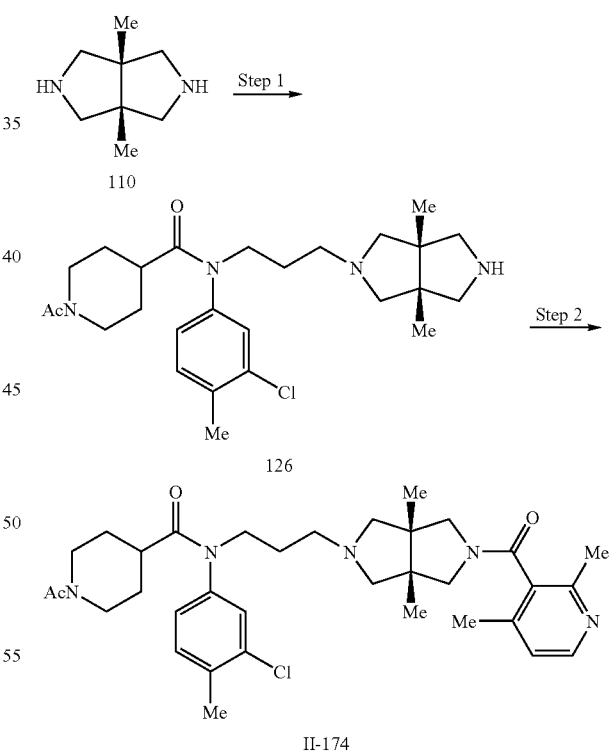

step 1—A mixture of 110 (1.2 g, 8 mmol), 18 (0.75 g, 2 mmol), KI (0.55 g, 3 mmol) and K$_2$CO$_3$ (0.825 g, 6 mmol) in DMF (30 mL) was stirred at 80° C. for 16 h before being partitioned between water and EtOAc. The aqueous layer was extracted twice with EtOAc. The combined organic layers were dried over (MgSO$_4$), filtered and evaporated. The residue was purified by flash chromatography on silica gel eluting with a gradient from 100% DCM to a 1:9 solution of DCM and DCM/MeOH/NH₄OH 60/10/1 to afford 0.100 g (3%) of 126: $^1$H NMR (CDCl$_3$) δ 1.53–2.46 (m, 15H), 2.56 (d, 2H, J=9 Hz), 2.67 (d, 2H, J=9 Hz), 2.78–2.95 (m, 3H), 3.48 (s, 6H), 4.52 (db, 1H, J=15 Hz), 6.97 (dd, 1H, J=9; 3 Hz), 7.18 (d, 1H, J=3 Hz), 7.31 (d, 1H, J=3 Hz); MS (ES+) m/z 608 (M+H)$^+$.

step 2—DIPEA (73 μL, 0.42 mmol) was added at RT to a solution of 126 (100 mg, 0.21 mmol), 2,4-dimethyl-3-pyridyl carboxylic acid (32 mg, 0.21 mmol), EDCI (48 mg, 0.25 mmol) and HOBT (34 mg, 0.25 mmol) in DMF (1 mL). The resulting mixture was stirred at RT for 16 h then partitioned between EtOAc and water. The aqueous layer was extracted twice with EtOAc. The combined organic layers were dried (Na$_2$SO$_4$), filtered and evaporated. The residue was purified by SiO$_2$ flash chromatography eluting with a gradient of 100% DCM to a 1:1 mixture DCM of a solution of DCM/MeOH/NH₄OH (80/10/1) over 20 minutes, followed by 8/2 DCM/MeOH solution for 10 min, 15 mL/min) to afford 87 mg (64%) of II-174: $^1$H NMR (CD$_3$OD) δ δ 0.90–3.34 (m, 35H), 3.39–3.84 (m, 4H), 3.92 (m, 1H), 4.52 (bd, 1H, J=12 Hz), 6.97 (m, 2H), 7.17 (bs, 1H), 7.31 (d, 1H, J=6 Hz), 8.36 (d, 1H, J=3 Hz); $^{13}$C NMR (CDCl$_3$) δ 19.10, 19.18, 20.19, 20.82, 21.14, 21.77, 22.52, 22.62, 27.05, 28.71, 29.22, 39.76, 41.07, 45.91, 48.41, 49.35, 49.38, 50.12, 50.69, 53.36, 58.30, 60.95, 67.41, 67.72, 123.02, 123.10, 126.69, 128.83, 132.40, 133.10, 135.64, 136.91, 141.50, 143.49, 143.58, 149.17, 149.22, 153.88, 154.06, 167.45, 169.19, 174.27; MS (ES+) m/z 608 (M+H)$^+$.

EXAMPLE 41

1-Acetyl-piperidine-4-carboxylic acid (3-chloro-4-methyl-phenyl)-{3-[(5-(2,4-dimethyl-pyridine-3-carbonyl)-3a,6a-bis-hydroxymethyl-hexahydro-pyrrolo[3,4-c]pyrrol-2-yl]-propyl}-amide (II-190)

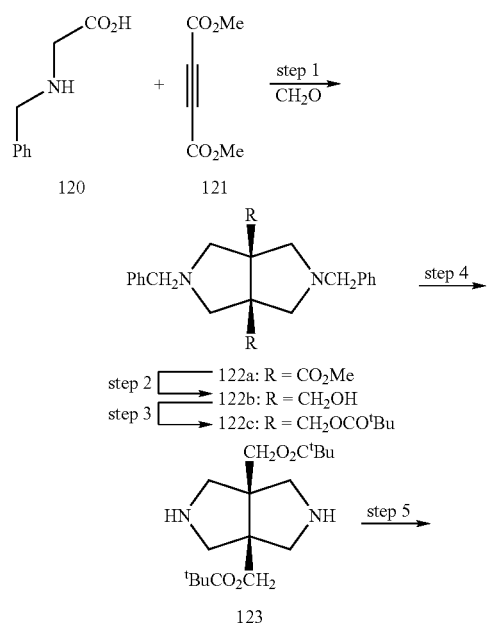

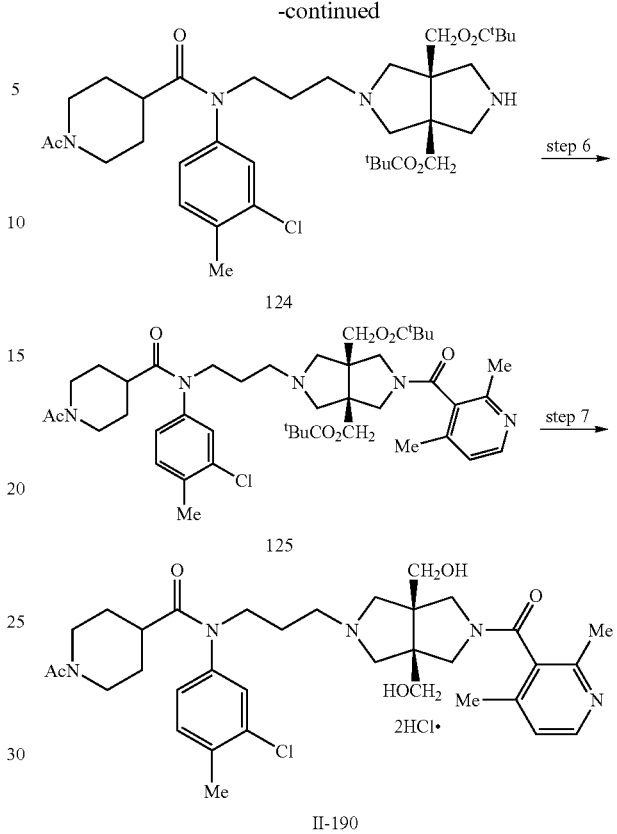

step—1-Formaldehyde (37 wt. % in water) was added dropwise over 3 h to a refluxing suspension of N-benzylglycine (10 g, 60.37 mmol) and dimethylacetylenedicarboxylate (3.7 mL, 30.19 mmol) in 200 mL of toluene. The resulting mixture stirred and heated to reflux for 14 h while water was continuously removed using a Dean Stark trap. The reaction mixture was cooled to RT and evaporated. The residue was purified by SiO$_2$ chromatography eluting with a hexane/EtOAc gradient (100% EtOAc to 75/25) over 40 minutes with and 80 mL/min flow rate to afford 3.4 g (28%) of 122a: $^1$H NMR (CDCl$_3$) δ 2.71 (d, 2H, J=9 Hz), 3.08 (d, 2H, J=9 Hz), 3.66 (s, 5H), 7.17–7.42 (m, 5H); MS (ES+) m/z 409 (M+H)$^{30}$.

step 2—An LAH solution (33 mL, 33 mmol, 1M solution in THF) was added to a solution of 122a (3.4 g, 8.323 mmol) and THF (100 mL) cooled to 0° C. and maintained under nitrogen. The resulting reaction mixture was stirred at 0° C. for 2 h before being quenched by addition of saturated NaHCO$_3$. The aqueous layer was extracted twice with EtOAc and combined organic layers were dried (Na$_2$SO$_4$), filtered and evaporated to afford 2.9 g (99%) of 122b: $^1$H NMR (CDCl$_3$) δ 2.56 (s, 4H), 3.58 (s, 2H), 3.63 (s, 2H), 7.18–7.38 (m, 5H); MS (ES+) m/z 353 (M+H)$^+$.

step 3—Trimethylacetyl chloride (1.7 mL, 13.8 mmol) was added to a solution of 122b (1.9 g, 5.39 mmol) in DCM (25 mL) and pyridine (2 mL). The resulting mixture was stirred at RT for 24 h before adding 5 mL of MeOH. After stirring at RT for 1 h, the reaction mixture was diluted with DCM and washed with 1M aqueous HCl, aqueous saturated NaHCO$_3$ and water. The organic layer was dried (Na$_2$SO$_4$), filtered and evaporated. The residue was purified by SiO$_2$ chromatography eluting with a hexane/EtOAc gradient (100% hexane to 10% EtOAc) to afford 1.14 g (41% theory) of 122c: $^1$H NMR (CDCl$_3$) δ 1.15 (s, 9H), 2.53 (d, 2H, J=9 Hz), 2.57 (d, 2H, J=9 Hz), 3.58 (s, 2H), 4.12 (s, 2H), 7.18–7.34 (m, 5H); MS (ES+) m/z 521 (M+H)$^+$.

step 4—A mixture of 122c (1.14 g, 2.189 mmol) and Pd(OH)$_2$/C (0.5 g; 20 wt. % on carbon) in EtOH (40 mL) and 10 mL of cyclohexane was heated to reflux with stirring for 24 h. The reaction mixture was cooled to RT, filtered and evaporated. The residue was dissolved in DCM and 5 mL of 1M HCl in Et$_2$O were added. The precipitate was filtered off and rinsed with DCM to afford 0.365 g (40%) of 123 as a light brown solid: $^1$H NMR (DMSO-d$_6$) δ 1.18 (s, 9H), 3.37 (d, 2H, J=9 Hz), 3.60 (d, 2H, J=9 Hz), 4.26 (s, 2H), 10.01 (bs, 1H); MS (ES+) m/z 341 (M+H)$^+$.

step 5—A mixture of 123 (90 mg, 0.242 mmol) and KI (44 mg, 0.266 mmol) in DMF (1 mL) was stirred at 80° C. for 8 h then added to a mixture of chloride 18 (0.1 g, 0.242 mmol), DIPEA (110 µL, 0.605 mmol) in DMF (1 mL). The resulting cloudy mixture was stirred at 40° C. for 15 h and then at 80° C. degrees for 2 h before being cooled to RT and diluted with EtOAc. The organic layer was washed with water and the aqueous layer was back extracted once with EtOAc. Combined organic layers were dried over (Na$_2$SO$_4$), filtered and evaporated. The residue was purified by SiO$_2$ chromatography gel eluting with a gradient from 100% DCM to a 1:1 solution of DCM and DCM/MeOH/NH$_4$OH 60/10/1 over 20 minutes at a 25 mL/min flow rate to afford 0.064 g (39%) of 124: MS (ES+) m/z 341 (M+H)$^+$.

step 6—2,4-Dimethyl-nicotinoyl chloride hydrochloride (39 mg/188.7 µmol) prepared from 2,4-dimethyl-nicotinic acid was added to a mixture of 124 (64 mg/94.33 µmol) and DIPEA (30 µL/188.7 µmol) in 0.5 mL of DCM. The resulting reaction mixture was stirred at RT for 5 h before being diluted with DCM, and washed with water. The aqueous layer was extracted once with DCM. Combined organic layers were dried over sodium sulfate, filtered and evaporated. The residue was purified by SiO$_2$ chromatography eluting with a gradient from 100% DCM to a 1:1 solution of DCM and DCM/MeOH/NH$_4$OH 60/10/1 over 20 minutes at a 25 mL/min flow rate to afford 0.062 g (81%) of 125: $^1$H NMR (CDCl$_3$) δ, mixture of rotamers, selected data: 4.51 (bd, 1H, J=12 Hz), 6.93–7.04 (m, 2H), 7.16 (m, 1H), 7.32 (d, 1H, J=9 Hz), 8.37 (dd, 1H, J=3, 1 Hz); MS (ES+) m/z 808 (M+H)$^+$.

step 7—Sodium methoxide (0.5 mL, 25 wt. % in MeOH) was added at RT to a solution of 125 (0.060 g, 74.21 µmol) in MeOH (4 mL). The resulting mixture was stirred at RT overnight then neutralized by addition of Dowex 50WX$^8$-200. The resin was filtered and rinsed with MeOH. The filtrate was evaporated and the residue was purified by SiO$_2$ chromatography (13 g RediSep column, DCM/[DCM/MeOH/NH$_4$OH 60/10/1] 10/0 to 1/1 over 20 minutes, 25 mL/min) to afford 23 mg (48%) of II-190 as a white foam: $^1$H NMR (CDCl$_3$) δ 1.51–1.85 (m, 6H), 2.05 (s, 3H), 2.22–2.56 (m, 16H), 2.61 (m, 1H), 2.84 (m, 1H), 3.07 (m, 1H), 3.39 (m, 1H), 3.51 (m, 1H), 3.38–3.57 (m, 8H), 4.51 (bd, 1H, J=12 Hz), 6.96 (dd, 1H, J=9, 1 Hz), 6.99 (dd, 1H, J=3, 1 Hz), 7.17 (m, 1H), 7.32 (d, 1H, J=9 Hz), 8.34 (t, 1H, J=3 Hz); $^{13}$C NMR (CDCl$_3$) δ 19.09, 19.31, 20.20, 21.76, 22.41, 22.68, 26.87, 28.72, 29.22, 30.08, 39.73, 41.07, 45.91, 48.16, 52.60, 53.82, 55.07, 55.13, 55.97, 56.05, 56.48, 63.91, 64.16, 123.16, 123.24, 126.61, 128.73, 132.48, 135.72, 137.07, 141.35, 149.09, 149.24, 153.73, 167.70, 167.92, 169.24, 174.37; MS (ES+) m/z 640 (M+H)$^+$.

EXAMPLE 42

Human CCR5 Receptor-ligand Binding Assay Protocol

Human CCR5 receptor (Genebank ID: 29169292) was cloned into mammalian expression vector, pTarget (Promega). The construct was transfected into CHO-G$_{\alpha16}$ cells by using Fugene Reagent (Roche). Clones were selected under antibiotic pressure (G418 and Hygromycin) and sorted 4 times with a fluorescence activates cell sorter and a monoclonal antibody specific for CCR5 receptor (BD Biosciences Pharmigen, Mab 2D7, Cat. No. 555993). The clone with highest expression (100,000 copies per cell) was chosen for the binding assays.

Adherent cells in 225 mL tissue culture flask (~90% confluent) were harvested using 1 mM EDTA in PBS (phosphate-buffered saline) without Ca$^{2+}$ and Mg$^{2+}$. Cells were washed twice with PBS containing no Ca$^{2+}$ and Mg$^{2+}$. CHO-G$_{\alpha16}$-hCCR5 cells were then resuspended (1×10$^6$/ml) in ice cold binding buffer (50 mM HEPES, 1 mM CaCl$_2$, 5 mM MgCl$_2$, 0.5% BSA, 0.05% NaN$_3$, pH 7.24), pH 7.4), supplemented with freshly made 0.5% BSA and 0.05% NaN$_3$.

Eighty µl CHO-G$_{\alpha16}$-hCCR5 (1×10$^6$/ml) cells were added to 96 well plates. All dilutions were made in binding buffer (50 mM HEPES, 1 mM CaCl$_2$, 5 mM MgCl$_2$, 0.5% BSA, 0.05% NaN$_3$, pH 7.24).

The plates were incubated on a cell shaker at RT for 2 h with a final concentration of 0.1 nM $^{125}$I RANTES or $^{125}$I MIP-1α or $^{125}$I MIP-1β. The compound dilutions were made in PBS, 1% BSA. Total reaction volume was 100 µl per well. The test compounds were added to the cells prior to the addition of radioligand.

After incubation, the cells were harvested onto GF/C filter plates using Packard cell harvester. Filters were pretreated with 0.3% PEI/0.2% BSA for 30 min. The filter plate was washed rapidly 5 times with 25 mM HEPES, 500 mM NaCl, 1 mM CaCl$_2$ and 5 mM MgCl$_2$ adjusted to pH 7.1. Plates were dried in oven (70° C.) for 20 min, added with 40 µl scintillation fluid and sealed with Packard TopSeal-A. Packard Top Count was used to measure of the radioactivity for 1 min per well.

Total binding was determined with control wells added with radioisotope and buffer and the non-specific binding was determined using an excess cold RANTES to some of the control wells. Specific binding was determined by subtracting the non-specific form total binding. Results are expressed as the percentage of specific $^{125}$I RANTES binding. IC$_{50}$ values were determined using varying concentrations of the test ligand in triplicates and the data was analyzed using GraphPad Prism (GraphPad, San Diego, Calif.).

| Compound No. | Binding IC$_{50}$ (µM) RANTES | Compound No. | Binding IC$_{50}$ (µM) RANTES |
|---|---|---|---|
| II-303 | 0.1019 | II-279 | 0.0015 |
| I-466 | 0.011 | I-39 | 0.0032 |
| I-449 | 0.001 | II-152 | 0.0022 |
| II-3 | 0.0184 | II-355 | 0.0027 |
| I-78 | 0.037 | II-182 | 0.0028 |
| II-1 | 0.0042 | I-52 | 0.0028 |
| I-29 | 0.016 | II-175 | 0.0029 |
| I-4 | 0.0191 | I-47 | 0.0037 |
| I-14 | 0.0019 | | |

EXAMPLE 43

Formulations

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations (G)

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 24 sprays every 4–12 hours.

REFERENTIAL EXAMPLE (2,4-Dimethyl-pyridin-3-yl)-(hexahydro-pyrrolo[3,4-c]pyrrol-2-yl)-methanone (54)

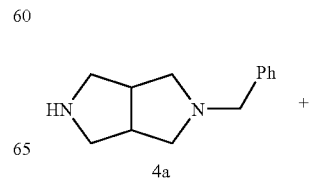

4a

-continued

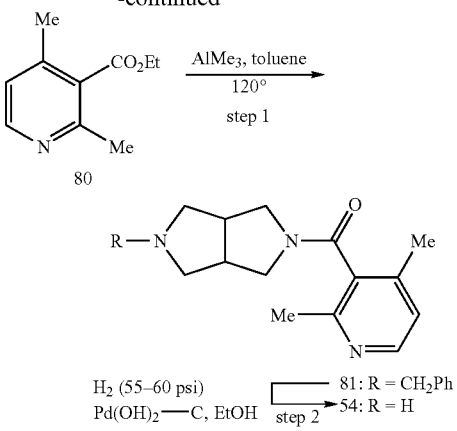

H₂ (55–60 psi)
Pd(OH)₂—C, EtOH
step 2

81: R = CH₂Ph
54: R = H step 1—A 25 mL 3-neck flask equipped with stir bar, addition funnel, N₂ inlet tube and reflux condenser was charged with 4a (1.0 g, 4.94 mmol) and (dry) toluene (4 mL) and cooled to 0° C. Trimethylaluminum (2.5 mL of a 2.0 M toluene solutionn, 5.0 mmol) was added dropwise, then allowed to warm to RT. 2,4-Dimethyl-nicotinic acid ethyl ester (80, 0.93 g, 5.2 mmol) in toluene (1 mL) was added dropwise then heated at 120° C. for 18 h. The reaction mixture was cooled in an ice bath and MeOH (2 mL) was added. The mixture was brought to RT, heated at reflux for 10 min then recooled to RT. The mixture was filtered through a CELITE® pad. The filtrate was washed with brine, dried (MgSO₄) then concentrated in vacuo. The crude product was purified by flash chromatography on silica eluting with 7.5% MeOH (containing 2% NH₄OH)/DCM to afford 1.17 g, (71%) of 81 as a pale yellow liquid: ms (ES+) m/z 336 (M+H)⁺.

step 2—A solution of 81 (5.55 g, 16.5 mmol) in EtOH (250 mL) containing 20% Pd(OH)₂ (2.75 g) was hydrogenated at 55 psi to 60 psi for 18 hrs. The mixture was filtered through a CELITE® pad to remove the catalyst and the filtrate concentrated in vacuo to afford 3.88 g (95%) 54 as a dark viscous liquid: ms (ES+) m/z 246 (M+H)⁺.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound according to formula I wherein:

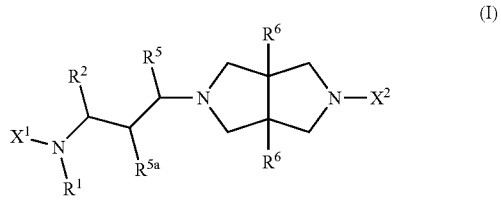

(I)

$X^1$ is selected from the group consisting —C(=O)R³ or —S(=O)₂R³;
$X^2$ is selected from the group consisting —C(=O)R⁴ or —S(=O)₂R⁴;
one of R¹ and R² is:
  (i) phenyl optionally substituted with one to four substituents selected independently in each incidence from the group consisting of halogen, $C_{1-6}$ alkyl and $C_{1-6}$ alkoxy;
the other of R¹ and R² is hydrogen;
R³ is selected from the group consisting of:
  (i) phenyl optionally substituted with one to four substituents selected independently in each incidence from the group consisting of:
    (a) $C_{1-10}$ alkyl,
    (b) $C_{1-10}$ heteroalkyl,
    (c) $C_{1-6}$ haloalkyl,
    (d) $C_{1-6}$ alkoxy,
    (e) $C_{1-6}$ thioalkyl,
    (f) amino,
    (g) $C_{1-6}$ alkyl amino,
    (h) $C_{1-6}$ dialkylamino,
    (g) $C_{1-6}$ acylamino,
    (i) carbamoyl, $N_{1-6}$ alkylcarbamoyl or N,N—$C_{1-6}$ dialkylcarbamoyl,
    (j) ureido,
    (k) nitro,
    (l) cyano,
    (m) halogen,
    (n) $C_{1-6}$ alkylsulfonyl,
    (o) sulfamoyl, N-$C_{1-6}$ alkylsulfamoyl or N,N—$C_{1-6}$ dialkylsulfamoyl,
    (p) $C_{1-6}$ alkylsulfonamido or optionally substituted phenylsulfonamido,
    (q) optionally substituted phenoxy,
    (r) —Y(CH₂)$_n$R¹¹ wherein R¹¹ is selected from the group consisting of cyano, —CO₂R¹², —CONR¹²R¹³, —SO₂N¹²R¹³, —NHSO₂R¹² and —NHSO₂NR¹²R¹³,
    (s) CO₂R¹²,
    (t) $C_{1-6}$ acyloxy,
    (u) $C_{1-6}$ alkylcarbonyl, and,
    (v) $C_{1-6}$ haloalkoxy;
  (ii) phenyl $C_{1-6}$ alkyl wherein phenyl as described in (i) above;
  (iii) $C_{3-7}$ cycloalkyl or bicyclohexyl, 4-oxo-cyclohexyl or 3-oxo-cyclobutyl said cycloalkyl optionally substituted with 1 to 4 fluorine, cyano, hydroxyl, $C_{1-3}$ alkyl or phenyl;
  (iv) $C_{1-3}$ alkyl-$C_{3-7}$ cycloalkyl said cycloalkyl optionally substituted with 1 to 4 fluorine, $C_{1-3}$ alkyl or phenyl;
  (v) NR¹⁴ᵃR¹⁴ᵇ; and R⁴ is heteroaryl selected from the group consisting of:
pyridinyl, pyridinyl N-oxide, pyrimidinyl, pyrazinyl, pyridazinyl, and cinnolin-4-yl optionally substituted with one to three substituents selected independently in each incidence from the group consisting of said heteroaryl optionally substituted with one to three subsituents selected independently in each incidence from the group consisting of (a) $C_{1-10}$alkyl, (b) phenyl optionally substituted with one to four substituents selected independently in each incidence from the group consisting of substituents (i)(a) to (i)(v) as described for R³ above, (c) benzyl, (d) acetyl, (e) amino, (f) $C_{1-6}$alkylamino, (g) $C_{1-6}$ dialkylamino, (h) aminobenzyl, (i) $C_{1-6}$ haloalkyl, (j) $C_{1-6}$ alkoxy, (k) $C_{1-6}$ thioalkyl, (l) $C_{1-6}$ alkylsulfonyl, (m) $C_{1-6}$ alkoxy carbonyl, (n) carboxyl, (o) carbamoyl, (p) nitro, (q) cyano, (r) sulfamoyl, (s) —$OCH_2CO_2R^{14c}$, (t)-$SCH_2CO_2R^{14c}$, and (u) halogen;

$R^5$ and $R^{5a}$ are hydrogen or $C_{1-6}$ alkyl;

$R^6$ is independently selected from the group consisting of hydrogen;

$R^{12}$ and $R^{13}$ (i) are independently hydrogen, $C_{1-6}$ alkyl or $C_{1-6}$ heteroalkyl;

$R^{14a}$ and $R^{14b}$ are independently hydrogen, $R^3$(i), $R^3$(ii), $R^3$(iii), $R^3$(iv), C(=O)OR$^{14c}$ and $C_{1-10}$ alkyl optionally independently substituted in each occurrence with one to three substituents independently selected at each occurrence from the group consisting of (a) hydroxy, (b) halogen, (c) $C_{1-6}$ alkoxy, (d) $C_{1-6}$ thioalkyl, (e) $C_{1-6}$ acyloxy, (f) $C_{1-6}$ alkoxycarbonyl, (g) $C_{1-6}$ acylamino, (h) N(R$^{14c}$)$_2$ wherein each R$^{14c}$ is selected independently, (i) cyano, (j) $C_{1-6}$ alkylsulfonyl, (k) N-methyl-methyl-sulfonamido, (l) carbamoyl, (m) $C_{1-6}$ alkoxycarbonyl, and (n) phenyl optionally substituted as defined in R³ (i) above;

$R^{14c}$ is hydrogen or $C_{1-6}$ alkyl;

Y is a direct bond, —O—, —S— or —NR$^{12}$—;

n is an integer from 1 to 6;

pharmaceutically acceptable salts, hydrates, solvates and stereoisomers thereof.

2. A compound according to claim 1 wherein is R¹ is optionally substituted phenyl, X¹ is —C(=O)R³ or —SO₂R³, X² is C(=O)R⁴ and R², R⁵, R⁵ᵃ and R⁶ are hydrogen.

3. A compound according to claim 2 wherein R³ is NR$^{14a}$R$^{14b}$.

4. A compound according to claim 3 wherein R$^{14a}$ is optionally substituted phenyl and R$^{14b}$ is hydrogen.

5. A compound according to claim 4 wherein R¹ is 4-methyl-3-chloro-phenyl, R$^{14a}$ is phenyl substituted by a carboxyl or $C_{1-6}$ alkoxycarbonyl and R$^{14b}$ is hydrogen.

6. A compound according to claim 1 wherein R² is optionally substituted phenyl, X¹ is —C(=O)R³ or —SO₂R³, X² is C(=O)R⁴ and R¹, R⁵, R⁵ᵃ and R⁶ are hydrogen.

7. A compound according to claim 6 wherein X¹ is —C(=O)R³, R³ is optionally substituted phenyl, optionally substituted phenyl, optionally substituted cycloalkyl, 4-oxo-cyclohexyl, or 3-oxo-cyclobutyl and R⁴ is a heteroaryl group wherein at least one atom adjacent to the atom linked to X² is a substituted carbon atom.

8. A compound according to claim 7 wherein X¹ is —C(=O)R³ and R³ is cycloalkyl optionally substituted with 1 to 4 fluorine atoms.

9. A compound according to claim 8 wherein R³ is cyclopentyl, 4,4-difluorocyclohexyl or 3,3-difluorocyclobutyl and R⁴ is selected from the group consisting of 2,6-dimethyl-pyrimidin-5-yl, 2,6-dimethyl-pyridine-3-yl and III.

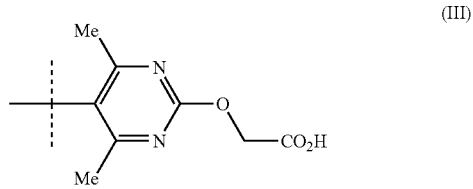

(III)

10. A compound according to claim 9 wherein R² is phenyl.

11. A compound according to claim 1 selected from the group consisting of:
cyclopentanecarboxylic acid {(S)-1-phenyl-3-[5-(pyridine-3-carbonyl)-hexahydro-pyrrolo[3,4-c]pyrrol-2-yl]-propyl}-amide; compound with trifluoro-acetic acid,
cyclopentanecarboxylic acid {(S)-3-[5-(4,6-dimethyl-pyrimidine-5-carbonyl)-hexahydro-pyrrolo[3,4-c]pyrrol-2-yl]-1-phenyl-propyl}-amide,
cyclopentanecarboxylic acid {(S)-3-[5-(2,4-dimethyl-pyridine-3-carbonyl)-hexahydro-pyrrolo[3,4-c]pyrrol-2-yl]-1-phenyl-propyl}-amide,
3-(3-(3-chloro-4-methyl-phenyl)-3-{3-[5-(4,6-dimethyl-pyrimidine-5-carbonyl)-hexahydro-pyrrolo[3,4-c]pyrrol-2-yl]-propyl}-ureido)-benzoic acid; compound with trifluoro-acetic acid
4,4-difluoro-cyclohexanecarboxylic acid {(S)-3-[5-(4,6-dimethyl-pyrimidine-5-carbonyl)-hexahydro-pyrrolo[3,4-c]pyrrol-2-yl]-1-phenyl-butyl}-amide, and,
(5-{5-[(S)-3-(cyclopentanecarbonyl-amino)-3-phenyl-propyl]-hexahydro-pyrrolo[3,4-c]pyrrole-2-carbonyl)}-4,6-dimethyl-pyrimidin-2-yloxy)-acetic acid; compound with trifluoro-acetic acid.

12. A pharmaceutical composition comprising a compound according to claim 1 admixed with at least one pharmaceutical acceptable carrier, diluent or excipient.

* * * * *